US011197862B2

(12) United States Patent
Huang et al.

(10) Patent No.: US 11,197,862 B2
(45) Date of Patent: Dec. 14, 2021

(54) METHODS OF PREVENTING TOXICITY OF PLATINUM DRUGS

(71) Applicant: XOMICS BIOPHARMA, INC., Menlo Park, CA (US)

(72) Inventors: Yong Huang, Milpitas, CA (US); Dominique P. Bridon, San Francisco, CA (US); Xuexiang Zhang, Fremont, CA (US); Chien-Ming Li, Fremont, CA (US)

(73) Assignee: XOMICS BIOPHARMA, INC., Menlo Park, CA (US)

( * ) Notice: Subject to any disclaimer, the term of this patent is extended or adjusted under 35 U.S.C. 154(b) by 0 days.

(21) Appl. No.: 15/744,485

(22) PCT Filed: Jul. 15, 2016

(86) PCT No.: PCT/US2016/042673
§ 371 (c)(1),
(2) Date: Jan. 12, 2018

(87) PCT Pub. No.: WO2017/011816
PCT Pub. Date: Jan. 19, 2017

(65) Prior Publication Data
US 2018/0207169 A1 Jul. 26, 2018

Related U.S. Application Data

(60) Provisional application No. 62/193,529, filed on Jul. 16, 2015.

(51) Int. Cl.
| | |
|---|---|
| *A61K 31/5365* | (2006.01) |
| *A61K 31/282* | (2006.01) |
| *A61K 31/40* | (2006.01) |
| *A61K 31/555* | (2006.01) |
| *A61P 25/02* | (2006.01) |
| *A61P 35/00* | (2006.01) |
| *A61K 45/06* | (2006.01) |
| *A61K 9/00* | (2006.01) |

(52) U.S. Cl.
CPC ........ *A61K 31/5365* (2013.01); *A61K 9/0019* (2013.01); *A61K 31/282* (2013.01); *A61K 31/40* (2013.01); *A61K 31/555* (2013.01); *A61K 45/06* (2013.01); *A61P 25/02* (2018.01); *A61P 35/00* (2018.01)

(58) Field of Classification Search
CPC .............. A61K 31/5362; A61K 9/0019; A61K 31/282; A61K 31/40; A61P 25/02
USPC ....................................................... 514/492
See application file for complete search history.

(56) References Cited

U.S. PATENT DOCUMENTS

| 2011/0052723 A1 | 6/2011 | Baeyens-Cabrera et al. |
| 2015/0087677 A1* | 3/2015 | Gaboyard-Niay ..... A61K 45/06 |
| | | 514/338 |

FOREIGN PATENT DOCUMENTS

| EP | 2090311 | * | 8/2009 |
| WO | WO 2009/032172 | * | 3/2009 |
| WO | WO-2011/047383 A1 | | 4/2011 |

OTHER PUBLICATIONS

Stein & Arnold. Oxaliplatin: a review of approved uses. Expert Opinion of Pharmacotherpay, 13:1, 125-137.*
Li et al. Role of Organic Cation Transporter I, OCT1 in the pharmacokinetics and toxicity of cis-diammine(pyridine)chloroplatinum (II ) and oxaliplatin in mice. Pharm. Res. 2011, 28: 610-625.*
Wang et al. Allosteric modulation of sigma-1 receptors elicit rapid antidepressant activity. CNS Neuroscience & Therapeutics, 22, 2016, 368-377.*
Albers, JW, et. al. (Feb. 16, 2011). "Interventions For Preventing Neuropathy Caused By Cisplatin and Related Compounds," *Cochrane Database Syst. Rev.* (2) Feb. 16, 2011, CD005228, 49 pages.
Argyriou, A.A., et al. (2012). "Chemotherapy-Induced Peripheral Neurotoxicity (CIPN): An Update," *Critical Reviews in Oncology/Hematology*. 82:51-77.
Argyriou, A. et. al. (Jan. 15, 2013, e-pub. Jul. 11, 2012). "Clinical Pattern and Associations of Oxaliplatin Acute Neurotoxicity," *Cancer*, pp. 438-444.
Argyriou, A.A. (May 29, 2015). "Updates on Oxaliplatin-Induced Peripheral Neurotoxicity (OXAIPN)," *Toxics*. 3:187-197.
Authier, N. et al. (Oct. 2009). "Animal Models of Chemotherapy-Evoked Painful Peripheral Neuropathies," *Neurotherapeutics* 6(4):620-629.
Avan, A. et al. (2015, e-pub. Mar. 12, 2015). "Platinum-Induced Neurotoxicity and Preventive Strategies: Past, Present, and Future," *The Oncologist*. 20:411-432.
Barabas, K. et al. (Mar. 2008). "Cisplatin: A Review Of Toxicities And Therapeutic Applications," *Veterinary and Comparative Oncology*, 6(1):1-18.
Belzer, M. et al. (Aug. 2013). "Substrate-Dependent Ligand Inhibition of the Human Organic Cation Transporter OCT2," *J. Pharmacol. Exp. Ther.* 346(2):300-310.
Boehmerle, W. et al. (Sep. 18, 2014). "Electrophysiological, Behavioral and Histological Characterization Of Paclitaxel, Cisplatin, Vincristine and Bortezomib-Induced Neuropathy In C57Bl/6 Mice," *Sci. Rep.* 4:6370, 9 pages.

(Continued)

*Primary Examiner* — Yevgeny Valenrod
(74) *Attorney, Agent, or Firm* — Morrison & Foerster LLP

(57) ABSTRACT

Methods for reducing platinum drug-induced toxicity in a cell expressing Organic Cation Transporter 2 (OCT2), methods for reducing platinum drug-induced toxicity in a subject, methods for treating cancer, methods for increasing efficacy of platinum drug treatment in a subject, and pharmaceutical compositions are described. The described methods and compositions include an OCT2 inhibitor where the OCT2 inhibitor is buflomedil or a salt thereof, dolutegravir or a salt thereof contains an imidazole, or is miconazole or a salt thereof.

22 Claims, 34 Drawing Sheets

(56) References Cited

OTHER PUBLICATIONS

Bourguinon, L. et al. (Apr. 2012, e-pub. Oct. 17, 2011). "The value Of Population Pharmacokinetics And Simulation For Postmarketing Safety Evaluation Of Dosing Guidelines For Drugs With A Narrow Therapeutic Index: Buflomedil As A Case Study," *Fundamental & Clinical Pharmacology*. 26(2):279-285.

Burger, H. (Feb. 2011). "Drug Transporters Of Platinum-Based Anticancer Agents And Their Clinical Significance," *Drug Resist. Updates* 14(1):22-34.

Carozzi, V.A. et al. (Dec. 2010, e-pub. Sep. 9, 2010). "Neurophysiological and Neuropathological Characterization Of New Murine Models Of Chemotherapy-Induced Chronic Peripheral Neuropathies," *Exp. Neurol.* 2010. 226(2):301-309.

Cavaletti, G. et al. (Feb. 2010, e-pub. Jan. 4, 2010). "Chemotherapy-Induced Peripheral Neurotoxicity Assessment: A Critical Revision Of The Currently Available Tools," *European Journal of Cancer* 46 (2010) 479-494.

Cavaletti, G. et al. (Aug. 21,2012). "The Chemotherapy-Induced Peripheral Neuropathy Outcome Measures Standardization Study: From Consensus To The First Validity And Reliability Findings," *Annals of Oncology* 24:454-462.

Cavaletti G. (Jun. 2014). "Chemotherapy-induced Peripheral Neurotoxicity (CIPN): What We Need and What We Know," *J. Peripher. Nerv. Syst.* 19(2):66-76.

Clinical Trial NCT01848457, (Jun. 11, 2015) "Preventing Nephrotoxicity and Otoxicity From Osteosarcoma Therapy," retrieved from <URL:https://clinicaltrials.gov/archive/NCT01848457/2015_06_11>, lasted visited Jun. 22, 2018.

Cottrell M.L. et al. (2013). "Clinical Pharmacokinetic, Pharmacodynamic and Drug-Interaction Profile of the Integrase Inhibitor Dolutegravir," *Clinical Pharmacokinetics* 52(11):981-994, 24 pages.

Ehrsson, H. et. al. (2002). "Pharmacokinetics Of Oxaliplatin In Humans," *Medical Oncology* 19(4):261-265.

Gauchan, P. et al. (2009). "Mechanical Allodynia Induced by Paclitaxel, Oxaliplatin and Vincristine: Different Effectiveness of Gabapentin and Different Expression of Voltage-Dependent Calcium Channel $\alpha_2\delta$-1 Subunit," *Bio. Pharm. Bull.* 32(4)732-734 (2009).

Griffith, K.A. et al. (May 2014). "Evaluation of Chemotherapy-Induced Peripheral Neuropathy Using Current Perception Threshold and Clinical Evaluations," *Support Care Cancer* 22(5):1161-1169, 18 pages.

Guidance For Industry: Drug Interaction Studies—Study Design, Data Analysis, Implications For Dosing, and Labeling Recommendations (Feb. 2012). *Clinical Pharmacology* 79 pages. Retrieved from <www.fda.gov/downloads/drugs/guidancecomplianceregulatoryinformation/guidances/ucm292362.pdf>. lasted visited Jul. 16, 2016.

Gunder-Remy, U. et al. (1981). "The Clinical Pharmacokinetics Of Buflomedil In Normal Subjects After Intravenous and Oral Administration," *European Journal of Clinical Pharmacology* 20(6):459-463.

Han, Y. et al. (Dec. 18, 2013). "Pathobiology Of Cancer Chemotherapy-Induced Peripheral Neuropathy (CIPN)," *Frontiers in Pharmacology*. 4(156):1-16.

Hargreaves, K.M. et al. (Jan. 1988). "A New and Sensitive Method For Measuring Thermal Nociception In Cutaneous Hyperalgesia," *Pain* 32(1):77-88.

Harrach, S. et al. (Apr. 24, 2015). "Role Of Transporters In The Distribution Of Platinum-Based Drugs," *Frontiers in Pharmacology* 6(85):1-7.

Heise et al. (2012). "Downregulation Of Organic Cation Transporters OCT1 (*SLC22A1*) and OCT3 (*SLC22A3*) in Human Hepatocellular Carcinoma And Their Prognostic Significance," *BMC Cancer* 12:109, 10 pages.

Hellberg et al. (Sep. 2015). "Immunohistochemical Localization Of OCT2 in The Cochlea Of Various Species," *Laryngoscope* 125:E320-325.

Hershman, D.L. et al. (Jun. 20, 2014, e-pub. Apr. 14, 2014). "Prevention and Management of Chemotherapy-Induced Peripheral Neuropathy in Survivors of Adult Cancers: American Society of Clinical Oncology Clinical Practice Guideline," *Journal Of Clinical Oncology* 32(18):1941-1970.

Hidalgo, M. et al. (Jun. 2003). "Pharmacokinetics and Pharmacodynamics: Maximizing The Clinical Potential Of Erlotinib (Tarceva)," *Seminars in Oncology* 30(3)(Suppl. 7):25-33.

Holmes, J. et. al. (1998). "Comparative Neurotoxicity of Oxaliplatin, Cisplatin, and Ormaplatin In A Wistar Rat Model," *Toxicological Sciences* 46:342-351.

Jahic, M. et. al. (2015). "Should Total Plasma Drug Concentration Be Used To Predict Transporter Mediated Drug-Drug Interactions For Highly Protein Bound Drugs," *13th European ISSX Meeting*, Glasgow, P164 Abstract.

Jensen, T.S et al. (Sep. 2014). "Allodynia and Hyperalgesia In Neuropathic Pain: Clinical Manifestations and Mechanisms," *Lancet Neural.* 13:924-935.

Karasawa, T. et al. (Sep. 17, 2015). "An Integrated View Of Cisplatin-Induced Nephrotoxicity and Ototoxicity," *Toxicology Letters* 237(3):219-227, 24 pages.

Katsuda, H. et al. (Nov. 2010). "Protecting Cisplatin-Induced Nephrotoxicity with Cimetidine Does Not Affect Antitumor Activity," *Biol. Pharm. Bull.* 33(11):1867-1871.

Kautio, A.-L. et. al. (Jan. 2008). "Amitriptyline in the Treatment of Chemotherapy-Induced Neuropathic Symptoms," *J. Pain Symptom Manage* 35(1):31-39.

Kautio, A.-L. et. al. (2009). "Amitriptyline In The Prevention Of Chemotherapy-Induced Neuropathic Symptoms," *Anticancer Res.* 29:2601-2606.

Kautio, A.-L. et al. (2011). "Oxaliplatin Scale and National Cancer Institute—Common Toxicity Criteria in the Assessment of Chemotherapy-induced Peripheral Neuropathy," *Anticancer Research* 31:3493-3496.

Kawashiri, T. et al. (Apr. 2011, e-pub. Sep. 9, 2010). "Prevention Of Oxaliplatin-Induced Mechanical Allodynia and Neurodegeneration By Neurotropin In The Rat Model," *European Journal of Pain* 15(4):344-350.

Kido, Y. et al. (Jul. 14, 2011) "Profiling Of A Prescription Drug Library For Potential Renal Drug-Drug Interactions Mediated By The Organic Cation Transporter 2," *Journal of Medicinal Chemistry* 54(13):4548-4558, 22 pages.

Kottschade, L.A. et al. (Nov. 2011). "The Use Of Vitamin E For The Prevention Of Chemotherapyinduced Peripheral Neuropathy: Results Of A Randomized Phase III Clinical Trial," *Support Care Cancer* 19(11):1769-1777, 14 pages.

Langer, T. et al. (Aug. 2013). "Understanding Platinum-Induced Ototoxicity," *Trends in Pharmacological Sciences* 34(8):458-469.

Lepist, E.-I. et al. (2014, e-pub. Mar. 19, 2014). "Contribution Of The Organic Anion Transporter OAT2 to The Renal Active Tubular Secretion Of Creatinine And Mechanism For Serum Creatinine Elevations Caused By Cobicistat," *Kidney International* 86:350-357.

Li, Q. et al. (2014). "Role Of Solute Carriers In Response To Anticancer Drugs," *Molecular and Cellular Therapies* 2:15, 14 pages.

Mikamo, H. et. al. (Jan. 1997). "Pharmacokinetics Of Miconazole In Serum and Exudate Of Pelvic Retroperitoneal Space After Radical Hysterectomy and Pelvic Lymphadenectomy," *International Journal of Antimicrobial Agents* 9(3):207-211.

Miller, R.P. et al. (Oct. 26, 2010). "Mechanisms of Cisplatin Nephrotoxicity," *Toxins* 2:2490-2518.

Miltenburg, N.C. et al. (2014). "Chemotherapy-Induced Neuropathy: A Comprehensive Survey," *Cancer Treatment Reviews* 40:872-882.

Min et. al. (Jan. 2010). "Pharmacokinetics and Safety Of S/GSK1349572, A Next-Generation HIV Integrase Inhibitor, in Healthy Volunteers," *Antimicrobial Agents And Chemotherapy* 54(1):254-258.

Molinaro, M. et. al. (Apr. 1994). "Evaluation Of Two Buflomedil Tablet Formulations In Patients With Atherosclerotic Disease," *Journal of Clinical Pharmacy and Therapeutics* 19(2):111-115.

(56) References Cited

OTHER PUBLICATIONS

Nakanishi, T. (2007). "Drug Transporters As Targets For Cancer Chemotherapy," *Cancer Genomics & Proteomics* 4:241-254.

Pace, A. et. al. (Mar. 1, 2003). "Neuroprotective Effect of Vitamin E Supplementation in Patients Treated With Cisplatin Chemotherapy," *J. Clin. Oncol.* 21 (5):927-931.

Reese, M.J. et al. (Feb. 2013). "In Vitro Investigations Into The Roles Of Drug Transporters And Metabolizing Enzymes In The Disposition And Drug Interactions Of Dolutegravir, A HIV integrase Inhibitor," *Drug Metabolism and Disposition* 41:353-361.

Renn, C.L. et al. (Apr. 26, 2011). "Multimodal Assessment Of Painful Peripheral Neuropathy Induced By Chronic Oxaliplatin-Based Chemotherapy In Mice," *Mol. Pain.* 7:29, 13 pages.

Sada, H. et al. (2012, e-pub. Mar. 29, 2012). "Repeated Administration Of Amitriptyline Reduces Oxaliplatin-Induced Mechanical Allodynia In Rats," *Journal of Pharmacological Sciences* 118:547-551.

Saif, M. et al. (2005). "Management Of Oxaliplatin-Induced Peripheral Neuropathy," *Therapeutics and Clinical Risk Management* 1 (4) 249-258.

Seretny, M. et al. (2014). "Incidence, Prevalence, and Predictors Of Chemotherapy-Induced Peripheral Neuropathy: A Systematic Review and Meta-Analysis," *PAIN* 155:2461-2470.

Sprowl, J.A. et al. (Jul. 2, 2013). "Oxaliplatin-induced Neurotoxicity Is Dependent On The Organic Cation Transporter OCT2," *Proc. Natl. Acad. Sci. USA* 110(27):11199-11204.

Sung, J.P. et al. (Jan. 1977). "Intravenous and Intrathecal Miconazole Therapy for Systemic Mycoses," *J. Med.* 126:5-13.

Ta, L.E. et al. (Feb. 26, 2009). "Mice With Cisplatin and Oxaliplatin-Induced Painful Neuropathy Develop Distinct Early Responses To Thermal Stimuli," *Mol. Pain* 5:9, 11 pages.

Tashima. (Jul. 27, 2015). "Possibilities of Cancer Chemotherapy Based on Transporter-Conscious Drug Design," *J. Carcinog. Mutagen* 6:4. 3 pages.

Ushio, S et al. (Jun. 2012, e-pub. Sep. 8, 2011). "Goshajinkigan reduces Oxaliplatin-Induced Peripheral Neuropathy Without Affecting Anti-Tumour Efficacy In Rodents," *European Journal of Cancer* 48(9):1407-1413.

Velasco, R., et al. (2014, e-pub. Jun. 29, 2013). "Early Predictors Of Oxaliplatin-Induced Cumulative Neuropathy In Colorectal Cancer Patients," *J. Neurol. Neurosurg. Psychiatry* 85:392-398.

Wensing, K. et al. (2013). "Saving Ears and Kidneys from Cisplatin," *Anticancer Research* 33:4183-4188.

Werling, L. (2007, e-pub. Jun. 30, 2007). "A Comparison Of The Binding Profiles Of Dextromethorphan, Memantine, Fluoxetine And Amitriptyline: Treatment Of Involuntary Emotional Expression Disorder," *Experimental Neurology* 207(2):248-257.

Wittwer M.B. et al. (Feb. 14, 2013). "Discovery of Potent, Selective Multidrug And Toxin Extrusion Transporter 1 (MATE1, SLC47A1) Inhibitors Through Prescription Drug Profiling and Computational Modeling," *Journal of Medicinal Chemistry* 56(3):781-795, 34 pages.

Wolf, S.L. et al. (Mar. 2012). "The Relationship Between Numbness, Tingling, and Shooting/Burning Pain In Patients With Chemotherapy-Induced Peripheral Neuropathy (CIPN) as Measured By The EORTC QLQ-CIPN20 Instrument, N06CA," *Support Care Cancer.* 20(3):625-632, 16 pages.

Yao, X et al. (2007). "Cisplatin Nephrotoxicity: A Review," *The American Journal of the Medical Sciences.* 334(2):115-124.

Yonesawa, A. et al. (Mar. 1, 2011, e-pub. Dec. 7, 2010). "Organic Cation Transporter OCT/SLC22A and H(+)/Organic Cation Antiporter MATE/SLC47A Are Key Molecules For Nephrotoxicity Of Platinum Agents," *Biochem. Pharmacology* 81(5):563-568.

Zhang, J. et al. (2015, e-pub. Mar. 27, 2015). "Population Pharmacokinetics Of Dolutegravir In HIV Infected Treatment-Naïve Patients," *British Journal of Clinical Pharmacology* 80(3):502-514.

Zhang Y. et al. (Apr. 2015). "Impact On Creatinine Renal Clearance By The Interplay Of Multiple Renal Transporters: A Case Study With INCB039110," *Drug Metab. Dispos.* 43(4):485-489.

International Preliminary Report On Patentability, dated Jan. 16, 2018, for PCT Application No. PCT/US2016/042673, filed Jul. 15, 2016, 10 pages.

International Search Report, dated Oct. 11, 2016, for PCT Application No. PCT/US2016/042673, filed Jul. 15, 2016, 5 pages.

Written Opinion, dated Oct. 11, 2016, for PCT Application No. PCT/US2016/042673, filed Jul. 15, 2016, 9 pages.

Barceló, R. et al. (2000). "Distal Ischemic Changes Related To Combination Chemotherapy With Cisplatin And Gemcitabine: Description Of Four Cases," *Annals of Oncology* 11:1191-1194.

Sprowl, J.A. et al. (Nov. 2013). "Conjunctive Therapy of Cisplatin With the OCT2 Inhibitor Cimetidine: Influence on Antitumor Efficacy and Systemic Clearance," *Clinical Pharmacology And Therapeutics*, 94(5):585-592, 19 pages.

European Extended Search Report, dated Jan. 8, 2019, for European Patent Application No. 16825297.1, 15 pages.

Amato, A.A. et al. (1998). "Neuropathies Associated with Malignancy," *Seminars in Neurology* 18(1):125-144.

Barretina, J. et al. (Sep. 29, 2012). "The Cancer Cell Line Encyclopedia Enables Predictive Modeling of Anticancer Drug Sensitivity," *Nature* 483(7391):603-607, 13 pages.

Bianchi, R. et al. (Apr. 15, 2006). "Protective Effect of Erythropoietin and Its Carbarnyalted Derivative in Experimental Cisplatin Peripheral Neurotoxicity," *Clin. Cancer Res.* 12(8):2607-2612.

Filipski, K.K. et al. (Oct. 2009). "Contribution of Organic Cation Transporter 2 (OCT2) to Cisplatin-Inducted Nephrotoxicity," *Clin. Pharmacol. Ther.* 86(4):396-402, 17 pages.

Kanat, O. et al. (Aug. 10, 2017). "Platinum-Induced Neurotoxicity: A Review of Possible Mechanisms," *World J. Clin. Oncol.* 8(4):329-335.

Koepsell, H. et al. (2004). "The SLC22 Drug Transporter Family," *Pflugers Arch.—Eur. J. Physiol.* 447:666-676.

Nies, A.T. et al. (2011, e-pub. Oct. 26, 2010). "Organic Cation Transporters (OCTs, MATEs), In Vitro and In Vivo Evidence for the Importance in Drug Therapy," *Drug Transporters* pp. 105-167.

NINDS (2018). "Peripheral Neuropathy Fact Sheet," NIH Publication No. 18-NS-4853, retrieved from https://www.ninds.nih.gov/Disorders/Patient-Caregiver-Education/Fact-Sheets/Peripheral-Neuropathy-Fact-Sheet, last visited Jul. 12, 2020, 12 pages.

Okabe, M. et al. (Sep. 2008). "Profiling SLCO and SLC22 Genes in the NCI-60 Cancer Cell Lines to Identify Drug Uptake Transporters," *Mol. Cancer Ther.* 7(9):3081-3091, 22 pages.

Starobova, H. et al. (May 31, 2017). "Pathophysiology of Chemotherapy-Induced Peripheral Neuropathy," *Frontiers in Molecular Neuroscience* 10(174):1-21.

Zajaczkowska, R. et al. (Mar. 22, 2019). "Mechanisms of Chemotherapy-Induced Peripheral Neuropathy," *International Journal of Molecular Sciences* 20(1451):1-29.

Zis, P. et al. (2017, e-pub. Jul. 1, 2017). "Painful Peripheral Neuropathy and Cancer," *Pain Ther.* 6:115-116.

Hashimoto, K. (2009). "Can the Sigma-1 Receptor Agonist Fluvoxamine Prevent Schizophrenia?," *CNS & Neurological Disorders—Drug Targets* 8:470-474.

Hashimoto, K. (2015, e-pub. Dec. 4, 2014). "Activation of Sigma-1 Receptor Chaperone in the Treatment of Neuropsychiatric Diseases and its Clinical Implication," *Journal of Pharmacological Sciences* 127:6-9.

Ishikawa, M. et al. (2009, e-pub. Jul. 2, 2009). "High Occupancy of σ1 Receptors in the Human Brain After Single Oral Administration of Donepezil: A Position Emission Tomography Study Using [11 C]SA4503," *International Journal of Neuropsychopharmacology* 12:1127-1131.

Jia, Y. et al. (Mar. 31, 2015). "The Latest Progress of Modern Clinical Cancer Diagnosis and Treatment, Ed. 1," Xi'an Jiaotong University Press, p. 357, 9 pages. English Translation.

Kishimoto, A. et al. (2010). "The Opposite Effects of Fluvoxamine and Sertraline in the Treatment of Psychotic Major Depression: A Case Report," *Annals of General Psychiatry* 9:23, 3 pages.

Kulkarni, S.K. et al. (2009). "σ-1 Receptors in Major Depression and Anxiety," *Expert Rev. Neurother.* 9 (7):1021-1034.

Lin, X. (Jan. 31, 2013). "Modern Diagnosis and Treatment of Liver Disease, Ed. 1," Military Medical Science Press pp. 217-218, 6 pages.. English Translation.

(56) References Cited

OTHER PUBLICATIONS

Werling, L. et al. (2007). "A comparison of the binding profiles of dextromethorphan, memantine, fluoxetine and amitriptyline: Treatment of involuntary emotional expression disorder," Experimental Neurology 207: 248-257.
Hershman, D. et al. (2014). "Prevention and Management of Chemotherapy-Induced Peripheral Neuropathy in Survivors of Adult Cancers: American Society of Clinical Oncology Clinical Practice Guideline," Journal of Clinical Oncology, 32(18): 1941-1967.
Clissold. S. et al. (1987). "Buflomedil: A Review of Its Pharmacodynamic and Pharmacokinetic Properties, and Therapeutic Efficacy in Peripheral and Cerebral Vascular Diseases," Drugs, 33: 430-460.

* cited by examiner

Figure 12
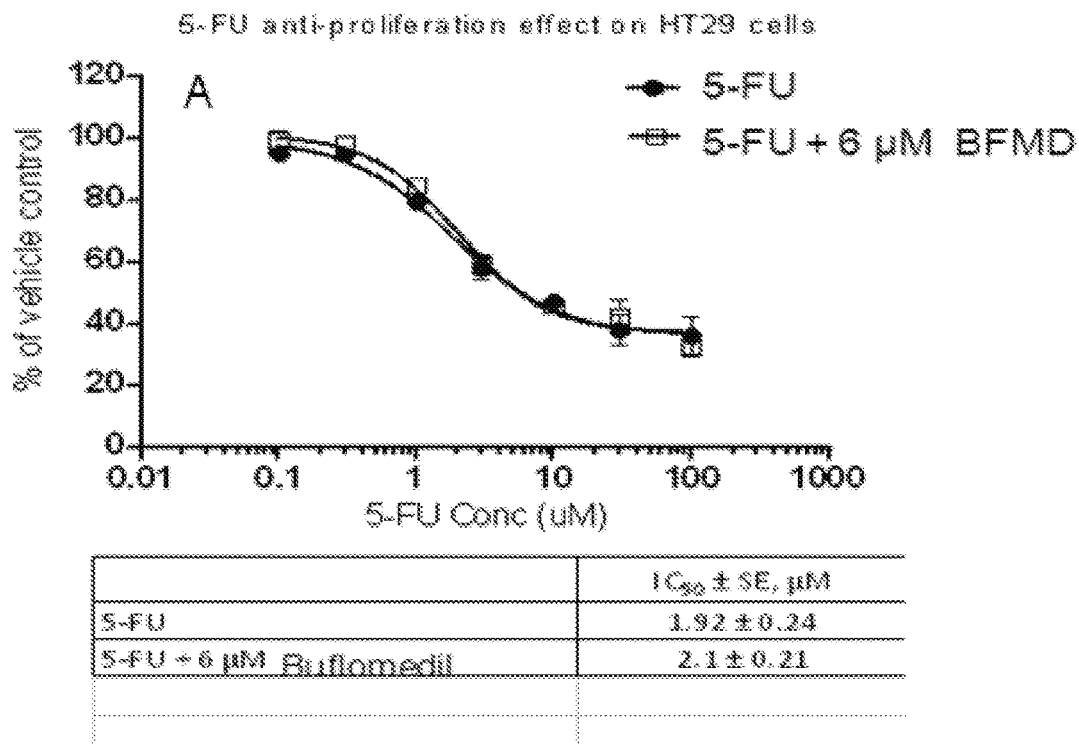
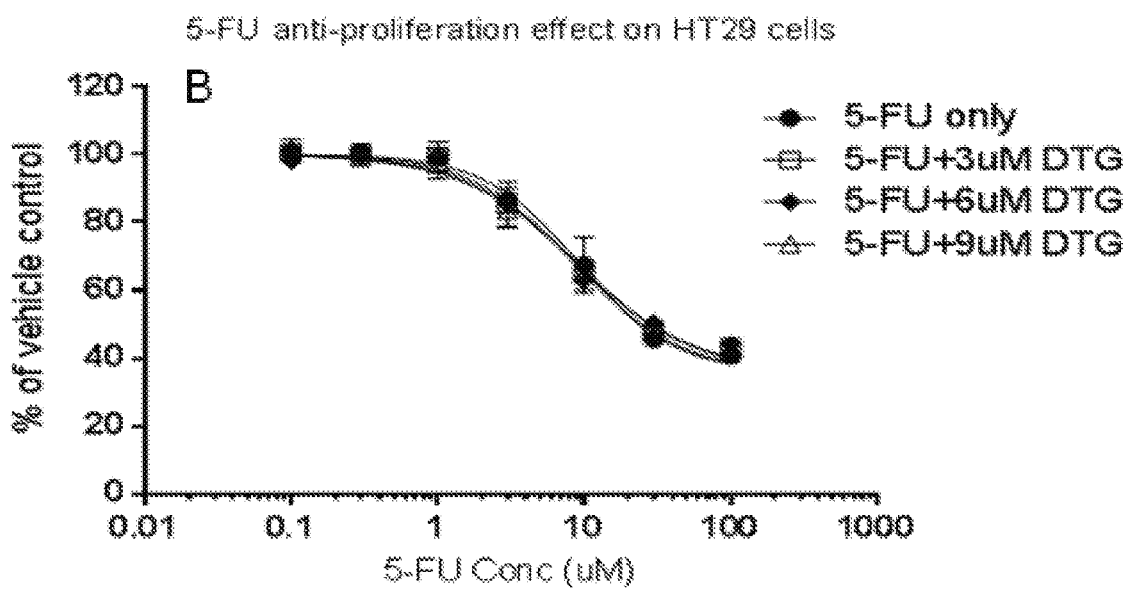

Figure 13
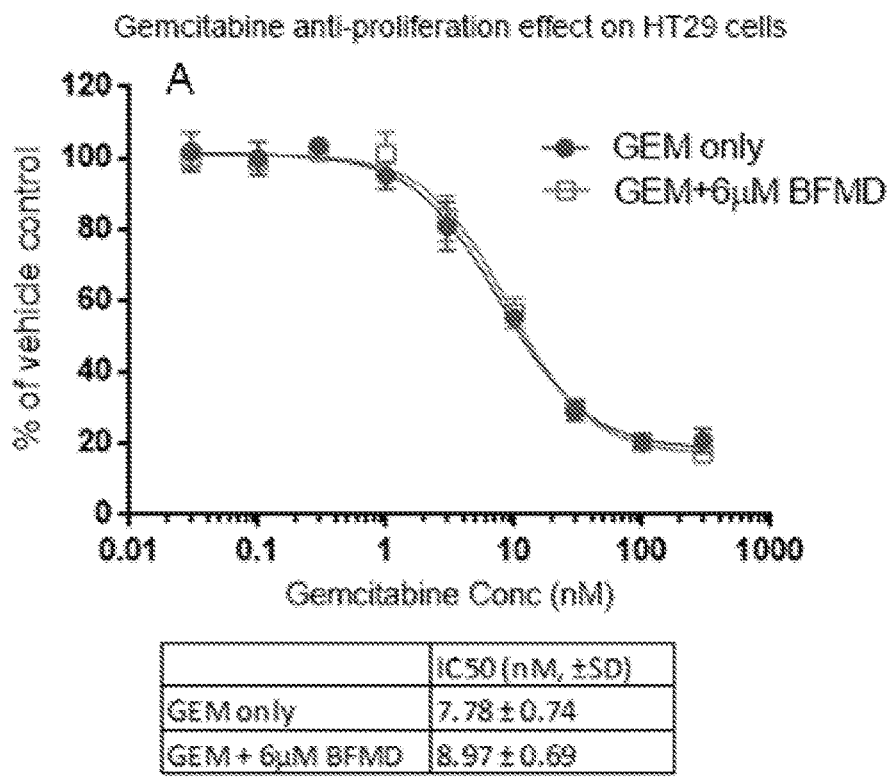
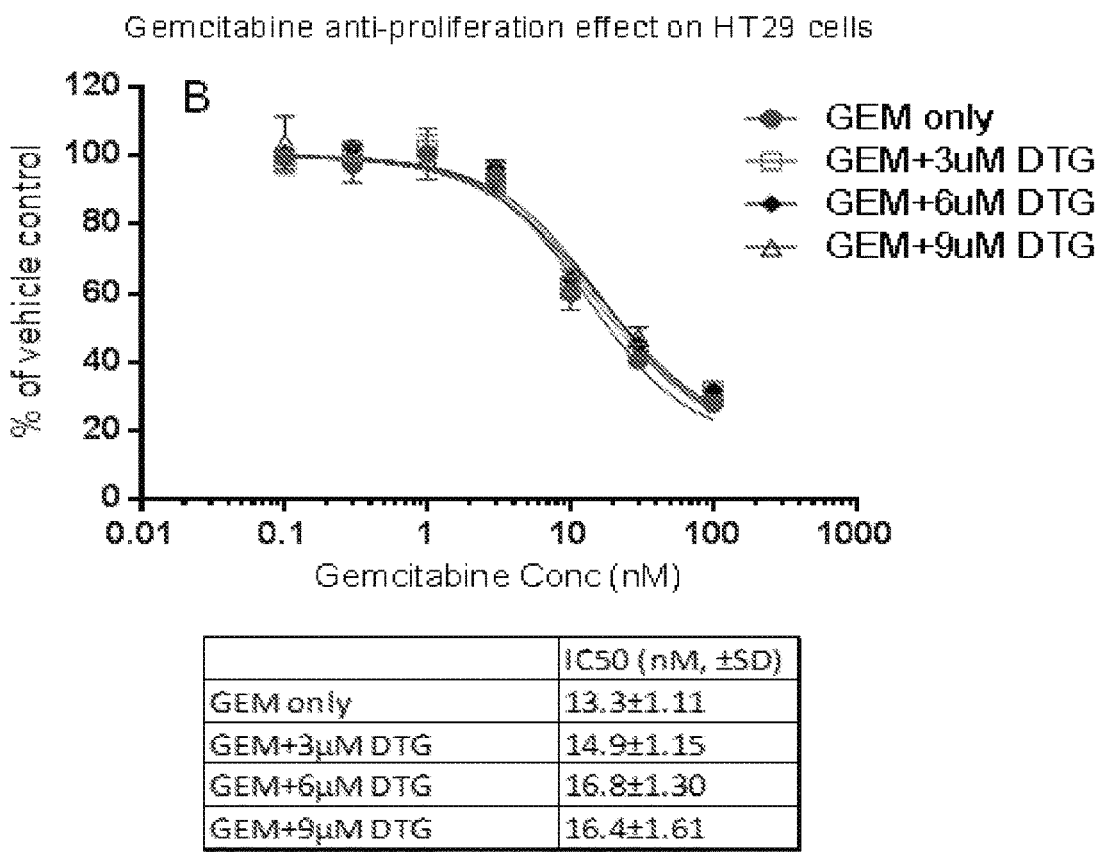

Figure 15
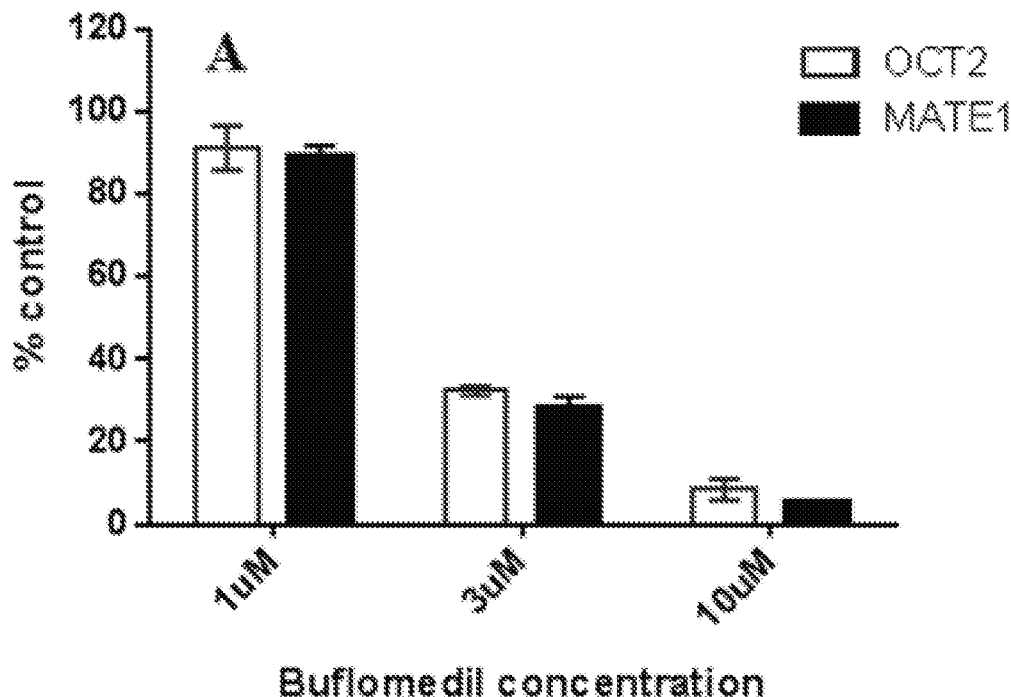
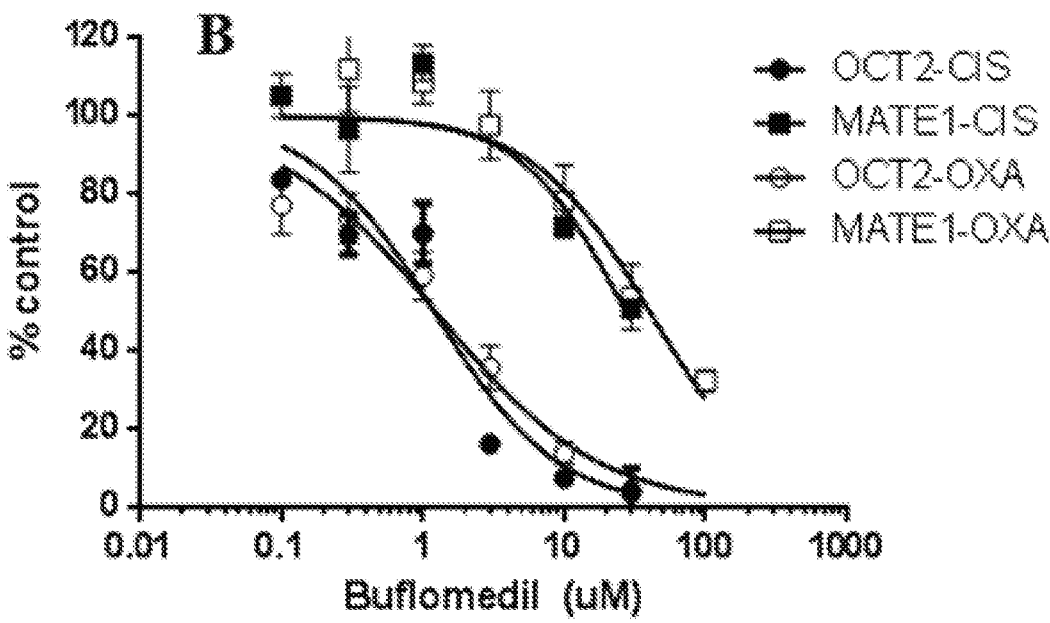

Figure 17
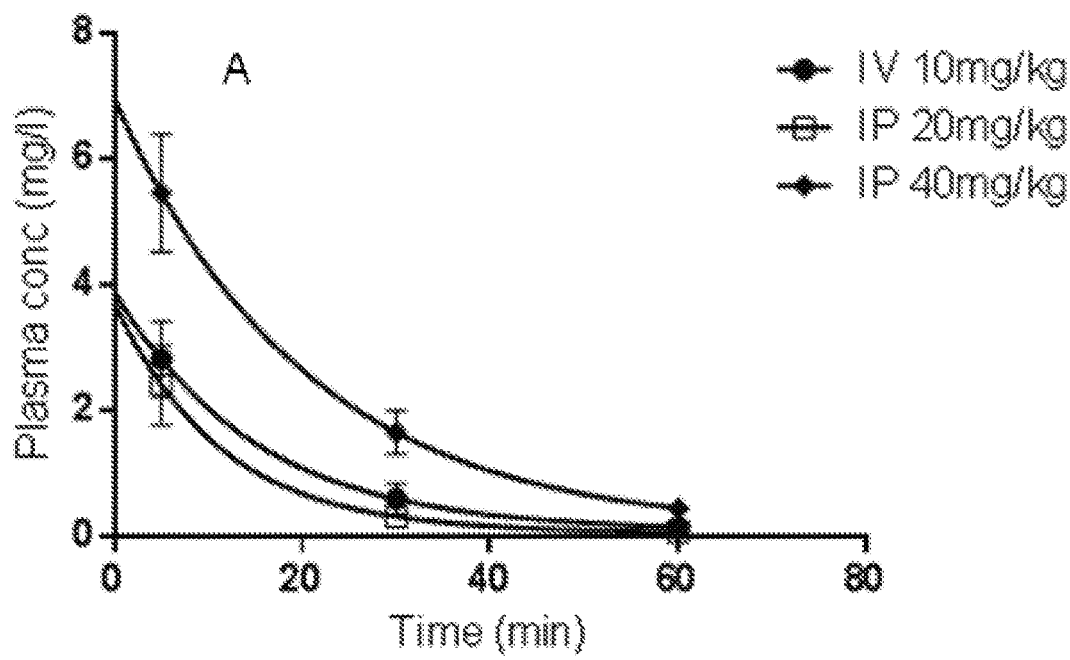
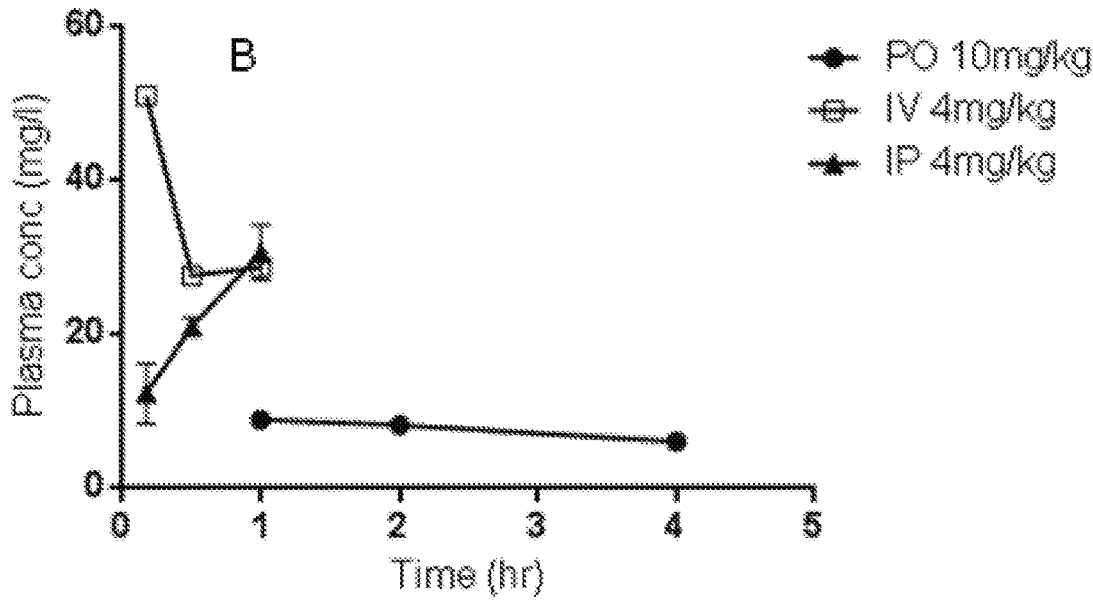

Figure 19
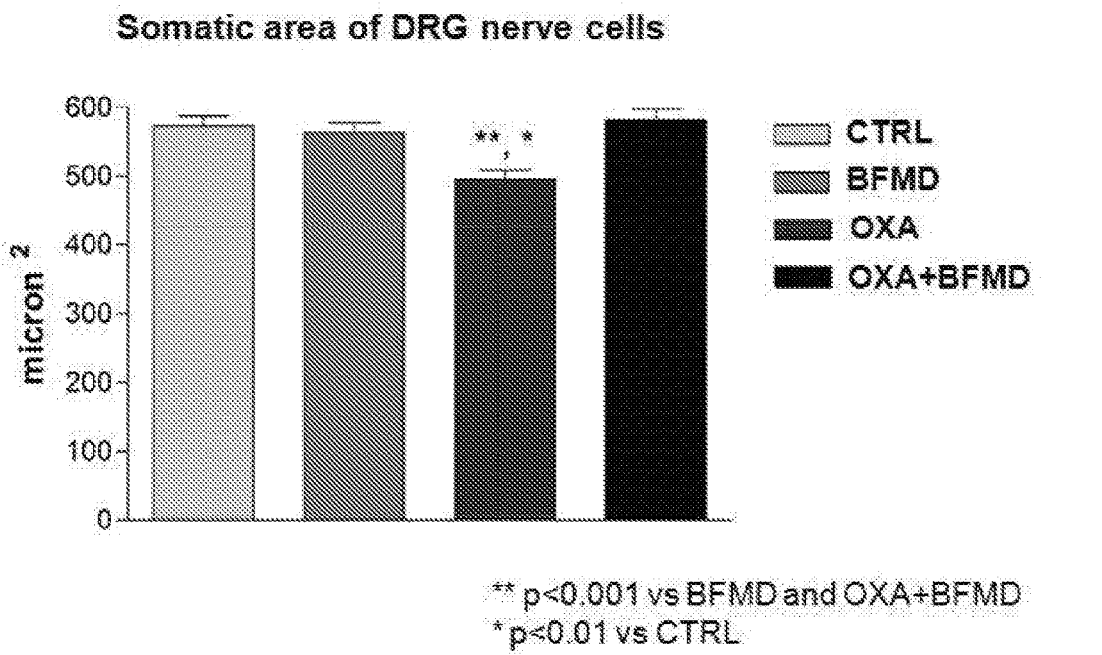
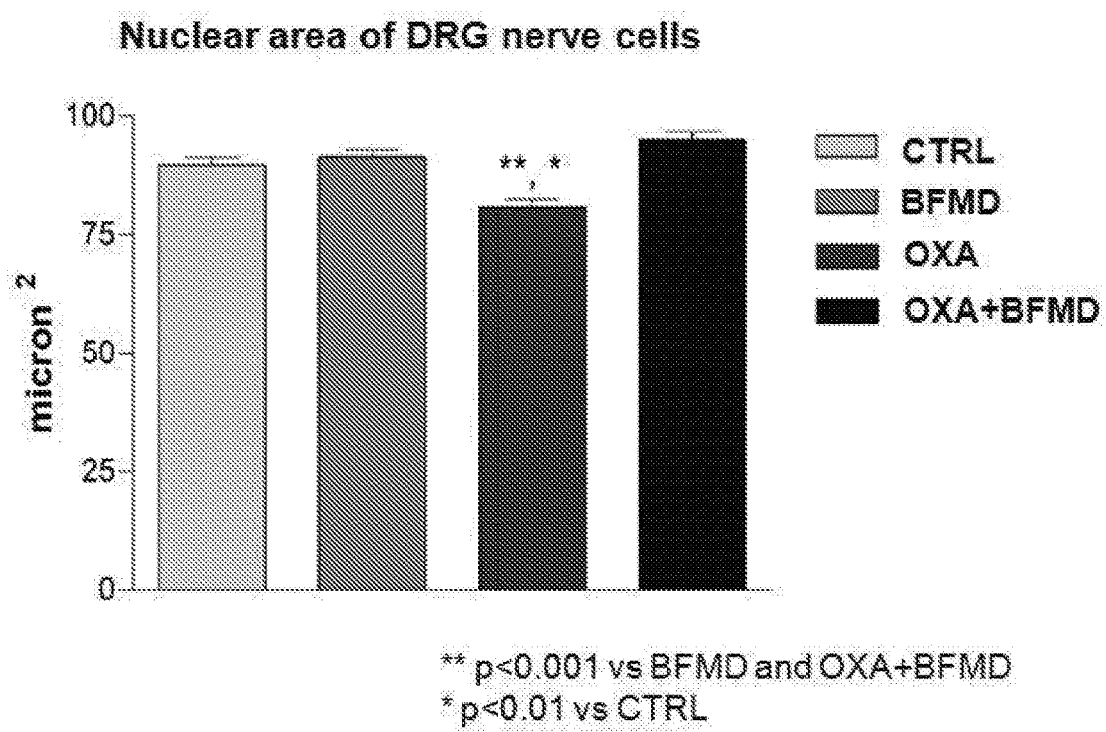

Figure 27

*Randomization:*
- OXA vehicle-treated controls (CTRL, N=5)
- Oxaliplatin 3.5 mg/kg, iv, 1qw (OXA, N=5)
- Chlophenesin, 4 mg/kg, iv, 1qw (CPC, N=5)
- Dolutegravir, 4 mg/kg, ip, 1qw (DTG, N=5)
- Oxaliplatin 3.5 mg/kg, iv + Chlophenesin, 4mg/kg, iv, 1qw (OXA+CPC, N=5)
- Oxaliplatin 3.5 mg/kg, iv + Dolutegravir, 4mg/kg, ip, 1qw (OXA+DTG, N=5)

OXA and CPC were co-administered intravenously while in the group co-treated with OXA and DTG, DTG will be injected intraperitoneally 1 hour before the intravenous administration of OXA.

*Parameters analyzed:*
- Behavioural test (dynamic test and cold plate test): 24h after administration
- Caudal amplitude and NCV: 48h after administration

*Statistical analysis:*
One way ANOVA

METHODS OF PREVENTING TOXICITY OF PLATINUM DRUGS

CROSS-REFERENCE TO RELATED APPLICATIONS

This application is a U.S. national phase application under 35 U.S.C. § 371 of International Application No. PCT/US2016/042673, filed on Jul. 15, 2016, which claims the priority benefit of U.S. Provisional Application No. 62/193,529, filed on Jul. 16, 2015, the disclosures of each of which are hereby incorporated by reference in their entirety.

FIELD OF THE INVENTION

The present invention relates to compounds that are able to reduce toxicity of platinum drugs.

BACKGROUND OF THE INVENTION

Platinum drugs, such as oxaliplatin and cisplatin and carboplatin are widely used highly effective chemotherapeutic drugs for treating a variety of cancers.

However, platinum drugs cause serious side effects, which deteriorate patients' quality of life, lead to early treatment termination, cause severe impairment and death. Besides hematotoxicity, nephrotoxicity, peripheral neuropathy and ototoxicity are three most prevalent toxicities associated with platinum drugs.

Nephrotoxicity is frequently seen in patients treated with cisplatin. It is estimated that 28%-36% of human patients receiving an initial dose of 50-100 mg/m$^2$ cisplatin develop acute kidney failure; most patients who develop some degree of cisplatin-induced kidney injury never fully recover [Barabas 2008]. In contrast, nephrotoxicity is rarely seen in patients treated with oxaliplatin and carboplatin. The clinical characteristics, mechanisms and management (including diagnosis, prevention and treatment) of platinum-induced nephrotoxicity are meticulously reviewed in [Barabas 2008, Yao 2007, Miller 2010, Karasawa 2015].

Ototoxicity is frequently associated with cisplatin and carboplatin, but rarely seen in oxaliplatin-treated patients. The incidence of overall cisplatin induced ototoxicity ranges from 42% to 62% [Langer 2013]. The clinical characteristics, mechanisms and management (including diagnosis, prevention and treatment) of platinum-induced ototoxicity are meticulously reviewed in [Langer 2013, Barabas 2008, Karasawa 2015].

Peripheral neuropathy (PN) or peripheral neurotoxicity is a very common adverse effect associated with many chemotherapeutics, including oxaliplatin and cisplatin. Peripheral neuropathies caused by different chemotherapeutic drugs often have distinct pathophysiology and clinical characteristics [Miltenburg 2014, Hershman 2014, Wolfgang 2014]. For example, unlike vincristine, which primarily causes axonal damage, the dorsal root ganglion (DRG) appears to be the primary site of neural damage caused by cisplatin and oxaliplatin [Miltenburg 2014, Holmes 1998]. Cisplatin PN is related to the cumulative dose and dose intensity. Most patients completing a full course of cisplatin treatment (usual cumulative dose 300-450 mg/m$^2$) develop moderate-to-severe (Grade 2 or higher) PN, with debilitating symptoms such as severe paresthesias and dysesthesias, sensory loss and sensory ataxia, which can last from months to years after treatment is discontinued. In contrast to cisplatin PN, oxaliplatin-induced PN (OXAIPN) has both acute and chronic forms. The chronic form has pathogenesis and clinical characteristics similar to cisplatin PN. Severe PN (Grade 3 or higher) has been observed with cumulative doses of oxaliplatin ranging from 510-765 mg/m$^2$ in up to 10% of patients. It is reported that approximately 50% of patients receiving cumulative doses of oxaliplatin above 1000 mg/m$^2$ develop severe PN [Argriou 2012]. Acute OXAIPN, which is a unique, acute, transient peripheral nerve hyperexcitability syndrome, is experienced by nearly all (up to 90%) patients. Distal and perioral cold-induced paresthesias and dysesthesias are the most commonly reported symptoms of acute OXAIPN. While acute and chronic OXAIPN appear to have distinct pathophysiology, studies have shown that patients with more acute symptoms eventually develop more severe chronic OXAIPN [Argyriou 2013]. The clinical characteristics, mechanisms and management (including diagnosis, prevention and treatment) of platinum-induced peripheral neuropathy and CIPN (chemotherapy induced peripheral neuropathy) are meticulously reviewed in [Hershman 2014, Argriou 2015, Argriou 2012, Avan 2015, Miltenburg 2014, Han 2013, Seretny 2014]. CIPN assessment, using patient reported outcome (PRO) based criteria, such as NCI-CTC v3.0, EORTC QLQ-CIPN20 and TNSc, and subjective quantitative measurements, such as nerve conduction studies and quantitative sensory testing (QST), are reviewed in [Cavaletti 2013, Griffth 2014].

Various agents have been proposed to prevent and/or treat CIPN. These include antioxidants, sodium channel blockers, opioid receptor analgesics, nerve growth factor (NGF) modulators, tricyclic antidepressants, neurotrophic agents, metal chelators, anticonvulsants (collectively reviewed in [Avan 2015]), sigma receptor ligands [US2011/0052723] and EGFR inhibitors [US 2015/0320861].

Despite CIPN being relatively distinct from other forms of neuropathic pain in many ways, including pathophysiology and symptoms [Hershman 2014, Wolf 2012], many of the agents aforementioned either have a record of efficacy for some neuropathic pain conditions or target pain signaling pathways. For example, tricyclic antidepressants amitriptyline and nortriptyline, which are also potent sigma receptor ligands [US2011/0052723, Werling 2007], are effective on various forms of neuropathic pains, but was ineffective on preventing nor treating PN symptoms induced by chemotherapeutic drugs including cisplatin and oxaliplatin [Kautio 2008, Kautio 2008].

In other clinical studies, antioxidant vitamin E, which was thought to be a protector against platinum assault in DRG, failed to reduce the incidence of sensory neuropathy in patients treated with platinum drugs [Pace 2003, Kottschade 2011].

After meticulous review of most clinical studies on agents for managing CIPN, American Society of Clinical Oncology (ASCO) concluded, in its critical 2014 guideline for CIPN prevention and management [Hershman 2014], "There are no established agents recommended for the prevention of CIPN in patients with cancer undergoing treatment with neurotoxic agents."

It has been long discovered and generally accepted that unwanted high accumulation of toxic platinum drugs in DRG is the primary mechanism of DRG nerve damage and hence CIPN related to treatment with platinum drugs [Miltenburg 2014, Holmes 1998]. A recent study suggests that oxaliplatin may accumulate in DRG cells via Organic Cation Transporter 2 (OCT2, SLC22A2), which is highly expressed in DRG neurons [Sprowl 2013]. Studies have shown several platinum agents, such as cisplatin, oxaliplatin and tetraplatin, are OCT2 substrates. OCT2 is also highly expressed in renal proximal tubule epithelium and cochlear epithelium [Hellberg 2015], potentially facilitating the uptake platinum agents and thus aggravating the cytotoxicity of cisplatin in these cells.

Besides OCT2, cisplatin and oxaliplatin are also transported by other transporters. Some of these transporters may potentiate anti-tumor efficacy; others may protect non-tumorous tissues from platinum toxicity [Burger 2011, Harrach 2015, Tashima 2015, Li 2014, Nakanishi 2007]. Therefore, it is critical to have a selective OCT2 inhibitor with desirable pharmacokinetic and safety profiles in order for it to be used clinically for minimizing cisplatin and oxaliplatin toxicities in normal tissues, without compromising their anti-tumor effectiveness.

SUMMARY

The present disclosure meets the need for reduced platinum drug-induced toxicity by providing methods for reducing platinum drug-induced toxicity in a cell expressing Organic Cation Transporter 2 (OCT2), for reducing platinum drug-induced toxicity in a subject, for treating cancer in a subject, and for increasing efficacy of platinum treatment in a subject, which include the step of providing an OCT2 inhibitor to a cell expressing OCT2 or to a subject comprising cells expressing OCT2. The present disclosure also meets the need for reduced platinum drug-induced toxicity by providing pharmaceutical compositions comprising a platinum drug and an OCT2 inhibitor.

The teachings herein demonstrate the discovery that inhibitors of OCT2 can reduce uptake of platinum drugs into healthy, non-cancer cells while leaving cancer cells, and the therapeutic toxic effect of platinum drugs on cancer cells, unaffected. FIG. 14 illustrates the inventive concept. OCT2 is critical for cellular uptake of platinum derivatives in certain cell types including kidney cells, neuronal cells, more specifically dorsal root ganglion on afferent neuronal cells, and cochlear cells. Therefore, OCT2 inhibitor provided to a non-cancerous kidney proximal tubule cell reduces the amount of platinum drug entering into the cell, and thus reduces platinum drug-induced toxicity in the cell by inhibiting uptake of platinum drug through OCT2. The contribution of other transporters like CTR1 to the uptake of platinum derivatives by kidney proximal tubule cells has not been validated yet. A similar scenario is expected to occur in Dorsal Root Ganglions where OCT2 is thought to be responsible for platinum accumulation and neurotoxicity with unknown contributions from other transporters. In contrast, if a colorectal cancer cell does not express OCT2, then an OCT2 inhibitor has no effect on this cell. Instead, the colorectal cancer cell typically expresses two other transporters, OCT1 and OCT3, that could mediate uptake of platinum drug into the cell, thereby allowing the platinum drug to remain therapeutically effective with respect to the cancer cell. If OCT2 is present on cancer cells and blocked by an OCT2 inhibitor, it is expected that the contributions of both OCT and 3 will be sufficient to preserve the uptake of platinum derivatives and therefore their anti-tumor activity. It is not known if other transporters are critical for the uptake of platinum derivatives in tumor cells.

Thus one aspect of the present disclosure includes methods for reducing platinum drug-induced toxicity in a cell expressing Organic Cation Transporter 2 (OCT2) comprising providing a platinum drug to the cell expressing OCT2; and providing an OCT2 inhibitor that reduces OCT2-mediated platinum drug uptake into the cell, wherein the OCT2 inhibitor is buflomedil or a buflomedil salt and reduces platinum drug induced toxicity in the cell.

Another aspect includes methods for reducing platinum drug-induced toxicity in a cell expressing Organic Cation Transporter 2 (OCT2) comprising providing a platinum drug to the cell expressing OCT2; and providing an OCT2 inhibitor that reduces OCT2-mediated platinum drug uptake into the cell, wherein the OCT2 inhibitor is dolutegravir or a dolutegravir salt and reduces platinum drug-induced toxicity in the cell.

Another aspect includes methods for reducing platinum drug-induced toxicity in a cell expressing Organic Cation Transporter 2 (OCT2) comprising providing a platinum drug to the cell expressing OCT2; and providing an OCT2 inhibitor that reduces OCT2-mediated platinum drug uptake into the cell, wherein the OCT2 inhibitor comprises imidazole and reduces platinum drug-induced toxicity in the cell. In some embodiments, the OCT2 inhibitor is miconazole or a salt thereof.

In some embodiments of the above aspects, the platinum drug and the OCT2 inhibitor are provided at the same time. In some embodiments, the OCT2 inhibitor is provided before the platinum drug. In some embodiments, the OCT2 inhibitor is provided after the platinum drug. In some embodiments, the cell expressing OCT2 is a cell selected from the group consisting of kidney cell, neuron cell, ear cell, and blood cell. In some embodiments, the cell is a sensory neuron cell. In some embodiments, the cell is a kidney cell. In some embodiments, the platinum drug is oxaliplatin. In some embodiments, the platinum drug is cisplatin. In some embodiments, the platinum drug is tetraplatin. In some embodiments, OCT2-mediated platinum drug uptake into the cell expressing OCT2 is inhibited by at least 50 percent, at least 70 percent or at least 90 percent as compared to OCT2-mediated platinum drug uptake into a cell not in the presence of the OCT2 inhibitor.

Another aspect of the present disclosure includes methods for reducing platinum drug-induced toxicity in a subject comprising providing a platinum drug to a subject comprising cells expressing Organic Cation Transporter 2 (OCT2); and providing an OCT2 inhibitor to the subject, wherein the OCT2 inhibitor is buflomedil or a buflomedil salt and reduces OCT2-mediated platinum drug uptake into the cells expressing OCT2, thereby reducing platinum drug-induced toxicity in the subject.

Another aspect includes methods for reducing platinum drug induced toxicity in a subject comprising providing a platinum drug to a subject comprising cells expressing Organic Cation Transporter 2 (OCT2); and providing an OCT2 inhibitor to the subject, wherein the OCT2 inhibitor is dolutegravir or a dolutegravir salt and reduces OCT2 mediated platinum drug uptake into the cells expressing OCT2, thereby reducing platinum drug induced toxicity in the subject.

Another aspect includes methods for reducing platinum drug-induced toxicity in a subject comprising providing a platinum drug to a subject comprising cells expressing Organic Cation Transporter 2 (OCT2); and providing an OCT2 inhibitor to the subject, wherein the OCT2 inhibitor comprises imidazole and reduces OCT2-mediated platinum drug uptake into the cells expressing OCT2, thereby reducing platinum drug-induced toxicity in the subject. In some embodiments, the OCT2 inhibitor is miconazole or a salt thereof.

Another aspect of the present disclosure includes methods for reducing platinum drug-induced toxicity in a subject, comprising providing an OCT2 inhibitor to a subject comprising cells expressing OCT2; wherein the OCT2 inhibitor is buflomedil or a buflomedil salt, the subject has been or will be provided with platinum drug and the OCT2 inhibitor reduces OCT2-mediated platinum drug uptake into the cells expressing OCT2, thereby reducing platinum drug-induced toxicity in the subject.

Another aspect includes methods for reducing platinum drug induced toxicity in a subject, comprising providing an OCT2 inhibitor to a subject comprising cells expressing OCT2; wherein the OCT2 inhibitor is dolutegravir or a dolutegravir salt, the subject has been or will be provided with platinum drug and the OCT2 inhibitor reduces OCT2 mediated platinum drug uptake into the cells expressing OCT2, thereby reducing platinum drug induced toxicity in the subject.

Another aspect includes methods for reducing platinum drug-induced toxicity in a subject, comprising providing an OCT2 inhibitor to a subject comprising cells expressing OCT2; wherein the OCT2 inhibitor comprises imidazole, the subject has been or will be provided with platinum drug and the OCT2 inhibitor reduces OCT2-mediated platinum drug uptake into the cells expressing OCT2, thereby reducing platinum drug-induced toxicity in the subject. In some embodiments, the OCT2 inhibitor is miconazole or a salt thereof.

In some embodiments of the above aspects, the platinum drug and the OCT2 inhibitor are provided at the same time. In some embodiments, the OCT2 inhibitor is provided before the platinum drug. In some embodiments, the OCT2 inhibitor is provided after the platinum drug. In some embodiments, the platinum drug is oxaliplatin. In some embodiments, the platinum drug is cisplatin. In some embodiments, the platinum drug is tetraplatin. In some embodiments, the amount of OCT2 inhibitor provided to the subject is at a less than a therapeutically effective dosage. In some embodiments, the amount of OCT2 inhibitor provided to the subject is 10 mg to 2000 mg per day. In some embodiments, the amount of platinum drug provided to the subject during one treatment session is greater than what is provided under standard clinical practices. In some embodiments, the cumulative amount of platinum drug provided to the subject over the entire course of treatment is greater than what is provided under standard clinical practices. In some embodiments, the platinum drug is provided at a greater frequency than under standard clinical practices. In some embodiments, the platinum drug-induced toxicity is selected from the group consisting of nephrotoxicity, neurotoxicity, hematoxicity, and ototoxicity. In some embodiments, the platinum drug-induced toxicity is neurotoxicity. In some embodiments, the neurotoxicity is peripheral neuropathy. In some embodiments, the peripheral neuropathy is Grade 3 or Grade 4 peripheral neuropathy. In some embodiments, the platinum drug-induced toxicity is nephrotoxicity. In some embodiments, the subject is a human or a non-human animal. In some embodiments, the OCT2 inhibitor is provided enterally, intravenously, intramuscularly, intraperitoneally, orally, or parenterally. In some embodiments, prevalence of platinum drug-induced toxicity in a group of subjects is reduced by at least 10% as compared to the prevalence of platinum drug-induced toxicity in a group of subjects not provided with an OCT2 inhibitor.

Another aspect of the present disclosure includes methods for treating cancer in a subject comprising providing a therapeutically effective amount of platinum drug to the subject having cancer, wherein the subject comprises a cancerous cell expressing platinum drug uptake transporters not inhibited by an Organic Cation Transporter 2 (OCT2) inhibitor; and providing an OCT2 inhibitor to the subject, wherein the OCT2 inhibitor is buflomedil or a buflomedil salt, thereby treating cancer in the subject.

Another aspect includes methods for treating cancer in a subject comprising providing a therapeutically effective amount of platinum drug to the subject having cancer, wherein the subject comprises a cancerous cell expressing platinum drug uptake transporters not inhibited by an Organic Cation Transporter 2 (OCT2) inhibitor; and providing an OCT2 inhibitor to the subject, wherein the OCT2 inhibitor is dolutegravir or a dolutegravir salt, thereby treating cancer in the subject.

Another aspect includes methods for treating cancer in a subject comprising providing a therapeutically effective amount of platinum drug to the subject having cancer, wherein the subject comprises a cancerous cell expressing platinum drug uptake transporters not inhibited by an Organic Cation Transporter 2 (OCT2) inhibitor; and providing an OCT2 inhibitor to the subject, wherein the OCT2 inhibitor comprises imidazole, thereby treating cancer in the subject. In some embodiments, the OCT2 inhibitor is miconazole or a salt thereof.

Another aspect includes methods for increasing efficacy of platinum drug treatment in a subject comprising providing a therapeutically effective amount of platinum drug to the subject having cancer, wherein the subject comprises a cancerous cell expressing platinum drug uptake transporters not inhibited by an OCT2 inhibitor; and providing an OCT2 inhibitor to the subject, wherein the OCT2 inhibitor is buflomedil or a buflomedil salt, thereby increasing efficacy of the platinum drug treatment.

Another aspect includes methods for increasing efficacy of platinum drug treatment in a subject comprising providing a therapeutically effective amount of platinum drug to the subject having cancer, wherein the subject comprises a cancerous cell expressing platinum drug uptake transporters not inhibited by an OCT2 inhibitor, and providing an OCT2 inhibitor to the subject, wherein the OCT2 inhibitor is dolutegravir or a dolutegravir salt, thereby increasing efficacy of the platinum drug treatment.

Another aspect includes methods for increasing efficacy of platinum drug treatment in a subject comprising providing a therapeutically effective amount of platinum drug to the subject having cancer, wherein the subject comprises a cancerous cell expressing platinum drug uptake transporters not inhibited by an OCT2 inhibitor, and providing an OCT2 inhibitor to the subject, wherein the OCT2 inhibitor comprises imidazole, thereby increasing efficacy of the platinum drug treatment. In some embodiments, the OCT2 inhibitor is miconazole or a salt thereof.

In some embodiments of the above aspects, the platinum drug and the OCT2 inhibitor are provided at the same time. In some embodiments, the OCT2 inhibitor is provided before the platinum drug. In some embodiments, the OCT2 inhibitor is provided after the platinum drug. In some embodiments, the platinum drug is oxaliplatin. In some embodiments, the platinum drug is cisplatin. In some embodiments, the platinum drug is tetraplatin. In some embodiments, the amount of OCT2 inhibitor provided to the subject is at a less than a therapeutically effective dosage. In some embodiments, the amount of OCT2 inhibitor provided to the subject is 10 mg to 2000 mg per day. In some embodiments, the amount of platinum drug provided to the subject during one treatment session is greater than what is provided under standard clinical practices. In some embodiments, the cumulative amount of platinum drug provided to the subject over the entire course of treatment is greater than what is provided under standard clinical practices. In some embodiments, the platinum drug is provided at a greater frequency than under standard clinical practices.

In some embodiments, the cancer is selected from the group consisting of adenocarcinoma of the pancreas, ampullary and periampullary carcinoma, adenocarcinoma of the anus, appendiceal carcinoma, hepatocellular carcinoma, carcinoma of the colon or rectum, epithelial ovarian carcinoma, fallopian tube carcinoma, primary peritoneal cancer, esophageal or esophagogastric junction carcinoma, gastric carcinoma, small bowel carcinoma, testicular cancer, cholangiocarcinoma, pancreatic adenocarcinoma, carcinoma of unknown primary origin, chronic lymphocytic leukemia/small lymphocytic lymphoma, non-Hodgkin's lymphoma, adult T-cell leukemia/lymphoma. AIDS-related B-cell lymphoma, diffuse large B-cell lymphoma, follicular lymphoma, gastric MALT lymphoma, nongastric MALT lymphoma, mantle cell lymphoma, mycosis fungoides/Sezary syndrome, splenic marginal zone lymphoma, peripheral T cell lymphoma, primary cutaneous B-cell lymphoma, primary cutaneous anaplastic large cell lymphoma (ALCL), lung cancer, liver cancer, and gallbladder cancer. In some embodiments, the cancer is carcinoma of the colon or rectum. In some embodiments, the cancer is liver cancer. In some embodiments, the cancer is lung cancer.

In some embodiments, the platinum drug uptake transporters not inhibited by an OCT2 inhibitor are Organic Cation Transporter 1 (OCT1) uptake transporters. In some embodiments, the platinum drug uptake transporters not inhibited by an OCT2 inhibitor are Organic Cation Transporter 3 (OCT3) uptake transporters. In some embodiments, the platinum drug uptake transporters not inhibited by an OCT2 inhibitor are Copper Transporter 1 (CTR1) uptake transporters.

In some embodiments, the method further comprises the step of determining whether the cancerous cell expresses platinum drug uptake transporters not inhibited by an OCT2 inhibitor. In some embodiments, the method further comprises providing a therapeutically effective amount of one or more additional chemotherapeutic agents to the subject in addition to the platinum drug. In some embodiments, the one or more additional chemotherapeutic agents is selected from the group consisting of 5-fluorouracil, bevacizumab, capecetabine, gemcitabine, irinotecan, and leucovorin. In some embodiments, the subject is a human or a non-human animal. In some embodiments, the OCT2 inhibitor is provided enterally, intravenously, intramuscularly, intraperitoneally, orally, or parenterally.

In another aspect the present disclosure includes pharmaceutical compositions comprising a platinum drug, an OCT2 inhibitor, wherein the OCT2 inhibitor is buflomedil or a buflomedil salt; and a pharmaceutically acceptable carrier. Another aspect includes pharmaceutical compositions comprising a platinum drug, an OCT2 inhibitor, wherein the OCT2 inhibitor is dolutegravir or a dolutegravir salt; and a pharmaceutically acceptable carrier. Another aspect includes pharmaceutical compositions comprising a platinum drug, an OCT2 inhibitor, wherein the OCT2 inhibitor comprises imidazole; and a pharmaceutically acceptable carrier. In some embodiments, the OCT2 inhibitor is miconazole or a salt thereof.

In some embodiments of the above aspects, the amount of platinum drug is greater than what is present in a standard pharmaceutical composition comprising platinum drug. In some embodiments, the pharmaceutical compositions further comprise a therapeutically effective amount of one or more additional chemotherapeutic agents in addition to the platinum drug. In some embodiments, the one or more additional chemotherapeutic agents is selected from the group consisting of 5-fluorouracil, bevacizumab, capecetabine, gemcitabine, irinotecan, and leucovorin. In some embodiments, the platinum drug is oxaliplatin. In some embodiments, the platinum drug is cisplatin. In some embodiments, the platinum drug is tetraplatin.

In some embodiments of the aspects where the OCT2 inhibitor comprises imidazole, the OCT2 inhibitor has a $C_{max,u}/IC_{50}$ or $C_{max}/IC_{50,app}$, of at least 1. In some embodiments, the OCT2 inhibitor has a $C_{max,u}/IC_{50}$ or $C_{max}/IC_{50,app}$ of at least 3. In some embodiments, the OCT2 inhibitor is not toxic to the cell at its clinical concentration. In some embodiments, the OCT2 inhibitor does not reduce anti-cancer activity of the platinum drug at its clinical concentration by more than 20% as compared to anti-cancer activity of the platinum drug at its clinical concentration in the absence of the OCT2 inhibitor. In some embodiments, the OCT2 inhibitor does not reduce uptake of the platinum drug at its clinical concentration into the cell via other transporters by more than 20% as compared to uptake of the platinum drug at its clinical concentration via other transporters in the absence of the OCT2 inhibitor. In some embodiments, the OCT2 inhibitor does not reduce the efflux of the platinum drug at its clinical concentration by more than 20% as compared to the efflux of the platinum drug at its clinical concentration in the absence of the OCT2 inhibitor. In some embodiments, the OCT2 inhibitor has a mean half-life that is greater than 2 hours.

Another aspect of the present disclosure includes methods of predicting the efficacy of a platinum drug and Organic Cation Transporter 2 (OCT2) inhibitor therapy in a subject having cancer comprising obtaining a sample comprising at least one cancerous cell; and determining whether the cancerous cell expresses platinum drug uptake transporters not inhibited by an OCT2 inhibitor, wherein platinum drug and OCT2 inhibitor therapy is likely to be effective in a subject where the cancerous cell expresses platinum drug uptake transporters not inhibited by an OCT2 inhibitor.

Another aspect includes methods of predicting the efficacy of platinum drug and Organic Cation Transporter 2 (OCT2) inhibitor therapy in a subject having cancer comprising obtaining a sample comprising at least one cancerous cell; and determining whether the cancerous cell expresses OCT2, wherein the platinum drug and OCT2 inhibitor therapy is not likely to be effective in a subject where the cancerous cell primarily expresses OCT2.

In some embodiments of the above aspects, the platinum drug is oxaliplatin. In some embodiments, the platinum drug is cisplatin. In some embodiments, the platinum drug is tetraplatin. In some embodiments, the OCT2 inhibitor therapy comprises administering buflomedil or a buflomedil salt. In some embodiments, the OCT2 inhibitor therapy comprises administering dolutegravir or a dolutegravir salt. In some embodiments, the OCT2 inhibitor therapy comprises administering an OCT2 inhibitor comprising imidazole. In some embodiments, the OCT2 inhibitor therapy comprises administering an OCT2 inhibitor comprising miconazole or a salt thereof.

The present disclosure provides a method for reducing platinum drug-induced neurotoxicity in a subject in need thereof comprising administering a platinum drug that is oxaliplatin to the subject in need thereof; and administering an effective dose of a selective Organic Cation Transporter 2 (OCT2) inhibitor to the subject in need thereof, wherein the subject in need thereof has a cancer.

The present disclosure provides a method for treating cancer in a subject in need thereof comprising administering a therapeutically effective amount of a platinum drug that is oxaliplatin to the subject in need thereof; and administering an effective dose of a selective Organic Cation Transporter 2 (OCT2) inhibitor to the subject in need thereof.

The present disclosure provides a method for increasing patient compliance for treating cancer in a subject in need thereof comprising administering a therapeutically effective amount of a platinum drug that is oxaliplatin to the subject in need thereof; and administering a selective Organic Cation Transporter 2 (OCT2) inhibitor to the subject in need thereof in a dose effective to reduce platinum drug-induced neurotoxicity in said subject in need thereof, whereby said subject completes treatment with a cumulative dose at least 500 mg/m$^2$.

In some embodiments, the therapeutically effective amount of platinum drug administered is known to cause platinum drug-induced neurotoxicity in subjects. In some embodiments, the neurotoxicity is peripheral neurotoxicity. In some embodiments, the neurotoxicity is damage to a sensory neuron. In some embodiments, the neurotoxicity is damage to a motor neuron. In some embodiments, the neurotoxicity is chronic neurotoxicity. In some embodiments, the neurotoxicity is acute syndrome transient neurotoxicity. In some embodiments, the neurotoxicity occurs 1 hour to seven days after first treatment. In some embodiments, the neurotoxicity occurs after a subject completes treatment with a cumulative dose of at least 500 mg/m$^2$. In some embodiments, the neurotoxicity is damage to dorsal root ganglia (DRG). In some embodiments, the dose of selective OCT2 inhibitor is effective to minimize platinum drug-induced neurotoxicity in said subject in need thereof.

In some embodiments, the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in patients treated with a cumulative dose of at least 100 mg/m$^2$. In some embodiments, the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in patients treated with a platinum drug dose intensity of at least 30 mg/week/m$^2$. In some embodiments, the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale. Total Neuropathy Score clinical version (TNSc) and European Organization for Research and Treatment of Cancer CIPN specific self-report questionnaire (EORTC QOL-CIPN20), in patients treated with a platinum drug dose of at least 80 mg/m$^2$.

In some embodiments, the method further comprises assessing platinum drug-induced neurotoxicity in a subject after administration of the platinum drug. In some embodiments, the neurotoxicity is assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20). In some embodiments, the neurotoxicity is assessed by a measurement selected from sensory nerve action potential, sensory nerve conduction velocity, cold pain threshold, heat pain threshold, mechanical pain threshold, cold detection threshold, warm detection threshold, mechanical detection threshold, vibration perception threshold, current perception threshold, pinprick sensibility, deep tendon reflexes and grip strength. In some embodiments, the neurotoxicity is assessed by measuring sensory nerve action potential in one of radial, dorsal sural, sural and ulnar nerves. In some embodiments, the method further comprises establishing the subject's baseline prior to administration of the platinum drug. In some embodiments, the platinum drug-induced neurotoxicity is assessed near the midpoint of treatment. In some embodiments, the platinum drug-induced neurotoxicity is assessed after treatment with a cumulative dose of 200 mg/m$^2$.

In some embodiments, the selective OCT2 inhibitor is selected from the group consisting of buflomedil, a buflomedil salt, dolutegravir, and a dolutegravir salt. In some embodiments, the selective OCT2 inhibitor is buflomedil, or a buflomedil salt. In some embodiments, the dose of buflomedil or a buflomedil salt administered in a subject is adjusted based on at least one of the factors of the said subject, body weight, body surface area, height, age, gender, alcohol use, tobacco use, life style, renal function, liver function, genetic polymorphism and co-medications. In some embodiments, the dose of buflomedil or a buflomedil salt results in its plasma level during the period of platinum administration at least 0.43 mg/l, 0.86 mg/l, 1.29 mg/l, 1.72 mg/l or 2.15 mg/l. In some embodiments, the dose of buflomedil or a buflomedil salt is at least 100 mg, 200 mg, 300 mg, 400 mg, 500 mg or 600 mg. In some embodiments, the dose of buflomedil or a buflomedil salt is at least 1 mg/kg, 2 mg/kg, 3 mg/kg, 4 mg/kg, 5 mg/kg, 6 mg/kg, 8 mg/kg or 10 mg/kg.

In some embodiments, the selective OCT2 inhibitor is dolutegravir or a dolutegravir salt. In some embodiments, the dose of dolutegravir or a dolutegravir salt results in its plasma level during the period of platinum administration at least 1.4 mg/l, 2.8 mg/l, 4.2 mg/l, 5.6 mg/l or 7.0 mg/l. In some embodiments, the dose of dolutegravir or a dolutegravir salt is at least 50 mg, 100 mg, 150 mg, 200 mg, 250 mg, 300 mg or 400 mg. In some embodiments, the dose of dolutegravir or a dolutegravir salt is at least 1 mg/kg, 2 mg/kg, 3 mg/kg, 4 mg/kg, 5 mg/kg or 6 mg/kg.

In some embodiments, the selective OCT2 inhibitor does not reduce the efficacy of the platinum drug. In some embodiments, the selective OCT2 inhibitor is administered at a dose that results in its plasma concentration during the period of platinum drug administration less than its maximum tolerated plasma concentration (MTC) and greater than 1×, 2×, 3×, 4× of its ICs value for OCT2-mediated transport of 20 μM oxaliplatin assessed in human serum or an assay buffer containing 4% bovine serum albumin. In some embodiments, the selective OCT2 inhibitor has an IC$_{50}$ for OCT2-mediated transport of 20 μM oxaliplatin in human serum or an assay solution containing 4% bovine serum albumin, of less than or equal to 2 μM. In some embodiments, the selective OCT2 inhibitor has an IC$_{50}$ for OCT2- mediated transport of 20.1M oxaliplatin in human serum or an assay solution containing 4% bovine serum albumin that is at least 15-fold less than the selective OCT2 inhibitor $IC_{50}$ for 20 µM oxaliplatin transport in human serum or an assay solution containing 4% bovine serum albumin mediated by OCT1-, OCT-3, and MATE-1.

In some embodiments, the subject in need thereof has a cancer expressing at least one of Organic Cation Transporter 1 (OCT1) or Organic Cation Transporter 3 (OCT3). In some embodiments, the selective OCT2 inhibitor is buflomedil, or a buflomedil salt. In some embodiments, the selective OCT2 inhibitor is dolutegravir, or a dolutegravir salt. In some embodiments, the platinum drug and the selective OCT2 inhibitor are administered at the same time. In some embodiments, the selective OCT2 inhibitor is administered before the platinum drug. In some embodiments, the selective OCT2 inhibitor is administered after the platinum drug. In some embodiments, the amount of platinum drug administered to the subject during one treatment session is greater than what is administered under standard clinical practices. In some embodiments, the cumulative amount of platinum drug administered to the subject in need thereof over the entire course of treatment is greater than what is administered under standard clinical practices. In some embodiments, the platinum drug is administered at a greater frequency than under standard clinical practices.

In some embodiments, the neurotoxicity is peripheral neuropathy. In some embodiments, the peripheral neuropathy is Grade 3 or Grade 4 peripheral neuropathy. In some embodiments, the subject in need thereof is a human or a non-human animal.

In some embodiments, the selective OCT2 inhibitor is administered enterally, intravenously, intramuscularly, intraperitoneally, orally, or parenterally. In some embodiments, the selective OCT2 inhibitor is administered via more than one route of administration. In some embodiments, the platinum drug and the selective OCT2 inhibitor are administered via the same route of administration. In some embodiments, the selective OCT2 inhibitor is administered via intravenous infusion. In some embodiments, the selective OCT2 inhibitor is administrated via intravenous injection and intravenous infusion. In some embodiments, intravenous infusion is over a period of time at least 1 hour. In some embodiments, the rate of intravenous infusion is constant. In some embodiments, the rate of intravenous infusion is variable.

In some embodiments, the cancer expresses OCT1. In some embodiments, the cancer expresses OCT3. In some embodiments, the cancer expresses OCT1 and OCT3. In some embodiments, the cancer is selected from the group consisting of adenocarcinoma of the pancreas, ampullary and periampullary carcinoma, adenocarcinoma of the anus, appendiceal carcinoma, hepatocellular carcinoma, carcinoma of the colon or rectum, epithelial ovarian carcinoma, fallopian tube carcinoma, primary peritoneal cancer, esophageal or esophagogastric junction carcinoma, gastric carcinoma, small bowel carcinoma, testicular cancer, cholangiocarcinoma, pancreatic adenocarcinoma, carcinoma of unknown primary origin, chronic lymphocytic leukemia/small lymphocytic lymphoma, non-Hodgkin's lymphoma, adult T-cell leukemia/lymphoma. AIDS-related B-cell lymphoma, diffuse large B-cell lymphoma, follicular lymphoma, gastric MALT lymphoma, nongastric MALT lymphoma, mantle cell lymphoma, mycosis fungoides/Sezary syndrome, splenic marginal zone lymphoma, peripheral T cell lymphoma, primary cutaneous B-cell lymphoma, primary cutaneous anaplastic large cell lymphoma (ALCL), lung cancer, liver cancer, head and neck cancer, prostate cancer, smooth muscle cancer and gallbladder cancer. In some embodiments, the cancer is ovarian cancer. In some embodiments, the cancer is head and neck cancer. In some embodiments, the cancer is prostate cancer. In some embodiments, the cancer is lymphoma. In some embodiments, the cancer is smooth muscle cancer. In some embodiments, the cancer is carcinoma of the colon or rectum. In some embodiments, the cancer is liver cancer. In some embodiments, the cancer is lung cancer.

In some embodiments, the method further comprises administering to the subject in need thereof a therapeutically effective amount of one or more additional cancer chemotherapeutic agents in addition to the platinum drug. In some embodiments, the one or more additional chemotherapeutic agents is selected from the group consisting of 5-fluorouracil, bevacizumab, capecetabine, gemcitabine, irinotecan, and leucovorin.

The present disclosure provides a pharmaceutical composition formulated for intravenous administration comprising a platinum drug that is oxaliplatin, a selective OCT2 inhibitor selected from the group consisting of buflomedil, a buflomedil salt, dolutegravir, and a dolutegravir salt, and a pharmaceutically acceptable carrier.

In some embodiments, the selective OCT2 inhibitor is buflomedil, or a buflomedil salt. In some embodiments, the OCT2 inhibitor is dolutegravir, or a dolutegravir salt. In some embodiments, the amount of the platinum drug is greater than what is present in a standard pharmaceutical composition comprising the platinum drug. In some embodiments, the pharmaceutical composition further comprises a therapeutically effective amount of one or more additional cancer chemotherapeutic agents in addition to the platinum drug. In some embodiments, the one or more additional chemotherapeutic agents is selected from the group consisting of 5-fluorouracil, bevacizumabh, capecetabine, gemcitabine, irinotecan, and leucovorin.

The present disclosure provides a kit comprising a therapeutically effective amount of a platinum drug that is oxaliplatin; a selective OCT2 inhibitor and instructions for use. In some embodiments, the kit further comprises instructions for determining a desirable dose of the selective OCT2 inhibitor for a subject in need. In some embodiments, the dose is determined based on at least one factor of the said subject selected from body weight, body surface area, height, age, gender, alcohol use, tobacco use, life style, renal function, liver function, genetic polymorphism and co-medications. In some embodiments, the dose is determined by monitoring plasma level of the OCT2 inhibitor in the said subject. In some embodiments, the selective OCT2 inhibitor is buflomedil or a buflomedil salt. In some embodiments, buflomedil or a buflomedil salt is present in an amount greater than 300 mg, 450 mg, 600 mg, 800 mg or 1000 mg. In some embodiments, the selective OCT2 inhibitor is dolutegravir or a dolutegravir salt. In some embodiments, dolutegravir or a dolutegravir salt is present in an amount greater than 50 mg, 75 mg, 100 mg, 150 mg, 200 mg or 300 mg. In some embodiments, the instructions state that the kit is intended for use in reducing platinum drug-induced neurotoxicity. In some embodiments, the instructions state that the kit is intended for use in treating cancer. In some embodiments, the kit further comprises a therapeutically effective amount of one or more additional cancer chemotherapeutic agents in addition to the platinum drug. In some embodiments, the one or more additional chemotherapeutic agents is selected from the group consisting of 5-fluorouracil, bevacizumab, capecetabine, gemcitabine, irinotecan, and leucovorin.

The present disclosure provides a method for reducing platinum drug-induced toxicity in a subject in need thereof comprising administering a platinum drug that is cisplatin to the subject in need thereof; and administering an effective dose of a selective Organic Cation Transporter 2 (OCT2) inhibitor to the subject in need thereof, wherein the toxicity is nephrotoxicity, ototoxicity or peripheral neuropathy, and wherein the subject in need thereof has a cancer.

The present disclosure provides a method for treating cancer in a subject in need thereof comprising administering a therapeutically effective amount of a platinum drug that is cisplatin to the subject in need thereof; and administering an effective dose of a selective Organic Cation Transporter 2 (OCT2) inhibitor to the subject in need thereof.

The present disclosure provides a method for increasing patient compliance for treating cancer in a subject in need thereof comprising administering a therapeutically effective amount of a platinum drug that is cisplatin to the subject in need thereof; and administering a selective Organic Cation Transporter 2 (OCT2) inhibitor to the subject in need thereof in a dose effective to reduce platinum drug-induced toxicity in said subject in need thereof, whereby said subject completes treatment with a cumulative dose of at least 100 mg/m².

The present disclosure provides a method for reducing platinum drug-induced toxicity in a subject in need thereof comprising determining an effective dose to achieve a plasma level of a selective Organic Cation Transporter 2 (OCT2) inhibitor that is buflomedil or a buflomedil salt in the subject in need thereof, wherein the plasma level is two to five times $IC_{50}$ of the selective Organic Cation Transporter 2 (OCT2) inhibitor that is buflomedil or a buflomedil salt; administering a platinum drug selected from the group consisting of oxaliplatin and cisplatin to the subject in need thereof; and administering an effective dose of a selective Organic Cation Transporter 2 (OCT2) inhibitor that is buflomedil or a buflomedil salt to the subject in need thereof, wherein the toxicity is nephrotoxicity, ototoxicity or peripheral neuropathy, and wherein the subject in need thereof has a cancer.

The present disclosure provides a method for treating cancer in a subject in need thereof comprising determining an effective dose to achieve a plasma level of a selective Organic Cation Transporter 2 (OCT2) inhibitor that is buflomedil or a buflomedil salt in the subject in need thereof, wherein the plasma level is two to five times $IC_{50}$ of the selective Organic Cation Transporter 2 (OCT2) inhibitor that is buflomedil or a buflomedil salt; administering a therapeutically effective amount of a platinum drug selected from the group consisting of oxaliplatin and cisplatin to the subject in need thereof; and administering an effective dose of a selective Organic Cation Transporter 2 (OCT2) inhibitor that is buflomedil or a buflomedil salt to the subject in need thereof.

The present disclosure provides a method for increasing patient compliance for treating cancer in a subject in need thereof comprising determining an effective dose to achieve a plasma level of a selective Organic Cation Transporter 2 (OCT2) inhibitor that is buflomedil or a buflomedil salt in the subject in need thereof, wherein the plasma level is two to five times $IC_{50}$ of the selective Organic Cation Transporter 2 (OCT2) inhibitor that is buflomedil or a buflomedil salt; administering a therapeutically effective amount of a platinum drug selected from the group consisting of oxaliplatin and cisplatin to the subject in need thereof; and administering a selective Organic Cation Transporter 2 (OCT2) inhibitor that is buflomedil or a buflomedil salt to the subject in need thereof in a dose effective to reduce platinum drug-induced toxicity in said subject in need thereof, whereby said subject completes treatment with a cumulative dose of at least 100 mg/m².

In some embodiments, the step of determining an effective dose to achieve a plasma level of a selective Organic Cation Transporter 2 (OCT2) inhibitor is performed by administering a pre-dose of the selective Organic Cation Transporter 2 (OCT2) inhibitor. In some embodiments, the step of determining an effective dose to achieve a plasma level of a selective Organic Cation Transporter 2 (OCT2) inhibitor is determined by a reference data chart based on subject characteristics.

The present disclosure provides a selective OCT2 inhibitor for use in the treatment of cancer in a subject in need thereof, wherein the OCT2 inhibitor is for use in combination with a platinum drug that is oxaliplatin. In some embodiments, the OCT2 inhibitor is for administration at a dose capable of reducing platinum drug-induced toxicity.

The present disclosure provides a selective OCT2 inhibitor for use in the treatment of cancer in a subject in need thereof, wherein the OCT2 inhibitor is for use in combination with a platinum drug that is cisplatin. In some embodiments, the OCT2 inhibitor is for administration at a dose capable of reducing platinum drug-induced toxicity.

The present disclosure provides a selective OCT2 inhibitor that is buflomedil or a buflomedil salt for use in the treatment of cancer in a subject in need thereof, wherein the OCT2 inhibitor is for use in combination with a platinum drug that is oxaliplatin or cisplatin. In some embodiments, the OCT2 inhibitor is for administration at a dose capable of reducing platinum drug-induced toxicity.

The present disclosure provides a use of a selective OCT2 inhibitor in the preparation of a medicament for the treatment of cancer, wherein the medicament is for use in combination with a platinum drug that is oxaliplatin. In some embodiments, the OCT2 inhibitor is for administration at a dose capable of reducing platinum drug-induced toxicity.

The present disclosure provides a use of a selective OCT2 inhibitor in the preparation of a medicament for the treatment of cancer, wherein the medicament is for use in combination with a platinum drug that is cisplatin. In some embodiments, the OCT2 inhibitor is for administration at a dose capable of reducing platinum drug-induced toxicity.

The present disclosure provides a use of a selective OCT2 inhibitor that is buflomedil or a buflomedil salt in the preparation of a medicament for the treatment of cancer, wherein the medicament is for use in combination with a platinum drug that is oxaliplatin or cisplatin. In some embodiments, the OCT2 inhibitor is for administration at a dose capable of reducing platinum drug-induced toxicity.

DESCRIPTION OF THE FIGURES

(FIG. 1B) Miconazole following intravenous injection [7]; (FIG. 1C) Buflomedil following oral administration of 300 mg tablet q12h(1) or 600 mg slow-release tablet qd(2) [9]; (FIG. 1D) Erlotinib following oral administration of 150 mg qd [10]; and (FIG. 1E) Dolutegravir following oral administration [15].

FIG. 6B), and dolutegravir (DTG) at 10 μM (FIG. 6C, FIG. 6D), but not 6 uM erlotinib (FIG. 6B) and 6 μM cimetidine (FIG. 6B), significantly reduced oxaliplatin (OXA) induced cytotoxicity in OCT2 expressing cells.

FIG. 12 depicts that buflomedil (BFMD) at 6 uM (FIG. 12A) and dolutegravir (DTG) at 3 uM, 6 μM and 9 μM (FIG. 12B) did not affect anti-tumor potency of 5-FU in HT-29 cells.

FIG. 13 depicts that buflomedil at 6 μM did not affect anti-tumor potency of gemcitabine in HT-29 cells.

FIG. 15 depicts buflomedil exhibited no selectivity between OCT2 and MATE1 when metformin is the substrate (FIG. 15A), whereas buflomedil exhibited great selectivity toward OCT2 when either cisplatin or oxaliplatin was used as the substrate, and furthermore, there was no/minimal difference in its $IC_{50}$s between using oxaliplatin or cisplatin as the substrate (FIG. 15B).

FIG. 17 depicts plasma levels of buflomedil (FIG. 17A) and dolutegravir (FIG. 17B) in balb/c mice under different dose and route of administration.

FIG. 19 depicts buflomedil was effective on preventing dorsal root ganglion (DRG) nerve cell injury in mice treated with 8 cycles of oxaliplatin at 3.5 mg/kg, based on morphometric assessment of DRG samples.

FIG. 27 depicts the design of study on the effect of dolutegravir and chlophenesin carbamate on reducing peripheral neurotoxicity after a single oxaliplatin administration.

DETAILED DESCRIPTION

Figure 1:
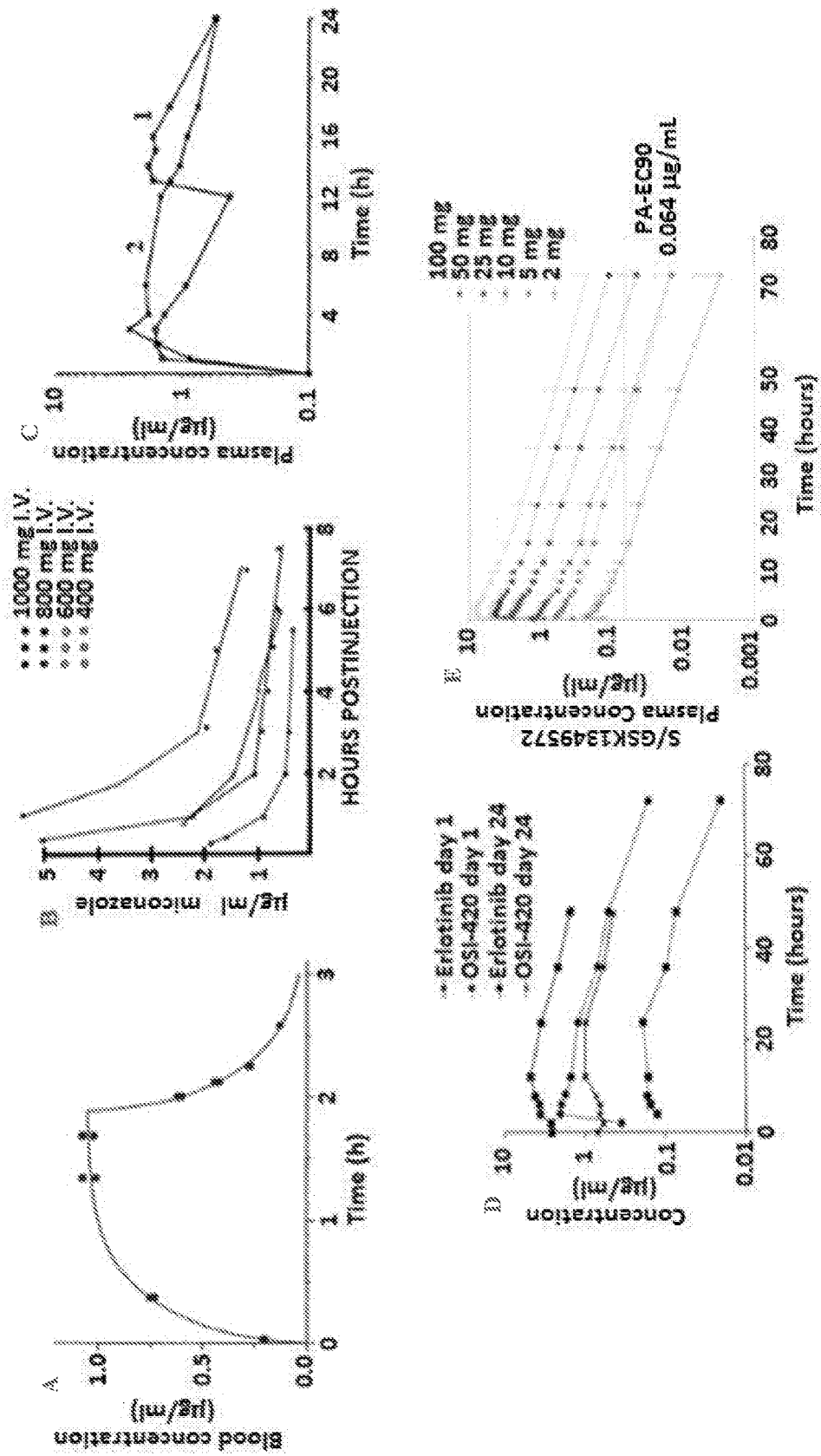
FIGS. 1 A-E depict the clinical plasma exposure of (FIG. 1A) Oxaliplatin following 2 hour intravenous infusion [6]

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

All references cited herein, including patent applications and publications, are hereby incorporated by reference in their entirety.

Methods of Reducing Platinum Drug-Induced Toxicity

In one aspect of the present disclosure, methods of reducing platinum drug-induced toxicity in a cell expressing OCT2, including the steps of providing a platinum drug to the cell expressing OCT2, and providing an OCT2 inhibitor that reduces OCT2-mediated platinum drug uptake into the cell, where the OCT2 inhibitor reduces platinum drug-induced toxicity in the cell are provided.

In another aspect, the present disclosure provides methods for reducing platinum drug-induced toxicity in a subject, including the steps of providing a platinum drug to a subject that contains cells expressing OCT2, and providing an OCT2 inhibitor to the subject, where the OCT2 inhibitor reduces OCT2-mediated platinum drug uptake into the cells expressing OCT2, thereby reducing platinum drug-induced toxicity in the subject. In another aspect, the present disclosure provides methods for reducing platinum drug-induced toxicity in a subject, including the step of providing an OCT2 inhibitor to a subject that contains cells expressing OCT2, where the subject has been or will be provided with platinum drug and where the OCT2 inhibitor reduces OCT2-mediated platinum drug uptake into the cells expressing OCT2, thereby reducing platinum drug-induced toxicity in the subject. In some embodiments, the subject is a human. In other embodiments, the subject is a non-human animal.

In another aspect, the present disclosure provides methods for reducing platinum drug-induced neurotoxicity in a subject in need thereof comprising administering a platinum drug that is oxaliplatin to the subject in need thereof; and administering an effective dose of a selective Organic Cation Transporter 2 (OCT2) inhibitor to the subject in need thereof, wherein the subject in need thereof has a cancer. In some embodiments, the selective Organic Cation Transporter 2 (OCT2) inhibitor is not buflomedil. In some embodiments, the method further comprises a step of determining whether the cancer expresses at least one of OCT1 or OCT3. In some embodiments, the cancer expresses at least one of OCT1 or OCT3.

In another aspect, the present disclosure provides methods for reducing platinum drug-induced toxicity in a subject in need thereof comprising administering a platinum drug that is cisplatin to the subject in need thereof; and administering an effective dose of a selective Organic Cation Transporter 2 (OCT2) inhibitor to the subject in need thereof, wherein the toxicity is nephrotoxicity, ototoxicity or peripheral neuropathy, and wherein the subject in need thereof has a cancer. In some embodiments, selective Organic Cation Transporter 2 (OCT2) inhibitor is not buflomedil. In some embodiments, the method further comprises a step of determining whether the cancer expresses at least one of OCT1 or OCT3. In some embodiments, the cancer expresses at least one of OCT1 or OCT3.

In another aspect, the present disclosure provides methods for reducing platinum drug-induced toxicity in a subject in need thereof comprising determining an effective dose to achieve a plasma level of a selective Organic Cation Transporter 2 (OCT2) inhibitor that is buflomedil or a buflomedil salt in the subject in need thereof, wherein the plasma level is two to five times $IC_{50}$ of the selective Organic Cation Transporter 2 (OCT2) inhibitor that is buflomedil or a buflomedil salt; administering a platinum drug selected from the group consisting of oxaliplatin and cisplatin to the subject in need thereof; and administering an effective dose of a selective Organic Cation Transporter 2 (OCT2) inhibitor that is buflomedil or a buflomedil salt to the subject in need thereof, wherein the toxicity is nephrotoxicity, ototoxicity or peripheral neuropathy, and wherein the subject in need thereof has a cancer. In some embodiments, the method further comprises a step of determining whether the cancer expresses at least one of OCT1 or OCT3. In some embodiments, the cancer expresses at least one of OCT1 or OCT3.

In another aspect, the present disclosure provides methods for reducing platinum drug-induced toxicity in a subject in need thereof comprising administering a selective Organic Cation Transporter 2 (OCT2) inhibitor which is selected from the group consisting of buflomedil, a buflomedil salt, dolutegravir, and a dolutegravir salt, to the subject in need thereof, wherein the subject in need thereof has a cancer expressing at least one of Organic Cation Transporter 1 (OCT1) or Organic Cation Transporter 3 (OCT3), and the subject in need thereof has been or will be administered with a platinum drug, such as cisplatin or oxaliplatin. In some embodiments, the method further comprises a step of determining whether the cancer expresses at least one of OCT1 or OCT3. In some embodiments the platinum drug is oxaliplatin and the platinum drug-induced toxicity is neurotoxicity. In some embodiments the platinum drug is cisplatin and the platinum drug-induced toxicity is neurotocicity, nephrotoxicity or ototoxicity.

In some embodiments, the therapeutically effective amount of platinum drug administered is known to cause platinum drug-induced toxicity in subjects. In some embodiments, the dose of selective OCT2 inhibitor is effective to reduce platinum drug-induced toxicity in a subject in need thereof by at least 10% compared to platinum drug-induced toxicity in subjects treated with the same treatment protocol but without administration of a selective OCT2 inhibitor.

Platinum Drug-Induced Toxicity

The methods of the present disclosure provide for a reduction of platinum drug-induced toxicity. Platinum drug-induced toxicity is a side-effect of treatment of cancer with platinum drugs. When administered to subjects, platinum drugs typically have a therapeutic anticancer activity in tumor cells but may have an unwanted toxic effect on healthy cells. This unwanted platinum drug-induced toxicity is mediated, at least in part, by transport of platinum drugs into healthy cells via OCT2.

Platinum drug-induced toxicity in a cell generally takes the form of a cytotoxic effect on the cell. Reduction of platinum drug-induced toxicity in a cell may be measured by any relevant technique or assay known to one of skill in the art. For example, toxicity in a cell may be assayed by assessing reduction in cell membrane integrity, which is a common effect of cytotoxic compounds. One such assay, an LDH assay, measures the release of lactate dehydrogenase from a cell which is normally sequestered inside the cell. Reduction of platinum drug-induced toxicity in a cell occurs when any amount of reduction occurs, as measured by the relevant assay. For example, toxicity in a cell may be reduced by at least 5%, at least 10%, at least 20%, at least 30%, at least 40%, at least 50%, at least 60%, at least 70%, at least 80%, or at least 90%.

Platinum drug-induced toxicity in a subject may manifest as toxicity in different physiological systems of the subject. Toxicity in a subject can be monitored by assessing parameters of general health of the subject before and throughout the periods that the subject is provided with OCT2 inhibitor and platinum drug. These parameters of general health may include, for example, weight, hair loss, gait, skin condition, and loss of appetite and other gastrointestinal issues. Toxicity may also be assessed by measuring the prevalence or frequency of toxicity among a group of subjects receiving the same platinum drug treatment. A reduction in toxicity may be assessed by comparing the prevalence or frequency of toxicity in such a group of subjects over time.

Platinum drug-induced toxicity may manifest as nephrotoxicity, neurotoxicity, hematoxicity, or ototoxicity. Nephrotoxicity may be monitored with a blood test to measure creatinine clearance, serum creatinine levels, or blood urea nitrogen levels. Decreased creatinine clearance, increased serum creatinine levels, and increased blood urea nitrogen levels indicate poor renal function. Neurotoxicity may be monitored by assessing neurotoxicity symptoms, such as limb weakness or numbness, loss of memory, vision, or intellect, uncontrollable obsessive and/or compulsive behaviors, delusions, headache, cognitive and behavioral problems and sexual dysfunction. In some embodiments where the platinum drug-induced toxicity is neurotoxicity, the neurotoxicity is peripheral neuropathy. In some embodiments, the peripheral neuropathy is Grade 3 or Grade 4 peripheral neuropathy. Ototoxicity may include cochleotoxicity characterized by high-frequency hearing loss and tinnitus. Ototoxicity may be analyzed by measuring auditory brainstem responses. Chemotherapy-induced hematotoxicity is a complex manifestation involving multiple mechanisms. It is however known in the art that reduction of neurotoxicity could also reduce hematotoxicity. For example, it is known that chemotherapy-induced nerve injury (neurotoxicity) with platinum derivatives produces a critical lesion in the bone marrow, which impairs hematopoietic regeneration. Therefore, it is possible to indirectly shield hematopoietic cells from injury using an agent that protects neuronal cells.

Reduction of platinum drug-induced toxicity in a subject occurs when any amount of reduction occurs, as measured by the relevant assays or tests. In some embodiments, prevalence of platinum drug-induced toxicity in a group of subjects is reduced by at least 10%, by at least 20%, by at least 30%, by at least 40%, or by at least 50% as compared to the prevalence of platinum drug-induced toxicity in a group of subjects not provided with an OCT2 inhibitor.

Platinum Drug-Induced Neurotoxicity

The methods of the present disclosure provide for a reduction of platinum drug-induced neurotoxicity. The methods of the present disclosure provide for a delay of onset of platinum drug-induced neurotoxicity. In some embodiments, the neurotoxicity is Grade 0 (normal), 1, 2, 3, or 4. In some embodiments, the delay is of onset of Grade 3 or higher. In some embodiments, the delay is of onset of Grade 2 or higher. In some embodiments, the neurotoxicity is damage to a motor neuron or sensory neuron. In some embodiments, the neurotoxicity is damage to a motor neuron. In some embodiments, the neurotoxicity is damage to a sensory neuron. In some embodiments, damage is to the DRG.

In some embodiments where the platinum drug-induced toxicity is neurotoxicity, the neurotoxicity is peripheral neurotoxicity. In some embodiments, the peripheral neurotoxicity is Grade 3 or Grade 4 peripheral neuropathy. In some embodiments, the peripheral neurotoxicity is Grade 2 peripheral neuropathy.

Neurotoxicity can be assessed by NCI-CTCAE (National Cancer Institute-Common Terminology Criteria for Adverse Events), as shown in the table below. In some embodiments, the neurotoxicity is assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20).

| Toxicity | Grade 1 | Grade 2 | Grade 3 | Grade 4 | Grade 5 |
| --- | --- | --- | --- | --- | --- |
| Cranial neuropathy (any) | Asymptomatic, detected on exam/testing only; intervention not indicated | Moderate symptoms; limiting instrumental ADL (activities of daily life) | Severe symptoms; limiting self-care ADL activities of daily life) | Life-threatening consequences; urgent intervention indicated | Death |
| Motor neuropathy | Asymptomatic, clinical or diagnostic observations only; intervention not indicated | Moderate symptoms; limiting instrumental ADL activities of daily life) | Severe symptoms; limiting self-care ADL activities of daily life); assistive device indicated | Life-threatening consequences; urgent intervention indicated | Death |
| Sensory neuropathy | Asymptomatic; loss of deep tendon reflexes or paresthesia | Moderate symptoms; limiting instrumental ADL activities of daily life) | Severe symptoms; limiting self-care ADL activities of daily life) | Life-threatening consequences; urgent intervention indicated | Death |
| Paresthesias | Mild symptoms | Moderate symptoms; limiting instrumental ADL activities of daily life) | Severe symptoms; limiting self-care ADL activities of daily life) | | |

In peripheral neuropathy, symptoms can range from numbness or tingling, to pricking sensations (paresthesia), or muscle weakness. Areas of the body may become abnormally sensitive leading to an exaggeratedly intense or distorted experience of touch (allodynia). In such cases, pain may occur in response to a stimulus that does not normally provoke pain. Severe symptoms may include burning pain (especially at night), muscle wasting, paralysis, or organ or gland dysfunction. Damage to nerves that supply internal organs may impair digestion, sweating, sexual function, and urination. In the most extreme cases, breathing may become difficult, or organ failure may occur.

In some embodiments, the neurotoxicity is assessed by a measurement selected from sensory nerve action potential, sensory nerve conduction velocity, cold pain threshold, heat pain threshold, mechanical pain threshold, cold detection threshold, warm detection threshold, mechanical detection threshold, vibration perception threshold, current perception threshold, pinprick sensibility, deep tendon reflexes and grip strength. These methods are described in Griffith, K. et. al., Support Care Cancer 2014, 22(5): 1161-1169 and Chong, P S, and Cros, D P. Technology literature review: quantitative sensory testing. Muscle & nerve [0148-639X] Chong, Peter Siao Tick yr: 2004 vol: 29 issue: 5 pg: 734-747.

In some embodiments where the platinum drug-induced toxicity is neurotoxicity, the neurotoxicity is chronic peripheral neuropathy. In certain instances, in chronic peripheral neuropathy, the symptoms would have been occurring for more than or about 2, 3, 4, 6, 7, 8, 9, 10, 11 or 12 months. In some embodiments, the neurotoxicity is chronic neurotoxicity. In some embodiments, the neurotoxicity is acute syndrome transient neurotoxicity. In some embodiments, the neurotoxicity occurs 1 hour to seven days after first treatment. In some embodiments, the neurotoxicity occurs 1, 2, 3, 4, 5, 6, 7, 8, 9, 10, 11, 12, 13, 14, 15, 16, 17, 18, 19, 20, 21, 22, 23 hours after first treatment. In some embodiments, the neurotoxicity occurs 1, 2, 3, 4, 5, 6, or 7 days after first treatment. In some embodiments, the neurotoxicity occurs after a subject completes treatment with a cumulative dose of at least 500 mg/m$^2$. In some embodiments, the neurotoxicity occurs after a subject completes treatment with a cumulative dose of at least 500, 600, 700, or 800 mg/m$^2$.

Some peripheral neuropathies are due to damage to the axons, while others due to damage to the myelin sheath, the fatty protein that coats and insulates the axon. Peripheral neuropathies may also be caused by a combination of both axonal damage and demyelination. Electrodiagnostic studies can help healthcare providers determine the type of damage involved.

In some embodiments, neurotoxicity is damage to the dorsal root ganglion. A dorsal root ganglion (or spinal ganglion) (also known as a posterior root ganglion), is a cluster of nerve cell bodies (a ganglion) in a posterior root of a spinal nerve. The dorsal root ganglia contain the cell bodies of sensory (afferent) neurons.

Forms of Peripheral Neuropathy

Oxaliplatin "induces two clinically distinct forms of peripheral neuropathy; the neuromyotonia-like, acute, transient syndrome characterized by cold-induced distal or perioral paresthesias and pharyngolaryngeal dysesthesias and the chronic form that, in most cases, is a pure sensory, axonal neuropathy with a stocking-and-glove distribution." (Argyriou, A., et. al., Cancer January 2013, 438-444). Cisplatin predominantly induces chronic peripheral neruropathy. The forms of chronic peripheral neuropathy are similar for oxaliplatin and cisplatin.

Acute OXAIPN is a transient peripheral nerve hyperexcitability syndrome that occurs shortly after the infusion of oxaliplatin. This form of neuropathy usually occurs with low total cumulative doses and can be triggered or exacerbated by exposure to cold stimuli. Patients typically experience paresthesia and dysesthesia of the hands and feet, as well as of the larynx and jaw. These symptoms tend to occur within hours of exposure and are reversible over time, especially over the next few hours and days.

Chronic OXAIPN occurs mainly in extremities and present with symptoms similar to those of cisplatin-induced neuropathy. The development of chronic OXAIPN is reported to correlate with the cumulative oxaliplatin dose. A loss of sensation, dysesthesia, and even functional impairment can develop progressively after several cycles of oxaliplatin-based therapy. These effects are usually reversible over time, but might last for several months and have had a significant impact on the continuation of oxaliplatin-based treatment, as these painful symptoms often disrupt the chemotherapy schedule.

Providing a Platinum Drug

In some aspects of methods of the present disclosure, a platinum drug is provided to a cell expressing OCT2 or a platinum drug is provided to a subject comprising cells expressing OCT2. The platinum drug may be any compound that contains a platinum (II) or (IV) center, two substituted or non-substituted cis-amines and two leaving groups. In some embodiments, the platinum drug is oxaliplatin. In some embodiments, the platinum drug is cisplatin. In some embodiments, the platinum drug is tetraplatin.

The cell or cells expressing OCT2 may include, for example, a kidney cell, a neuron cell, a sensory neuron cell, an ear cell, or a blood cell. OCT2 expression in a cell may be assessed by any method found useful by one of skill in the art, including assays measuring transcription of the oct2 gene in the cell, assays measuring the presence of OCT2 protein in the cell, and analysis of published data containing such measurements for various cell types.

The platinum drug may be provided to the cell expressing OCT2 or to the subject comprising cells expressing OCT2 by any methods typically carried out in the lab or in a health care setting to administer drugs to a cell or to a subject. For example, cells may be incubated with the platinum drug, or cells may be provided the platinum drug via the same methods that are used to administer drugs to a subject. The platinum drug may be provided to the subject, for example, enterally, intravenously, intramuscularly, intraperitoneally, orally, or parenterally.

In some embodiments, the amount of platinum drug provided to the subject during one treatment session is greater than what is provided under standard clinical practices. For example, a typical dose of oxaliplatin that is provided under standard clinical practices is 60-130 mg/m$^2$ per treatment cycle. In some embodiments, the cumulative amount of platinum drug provided to the subject over the entire course of treatment is greater than what is provided under standard clinical practices. For example, a typical cumulative dose of oxalipalatin over the entire course of treatment under standard clinical practices is 780-850 mg/m$^2$, or, in rare cases, >1000 mg/m$^2$. In some embodiments, the platinum drug is provided at a greater frequency than under standard clinical practices. For example, under standard clinical practices oxaliplatin is typically provided to the subject every two or three weeks for 8-12 cycles over 6 months.

Providing an OCT2 Inhibitor

In some aspects of methods of the present disclosure, an OCT2 inhibitor is provided that reduces OCT2-mediated platinum drug uptake into the cell expressing OCT2. OCT2-mediated platinum drug uptake into a cell expressing OCT2 may be measured by any method deemed appropriate by one of skill in the art. For example, the methods described in Examples 1 and 2 below may be used. In some embodiments, OCT2-mediated platinum drug uptake into the cell expressing OCT2 is inhibited by at least 50 percent, at least 60 percent, at least 70 percent, at least 80 percent, or at least 90 percent as compared to OCT2-mediated platinum drug uptake into a cell not in the presence of the OCT2 inhibitor.

In some aspects of the methods of the present disclosure, an OCT2 inhibitor is provided to the subject. In some embodiments, the OCT2 inhibitor is buflomedil or a buflomedil salt. In other embodiments, the OCT2 inhibitor comprises imidazole. In some embodiments, the OCT2 inhibitor is miconazole or a salt thereof. In some embodiments, the OCT2 inhibitor is dolutegravir or a salt thereof.

The OCT2 inhibitor may be provided to the subject, for example, enterally, intravenously, intramuscularly, intraperitoneally, orally, or parenterally. The amount of OCT2 inhibitor provided varies but is typically just enough in order to reduce platinum drug-induced toxicity. In some embodiments, the amount of OCT2 inhibitor provided to the subject is at a less than therapeutically effective dosage. With respect to the OCT2 inhibitor, a therapeutically effective dosage is a dosage that is effective to achieve a desired therapeutic or prophylactic result other than reduction of platinum drug-induced toxicity. For example, buflomedil is typically used to treat claudication or the symptoms of peripheral arterial disease. Accordingly, for example, in some embodiments, the amount of OCT2 inhibitor provided to the subject is at a dosage less than that could be therapeutically effective for treatment of claudication. In some embodiments, the amount of OCT2 inhibitor provided to the subject is 10 mg to 2000 mg per day. In some embodiments where the OCT2 inhibitor is buflomedil or a buflomedil salt, the amount of buflomedil or buflomedil salt provided to the subject is 150 mg to 900 mg per day. In some embodiments where the OCT2 inhibitor is miconazole or a miconazole salt, the amount of miconazole or miconazole salt provided to the subject is up to 2000 mg per day. In some embodiments where the OCT2 inhibitor is dolutegravir or a dolutegravir salt, the amount of dolutegravir or dolutegravir salt provided to the subject is 10 mg to 200 mg per day.

The platinum drug and the OCT2 inhibitor may be provided to the subject in any order or with any amount of overlap. In some embodiments, the platinum drug and the OCT2 inhibitor are provided at the same time. In some embodiments, the OCT2 inhibitor is provided to the subject before the platinum drug. In some embodiments, the OCT2 inhibitor is provided to the subject after the platinum drug. Drug pharmacokinetics can be modified by using different administration routines and/or different formulations. For example, slow intravenous infusion using drip-infusion pump or similar methods can be used to maintain desirable plasma concentrations of OCT2 inhibitors, including miconazole, dolutegravir, and buflomedil, over the course of platinum drug infusion for the purpose of reducing platinum drug-induced toxicities.

In embodiments of the present disclosure where the OCT2 inhibitor comprises imidazole, the OCT2 inhibitor may have certain characteristics and functional attributes. In some embodiments, the OCT2 inhibitor has a $C_{max,u}/IC_{50}$ or $C_{max}/IC_{50,app}$, of at least 1. In some embodiments, the OCT2 inhibitor has a $C_{max,u}/IC_{50}$ or $C_{max}/IC_{50,app}$ of at least 3. $C_{max}$ and $C_{max,u}$ denote the maximum total and unbound plasma concentration of a drug, respectively. $IC_{50}$ denotes the half maximal inhibitory concentration assessed in vitro in protein-free assay buffer. $IC_{50,app}$ denotes the half maximal inhibitory concentration assessed in vitro in serum or assay buffer containing serum binding protein(s) such as albumin.

In some embodiments, the OCT2 inhibitor is not toxic to the cell at its clinical concentration. Toxicity of the OCT2 inhibitor to the cell refers to any cytotoxic effect on the cell measurable by any method known to one of skill in the art. In some embodiments, the OCT2 inhibitor does not reduce anti-cancer activity of the platinum drug at its clinical concentration by more than 20% as compared to anti-cancer activity of the platinum drug at its clinical concentration in the absence of the OCT2 inhibitor. Anti-cancer activity refers to the chemotherapeutic effect of a platinum drug on cancer cells. Platinum drugs typically generate crosslinks in cancer cell DNA leading to apoptosis and cell growth inhibition. Anti-cancer activity may be measured by, for example, cytotoxicity assays on cancer cells.

In some embodiments, the OCT2 inhibitor does not reduce uptake of the platinum drug at its clinical concentration into the cell via transporters other than OCT2 by more than 20% as compared to uptake of the platinum drug at its clinical concentration via transporters other than OCT2 in the absence of the OCT2 inhibitor. In some embodiments, the OCT2 inhibitor does not reduce the efflux of the platinum drug at its clinical concentration by more than 20% as compared to the efflux of the platinum drug at its clinical concentration in the absence of the OCT2 inhibitor. Uptake of the platinum drug into the cell via transporters other than OCT2 and efflux of the platinum drug may be measured by any assay deemed suitable by one of skill in the art, including, for example, the in vitro transporter assays described in Examples 3 and 4. "Clinical concentration" refers to a drug's plasma or serum concentration when the drug is dosed at a clinically relevant range, which is below its maximum tolerated dose (MTD).

In some embodiments, the OCT2 inhibitor has a mean half-life that is greater than 2 hours. Half-life refers to the amount of time it takes for a substance, such as a drug or other molecule, to lose one-half of its pharmacologic, physiologic, or radiological activity. The half-life may also describe the time that it takes for the blood plasma concentration of a substance to decrease by half.

Methods for Treating Cancer and for Increasing Efficiency of Platinum Drug Treatment In one aspect, the present disclosure provides methods for treating cancer in a subject including the steps of providing a therapeutically effective amount of platinum drug to the subject having cancer, where the subject comprises a cancerous cell expressing platinum drug uptake transporters not inhibited by an Organic Cation Transporter 2 (OCT2) inhibitor; and providing an OCT2 inhibitor to the subject, thereby treating cancer in the subject. In some embodiments, the cancer is a type of cancer that is known to those skilled in the art to be amenable to treatment with/often treated with platinum drugs in standard treatment protocols, including platinum drugs such as oxaliplatin and/or cisplatin. In some embodiments, the OCT2 inhibitor is buflomedil or a buflomedil salt. In other embodiments, the OCT2 inhibitor contains imidazole. In some embodiments, the OCT2 inhibitor is miconazole or a salt thereof. In some embodiments, the OCT2 inhibitor is dolutegravir or a salt thereof. In some embodiments the subject is a human. In other embodiments, the subject is a non-human animal. In some embodiments, the subject has a cancer who is or will be undergoing cancer treatment that includes administration of a platinum drug, such as oxaliplatin or cisplatin. In some embodiments, the OCT2 inhibitor is not buflomedil or a buflomedil salt.

In another aspect, the present disclosure provides methods for treating cancer in a subject in need thereof comprising administering a therapeutically effective amount of a platinum drug that is oxaliplatin to the subject in need thereof; and administering an effective dose of a selective Organic Cation Transporter 2 (OCT2) inhibitor to the subject in need thereof. In some embodiments, the selective Organic Cation Transporter 2 (OCT2) inhibitor is not buflomedil. In some embodiments, the method further comprises a step of determining whether the cancer expresses at least one of OCT1 or OCT3. In some embodiments, the cancer expresses at least one of OCT1 or OCT3.

In another aspect, the present disclosure provides methods for treating cancer in a subject in need thereof comprising administering a therapeutically effective amount of a platinum drug that is cisplatin to the subject in need thereof; and administering an effective dose of a selective Organic Cation Transporter 2 (OCT2) inhibitor to the subject in need thereof. In some embodiments, the selective Organic Cation Transporter 2 (OCT2) inhibitor is not buflomedil. In some embodiments, the method further comprises a step of determining whether the cancer expresses at least one of OCT1 or OCT3. In some embodiments, the cancer expresses at least one of OCT1 or OCT3.

In another aspect, the present disclosure provides methods for treating cancer in a subject in need thereof comprising determining an effective dose to achieve a plasma level of a selective Organic Cation Transporter 2 (OCT2) inhibitor that is buflomedil or a buflomedil salt in the subject in need thereof, wherein the plasma level is two to five times the $IC_{50}$ of the selective Organic Cation Transporter 2 (OCT2) inhibitor that is buflomedil or a buflomedil salt; administering a therapeutically effective amount of a platinum drug selected from the group consisting of oxaliplatin and cisplatin to the subject in need thereof; and administering an effective dose of a selective Organic Cation Transporter 2 (OCT2) inhibitor that is buflomedil or a buflomedil salt to the subject in need thereof. In some embodiments, the methods further comprise a step of determining whether the cancer expresses at least one of OCT1 or OCT3. In some embodiments, the cancer expresses at least one of OCT1 or OCT3.

Treating cancer refers to clinical intervention in an attempt to alter the natural course of the subject or cell being treated during the course of clinical pathology. Desirable effects of treatment include, but are not limited to, decreasing the rate of disease progression, ameliorating or palliating the disease state, and remission or improved prognosis. For example, an individual is successfully "treated" if one or more symptoms associated with cancer are mitigated or eliminated, including, but not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of subjects.

In another aspect, the present disclosure provides methods for increasing efficacy of platinum drug treatment in a subject including the steps of providing a therapeutically effective amount of platinum drug to the subject having cancer, where the subject comprises a cancerous cell expressing platinum drug uptake transporters not inhibited by an OCT2 inhibitor; and providing an OCT2 inhibitor to the subject, thereby increasing efficacy of the platinum drug treatment. In some embodiments, the OCT2 inhibitor is buflomedil or a buflomedil salt. In other embodiments, the OCT2 inhibitor contains imidazole. In some embodiments, the OCT2 inhibitor is miconazole or a salt thereof. In some embodiments, the OCT2 inhibitor is dolutegravir or a salt thereof.

Efficacy of platinum drug treatment refers to the ability of the platinum drug treatment to have the desired chemotherapeutic effect in the subject. Efficacy is typically assessed by progression free survival (PFS), which is the length of time during or after treatment that a patient lives with a disease but it does not get worse, or by overall survival (OS), which is the length of time from either the date of diagnosis or the start of treatment for a disease that the patient with the disease is still alive.

The platinum drug and the OCT2 inhibitor may be provided to the subject in any order or with any amount of overlap. In some embodiments, the platinum drug and the OCT2 inhibitor are provided at the same time. In some embodiments, the OCT2 inhibitor is provided to the subject before the platinum drug. In some embodiments, the OCT2 inhibitor is provided to the subject after the platinum drug. Drug pharmacokinetics can be modified by using different administration routines and/or different formulations. For example, slow intravenous infusion using drip-infusion pump or similar methods can be used to maintain desirable plasma concentrations of OCT2 inhibitors, including miconazole, dolutegravir, and buflomedil, over the course of platinum drug infusion for the purpose of treating cancer in the subject or increasing efficacy of platinum drug treatment in a subject.

The OCT2 inhibitor may be provided to the subject, for example, enterally, intravenously, intramuscularly, intraperitoneally, orally, or parenterally. The amount of OCT2 inhibitor provided varies but is typically just enough in order to increase efficacy of platinum drug treatment in the subject. In some embodiments, the amount of OCT2 inhibitor provided to the subject is at a less than therapeutically effective dosage. With respect to the OCT2 inhibitor, a therapeutically effective dosage is a dosage that is effective to achieve a desired therapeutic or prophylactic result other than treatment of cancer or increasing efficacy of platinum drug treatment in the subject. For example, buflomedil is typically used to treat claudication or the symptoms of peripheral arterial disease. Accordingly, for example, in some embodiments, the amount of OCT2 inhibitor provided to the subject is at a dosage less than that could be therapeutically effective for treatment of claudication. In some embodiments, the amount of OCT2 inhibitor provided to the subject is 10 mg to 2000 mg per day.

The platinum drug may be any compound that contains a square-planar platinum (II) or (IV) center, two substituted or non-substituted cis-amines and two leaving groups. In some embodiments, the platinum drug is oxaliplatin. In some embodiments, the platinum drug is cisplatin. In some embodiments, the platinum drug is tetraplatin. The platinum drug may be provided to the subject, for example, enterally, intravenously, intramuscularly, intraperitoneally, orally, or parenterally.

A therapeutically effective amount of a platinum drug refers to an amount of the drug that is effective to achieve a desired therapeutic or prophylactic result. Typically, the desired therapeutic result in providing platinum drug to a subject is toxicity to cancer cells in the subject. In some embodiments, the amount of platinum drug provided to the subject during one treatment session is greater than what is provided under standard clinical practices. For example, a typical dose of oxaliplatin that is provided under standard clinical practices is 60-130 mg/m$^2$ per treatment cycle. In some embodiments, the cumulative amount of platinum drug provided to the subject over the entire course of treatment is greater than what is provided under standard clinical practices. For example, a typical cumulative dose of oxaliplatin over the entire course of treatment under standard clinical practices is 780-850 mg/m$^2$, or, in rare cases, >1000 mg/m$^2$. In some embodiments, the platinum drug is provided at a greater frequency than under standard clinical practices. For example, under standard clinical practices oxaliplatin is typically provided to the subject every two or three weeks for 8-12 cycles over 6 months.

In some embodiments, the methods further comprise a step of providing a therapeutically effective amount of one or more additional chemotherapeutic agents to the subject in addition to the platinum drug. The one or more additional chemotherapeutic agents may be, for example, 5-fluorouracil, bevacizumab, capecitabine, gemcitabine, irinotecan, and leucovorin.

Types of Cancer

The methods of the present disclosure for treating cancer and for increasing efficacy of platinum drug treatment may be used in subjects having any type of cancer that responds to platinum drug treatment. For example, the cancer may be adenocarcinoma of the pancreas, ampullary and periampullary carcinoma, hepatocellular carcinoma, adenocarcinoma of the anus, appendiceal carcinoma, carcinoma of the colon or rectum, epithelial ovarian carcinoma, fallopian tube carcinoma, primary peritoneal cancer, esophageal or esophagogastric junction carcinoma, gastric carcinoma, small bowel carcinoma, testicular cancer, cholangiocarcinoma, pancreatic adenocarcinoma, carcinoma of unknown primary origin, chronic lymphocytic leukemia/small lymphocytic lymphoma, non-Hodgkin's lymphoma, adult T-cell leukemia/lymphoma, AIDS-related B-cell lymphoma, diffuse large B-cell lymphoma, follicular lymphoma, gastric MALT lymphoma, nongastric MALT lymphoma, mantle cell lymphoma, mycosis fungoides/Sezary syndrome, splenic marginal zone lymphoma, peripheral T cell lymphoma, primary cutaneous B-cell lymphoma, primary cutaneous anaplastic large cell lymphoma (ALCL), lung cancer, liver cancer, and gallbladder cancer.

In some embodiments, the cancer may be adenocarcinoma of the pancreas, ampullary and periampullary carcinoma, hepatocellular carcinoma, adenocarcinoma of the anus, appendiceal carcinoma, carcinoma of the colon or rectum, epithelial ovarian carcinoma, fallopian tube carcinoma, primary peritoneal cancer, esophageal or esophagogastric junction carcinoma, gastric carcinoma, small bowel carcinoma, testicular cancer, cholangiocarcinoma, pancreatic adenocarcinoma, carcinoma of unknown primary origin, chronic lymphocytic leukemia/small lymphocytic lymphoma, non-Hodgkin's lymphoma, adult T-cell leukemia/lymphoma, AIDS-related B-cell lymphoma, diffuse large B-cell lymphoma, follicular lymphoma, gastric MALT lymphoma, nongastric MALT lymphoma, mantle cell lymphoma, mycosis fungoides/Sezary syndrome, splenic marginal zone lymphoma, peripheral T cell lymphoma, primary cutaneous B-cell lymphoma, primary cutaneous anaplastic large cell lymphoma (ALCL), lung cancer, liver cancer, head and neck cancer, prostate cancer, or smooth muscle cancer, or gallbladder cancer.

In certain embodiments, the cancer is carcinoma of the colon or rectum. In certain embodiments, the cancer is liver cancer. In certain embodiments, the cancer is lung cancer. In certain embodiments, the cancer is ovarian cancer. In certain embodiments, the cancer is head and neck cancer. In certain embodiments, the cancer is prostate cancer. In certain embodiments, the cancer is lymphoma. In certain embodiments, the cancer is smooth muscle cancer.

In some embodiments, the cancer is treatable with oxaliplatin. In some embodiments, the cancer is treatable with cisplatin.

In some embodiments, the methods of the present disclosure for treating cancer and for increasing efficacy of platinum drug treatment may be used in subjects having a cancer expressing at least one of Organic Cation Transporter 1 (OCT1) or Organic Cation Transporter 3 (OCT3). In some embodiments, the cancer expresses OCT1. In some embodiments, the cancer expresses OCT3. In some embodiments, the cancer expresses OCT1 and OCT3.

Platinum Drug Uptake Transporters

In methods of the present disclosure for treating cancer and for increasing efficiency of platinum drug treatment, the subject comprises a cancerous cell expressing platinum drug uptake transporters not inhibited by an OCT2 inhibitor. In some embodiments, the method further comprises the step of determining whether the cancerous cell expresses platinum drug uptake transporters not inhibited by an OCT2 inhibitor. Whether or not a platinum drug uptake transporter is inhibited by an OCT2 inhibitor may be determined by assays known to one of skill in the art. The step of determining whether the cancerous cell expresses platinum drug uptake transporters not inhibited by an OCT2 inhibitor may also be carried out by reviewing published gene and/or protein expression data from various cancer cell types. In some embodiments, the platinum drug uptake transporters not inhibited by an OCT2 inhibitor are Organic Cation Transporter 1 (OCT1) uptake transporters. In some embodiments, the platinum drug uptake transporters not inhibited by an OCT2 inhibitor are Organic Cation Transporter 3 (OCT3) uptake transporters. In some embodiments, the platinum drug uptake transporters not inhibited by an OCT2 inhibitor are Copper Transporter I (CTR1) uptake transporters.

Methods of Predicting Efficacy

In one aspect the present disclosure provides methods of predicting the efficacy of a platinum drug and Organic Cation Transporter 2 (OCT2) inhibitor therapy in a subject having cancer including the steps of obtaining a sample comprising at least one cancerous cell; and determining whether the cancerous cell expresses platinum drug uptake transporters not inhibited by an OCT2 inhibitor, where platinum drug and OCT2 inhibitor therapy is likely to be effective in a subject where the cancerous cell expresses platinum drug uptake transporters not inhibited by an OCT2 inhibitor.

In another aspect the present disclosure provides methods of predicting the efficacy of platinum drug and Organic Cation Transporter 2 (OCT2) inhibitor therapy in a subject having cancer including the steps of obtaining a sample comprising at least one cancerous cell; and determining whether the cancerous cell expresses OCT2, where platinum drug and OCT2 inhibitor therapy is not likely to be effective in a subject where the cancerous cell primarily expresses OCT2.

In another aspect, the present disclosure provides methods of predicting the efficacy of a platinum drug and Organic Cation Transporter 2 (OCT2) inhibitor therapy in a subject having cancer comprising determining whether the cancer expresses platinum drug uptake transporters not inhibited by a selective OCT2 inhibitor, wherein platinum drug and the selective OCT2 inhibitor therapy is likely to be effective in a subject where the cancerous cell expresses platinum drug uptake transporters not inhibited by a selective OCT2 inhibitor. In some embodiments, the uptake transporter is OCT1 or OCT3.

In another aspect, the present disclosure provides methods of predicting the efficacy of platinum drug and Organic Cation Transporter 2 (OCT2) inhibitor therapy in a subject having cancer comprising determining whether the cancerous cell expresses OCT2, wherein the platinum drug and a selective OCT2 inhibitor therapy is not likely to be effective in a subject where the cancer primarily expresses OCT2. In some embodiments, the uptake transporter is OCT1 or OCT3.

Predicting the efficacy of platinum drug and selective OCT2 inhibitor therapy refers to the likelihood that the platinum drug and selective OCT2 inhibitor therapy will have the desired chemotherapeutic effect in the subject. Efficacy is typically assessed by progression free survival (PFS), which is the length of time during or after treatment that a patient lives with a disease but it does not get worse, or by overall survival (OS), which is the length of time from either the date of diagnosis or the start of treatment for a disease that the patient with the disease is still alive.

The methods of predicting efficacy as disclosed herein may be used in a subject having any type of cancer. In some embodiments, the platinum drug is oxaliplatin. In some embodiments, the platinum drug is cisplatin. In some embodiments, the platinum drug is tetraplatin. In some embodiments, the selective OCT2 inhibitor therapy includes administering buflomedil or a buflomedil salt. In some embodiments, the selective OCT2 inhibitor therapy includes administering an OCT2 inhibitor comprising imidazole. In some embodiments, the selective OCT2 inhibitor therapy includes administering miconazole or a salt thereof. In some embodiments, the OCT2 inhibitor therapy includes administering dolutegravir or a dolutegravir salt.

Obtaining Samples

The methods of predicting efficacy as described herein include the step of obtaining a sample comprising at least one cancerous cell. Samples may be obtained by any method known in the art, including biopsy, aspiration, surgery, or sampling of a bodily fluid from the subject such as blood, cerebral spinal fluid, amniotic fluid, peritoneal fluid, or interstitial fluid. Typically the sample is obtained from a diseased tissue or organ. The at least one cancerous cell may be detected, for example, by analyzing the sample under a microscope or by detecting the expression or presence of certain cancer markers in the sample.

Determining Step

In one aspect the methods of predicting efficacy as described herein include the step of determining whether the cancerous cell expresses platinum drug uptake transporters not inhibited by an OCT2 inhibitor. Determining whether the cancerous cell expresses a platinum drug uptake transporter not inhibited by an OCT2 inhibitor may involve any assays known to one of skill in the art for detecting the presence of specific platinum drug uptake transporters or their expression in a cell. The step of determining whether the cancerous cell expresses platinum drug uptake transporters not inhibited by an OCT2 inhibitor may also be carried out by reviewing published gene and/or protein expression data from various cancer cell types. In some embodiments, the platinum drug uptake transporters not inhibited by an OCT2 inhibitor are Organic Cation Transporter 1 (OCT1) uptake transporters. In some embodiments, the platinum drug uptake transporters not inhibited by an OCT2 inhibitor are Organic Cation Transporter 3 (OCT3) uptake transporters. In some embodiments, the platinum drug uptake transporters not inhibited by an OCT2 inhibitor are Copper Transporter I (CTR1) uptake transporters.

In one aspect the methods of predicting efficacy as described herein include the step of determining whether the cancerous cell expresses OCT2. Determining whether the cancerous cell expresses OCT2 may involve any assays known to one of skill in the art for detecting the presence of OCT2 or its expression in a cell. The step of determining whether the cancerous cell expresses OCT2 may also be carried out by reviewing published gene and/or protein expression data from various cancer cell types.

Screening of Compounds for Reducing Platinum Drug-Induced Toxicity

Ideal properties for a platinum protective agent, composition, and/or regimen include: (i) maximum reduction, prevention, mitigation, and/or delay in onset of platinum-associated toxicities (and associated treatment interruptions, delays or dose modifications due to such toxicities); (ii) a lack of interference with anti-tumor activity and lack of tumor desensitization to cytotoxic effects of platinum therapy; (iii) a safety profile that is medically acceptable; (iv) exploitation of biochemical and pharmacological mechanisms to reduce, prevent, mitigate, and/or delay platinum-associated toxicity; and (v) increases in chemotherapeutic index by allowing increases in dose, frequency, and/or duration of primary platinum treatment.

As used herein, a selective OCT2 inhibitor has an $IC_{50}$ for OCT2-mediated transport of 201 µM oxaliplatin in human serum or an assay solution containing 4% bovine serum albumin, of less than or equal to 5 µM; and has an $IC_{50}$ for OCT2-mediated transport of 20 µM oxaliplatin in human serum or an assay solution containing 4% bovine serum albumin that is at least 10-fold less than the selective OCT2 inhibitor $IC_{50}$ for 20 µM oxaliplatin transport in human serum or an assay solution containing 4% bovine serum albumin mediated by OCT-1, OCT-3, and MATE-1.

In some embodiments, a selective OCT2 inhibitor has an $IC_{50}$ for OCT2-mediated transport of 20 µM oxaliplatin in human serum or an assay solution containing 4% bovine serum albumin, of less than or equal to 2, 3, or 4 µM.

In some embodiments, a selective OCT2 inhibitor has an $IC_{50}$ for OCT2-mediated transport of 20 µM oxaliplatin in human serum or an assay solution containing 4% bovine serum albumin that is at least 15, 20, 25-fold less than the selective OCT2 inhibitor $IC_{50}$ for 20 µM oxaliplatin transport in human serum or an assay solution containing 4% bovine serum albumin mediated by OCT-1. OCT-3, and MATE-1.

In some embodiments, a selective OCT2 inhibitor has the one or more of the following additional criteria:

1) $C_{ma}$ under standard or current use is 2 times of OCT2 $IC_{50}$; and 2) maximum tolerated plasma concentration (MTC) is greater than 15 times OCT2 $IC_{50}$, or 4 times of calculated OCT2 $IC_{90}$.

In some embodiments, another criterion is that the selective OCT2 inhibitor does not reduce the efficacy of the platinum drug.

If a platinum-protective agent is capable of increasing the therapeutic index of an active, but otherwise toxic, platinum drug, composition, and/or regimen, it may lead to significant benefit to the subject by increasing tumor response rate, increasing time to tumor progression, and overall patient survival. Prevention of OXA-IPN includes complete or partial prevention. If partial prevention is obtained, it should be sufficient to observe some clinical improvement in presence of drug. Long term toxicity being related to platinum levels in DRG, prevention could also mean a decrease in platinum uptake in DRG while keeping the uptake of OXA constant in the tumor. Another way to measure successful prevention is to improve the ratio of uptake between tumor and DRG (Tumor/DRG) and keeping that ratio above its original value measured in absence of drug.

OCTs the transporters involved in the uptake of oxaliplatin, with OCT2 being responsible for the uptake of oxaliplatin into DRG and kidney cells whereas OCT1 is mostly responsible for the uptake of oxaliplatin into tumor cells. A ratio of blockage called DRG/tumor by calculating the ratio OCT2/OCT1 uptake ratio can be established and is useful for screening.

A large series of compounds were screened to find compounds that blocks OCT2-mediated, but not OCT1-mediated, uptake of oxaliplatin in cells (and thus are selective OCT2 inhibitors). Preferably, the compounds tested were studied for their DRG/tumor ratio expressed in terms of OCT2/OCT1 binding ratio.

A particularity of the OCT2 transporter has been described in the literature by Belzer (Belzer, M., et. al. J Pharmacol Exp Ther. 2013 August; 346(2): 300-310). Indeed OCT2 is known to have several binding sites and therefore inhibitors for the OCT2 transporters are known to be substrate dependent. Belzer's observations were tested by comparing the effect of several inhibitors on a selection of substrates. Consistent with the results from Belzer, a compound's inhibitory potency of OCT2-mediated transport varies significantly depending on the OCT2 substrates being investigated. Therefore, a skilled artisan should not rely on the published OCT2 inhibitory values unless oxaliplatin was used as a substrate.

Platinum Drugs

Platinum drugs are compounds that contain a platinum (II) or (IV) center, two substituted or non-substituted cis-amines and two leaving groups. They form highly reactive, charged, platinum complexes which bind to nucleophilic groups in DNA, inducing intra- and inter-strand DNA cross-links resulting in apoptosis and cell growth inhibition. Commonly used platinum drugs include cisplatin (structure: square-planar platinum (II) center, containing two cis-amines and two chloride groups), carboplatin (structure: square-planar platinum (II) center, containing two cis-amines and bidentate dicarboxylate), and oxaliplatin (structure: square-planar platinum (II) center, bidentate ligand 1,2-diaminocyclohexane and a bidentate oxalate group). Additional platinum drugs include lipoplatin, nedaplatin, eptaplatin (heptaplatin), picoplatin, satraplatin, tetraplatin, iproplatin, lobaplatin, and triplatin.

Structures of platinum drugs include, for example,

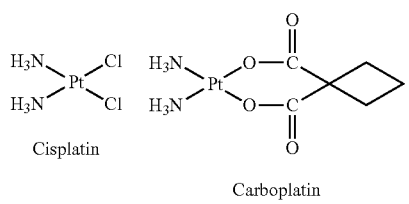
Cisplatin
Carboplatin

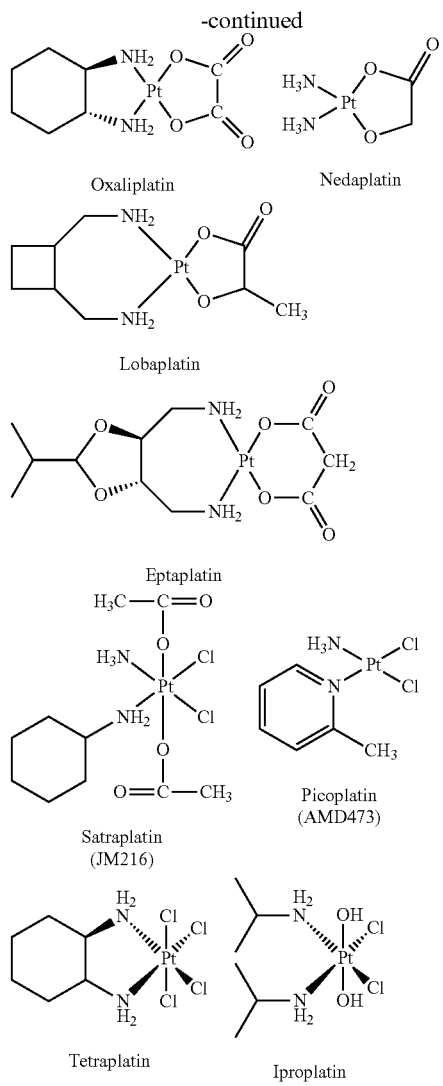
Oxaliplatin
Nedaplatin
Lobaplatin
Eptaplatin
Satraplatin (JM216)
Picoplatin (AMD473)
Tetraplatin
Iproplatin Several of these platinum drugs are drugs on various world markets. Others are drug candidates currently undergoing human clinical trials. In some embodiments, the platinum drug is one that has resulted in intolerable levels of toxicity when administered in clinical trials. For example, tetraplatin (ormaplatin) failed in human clinical trials due to an intolerable level of neurotoxicity. Anti-cancer therapy with such drugs would greatly benefit from the methods disclosed herein.

In some embodiments, oxaliplatin is provided as a powder or a solution. Oxaliplatin may be administered as an intravenous infusion or injection. Oxaliplatin can be obtained from commercial sources (Ranbaxy Limited, Mumbai, India; Accord Healthcare Limited. Durham, N.C.; Actavis, Parsippany-Troy Hills, N.J.; and Hospira, San Jose, Calif.).

In some embodiments, cisplatin is provided as a solution. Cisplatin may be administered as an intravenous infusion. Cisplatin can be obtained from commercial sources (Accord Healthcare Limited. Durham, N.C.; Hospira, San Jose, Calif.; and Sandoz, Holzkirchen, Upper Bavaria. Germany).

Uptake of platinum drugs by transporters typically involves uptake of the metabolites of the drug. Platinum drugs are metabolized and then these metabolites are transported into cells. For example, OCT2 may transport cisplatin analog(s) more efficiently than transporting cisplatin itself.

OCT2 Inhibitors

In some embodiments, the selective OCT2 inhibitor is buflomedil or a buflomedil salt. The structure of buflomedil is

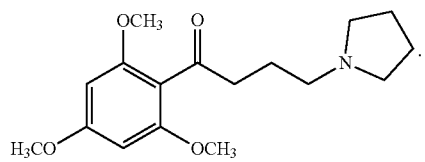

Its IUPAC name is 4-pyrrolidin-1-yl-1-(2,4,6-trimethoxy-phenyl)butan-1-one. In some embodiments, buflomedil is provided as a solution. Buflomedil may be administered orally or intravenously. Buflomedil can be obtained from commercial sources (Loftyl™, Abbott, Chicago, Ill.).

Buflomedil is a vasoactive drug and has been used to treat claudication or symptoms of peripheral arterial disease. The standard of care for buflomedil is 300 mg orally per day with a maximum of 600 mg per day; or intravenous bolus of 200 mg maximum per day for a patient. The MTC (maximum tolerable concentration) is 10 mg/l.

In some embodiments, the OCT2 inhibitor comprises imidazole. Imidazoles are organic compounds with the formula (CH)2N(NH)CH, are planar heterocyclic (five-member ring), and are water soluble. Imidazoles are part of the class of azole antifungal drugs. They include, for example, bifonazole, butoconazole, clotrimazole, econazole, fenticonazole, isoconazole, ketoconazole, luliconazole, miconazole, omoconazole, oxiconazole, sertaconazole, sulconazole, tioconazole, imidazole antibiotics (Nitroimidazoles) such as 6-Amino PA824, azanidazole, benznidazole, dimetridazole, megazol, metronidazole, nimorazole, omidazole, tinidazole, and the imidazole sedative, midazolam. In some embodiments, the selective OCT2 inhibitor is a salt of an imidazole.

In some embodiments, imidazole contains the following structure:

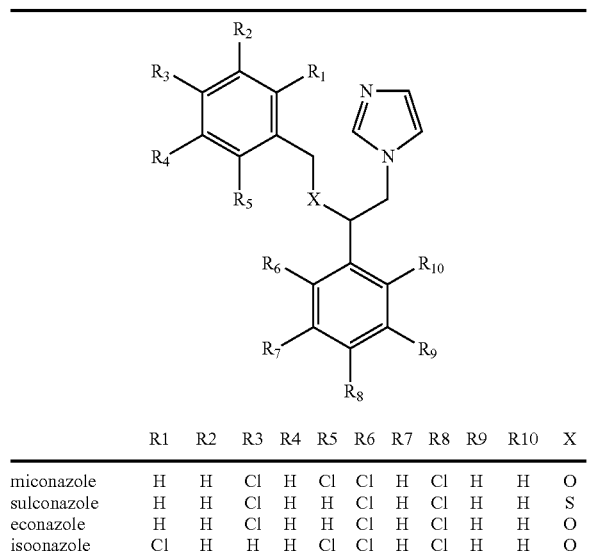

| | R1 | R2 | R3 | R4 | R5 | R6 | R7 | R8 | R9 | R10 | X |
|---|---|---|---|---|---|---|---|---|---|---|---|
| miconazole | H | H | Cl | H | Cl | Cl | H | Cl | H | H | O |
| sulconazole | H | H | Cl | H | H | Cl | H | Cl | H | H | S |
| econazole | H | H | Cl | H | H | Cl | H | Cl | H | H | O |
| isoonazole | Cl | H | H | H | Cl | Cl | H | Cl | H | H | O |

In some embodiments, imidazoic contains the following structure:

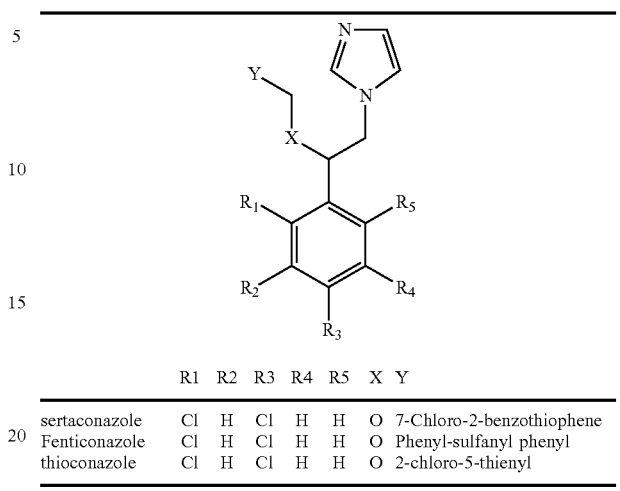

| | R1 | R2 | R3 | R4 | R5 | X | Y |
|---|---|---|---|---|---|---|---|
| sertaconazole | Cl | H | Cl | H | H | O | 7-Chloro-2-benzothiophene |
| Fenticonazole | Cl | H | Cl | H | H | O | Phenyl-sulfanyl phenyl |
| thioconazole | Cl | H | Cl | H | H | O | 2-chloro-5-thienyl |

In some embodiments, the selective OCT2 inhibitor is dolutegravir or a salt of dolutegravir. The structure of dolutegravir is

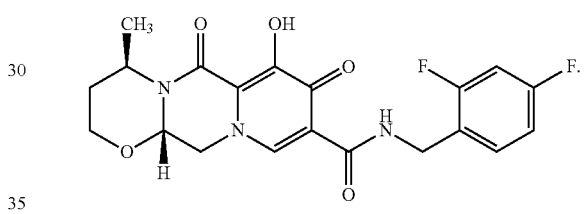

In some embodiments, dolutegravir (Trivicay™, Viiv Healthcare, UK) is provided as a tablet. Dolutegravir may be administered orally. Dolutegravir can be obtained from commercial sources (Trivicay™, Viiv Healthcare, UK).

Effective Dose of Selective OCT2 Inhibitor

An effective dose of a selective OCT2 inhibitor refers to an amount of a selective OCT2 inhibitor that can sufficiently reduce OCT2 transport of a platinum drug into a cell. In some embodiments, the amount of a selective OCT2 inhibitor can completely block transport of a platinum drug into a cell or block 99, 98, 97, 96, 95, 94, 93, 92, 91, 90, 85, 80, 75, or 70% of transport of a platinum drug into a cell. In some embodiments, the platinum drug which is a substrate for the determination is oxaliplatin. Measurement is performed by comparing platinum accumulation in cells that express OCT2 and without OCT2 expression (control cells). A 100% blockage means platinum amount in the OCT2 cells and control cells are the same In some embodiments, the dose of selective OCT2 inhibitor is effective to reduce platinum drug-induced toxicity in said subject in need thereof by at least 10% compared to platinum drug-induced toxicity in subjects treated with the same treatment protocol but without administration of a selective OCT2 inhibitor.

In some embodiments, the dose of selective OCT2 inhibitor is effective to minimize platinum drug-induced neurotoxicity in said subject in need thereof.

In some embodiments, the dose of selective OCT2 inhibitor is effective to prevent platinum drug-induced neurotoxicity of Grade 3 or higher, as assessed by a method selected from the group consisting of National Cancer Institute- Common Toxicity Criteria (NCI-CTC) sensory scale, National Cancer Institute-Common Toxicity Criteria (NCI-CTC) motor scale, Total Neuropathy Score clinical version (TNSc), and European Organization for Research and Treatment of Cancer CIPN specific self-report questionnaire (EORTC QOL-CIPN20), in a patient treated with a cumulative dose of at least 100 mg/m$^2$. In some embodiments, the cumulative dose at least 100 mg/m$^2$, 200 mg/m$^2$, 300 mg/m$^2$, 400 mg/m$^2$ or 500 mg/m$^2$. In some embodiments, the dose of selective OCT2 inhibitor is effective to prevent platinum drug-induced neurotoxicity of Grade 2 or higher. In some embodiments, the prevention is a delay of onset or delay of promotion to the next grade of neurotoxicity.

In some embodiments, the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in a patient treated with a platinum drug dose intensity of at least 30 mg/week/m$^2$. In some embodiments, the platinum drug dose intensity is at least 30 mg/week/m$^2$, 40 mg/week/m$^2$. 50 mg/week/m$^2$ or 60 mg/week/m$^2$. In some embodiments, the platinum drug dose intensity is at least 30 mg/week/m$^2$ to 50 mg/week/m$^2$. In some embodiments, the dose of selective OCT2 inhibitor is effective to prevent platinum drug-induced neurotoxicity of Grade 2 or higher. In some embodiments, the prevention is a delay of onset or delay of promotion to the next grade of neurotoxicity.

In some embodiments, the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in a patient treated with a platinum drug dose of at least 80 mg/m$^2$. In some embodiments, the platinum drug dose is at least 80 mg/m$^2$, 90 mg/m$^2$, 100 mg/m$^2$, 110 mg/m$^2$. 120 mg/m$^2$. 130 mg/m$^2$, or 140 mg/m$^2$. In some embodiments, the dose of selective OCT2 inhibitor is effective to prevent platinum drug-induced neurotoxicity of Grade 2 or higher. In some embodiments, the prevention is a delay of onset or delay of promotion to the next grade of neurotoxicity.

Prevention, as used herein, can refer to any action providing a benefit to a subject at risk of being afflicted with a condition or disease, including avoidance of the development of the condition or disease or a decrease of one or more symptoms of the condition or disease. With regard to prevention of platinum drug-induced neurotoxicity of a certain grade, the promotion or progression to the next grade for the subject is avoided.

In some embodiments, the selective OCT2 inhibitor is administered in a dose effective to reduce neurotoxicity. Neurotoxicity can result in sensitivities to touching cold items, difficulty swallowing cold liquids, throat discomfort, and muscle cramps. In some embodiments, the neurotoxicity is Grade 0, 1, 2, 3, or 4. In some embodiments, the neurotoxicity is damage to a motor neuron or sensory neuron. In some embodiments, the selective OCT2 inhibitor is administered in a dose effective to minimize damage to dorsal root ganglia (DRG).

In some embodiments, neurotoxicity is assessed by determining nerve conduction. In some embodiments, the nerve conduction study is conducted in one of radial, dorsal sural, sural and ulnar nerves. These methods are discussed in Velasco, R., et. al. J Neurol Neurosyrg Psychiatry 2014, 85:392-398.

In some embodiments, the nerve conduction study comprises measuring sensory nerve action potential (SNAP). In some embodiments, the nerve condition study comprises measuring nerve conduction velocity (NCV). In some embodiments, neurotoxicity is assessed by determining sensitivity to cold temperature. In some embodiments, neurotoxicity is assessed by determining sensitivity to a mechanical stimulus.

In some embodiments, neurotoxicity is assessed by a test method selected from thermal detection threshold, mechanical detection threshold, vibration perception threshold, current perception threshold, pinprick sensibility, deep tendon reflexes and grip strength. These methods are discussed in Griffith, K. et. al., Support Care Cancer 2014, 22(5): 1161-1169.

In some embodiments, neurotoxicity is assessed by National Cancer Institute-Common Toxicity Criteria (NCI-CTC) sensory scale. In some embodiments, neurotoxicity is assessed by Total Neuropathy Score clinical version (TNSc). In some embodiments, neurotoxicity is assessed by the European Organization for Research and Treatment of Cancer CIPN specific self-report questionnaire (EORTC QOL-CIPN20). These methods are discussed in Kauto et al. "Oxaliplatin and National Cancer Institute-Common Toxicity Criteria in the Assessment of Chemotherapy-induced Peripheral Neuropathy" Anticancer Research 31: 3493-3496 (2011); and Cavaletti, G., et. al., European Journal of Cancer 46 (2010) 479-494.

Figure 33:
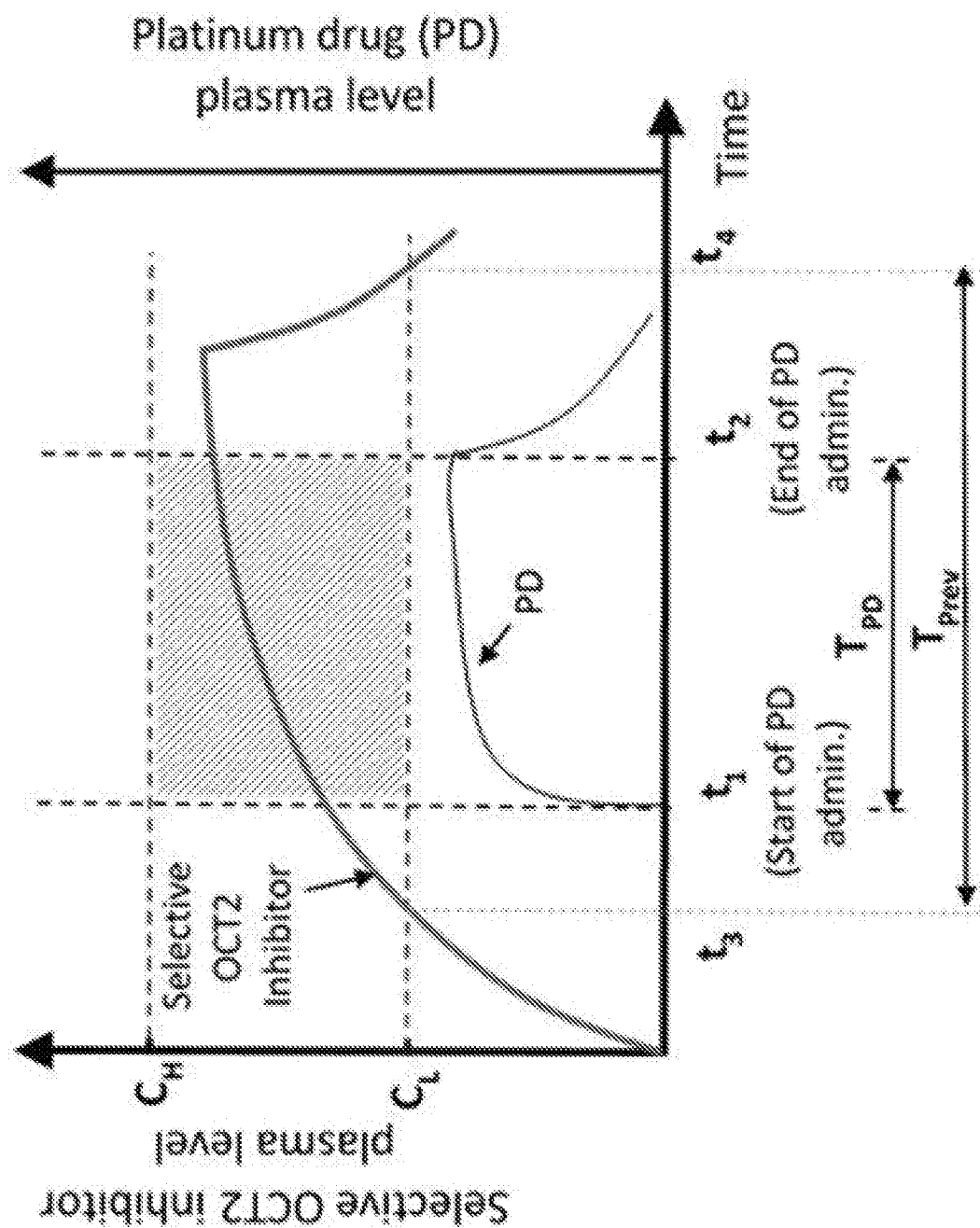
FIG. 33 depicts a desirable plasma level profile of a selective OCT2 inhibitor for reducing toxicity of a platinum drug while minimizing its own adverse effect.

Time-Concentration Profile of a Selective OCT2 Inhibitor Under Clinical Settings Clinically, platinum-based anti-cancer agents, including oxaliplatin and cisplatin, are administered via intravenous infusion over a period of time (typically 2-4 hours, $T_{PD}$ in Figure A) in a treatment cycle, during which platinum drugs reach high plasma levels and are more likely to cause adverse effects, including peripheral neuropathy and nephrotoxicity. Therefore, it is important that during the course of platinum drug administration ($T_{PD}$), the plasma level of a selective OCT2 inhibitor is maintained between two predetermined levels ($C_L$ and $C_H$ in FIG. 33) in order to achieve desirable protective effects while at the same time, minimizing the adverse effects of the OCT2 inhibitor itself. This therapeutic window is depicted in Figure A as the hatched area. Another way to describe such pharmacokinetic profile is through defining a preventive time period ($T_{prev}$) during which the plasma level of the OCT2 inhibitor is maintained between $C_L$ and $C_H$, and $T_{prev}$ should cover the entire period ($T_{PD}$) of platinum drug administration as depicted in Figure A. Outside of $T_{prev}$, it is desirable to keep inhibitor level as low as possible so as to minimize its other pharmacological effects including adverse effects. Such desirable time-plasma level profile can be achieved through applying commonly practiced drug administration techniques such as oral, intravenous injection, intravenous infusion, or combination of such; and through optimizing the formulation of the selective OCT2 inhibitor such as extended release.

It is important to note that the approach above for eliciting optimal protective effects of a selective OCT2 inhibitor against platinum-drug-induced toxicities is in contrast to most other therapeutic interventions whereas treatment efficacy of a drug is primarily driven by its accumulative plasma exposure (drug plasma level integrated over time, typically 12-24 hours, which is commonly referred as area under the curve/AUC) [Benet, L, and Hoener, B., Clin Pharmacol Ther 2002; 71:115-21].

The desirable plasma concentration range of a selective OCT2 inhibitor can be determined as follow: $C_L$ can be determined based on the inhibitor's in vitro OCT2 $IC_{50}$ value, which is measured in 100% human serum or assay buffer containing physiological level of serum albumin. Depending on the level of OCT2 inhibition during the course of platinum drug administration, $C_L$ may be set to a value that is not lower than the in vitro OCT2 $IC_{50}$ value, which corresponds to an estimated 50% reduction of OCT2 mediated transport of a platinum drug in vivo. More preferably, $C_L$ may be set to two times or four times the in vitro OCT2 $IC_{50}$ value, which corresponds to estimated 70% and 90% OCT2 inhibition, respectively. For example, for buflomedil with measured $IC_{50}$ value of 1.4±0.2 uM (Table 4), the $C_L$ may be set to 1.4 uM (0.43 mg/l); or more preferably, 2.8 uM (0.86 mg/l) or 5.6 uM (1.72 mg/l) for eliciting more protective effects. In the case of dolutegravir, the measured $IC_{50}$ value is 3.4±1.0 uM (Table 4), thus the $C_L$ may be set to 1× (3.4 uM or 1.4 mg/l), 2× (6.8 uM or 2.8 mg/l) or 4× (13.6 uM or 5.6 mg/l) the $IC_{50}$ value.

$C_H$ can be determined based on clinical and preclinical toxicity studies of a selective OCT2 inhibitor, such as the $C_{max}$ of a drug under its clinical maximum tolerated dose (MTD). For example, it is well documented that buflomedil overdose can lead to fatal cardio- and neuro-toxicity [European Medicines Agency 2012, Bucolo 2012], which contributed to its marketing suspension in Europe and in a number of other countries. It's documented that the serious toxicities are associated with buflomedil plasma levels above 10 mg/l (32.5 uM) [European Medicines Agency 2012, Bourguignon 2012]. Hence, it is critical to ensure that buflomedil plasma level stay below the toxicity-triggering level by setting $C_H$ to 10 mg/l or lower. In the case of dolutegravir, a preclinical 14-week toxicity study in monkey reported that at the NOAEL (no-observed-adverse-effect-level) dose, the mean plasma $C_m$ in females is 23.5 mg/l (54.8 uM) [PMDA 2012], thus Cu can be set to equal or to be below this value.

Dose Adjustment of a Selective OC72 Inhibitor

Figure 34:
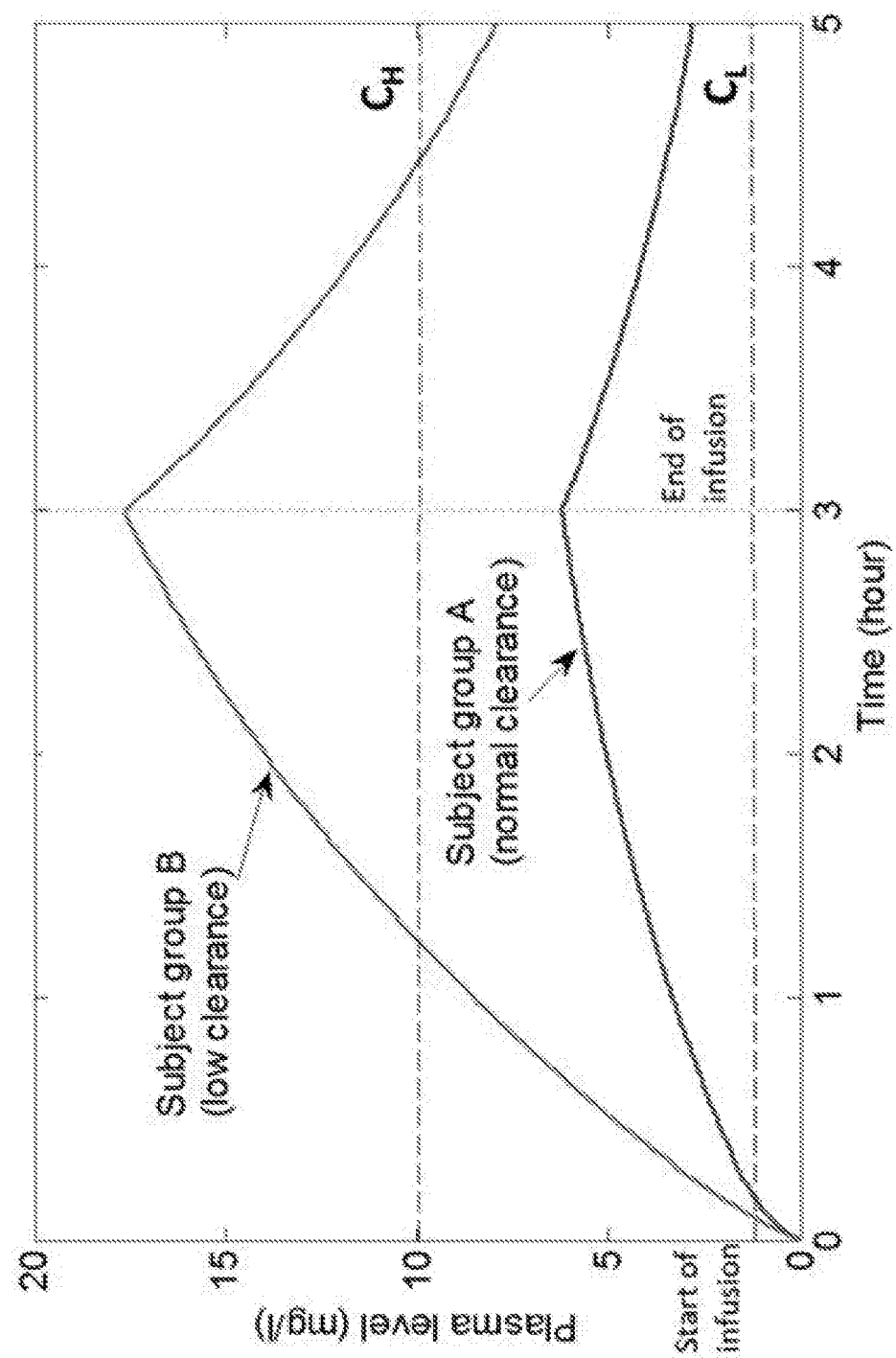
FIG. 34 depicts simulated buflomedil plasma level in two different group of subjects with different reported drug clearance rate, under the same buflomedil treatment (intravenous infusion at a constant rate of 150 mg/hour, 3 hours).

The plasma level of a drug is affected by many factors, including but not limited to: body weight, gender, age and function of major drug clearance organs such as kidney and liver function [FDA, Guidance for Industry: Population Pharmacokinetics, 1999]. Therefore, significant variabilities in drug plasma levels are often seen in subjects under the same drug dose and route of administration. Such inter-individual variabilities not only can influence the protective effects of a selective OCT2 inhibitor, but more importantly, could lead to serious adverse effects when the inhibitor stays above its safe level $C_{11}$. This is particularly important for drugs such as buflomedil because high plasma exposure is reported to cause severe toxicities and mortality [European Medicines Agency, Procedure number: EMEA/H/A-107/1293 (http://www.ema.eurpa.eu/docs/en_GB/document_library/Referrals_document/Buflomedil_107/WC500128578.pdf) 2012; Bucolo, C., et. al., pharmacoepidemiology and drug safety 2012; 21: 1190-1196]. To demonstrate the need for dose adjustment, we conducted a pharmacokinetic simulation in two group of subjects administrated with 450 mg buflomedil through a constant rate intravenous (IV) infusion (150 mg/hour over 3 hours). Pharmacokinetic parameters used in the simulation are from two distinct (by weight, age and height) groups of patients, which exhibited significantly difference in average buflomedil clearance (Group A 292 ml/min vs. Group B 99.5 ml/min) [Gundert-Remy, U., et. al., Eur J Clin Pharmacol (1981) 20: 459-463; Bourguignon. L., et. al., *Fundam Clin Pharmacol.* 2012 April; 26(2):279-85]. As shown in FIG. 34, despite the plasma levels of buflomedil of Group A subjects are in the desirable range defined by $C_L$ and $C_H$, however, in Group B subjects of seniors (average age 82 yrs) with impaired renal clearance, the same dose results in dangerously high levels of buflomedil (>10 mg/l). The PK simulation also suggests a nearly 70% dose reduction for the Group B subjects in order to achieve similar plasma level of buflomedil in Group A subjects. The PK simulation also demonstrates that IV infusion of buflomedil at a constant rate results in slow change in its plasma level over time. Combining an IV bolus injection and an IV infusion, or using variable rate IV infusion, or using other methods described in [Shargel. L., et. al. Applied Biopharmaceutics and Pharmacokinetics, $6^{th}$, 2012] may be applied in order to achieve more consistent plasma level of a selective OCT2 inhibitor during the course of administration.

Many approaches can be used to tailor drug dose for individuals [Klotz. U., *J Clin Chem Clin Biochem.* 1983 November; 21(11):649-58; Jelliffe, R., Ther Drug Monit. 2000 June; 22(3):325-9]. For example, a clinical approach may involve applying a low or normal dose to a subject, followed by measuring the plasma drug level, which can be used to guide dose adjustment for that subject as needed. As another example, dose adjustment can also be guided by population pharmacokinetics analysis [FDA, Guidance for Industry: Population Pharmacokinetics, 1999], which is commonly practiced to identify measurable factors that are associated with variabilities in drug level. Such factors include, but are not limited to, weight, body surface area, height, age, gender, alcohol use, smoking, life style, renal function (commonly assessed by creatinine clearance test), liver function (commonly assessed with Indocyanine-green clearance test), genetic polymorphism and co-medications.

Pharmacokinetic Profile of OCT2 Inhibitor Concentration

The present disclosure provides the disclosed methods, in which the selective OCT2 inhibitor is administered at a dose that results in its plasma concentration during the period of platinum drug administration is less than its maximum tolerated plasma concentration (MTC) and greater than 1×, 2×, 3×, 4× of its $IC_{50}$ value for OCT2-mediated transport of 20 μM oxaliplatin assessed in human serum or an assay buffer containing 4% bovine serum albumin.

In some embodiments, the dose of buflomedil or a buflomedil salt administered in a subject is adjusted based on at least one of the factors of the subject, including body weight, body surface area, height, age, gender, alcohol use, tobacco use, life style, renal function, liver function, genetic polymorphism and co-medications. In some embodiments, the dose of buflomedil or a buflomedil salt results in its plasma level during the period of platinum administration at least 0.43 mg/l, 0.86 mg/l, 1.29 mg/l, 1.72 mg/l or 2.15 mg/l. In some embodiments, the dose of buflomedil or a buflomedil salt is at least 50, 75, 100, 125, 150, 175, 200, 225, 250, 275, 300, 325, 350, 375, 400, 425, 450, 475, 500, 525, 550, 575, or 600 mg. In some embodiments, the dose of buflomedil or a buflomedil salt is at least 100 mg, 200 mg, 400 mg or 600 mg. In some embodiments, the dose of buflomedil or a buflomedil salt is at least 300 mg, 450 mg, 600 mg, 800 mg or 1000 mg. In some embodiments, the dose of buflomedil or a buflomedil salt is at least 1 mg/kg, 2 mg/kg, 3 mg/kg, 4 mg/kg, 5 mg/kg, 6 mg/kg, 8 mg/kg or 10 mg/kg.

In some embodiments, the dose of dolutegravir or a dolutegravir salt results in its plasma level during the period of platinum administration at least 1.4 mg/l, 2.8 mg/l, 4.2 mg/l, 5.6 mg/l or 7.0 mg/l. In some embodiments, the dose of dolutegravir or a dolutegravir salt is at least 50 mg, 100 mg, 150 mg, 200 mg, 250 mg, 300 mg or 400 mg. In some embodiments, the dose of dolutegravir or a dolutegravir salt is at least 50 mg, 75 mg, 100 mg, 150 mg, 200 mg or 300 mg. In some embodiments, the dose of dolutegravir or a dolutegravir salt is at least 1 mg/kg, 2 mg/kg, 3 mg/kg, 4 mg/kg, 5 mg/kg or 6 mg/kg.

In some embodiments, the dose adjustment is based on the characteristics of the subject as described above with reference to the data charts described herein as development for individual drugs.

Pharmaceutical Compositions

In one aspect the present disclosure provides pharmaceutical compositions containing a platinum drug, an OCT2 inhibitor, and a pharmaceutically acceptable carrier. In some embodiments, the OCT2 inhibitor is buflomedil or a buflomedil salt. In other embodiments, the OCT2 inhibitor contains imidazole. In some embodiments, the OCT2 inhibitor is miconazole or a salt thereof. In some embodiments, the OCT2 inhibitor is dolutegravir or a salt thereof. In some embodiments, the platinum drug is oxaliplatin or cisplatin. In some embodiments, the platinum drug is oxaliplatin. In some embodiments, the platinum drug is cisplatin. In some embodiments, a pharmaceutical composition is formulated for intravenous administration comprising a platinum drug that is oxaliplatin, a selective OCT2 inhibitor selected from the group consisting of buflomedil, a buflomedil salt, dolutegravir, and a dolutegravir salt, and a pharmaceutically acceptable carrier.

In some embodiments, a pharmaceutical composition is formulated for intravenous administration comprising a platinum drug that is oxaliplatin or cisplatin, a selective OCT2 inhibitor selected from the group consisting of buflomedil, a buflomedil salt, dolutegravir, and a dolutegravir salt, and a pharmaceutically acceptable carrier.

In some embodiments, a pharmaceutical composition is formulated for intravenous administration comprising a platinum drug that is oxaliplatin or cisplatin, a selective OCT2 inhibitor that is buflomedil or a buflomedil salt, and a pharmaceutically acceptable carrier.

In some embodiments, the platinum drug is oxaliplatin. In some embodiments, the platinum drug is cisplatin. In some embodiments, the platinum drug is tetraplatin. In some embodiments, the amount of platinum drug is greater than what is present in a standard pharmaceutical composition containing a platinum drug. For example, a standard pharmaceutical composition containing oxaliplatin is usually dosed as a powder to be reconstituted with water with the following strengths: 50 mg/vial, 100 mg/vial, or 200 mg/vial. A standard pharmaceutical composition containing cisplatin is usually provided as a 1 mg/ml solution ready for injection in large vial containing 200 mg/200 ml. Tetraplatin is not an approved drug but the injected amount is expected to be similar to cisplatin (5 mg/kg) with a similar formulation.

In some embodiments, the pharmaceutical composition further contains a therapeutically effective amount of one or more additional chemotherapeutic agents in addition to the platinum drug. The additional chemotherapeutic agent may be, for example, 5-fluorouracil, bevacizumab, capecetabine, gemcitabine, irinotecan, or leucovorin.

Any pharmaceutically acceptable carrier may be used. In some embodiments, compositions of the present disclosure are formulated in a conventional manner using one or more physiologically acceptable carriers including, e.g., excipients and auxiliaries which facilitate processing of the active compounds into preparations which are suitable for pharmaceutical use. Suitable pharmaceutically acceptable carriers include, without limitation, physiological saline, aqueous buffer solutions, water for injection use, dextrose solution, solvents and/or dispersion media. The use of such carriers is well known in the art. The carrier is preferably sterile. In some embodiments, the carrier is stable under the conditions of manufacture and storage and preserved against the contaminating action of microorganisms, such as bacteria and fungi, through the use of, for example and without limitation, parabens, chlorobutanol, phenol, ascorbic acid, or thimerosal.

Examples of materials and solutions that can serve as pharmaceutically acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil: (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water: (17) isotonic saline; (18) Ringer's solution: (19) ethyl alcohol; (20) pH buffered solutions; (21) polyesters, polycarbonates and/or polyanhydrides; and (22) other non-toxic compatible substances employed in pharmaceutical formulations.

Proper formulation of the compositions of the present disclosure may be dependent upon the route of administration chosen. A summary of pharmaceutical compositions described herein is found, for example, in Remington: The Science and Practice of Pharmacy, Nineteenth Ed (Easton. Pa.: Mack Publishing Company, 1995); Hoover, John E., Remington's Pharmaceutical Sciences, Mack Publishing Co., Easton. Pa. 1975; Liberman, H. A, and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999). In some embodiments, the pharmaceutical composition is formulated for enteral, intravenous, intramuscular, intraperitoneal, oral, or parenteral administration. In some embodiments, the pharmaceutical composition is formulated for intravenous administration. In certain embodiments, multiple compositions are provided and formulated for different routes of administration.

Articles of Manufacture

The present disclosure relates to a kit comprising a platinum drug that is oxaliplatin or cisplatin; a selective OCT2 inhibitor; and instructions for use. The kit may further comprise instructions for use, e.g., for reducing platinum drug-induced neurotoxicity; treating cancer; or creasing patient compliance for treating cancer. The instructions for use are generally written instructions, although electronic storage media (e.g., magnetic diskette or optical disk) containing instructions are also acceptable.

The present disclosure relates to a kit comprising a platinum drug that is oxaliplatin; a selective OCT2 inhibitor; and instructions for use. In some embodiments, the present disclosure relates to a kit comprising a platinum drug that is oxaliplatin; a selective OCT2 inhibitor selected from the group consisting of buflomedil, a buflomedil salt, dolutegravir, and a dolutegravir salt; and instructions for use. The kit may further comprise instructions for use, e.g., for reducing platinum drug-induced neurotoxicity; treating cancer; or creasing patient compliance for treating cancer. The instructions for use are generally written instructions, although electronic storage media (e.g., magnetic diskette or optical disk) containing instructions are also acceptable.

The present disclosure relates to a kit comprising a platinum drug that is cisplatin; a selective OCT2 inhibitor; and instructions for use. In some embodiments, the present disclosure relates to a kit comprising a platinum drug that is cisplatin, a selective OCT2 inhibitor selected from the group consisting of buflomedil, a buflomedil salt, dolutegravir, and a dolutegravir salt; and instructions for use. The kit may further comprise instructions for use, e.g., for reducing platinum drug-induced neurotoxicity; treating cancer; or creasing patient compliance for treating cancer. The instructions for use are generally written instructions, although electronic storage media (e.g., magnetic diskette or optical disk) containing instructions are also acceptable.

The present disclosure relates to a kit comprising a platinum drug that is oxaliplatin or cisplatin, a selective OCT2 inhibitor selected from the group consisting of buflomedil and a buflomedil salt; and instructions for use. The kit may further comprise instructions for use, e.g., for reducing platinum drug-induced neurotoxicity; treating cancer; or creasing patient compliance for treating cancer. The instructions for use are generally written instructions, although electronic storage media (e.g., magnetic diskette or optical disk) containing instructions are also acceptable.

In some embodiments, the kit further comprises a therapeutically effective amount of one or more additional cancer chemotherapeutic agents in addition to the platinum drug. In some embodiments, the one or more additional chemotherapeutic agents is selected from the group consisting of 5-fluorouracil, bevacizumab, capecetabine, gemcitabine, irinotecan, and leucovorin.

The present disclosure also relates to a pharmaceutical kit comprising one or more containers comprising a platinum drug that is oxaliplatin or cisplatin; and one or more containers comprising a selective OCT2 inhibitor selected from the group consisting of buflomedil, a buflomedil salt, dolutegravir, and a dolutegravir salt. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies). In certain embodiments, multiple dosage forms are provided and formulated for different routes of administration.

Also disclosed are articles of manufacture comprising a unit dosage of the compositions, in suitable packaging for use in the methods described herein. Suitable packaging is known in the art and includes, for example, vials, vessels, ampules, bottles, jars, flexible packaging and the like. An article of manufacture may further be sterilized and/or sealed. In certain embodiments, multiple compositions are provided and formulated for different routes of administration.

Where the administration involves more than one active agent for use in combination, generally, the agents may be formulated separately or in a single dosage form, depending on the prescribed most suitable administration regime for each of the agents concerned.

The instructions can include instructions for determining a desirable dose of the selective OCT2 inhibitor for a subject in need. For example, the instructions can include determining a dose based on at least one factor of the subject, including, but not limited to, body weight, body surface area, height, age, gender, alcohol use, tobacco use, life style, renal function, liver function, genetic polymorphism and co-medications. In some embodiments, the instructions include determining a dose by monitoring plasma level of the OCT2 inhibitor in the said subject.

Administration of Platinum Drug and OCT2

In some embodiments, the method comprises a step prior to the administration of the drugs, wherein the step is determining an effective dose to achieve a plasma level of a selective Organic Cation Transporter 2 (OCT2) inhibitor that is buflomedil or a buflomedil salt in the subject in need thereof, wherein the plasma level is two to five times $IC_{50}$ of the selective Organic Cation Transporter 2 (OCT2) inhibitor that is buflomedil or a buflomedil salt.

In some embodiments, the step of determining an effective dose to achieve a plasma level of a selective Organic Cation Transporter 2 (OCT2) inhibitor is performed by administering a pre-dose of the selective Organic Cation Transporter 2 (OCT2) inhibitor. A pre-dose is a normal or low dose. The plasma level can thus be determined for the particular subject who is dosed.

In some embodiments, the step of determining an effective dose to achieve a plasma level of a selective Organic Cation Transporter 2 (OCT2) inhibitor is determined by reference data chart based on subject characteristics. Subject characteristics are particular to an individual and can include body weight, kidney function, liver function, and body surface area. A reference data chart based on subject characteristics can be generated by guidelines from the FDA [FDA, Guidance for Industry: Population Pharmacokinetics, 1999].

In some embodiments, the platinum drug and the selective OCT2 inhibitor are administered at the same time. In some embodiments, the selective OCT2 inhibitor is administered before the platinum drug. In some embodiments, the selective OCT2 inhibitor is administered after the platinum drug.

In some embodiments, the selective OCT2 inhibitor is administered via more than one route of administration. In some embodiments, the platinum drug and the selective OCT2 inhibitor are administered via the same route of administration.

In some embodiments, the selective OCT2 inhibitor is administered via intravenous infusion. In some embodiments, the selective OCT2 inhibitor is administered via intravenous injection and intravenous infusion. In some embodiments, the intravenous infusion is over a period of time at least 1 hour, such as at least 1, 2, 3, 4, 5 or 6 hours. In some embodiments, the rate of intravenous infusion is constant. In some embodiments, the rate of intravenous infusion is variable.

In some embodiments, the amount of selective OCT2 inhibitor administered to the subject in need thereof is at least one to five times the OCT2 $IC_{50}$ of the selective OCT2 inhibitor In some embodiments, the amount of selective OCT2 inhibitor administered to the subject in need thereof is 50 mg to 600 mg per day.

In some embodiments, the amount of platinum drug administered to the subject during one treatment session is greater than what is administered under standard clinical practices.

In some embodiments, the cumulative amount of platinum drug administered to the subject in need thereof over the entire course of treatment is greater than what is administered under standard clinical practices.

In some embodiments, the platinum drug is administered at a greater frequency than under standard clinical practices.

Enhancing Patient Compliance

The present disclosure provides a method for enhancing patient compliance. In some embodiments, administration of a platinum drug to a subject would result in pain. In some embodiments, the therapeutically effective amount of platinum drug administered is known to cause platinum drug-induced toxicity in subjects. Since the compositions are useful in reducing pain in a subject, a method using the compositions can achieve increased patient compliance.

In some embodiments, the present disclosure provides methods for increasing patient compliance for treating cancer in a subject in need thereof comprising administering a therapeutically effective amount of a platinum drug that is oxaliplatin to the subject in need thereof; and administering a selective Organic Cation Transporter 2 (OCT2) inhibitor to the subject in need thereof in a dose effective to reduce platinum drug-induced neurotoxicity in said subject in need thereof, whereby said subject completes treatment with a cumulative dose at least 500 mg/m$^2$. In some embodiments, subject completes treatment with a cumulative dose at least 500, 600, 700 or 800 mg/m$^2$. In some embodiments, subject completes treatment with a cumulative dose at least 500 to 800 mg/m$^2$. In some embodiments, the selective Organic Cation Transporter 2 (OCT2) inhibitor is not buflomedil. In some embodiments, the method further comprises a step of determining whether the cancer expresses at least one of OCT1 or OCT3. In some embodiments, the cancer expresses at least one of OCT1 or OCT3.

In some embodiments, the present disclosure provides methods for increasing patient compliance for treating cancer in a subject in need thereof comprising administering a therapeutically effective amount of a platinum drug that is cisplatin to the subject in need thereof; and administering a selective Organic Cation Transporter 2 (OCT2) inhibitor to the subject in need thereof in a dose effective to reduce platinum drug-induced toxicity in said subject in need thereof, whereby said subject completes treatment with a cumulative dose of at least 100 mg/m$^2$. In some embodiments, subject completes treatment with a cumulative dose of 100 mg/m$^2$, 200 mg/m$^2$, 300 mg/m$^2$, 400 mg/m$^2$, 500 mg/m$^2$ or 600 mg/m$^2$. In some embodiments, subject completes treatment with a cumulative dose of at least 100 mg/m$^2$. In some embodiments, subject completes treatment with a cumulative dose of at least 300 mg/m$^2$. In some embodiments, subject completes treatment with a cumulative dose of at least 100 to 300 mg/m$^2$. In some embodiments, the selective Organic Cation Transporter 2 (OCT2) inhibitor is not buflomedil. In some embodiments, the method further comprises a step of determining whether the cancer expresses at least one of OCT1 or OCT3. In some embodiments, the cancer expresses at least one of OCT1 or OCT3.

In some embodiments, the present disclosure provides method for increasing patient compliance for treating cancer in a subject in need thereof comprising determining an effective dose to achieve a plasma level of a selective Organic Cation Transporter 2 (OCT2) inhibitor that is buflomedil or a buflomedil salt in the subject in need thereof, wherein the plasma level is two to five times IC$_{50}$ of the selective Organic Cation Transporter 2 (OCT2) inhibitor that is buflomedil or a buflomedil salt; administering a therapeutically effective amount of a platinum drug selected from the group consisting of oxaliplatin and cisplatin to the subject in need thereof; and administering a selective Organic Cation Transporter 2 (OCT2) inhibitor that is buflomedil or a buflomedil salt to the subject in need thereof in a dose effective to reduce platinum drug-induced toxicity in said subject in need thereof, whereby said subject completes treatment with a cumulative dose of at least 100 mg/m$^2$. In some embodiments, subject completes treatment with a cumulative dose at least 200, 300, 400, 500, 600, 700, or 800 mg/m$^2$. In some embodiments, subject completes treatment with a cumulative dose at least 500 to 800 mg/m$^2$. In some embodiments, subject completes treatment with a cumulative dose of at least 100 mg/m$^2$. In some embodiments, subject completes treatment with a cumulative dose of at least 300 mg/m$^2$. In some embodiments, subject completes treatment with a cumulative dose of at least 100 to 300 mg/m. In some embodiments, the method further comprises a step of determining whether the cancer expresses at least one of OCT1 or OCT3. In some embodiments, the cancer expresses at least one of OCT1 or OCT3.

Interim Assessments of Protection Against CIPN to Avoid Unnecessary Continued Exposure to a Selective OCT2 Inhibitor In the prevention of CIPN and neuronal cell damage or death due to platinum drug (e.g., oxaliplatin and cisplatin), it is important to limit the maximal exposure of a protective agent such as buflomedil and dolutegravir that may have inherent toxicities. These toxicities are most evident when the plasma level of a selective OCT2 inhibitor exceeds the safe level defined as $C_H$ in FIG. 33, especially if it is exceeded repeatedly. To limit these toxicities it is important to either monitor plasma level of a selective OCT2 inhibitor to ensure it does not exceed $C_H$ or to discontinue treatment with the inhibitor if it is found not to be effective on reducing platinum drug (e.g., oxaliplatin or cisplatin) toxicities at some interim point. Since patients require many cycles (typically, 10-12 for oxaliplatin, 4-8 for cisplatin) of treatment over months, avoiding unnecessary exposure to high plasma level of a selective OCT2 inhibitor (e.g., buflomedil and dolutegravir) is important.

Fortunately there are recognized and well validated intermediate objective measures that can be employed to estimate whether the preventative therapy reduces peripheral neuropathy caused by oxaliplatin and cisplatin, using methods described in Velasco (Velasco R. Bruna J, Briani C. et al. J Neurol Neurosurg Psychiatry 2014; 85:392-398.). The interim point to make these assessments is after as few as 3 or 4 cycles of platinum drug (e.g., oxaliplatin) treatment. If there is no protection by these measures then it is futile to continue with a selective OCT2 inhibitor such as buflomedil or dolutegravir. The method would employ such methods are described in Velasco 2014. Velasco found that three variables obtained at intermediate follow-up, namely, the number of acute symptoms (OR 1.9: CI 95% 1.2 to 3.2; p=0.012) and the >30% decrease in sensory nerve action potential amplitude from the baseline value in radial (OR 41.4; CI 95% 4.98 to 343.1; p=0.001) and dorsal sural nerves (OR 24.96; CI 95% 2.6 to 239.4; p=0.005) were independently associated with the risk of developing severe OXA-IPN. So if there has been significant deterioration in these parameters after 3, 4 or 6 platinum drug (e.g., oxaliplatin) cycles (despite being treated with a selective OCT2 inhibitor), discontinuation of administration of the selective OCT2 inhibitor (e.g., buflomedil or dolutegravir) at the interim point to avoid further exposure to an unnecessary and potentially harmful agent. Similar approach can be applied to cisplatin, which typically triggers peripheral neuropathy after the administration of 250-350 mg/m2 (Argyriou. et. al., Critical Reviews in Oncology/Hematology 82 (2012)51-77).

The present disclosure provides the disclosed methods, in which the platinum drug-induced toxicity is assessed after administration of the OCT2 inhibitor. In some embodiments, the present disclosure provides the disclosed methods, in which the platinum drug-induced toxicity is assessed by establishing the subject's baseline of sensory nerve action potential or sensory nerve conduction prior to administration of the platinum drug. In some embodiments, the platinum drug-induced toxicity is assessed near the midpoint of treatment. In some embodiments, the platinum drug-induced toxicity is assessed after treatment with a cumulative dose of 200 mg/m$^2$. In some embodiments, the platinum drug-induced toxicity is assessed after treatment with a cumulative dose of 200 mg/m$^2$, 300 mg/m$^2$, 400 mg/m$^2$, 500 mg/m$^2$, 600 mg/m$^2$, 700 mg/m$^2$ or 800 mg/m$^2$.

Medical Uses

As described herein, selective OCT2 inhibitors may be used according to the teachings herein for use in the treatment of cancer in a subject in need thereof, wherein the OCT2 inhibitor is for use in combination with a platinum drug selected from the group consisting of oxaliplatin and cisplatin, and with respect to the variations as described for the methods taught herein.

Use of a selective OCT2 inhibitor in the preparation of a medicament for the treatment of cancer, wherein the medicament is for use in combination with a platinum drug selected from the group consisting of oxaliplatin and cisplatin is also contemplated based on the teachings provided herein and with respect to the variations as described for the methods taught herein.

Use of a platinum drug selected from the group consisting of oxaliplatin and cisplatin in the preparation of a medicament for the treatment of cancer, wherein the medicament is for use in combination with a selective OCT2 inhibitor is also contemplated based on the teachings provided herein and with respect to the variations as described for the methods taught herein.

In certain embodiments of the uses described above, the OCT2 inhibitor is for administration at a dose capable of reducing platinum drug-induced toxicity. In certain embodiments, the OCT2 inhibitor is for administration at a dose of between X and Y mg/kg per day.

EXEMPLARY EMBODIMENTS

Embodiment I-1

In one embodiment, the present disclosure provides methods for reducing platinum drug-induced toxicity in a cell expressing Organic Cation Transporter 2 (OCT2) comprising
providing a platinum drug to the cell expressing OCT2; and
providing an OCT2 inhibitor that reduces OCT2-mediated platinum drug uptake into the cell,
    wherein the OCT2 inhibitor is buflomedil or a buflomedil salt and reduces platinum drug induced toxicity in the cell.

Embodiment I-2

In one embodiment, the present disclosure provides a method for reducing platinum drug-induced toxicity in a cell expressing Organic Cation Transporter 2 (OCT2) comprising
providing a platinum drug to the cell expressing OCT2; and
providing an OCT2 inhibitor that reduces OCT2-mediated platinum drug uptake into the cell,
    wherein the OCT2 inhibitor is dolutegravir or a dolutegravir salt and reduces platinum drug-induced toxicity in the cell.

Embodiment I-3

In one embodiment, the present disclosure provides a method for reducing platinum drug-induced toxicity in a cell expressing Organic Cation Transporter 2 (OCT2) comprising
providing a platinum drug to the cell expressing OCT2; and
providing an OCT2 inhibitor that reduces OCT2-mediated platinum drug uptake into the cell,
wherein the OCT2 inhibitor comprises imidazole and reduces platinum drug-induced toxicity in the cell.

Embodiment I-4

In a further embodiment of embodiment I-3, the OCT2 inhibitor is miconazole or a salt thereof.

Embodiment I-5

In a further embodiment of any of embodiments I-1 to I-4, the platinum drug and the OCT2 inhibitor are provided at the same time.

Embodiment I-6

In a further embodiment of any of embodiments I-1 to I-4, the OCT2 inhibitor is provided before the platinum drug.

Embodiment I-7

In a further embodiment of any of embodiments I-1 to I-4, the OCT2 inhibitor is provided after the platinum drug.

Embodiment I-8

In a further embodiment of any of embodiments I-1 to I-7, the cell expressing OCT2 is a cell selected from the group consisting of kidney cell, neuron cell, ear cell, and blood cell.

Embodiment I-9

In a further embodiment of embodiment I-8, the cell is a sensory neuron cell

Embodiment I-10

In a further embodiment of embodiment I-8, wherein the cell is a kidney cell.

Embodiment I-11

In a further embodiment of any of embodiments I-1 to I-10, the platinum drug is oxaliplatin.

Embodiment I-12

In a further embodiment of any of embodiments I-1 to I-10, the platinum drug is cisplatin.

Embodiment I-13

In a further embodiment of any of embodiments I-1 to I-10, the platinum drug is tetraplatin.

Embodiment I-14

In a further embodiment of any of embodiments I-1 to I-13, OCT2-mediated platinum drug uptake into the cell expressing OCT2 is inhibited by at least 50 percent, at least 70 percent or at least 90 percent as compared to OCT2-mediated platinum drug uptake into a cell not in the presence of the OCT2 inhibitor.

Embodiment I-15

In one embodiment, the present disclosure provides a method for reducing platinum drug-induced toxicity in a subject comprising
providing a platinum drug to a subject comprising cells expressing Organic Cation Transporter 2 (OCT2); and
providing an OCT2 inhibitor to the subject,
wherein the OCT2 inhibitor is buflomedil or a buflomedil salt and reduces OCT2-mediated platinum drug uptake into the cells expressing OCT2, thereby reducing platinum drug-induced toxicity in the subject.

Embodiment I-16

In one embodiment, the present disclosure provides a method for reducing platinum drug induced toxicity in a subject comprising
providing a platinum drug to a subject comprising cells expressing Organic Cation Transporter 2 (OCT2); and
providing an OCT2 inhibitor to the subject,
wherein the OCT2 inhibitor is dolutegravir or a dolutegravir salt and reduces OCT2 mediated platinum drug uptake into the cells expressing OCT2, thereby reducing platinum drug induced toxicity in the subject.

Embodiment I-17

In one embodiment, the present disclosure provides a method for reducing platinum drug-induced toxicity in a subject comprising
providing a platinum drug to a subject comprising cells expressing Organic Cation Transporter 2 (OCT2); and
providing an OCT2 inhibitor to the subject,
wherein the OCT2 inhibitor comprises imidazole and reduces OCT2-mediated platinum drug uptake into the cells expressing OCT2, thereby reducing platinum drug-induced toxicity in the subject.

Embodiment I-18

In a further embodiment of embodiment I-17, the OCT2 inhibitor is miconazole or a salt thereof.

Embodiment I-19

In one embodiment, the present disclosure provides methods for reducing platinum drug-induced toxicity in a subject, comprising
providing an OCT2 inhibitor to a subject comprising cells expressing OCT2; wherein the OCT2 inhibitor is buflomedil or a buflomedil salt, the subject has been or will be provided with platinum drug and the OCT2 inhibitor reduces OCT2-mediated platinum drug uptake into the cells expressing OCT2, thereby reducing platinum drug-induced toxicity in the subject.

Embodiment I-20

In one embodiment, the present disclosure provides a method for reducing platinum drug induced toxicity in a subject, comprising
providing an OCT2 inhibitor to a subject comprising cells expressing OCT2; wherein the OCT2 inhibitor is dolutegravir or a dolutegravir salt, the subject has been or will be provided with platinum drug and the OCT2 inhibitor reduces OCT2 mediated platinum drug uptake into the cells expressing OCT2, thereby reducing platinum drug induced toxicity in the subject.

Embodiment I-21

In one embodiment, the present disclosure provides a method for reducing platinum drug-induced toxicity in a subject, comprising
providing an OCT2 inhibitor to a subject comprising cells expressing OCT2;
wherein the OCT2 inhibitor comprises imidazole, the subject has been or will be provided with platinum drug and the OCT2 inhibitor reduces OCT2-mediated platinum drug uptake into the cells expressing OCT2, thereby reducing platinum drug-induced toxicity in the subject.

Embodiment I-22

In a further embodiment of embodiment I-21, the OCT2 inhibitor is miconazole or a salt thereof.

Embodiment I-23

In a further embodiment of any of embodiments I-15 to I-22, the platinum drug and the OCT2 inhibitor are provided at the same time.

Embodiment I-24

In a further embodiment of any of embodiments I-15 to I-22, the OCT2 inhibitor is provided before the platinum drug.

Embodiment I-25

In a further embodiment of any of embodiments I-15 to I-22, the OCT2 inhibitor is provided after the platinum drug.

Embodiment I-26

In a further embodiment of any of embodiments I-15 to I-25, the platinum drug is oxaliplatin.

Embodiment I-27

In a further embodiment of any of embodiments I-15 to I-25, the platinum drug is cisplatin.

Embodiment I-28

In a further embodiment of any of embodiments I-15 to I-25, the platinum drug is tetraplatin.

Embodiment I-29

In a further embodiment of any of embodiments I-15 to I-28, the amount of OCT2 inhibitor provided to the subject is at a less than a therapeutically effective dosage.

Embodiment I-30

In a further embodiment of any of embodiments I-15 to I-29, the amount of OCT2 inhibitor provided to the subject is 10 mg to 2000 mg per day.

Embodiment I-31

In a further embodiment of any of embodiments I-15 to I-30, the amount of platinum drug provided to the subject during one treatment session is greater than what is provided under standard clinical practices.

Embodiment I-32

In a further embodiment of any of embodiments I-15 to I-31, the cumulative amount of platinum drug provided to the subject over the entire course of treatment is greater than what is provided under standard clinical practices.

Embodiment I-33

In a further embodiment of any of embodiments I-15 to I-32, the platinum drug is provided at a greater frequency than under standard clinical practices.

Embodiment I-34

In a further embodiment of any of embodiments I-15 to I-33, the platinum drug-induced toxicity is selected from the group consisting of nephrotoxicity, neurotoxicity, hematoxicity, and ototoxicity.

Embodiment I-35

In a further embodiment of embodiment I-34, the platinum drug-induced toxicity is neurotoxicity.

Embodiment I-36

In a further embodiment of embodiment I-35, the neurotoxicity is peripheral neuropathy.

Embodiment I-37

In a further embodiment of embodiment I-36, the peripheral neuropathy is Grade 3 or Grade 4 peripheral neuropathy.

Embodiment I-38

In a further embodiment of embodiment I-34, the platinum drug-induced toxicity is nephrotoxicity.

Embodiment I-39

In a further embodiment of any of embodiments I-15 to I-38, the subject is a human or a non-human animal.

Embodiment I-40

In a further embodiment of any of embodiments I-15 to I-39, the OCT2 inhibitor is provided enterally, intravenously, intramuscularly, intraperitoneally, orally, or parenterally.

Embodiment I-41

In a further embodiment of any of embodiments I-15 to I-40, prevalence of platinum drug-induced toxicity in a group of subjects is reduced by at least 10% as compared to the prevalence of platinum drug-induced toxicity in a group of subjects not provided with an OCT2 inhibitor.

Embodiment I-42

In one embodiment, the present disclosure provides methods for treating cancer in a subject comprising;
providing a therapeutically effective amount of platinum drug to the subject having cancer,
wherein the subject comprises a cancerous cell expressing platinum drug uptake transporters not inhibited by an Organic Cation Transporter 2 (OCT2) inhibitor; and providing an OCT2 inhibitor to the subject,
wherein the OCT2 inhibitor is buflomedil or a buflomedil salt, thereby treating cancer in the subject.

Embodiment I-43

In one embodiment, the present disclosure provides methods for treating cancer in a subject comprising;
providing a therapeutically effective amount of platinum drug to the subject having cancer,
wherein the subject comprises a cancerous cell expressing platinum drug uptake transporters not inhibited by an Organic Cation Transporter 2 (OCT2) inhibitor; and
providing an OCT2 inhibitor to the subject,
wherein the OCT2 inhibitor is dolutegravir or a dolutegravir salt, thereby treating cancer in the subject.

Embodiment I-44

In one embodiment, the present disclosure provides a method for treating cancer in a subject comprising;
providing a therapeutically effective amount of platinum drug to the subject having cancer,
wherein the subject comprises a cancerous cell expressing platinum drug uptake transporters not inhibited by an Organic Cation Transporter 2 (OCT2) inhibitor; and
providing an OCT2 inhibitor to the subject,
wherein the OCT2 inhibitor comprises imidazole, thereby treating cancer in the subject.

Embodiment I-45

In a further embodiment of embodiment I-44, the OCT2 inhibitor is miconazole or a salt thereof.

Embodiment I-46

In one embodiment, the present disclosure provides a method for increasing efficacy of platinum drug treatment in a subject comprising providing a therapeutically effective amount of platinum drug to the subject having cancer,
wherein the subject comprises a cancerous cell expressing platinum drug uptake transporters not inhibited by an OCT2 inhibitor; and
providing an OCT2 inhibitor to the subject,
 wherein the OCT2 inhibitor is buflomedil or a buflomedil salt,
 thereby increasing efficacy of the platinum drug treatment.

Embodiment I-47

In one embodiment, the present disclosure provides a method for increasing efficacy of platinum drug treatment in a subject comprising
providing a therapeutically effective amount of platinum drug to the subject having cancer,
wherein the subject comprises a cancerous cell expressing platinum drug uptake transporters not inhibited by an OCT2 inhibitor; and
providing an OCT2 inhibitor to the subject,
 wherein the OCT2 inhibitor is dolutegravir or a dolutegravir salt,
thereby increasing efficacy of the platinum drug treatment.

Embodiment I-48

In one embodiment, the present disclosure provides a method for increasing efficacy of platinum drug treatment in a subject comprising
providing a therapeutically effective amount of platinum drug to the subject having cancer, wherein the subject comprises a cancerous cell expressing platinum drug uptake transporters not inhibited by an OCT2 inhibitor; and
providing an OCT2 inhibitor to the subject,
 wherein the OCT2 inhibitor comprises imidazole,
 thereby increasing efficacy of the platinum drug treatment.

Embodiment I-49

In a further embodiment of embodiment I-48, the OCT2 inhibitor is miconazole or a salt thereof.

Embodiment I-50

In a further embodiment of any of embodiments I-42 to I-49, the platinum drug and the OCT2 inhibitor are provided at the same time.

Embodiment I-51

In a further embodiment of any of embodiments I-42 to I-49, the OCT2 inhibitor is provided before the platinum drug.

Embodiment I-52

In a further embodiment of any of embodiments I-42 to I-49, the OCT2 inhibitor is provided after the platinum drug.

Embodiment I-53

In a further embodiment of any of embodiments I-42 to I-52, the platinum drug is oxaliplatin.

Embodiment I-54

In a further embodiment of any of embodiments I-42 to I-52, the platinum drug is cisplatin.

Embodiment I-55

In a further embodiment of any of embodiments I-42 to I-52, the platinum drug is tetraplatin.

Embodiment I-56

In a further embodiment of any of embodiments I-42 to I-54, the amount of OCT2 inhibitor provided to the subject is at a less than a therapeutically effective dosage.

Embodiment I-57

In a further embodiment of any of embodiments I-42 to I-56, the amount of OCT2 inhibitor provided to the subject is 10 mg to 2000 mg per day.

Embodiment I-58

In a further embodiment of any of embodiments I-42 to I-57, the amount of platinum drug provided to the subject during one treatment session is greater than what is provided under standard clinical practices.

Embodiment I-59

In a further embodiment of any of embodiments I-42 to I-58, the cumulative amount of platinum drug provided to the subject over the entire course of treatment is greater than what is provided under standard clinical practices.

Embodiment I-60

In a further embodiment of any of embodiments I-42 to I-59, the platinum drug is provided at a greater frequency than under standard clinical practices.

Embodiment I-61

In a further embodiment of any of embodiments I-42 to I-60, the cancer is selected from the group consisting of adenocarcinoma of the pancreas, ampullary and periampullary carcinoma, adenocarcinoma of the anus, appendiceal carcinoma, hepatocellular carcinoma, carcinoma of the colon or rectum, epithelial ovarian carcinoma, fallopian tube carcinoma, primary peritoneal cancer, esophageal or esophagogastric junction carcinoma, gastric carcinoma, small bowel carcinoma, testicular cancer, cholangiocarcinoma, pancreatic adenocarcinoma, carcinoma of unknown primary origin, chronic lymphocytic leukemia/small lymphocytic lymphoma, non-Hodgkin's lymphoma, adult T-cell leukemia/lymphoma, AIDS-related B-cell lymphoma, diffuse large B-cell lymphoma, follicular lymphoma, gastric MALT lymphoma, nongastric MALT lymphoma, mantle cell lymphoma, mycosis fungoides/Sezary syndrome, splenic marginal zone lymphoma, peripheral T cell lymphoma, primary cutaneous B-cell lymphoma, primary cutaneous anaplastic large cell lymphoma (ALCL), lung cancer, liver cancer, and gallbladder cancer.

Embodiment I-62

In a further embodiment of embodiment I-61, the cancer is carcinoma of the colon or rectum.

Embodiment I-63

In a further embodiment of embodiment I-61, the cancer is liver cancer.

Embodiment I-64

In a further embodiment of embodiment I-61, the cancer is lung cancer.

Embodiment I-65

In a further embodiment of any of embodiments I-42 to I-64, the platinum drug uptake transporters not inhibited by an OCT2 inhibitor are Organic Cation Transporter 1 (OCT1) uptake transporters.

Embodiment I-66

In a further embodiment of any of embodiments I-42 to I-64, the platinum drug uptake transporters not inhibited by an OCT2 inhibitor are Organic Cation Transporter 3 (OCT3) uptake transporters.

Embodiment I-67

In a further embodiment of any of embodiments I-42 to I-64, the platinum drug uptake transporters not inhibited by an OCT2 inhibitor are Copper Transporter I (CTR1) uptake transporters.

Embodiment I-68

In a further embodiment of any of embodiments I-42 to I-67, the method further comprises the step of determining whether the cancerous cell expresses platinum drug uptake transporters not inhibited by an OCT2 inhibitor.

Embodiment I-69

In a further embodiment of any of embodiments I-42 to I-68, further comprising providing a therapeutically effective amount of one or more additional chemotherapeutic agents to the subject in addition to the platinum drug.

Embodiment I-70

In a further embodiment of embodiment I-69, the one or more additional chemotherapeutic agents is selected from the group consisting of 5-fluorouracil, bevacizumab, capecitabine, gemcitabine, irinotecan, and leucovorin.

Embodiment I-71

In a further embodiment of any of embodiments I-42 to I-70, the subject is a human or a non-human animal.

Embodiment I-72

In a further embodiment of any of embodiments I-42 to I-71, the OCT2 inhibitor is provided enterally, intravenously, intramuscularly, intraperitoneally, orally, or parenterally.

Embodiment I-73

In one embodiment, the present disclosure provides pharmaceutical compositions comprising;
a platinum drug,
an OCT2 inhibitor, wherein the OCT2 inhibitor is buflomedil or a buflomedil salt; and
a pharmaceutically acceptable carrier.

Embodiment I-74

In one embodiment, the present disclosure provides a pharmaceutical composition comprising:
a platinum drug,
an OCT2 inhibitor, wherein the OCT2 inhibitor is dolutegravir or a dolutegravir salt; and
a pharmaceutically acceptable carrier.

Embodiment I-75

In one embodiment, the present disclosure provides a pharmaceutical composition comprising;
a platinum drug,
an OCT2 inhibitor, wherein the OCT2 inhibitor comprises imidazole; and
a pharmaceutically acceptable carrier.

Embodiment I-76

In a further embodiment of embodiment I-75, the OCT2 inhibitor is miconazole or a salt thereof.

Embodiment I-77

In a further embodiment of any of embodiments I-73 to I-76, the amount of platinum drug is greater than what is present in a standard pharmaceutical composition comprising platinum drug.

Embodiment I-78

In a further embodiment of any of embodiments I-73 to I-77, further comprising a therapeutically effective amount of one or more additional chemotherapeutic agents in addition to the platinum drug.

Embodiment I-79

In a further embodiment of embodiment I-78, the one or more additional chemotherapeutic agents is selected from the group consisting of 5-fluorouracil, bevacizumab, capecitabine, gemcitabine, irinotecan, and leucovorin.

Embodiment I-80

In a further embodiment of any of embodiments I-73 to I-79, the platinum drug is oxaliplatin.

Embodiment I-81

In a further embodiment of any of embodiments I-73 to I-79, the platinum drug is cisplatin.

Embodiment I-82

In a further embodiment of any of embodiments I-73 to I-79, the platinum drug is tetraplatin.

Embodiment I-83

In a further embodiment of any of embodiments I-3, I-17, I-21, I-44, or I-48, the OCT2 inhibitor has a $C_{max,u}/IC_{50}$ or $C_{max}/IC_{50,app}$ of at least 1.

Embodiment I-84

In a further embodiment of any of embodiments I-3, I-17, I-21, I-44, or I-48, the OCT2 inhibitor has a $C_{max,u}/IC_{50}$ or $C_{max}/IC_{50,app}$ of at least 3.

Embodiment I-85

In a further embodiment of any of embodiments I-3, I-17, I-21, I-44, I-48, I-83, or I-84, the OCT2 inhibitor is not toxic to the cell at its clinical concentration.

Embodiment I-86

In a further embodiment of any of embodiments I-3, I-17, I-21, I-44, I-48, or I-83 to I-85, the OCT2 inhibitor does not reduce anti-cancer activity of the platinum drug at its clinical concentration by more than 20% as compared to anti-cancer activity of the platinum drug at its clinical concentration in the absence of the OCT2 inhibitor.

Embodiment I-87

In a further embodiment of any of embodiments I-3, I-17, I-21, I-44, I-48, or I-83 to I-86, the OCT2 inhibitor does not reduce uptake of the platinum drug at its clinical concentration into the cell via other transporters by more than 20% as compared to uptake of the platinum drug at its clinical concentration via other transporters in the absence of the OCT2 inhibitor.

Embodiment I-88

In a further embodiment of any of embodiments I-3, I-17, I-21, I-44, I-48, or I-83 to I-87, the OCT2 inhibitor does not reduce the efflux of the platinum drug at its clinical concentration by more than 20% as compared to the efflux of the platinum drug at its clinical concentration in the absence of the OCT2 inhibitor.

Embodiment I-89

In a further embodiment of any of embodiments I-3, I-17, I-21, I-44, I-48, or I-83 to I-88, the OCT2 inhibitor has a mean half-life that is greater than 2 hours.

Embodiment I-90

In a further embodiment of embodiment I-75, the OCT2 inhibitor has a $C_{max,u}/IC_{50}$ or $C_{max}/IC_{50,app}$ of at least 1.

Embodiment I-91

In a further embodiment of embodiment I-75, the OCT2 inhibitor has a $C_{max,u}/IC_{50}$ or $C_{max}/IC_{50,app}$ of at least 3.

Embodiment I-92

In a further embodiment of any of embodiments I-75, I-90, or I-91, the OCT2 inhibitor is not toxic to the cell at its clinical concentration.

Embodiment I-93

In a further embodiment of any of embodiments I-75 or I-90 to I-92, the OCT2 inhibitor does not reduce anti-cancer activity of the platinum drug at its clinical concentration by more than 20% as compared to anti-cancer activity of the platinum drug at its clinical concentration in the absence of the OCT2 inhibitor.

Embodiment I-94

In a further embodiment of any of embodiments I-75 or I-90 to I-93, the OCT2 inhibitor does not reduce uptake of the platinum drug at its clinical concentration into the cell via other transporters by more than 20% as compared to uptake of the platinum drug at its clinical concentration via other transporters in the absence of the OCT2 inhibitor.

Embodiment I-95

In a further embodiment of any of embodiments I-75 or I-90 to I-94, the OCT2 inhibitor does not reduce the efflux of the platinum drug at its clinical concentration by more than 20% as compared to the efflux of the platinum drug at its clinical concentration in the absence of the OCT2 inhibitor.

Embodiment I-96

In a further embodiment of any of embodiments I-75 or I-90 to I-95, the OCT2 inhibitor has a mean half-life that is greater than 2 hours.

Embodiment I-97

In one embodiment, the present disclosure provides a method of predicting the efficacy of a platinum drug and Organic Cation Transporter 2 (OCT2) inhibitor therapy in a subject having cancer comprising
obtaining a sample comprising at least one cancerous cell; and
determining whether the cancerous cell expresses platinum drug uptake transporters not inhibited by an OCT2 inhibitor, wherein platinum drug and OCT2 inhibitor therapy is likely to be effective in a subject where the cancerous cell expresses platinum drug uptake transporters not inhibited by an OCT2 inhibitor.

Embodiment I-98

In one embodiment, the present disclosure provides methods of predicting the efficacy of platinum drug and Organic Cation Transporter 2 (OCT2) inhibitor therapy in a subject having cancer comprising
obtaining a sample comprising at least one cancerous cell; and
determining whether the cancerous cell expresses OCT2,
  wherein the platinum drug and OCT2 inhibitor therapy is
    not likely to be effective in
  a subject where the cancerous cell primarily expresses OCT2.

Embodiment I-99

In a further embodiment of any of embodiments I-97 or I-98, the platinum drug is oxaliplatin.

Embodiment I-100

In a further embodiment of any of embodiments I-97 or I-98, the platinum drug is cisplatin.

Embodiment I-101

In a further embodiment of any of embodiments I-97 or I-98, the platinum drug is tetraplatin.

Embodiment I-102

In a further embodiment of any of embodiments I-97 or I-98, the OCT2 inhibitor therapy comprises administering buflomedil or a buflomedil salt.

Embodiment I-103

In a further embodiment of any of embodiments I-97 or I-98, the OCT2 inhibitor therapy comprises administering dolutegravir or a dolutegravir salt.

Embodiment I-104

In a further embodiment of any of embodiments I-97 or I-98, the OCT2 inhibitor therapy comprises administering an OCT2 inhibitor comprising imidazole.

Embodiment I-105

In a further embodiment of embodiment I-104, the OCT2 inhibitor therapy comprises administering an OCT2 inhibitor comprising miconazole or a salt thereof.

Exemplary Embodiments of Oxaliplatin and Neurotoxicity

Embodiment II-1

In one embodiment, the present disclosure provides methods for reducing platinum drug-induced neurotoxicity in a subject in need thereof comprising
administering a platinum drug that is oxaliplatin to the subject in need thereof; and
administering an effective dose of a selective Organic Cation Transporter 2 (OCT2) inhibitor to the subject in need thereof,
wherein the subject in need thereof has a cancer.

Embodiment II-2

In one embodiment, the present disclosure provides methods for treating cancer in a subject in need thereof comprising
administering a therapeutically effective amount of a platinum drug that is oxaliplatin to the subject in need thereof; and
administering an effective dose of a selective Organic Cation Transporter 2 (OCT2) inhibitor to the subject in need thereof.

Embodiment II-3

In one embodiment, the present disclosure provides methods for increasing patient compliance for treating cancer in a subject in need thereof comprising
administering a therapeutically effective amount of a platinum drug that is oxaliplatin to the subject in need thereof; and
administering a selective Organic Cation Transporter 2 (OCT2) inhibitor to the subject in need thereof in a dose effective to reduce platinum drug-induced neurotoxicity in said subject in need thereof, whereby said subject completes treatment with a cumulative dose at least 500 mg/m$^2$.

Embodiment II-4

The method of Embodiments II-2 or 3, wherein the therapeutically effective amount of platinum drug administered is known to cause platinum drug-induced neurotoxicity in subjects.

Embodiment II-5

The method of any of Embodiments II-1 or 3-4, wherein the neurotoxicity is peripheral neurotoxicity.

Embodiment II-6

The method of any of Embodiments II-1 or 3-4, wherein the neurotoxicity is damage to a sensory neuron.

Embodiment II-7

The method of any of Embodiments II-1 or 3-4, wherein the neurotoxicity is damage to a motor neuron.

Embodiment II-7a

The method of any of Embodiments II-1-7, wherein the neurotoxicity is chronic neurotoxicity.

Embodiment II-7b

The method of any of Embodiments II-1-7, wherein the neurotoxicity is acute syndrome transient neurotoxicity.

Embodiment II-7c

The method of any of Embodiments II-1-7, wherein the neurotoxicity occurs 1 hour to seven days after first treatment.

Embodiment II-7d

The method of any of Embodiments III-1-7, wherein the neurotoxicity occurs after a subject completes treatment with a cumulative dose of at least 500 mg/m$^2$

Embodiment II-8

The method of any of Embodiments II-1 or 3-4, wherein the neurotoxicity is damage to dorsal root ganglia (DRG).

Embodiment II-9

The method of any of Embodiments II-1-8, wherein the dose of selective OCT2 inhibitor is effective to minimize platinum drug-induced neurotoxicity in said subject in need thereof.

Embodiment II-10

The method of any of Embodiments II-1-8, wherein the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in patients treated with a cumulative dose of at least 100 mg/m$^2$.

Embodiment II-11

The method of any of Embodiments II-1-8, wherein the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale. National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in patients treated with a platinum drug dose intensity of at least 30 mg/week/m$^2$.

Embodiment II-12

The method of any of Embodiments II-1-8, wherein the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in patients treated with a platinum drug dose of at least 80 mg/m$^2$.

Embodiment II-13

The method of any of Embodiments II-1-12, further comprising assessing platinum drug-induced neurotoxicity in a subject after administration of the platinum drug.

Embodiment II-14

The method of Embodiment II-13, wherein the neurotoxicity is assessed by a method selected from National Cancer Institute-Common Toxicity Criteria (NCI-CTC) sensory scale. National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20).

Embodiment II-15

The method of Embodiment II-13, wherein the neurotoxicity is assessed by a measurement selected from sensory nerve action potential, sensory nerve conduction velocity, cold pain threshold, heat pain threshold, mechanical pain threshold, cold detection threshold, warm detection threshold, mechanical detection threshold, vibration perception threshold, current perception threshold, pinprick sensibility, deep tendon reflexes and grip strength.

Embodiment II-16

The method of Embodiment II-13, wherein the neurotoxicity is assessed by measuring sensory nerve action potential in one of radial, dorsal sural, sural and ulnar nerves.

Embodiment II-17

The method of any of Embodiments II-13-16, further compromising establishing the subject's baseline prior to administration of the platinum drug.

Embodiment II-18

The method of any of Embodiments II-13-16, wherein the platinum drug-induced neurotoxicity is assessed near the midpoint of treatment.

Embodiment II-19

The method of any of Embodiments II-13-16, wherein the platinum drug-induced neurotoxicity is assessed after treatment with a cumulative dose of 200 mg/m$^2$.

Embodiment II-20

The method of any of Embodiments II-1-8, wherein the selective OCT2 inhibitor is selected from the group consisting of buflomedil, a buflomedil salt, dolutegravir, and a dolutegravir salt.

Embodiment II-21

The method of Embodiment II-20, wherein the selective OCT2 inhibitor is buflomedil, or a buflomedil salt.

Embodiment II-22

The method of Embodiment II-21, wherein the dose of buflomedil or a buflomedil salt administered in a subject is adjusted based on at least one of the factors of the said subject, body weight, body surface area, height, age, gender, alcohol use, tobacco use, life style, renal function, liver function, genetic polymorphism and co-medications.

Embodiment II-23

The method of Embodiments II-21 or 22, wherein the dose of buflomedil or a buflomedil salt results in its plasma level during the period of platinum administration at least 0.43 mg/l, 0.86 mg/l, 1.29 mg/l, 1.72 mg/l or 2.15 mg/l.

Embodiment II-24

The method of any of Embodiments II-21-23, wherein the dose of buflomedil or a buflomedil salt is at least 100 mg, 200 mg, 300 mg, 400 mg, 500 mg or 600 mg.

Embodiment II-25

The method of any of Embodiments II-21-24, wherein the dose of buflomedil or a buflomedil salt is at least 1 mg/kg, 2 mg/kg, 3 mg/kg, 4 mg/kg, 5 mg/kg, 6 mg/kg, 8 mg/kg or 10 mg/kg.

Embodiment II-26

The method of Embodiment II-20, wherein the selective OCT2 inhibitor is dolutegravir or a dolutegravir salt.

Embodiment II-27

The method of Embodiment II-26, wherein the dose of dolutegravir or a dolutegravir salt results in its plasma level during the period of platinum administration at least 1.4 mg/l, 2.8 mg/l, 4.2 mg/l, 5.6 mg/l or 7.0 mg/l.

Embodiment II-28

The method of Embodiment II-26 or 27, wherein the dose of dolutegravir or a dolutegravir salt is at least 50 mg, 100 mg, 150 mg, 200 mg, 250 mg, 300 mg or 400 mg.

Embodiment II-29

The method of any of Embodiments II-26-28, wherein the dose of dolutegravir or a dolutegravir salt is at least 1 mg/kg, 2 mg/kg, 3 mg/kg, 4 mg/kg, 5 mg/kg or 6 mg/kg.

Embodiment II-30

The method of any of Embodiments II-1-29, wherein the selective OCT2 inhibitor does not reduce the efficacy of the platinum drug.

Embodiment II-31

The method of any of Embodiments II-1-30, wherein the selective OCT2 inhibitor is administered at a dose that results in its plasma concentration during the period of platinum drug administration less than its maximum tolerated plasma concentration (MTC) and greater than 1×, 2×, 3×, 4× of its $IC_{50}$ value for OCT2-mediated transport of 20 µM oxaliplatin assessed in human serum or an assay buffer containing 4% bovine serum albumin.

Embodiment II-32

The method of any of Embodiments II-1-19, 30 or 31, wherein the selective OCT2 inhibitor has an $IC_{50}$ for OCT2-mediated transport of 20 µM oxaliplatin in human serum or an assay solution containing 4% bovine serum albumin, of less than or equal to 2 µM.

Embodiment II-33

The method of Embodiment II-32, wherein the selective OCT2 inhibitor has an $IC_{50}$ for OCT2-mediated transport of 20 µM oxaliplatin in human serum or an assay solution containing 4% bovine serum albumin that is at least 15-fold less than the selective OCT2 inhibitor $IC_{50}$ for 20 µM oxaliplatin transport in human serum or an assay solution containing 4% bovine serum albumin mediated by OCT1-, OCT-3, and MATE-1.

Embodiment II-34

The method of any of Embodiments II-1-33, wherein the subject in need thereof has a cancer expressing at least one of Organic Cation Transporter 1 (OCT1) or Organic Cation Transporter 3 (OCT3).

Embodiment II-35

The method of any of Embodiments II-1-25 or 30-34, wherein the selective OCT2 inhibitor is buflomedil, or a buflomedil salt.

Embodiment II-36

The method of any of Embodiments II-1-20 or 26-34, wherein the selective OCT2 inhibitor is dolutegravir, or a dolutegravir salt.

Embodiment II-37

The method of any of Embodiments II-1-36, wherein the platinum drug and the selective OCT2 inhibitor are administered at the same time.

Embodiment II-38

The method of any of Embodiments II-1-36, wherein the selective OCT2 inhibitor is administered before the platinum drug.

Embodiment II-39

The method of any of Embodiments II-1-36, wherein the selective OCT2 inhibitor is administered after the platinum drug.

Embodiment II-40

The method of any of Embodiments II-1-39, wherein the amount of platinum drug administered to the subject during one treatment session is greater than what is administered under standard clinical practices.

Embodiment II-41

The method of any of Embodiments II-1-40, wherein the cumulative amount of platinum drug administered to the subject in need thereof over the entire course of treatment is greater than what is administered under standard clinical practices.

Embodiment II-42

The method of any of Embodiments II-1-41, wherein the platinum drug is administered at a greater frequency than under standard clinical practices.

Embodiment II-43

The method of any of Embodiments II-1 or 3-42, wherein the neurotoxicity is peripheral neuropathy.

Embodiment II-44

The method of Embodiment II-43, wherein the peripheral neuropathy is Grade 3 or Grade 4 peripheral neuropathy.

Embodiment II-45

The method of any of Embodiments II-1-44, wherein the subject in need thereof is a human or a non-human animal.

Embodiment II-46

The method of any of Embodiments II-1-45, wherein the selective OCT2 inhibitor is administered enterally, intravenously, intramuscularly, intraperitoneally, orally, or parenterally.

Embodiment II-47

The method of any of Embodiments II-1-46, wherein the selective OCT2 inhibitor is administered via more than one route of administration.

Embodiment II-48

The method of any of Embodiments II-1-46, wherein the platinum drug and the selective OCT2 inhibitor are administered via the same route of administration.

Embodiment II-49

The method of any of Embodiments II-1-45, wherein the selective OCT2 inhibitor is administered via intravenous infusion.

Embodiment II-50

The method of any of Embodiments II-1-45, wherein the selective OCT2 inhibitor is administrated via intravenous injection and intravenous infusion.

Embodiment II-51

The method of Embodiments II-49 or 50, wherein intravenous infusion is over a period of time at least 1 hour.

Embodiment II-52

The method of Embodiments II-49 or 50, wherein the rate of intravenous infusion is constant.

Embodiment II-53

The method of Embodiments II-49 or 50, wherein the rate of intravenous infusion is variable.

Embodiment II-54

The method of any of Embodiments II-1-53, wherein the cancer expresses OCT1.

Embodiment II-55

The method of any of Embodiments II-1-54, wherein the cancer expresses OCT3.

Embodiment II-56

The method of any of Embodiments II-1-55, wherein the cancer expresses OCT1 and OCT3.

Embodiment II-57

The method of any one of Embodiments II-1-56, wherein the cancer is selected from the group consisting of adenocarcinoma of the pancreas, ampullary and periampullary carcinoma, adenocarcinoma of the anus, appendiceal carcinoma, hepatocellular carcinoma, carcinoma of the colon or rectum, epithelial ovarian carcinoma, fallopian tube carcinoma, primary peritoneal cancer, esophageal or esophagogastric junction carcinoma, gastric carcinoma, small bowel carcinoma, testicular cancer, cholangiocarcinoma, pancreatic adenocarcinoma, carcinoma of unknown primary origin, chronic lymphocytic leukemia/small lymphocytic lymphoma, non-Hodgkin's lymphoma, adult T-cell leukemia/lymphoma, AIDS-related B-cell lymphoma, diffuse large B-cell lymphoma, follicular lymphoma, gastric MALT lymphoma, nongastric MALT lymphoma, mantle cell lymphoma, mycosis fungoides/Sezary syndrome, splenic marginal zone lymphoma, peripheral T cell lymphoma, primary cutaneous B-cell lymphoma, primary cutaneous anaplastic large cell lymphoma (ALCL), lung cancer, liver cancer, head and neck cancer, prostate cancer, smooth muscle cancer and gallbladder cancer.

Embodiment II-58

The method of Embodiment II-57, wherein the cancer is ovarian cancer.

Embodiment II-59

The method of Embodiment II-57, wherein the cancer is head and neck cancer.

Embodiment II-60

The method of Embodiment II-57, wherein the cancer is prostate cancer.

Embodiment II-61

The method of Embodiment II-57, wherein the cancer is lymphoma.

Embodiment II-62

The method of Embodiment II-57, wherein the cancer is smooth muscle cancer.

Embodiment II-63

The method of Embodiment II-57, wherein the cancer is carcinoma of the colon or rectum.

Embodiment II-64

The method of Embodiment II-57, wherein the cancer is liver cancer.

Embodiment II-65

The method of Embodiment II-57, wherein the cancer is lung cancer.

Embodiment II-66

The method of any of Embodiments II-1-65, further comprising administering to the subject in need thereof a therapeutically effective amount of one or more additional cancer chemotherapeutic agents in addition to the platinum drug.

Embodiment II-67

The method of Embodiment II-66, wherein the one or more additional chemotherapeutic agents is selected from the group consisting of 5-fluorouracil, bevacizumab, capecetabine, gemcitabine, irinotecan, and leucovorin.

Embodiment II-68

A pharmaceutical composition formulated for intravenous administration comprising
a platinum drug that is oxaliplatin,
a selective OCT2 inhibitor selected from the group consisting of buflomedil, a buflomedil salt, dolutegravir, and a dolutegravir salt, and
a pharmaceutically acceptable carrier.

Embodiment II-69

The pharmaceutical composition of Embodiment II-68, wherein the selective OCT2 inhibitor is buflomedil, or a buflomedil salt.

Embodiment II-70

The pharmaceutical composition of Embodiment II-68, wherein the OCT2 inhibitor is dolutegravir, or a dolutegravir salt.

Embodiment II-71

The pharmaceutical composition of any of Embodiments II-68-70, wherein the amount of the platinum drug is greater than what is present in a standard pharmaceutical composition comprising the platinum drug.

Embodiment II-72

The pharmaceutical composition of any of Embodiments II-68-71, further comprising a therapeutically effective amount of one or more additional cancer chemotherapeutic agents in addition to the platinum drug.

Embodiment II-73

The pharmaceutical composition of Embodiment II-72, wherein the one or more additional chemotherapeutic agents is selected from the group consisting of 5-fluorouracil, bevacizumab, capecetabine, gemcitabine, irinotecan, and leucovorin.

Embodiment II-74

A kit comprising a therapeutically effective amount of a platinum drug that is oxaliplatin; a selective OCT2 inhibitor and instructions for use.

Embodiment II-75

The kit of Embodiment II-74, further comprising instructions for determining a desirable dose of the selective OCT2 inhibitor for a subject in need.

Embodiment II-76

The kit of Embodiment II-75, wherein the dose is determined based on at least one factor of the said subject selected from body weight, body surface area, height, age, gender, alcohol use, tobacco use, life style, renal function, liver function, genetic polymorphism and co-medications.

Embodiment II-77

The kit of Embodiment II-75, wherein the dose is determined by monitoring plasma level of the OCT2 inhibitor in the said subject.

Embodiment II-78

The kit of any one of Embodiments II-74-77, wherein the selective OCT2 inhibitor is buflomedil or a buflomedil salt.

Embodiment II-79

The kit of Embodiment II-78, wherein buflomedil or a buflomedil salt is present in an amount greater than 300 mg, 450 mg, 600 mg, 800 mg or 1000 mg.

Embodiment II-80

The kit of any of Embodiments II-74-77, wherein the selective OCT2 inhibitor is dolutegravir or a dolutegravir salt.

Embodiment II-81

The kit of Embodiment II-80, wherein dolutegravir or a dolutegravir salt is present in an amount greater than 50 mg, 75 mg, 100 mg, 150 mg, 200 mg or 300 mg.

Embodiment II-82

The kit of any of Embodiments II-74-81, wherein the instructions state that the kit is intended for use in reducing platinum drug-induced neurotoxicity.

Embodiment II-83

The kit of Embodiment II-74-80, wherein the instructions state that the kit is intended for use in treating cancer.

Embodiment II-84

The kit of any of Embodiments II-74-83, further comprising a therapeutically effective amount of one or more additional cancer chemotherapeutic agents in addition to the platinum drug.

Embodiment II-85

The kit of Embodiment II-84, wherein the one or more additional chemotherapeutic agents is selected from the group consisting of 5-fluorouracil, bevacizumab, capecetabine, gemcitabine, irinotecan, and leucovorin.

Exemplary Embodiments of Cisplatin and Toxicities

Embodiment III-1

In one embodiment, the present disclosure provides methods for reducing platinum drug-induced toxicity in a subject in need thereof comprising
administering a platinum drug that is cisplatin to the subject in need thereof; and
administering an effective dose of a selective Organic Cation Transporter 2 (OCT2) inhibitor to the subject in need thereof, wherein the toxicity is nephrotoxicity, ototoxicity or peripheral neuropathy, and wherein the subject in need thereof has a cancer.

Embodiment III-2

In one embodiment, the present disclosure provides methods for treating cancer in a subject in need thereof comprising administering a therapeutically effective amount of a platinum drug that is cisplatin to the subject in need thereof; and administering an effective dose of a selective Organic Cation Transporter 2 (OCT2) inhibitor to the subject in need thereof.

Embodiment III-3

In one embodiment, the present disclosure provides methods for increasing patient compliance for treating cancer in a subject in need thereof comprising administering a therapeutically effective amount of a platinum drug that is cisplatin to the subject in need thereof; and administering a selective Organic Cation Transporter 2 (OCT2) inhibitor to the subject in need thereof in a dose effective to reduce platinum drug-induced toxicity in said subject in need thereof, whereby said subject completes treatment with a cumulative dose of at least 100 mg/m$^2$.

Embodiment III-4

The method of Embodiment III-2 or 3, wherein the therapeutically effective amount of platinum drug administered is known to cause platinum drug-induced neurotoxicity in subjects.

Embodiment III-5

The method of Embodiment III-4, wherein the neurotoxicity is peripheral neurotoxicity.

Embodiment III-6

The method of Embodiment III-4, wherein the neurotoxicity is damage to a sensory neuron.

Embodiment III-7

The method of Embodiment III-4, wherein the neurotoxicity is damage to a motor neuron.

Embodiment III-7a

The method of any of Embodiments III-1-7, wherein the neurotoxicity is chronic neurotoxicity.

Embodiment III-7b

The method of any of Embodiments III-1-7, wherein the neurotoxicity is acute syndrome transient neurotoxicity.

Embodiment III-7c

The method of any of Embodiments II-1-7, wherein the neurotoxicity occurs 1 hour to seven days after first treatment.

Embodiment III-7d

The method of any of Embodiments III-1-7, wherein the neurotoxicity occurs after a subject completes treatment with a cumulative dose of at least 500 mg/m$^2$

Embodiment III-8

The method of Embodiment III-4, wherein the neurotoxicity is damage to dorsal root ganglia (DRG).

Embodiment III-9

The method of any of Embodiments III-1-8, wherein the dose of selective OCT2 inhibitor is effective to minimize platinum drug-induced neurotoxicity in said subject in need thereof.

Embodiment III-10

The method of any of Embodiments III-1-8, wherein the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in patients treated with a cumulative dose of at least 100 mg/m$^2$.

Embodiment III-11

The method of any of Embodiments III-1-8, wherein the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in patients treated with a platinum drug dose intensity of at least 30 mg/week/m$^2$.

Embodiment III-12

The method of any of Embodiments III-1-8, wherein the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in patients treated with a platinum drug dose of at least 80 mg/m$^2$.

Embodiment III-13

The method of any of Embodiments II-1-12, further comprising assessing platinum drug-induced neurotoxicity in a subject after administration of the platinum drug.

Embodiment III-14

The method of Embodiment III-13, wherein the neurotoxicity is assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20).

Embodiment III-15

The method of Embodiment III-13, wherein the neurotoxicity is assessed by a measurement selected from sensory nerve action potential, sensory nerve conduction velocity, cold pain threshold, heat pain threshold, mechanical pain threshold, cold detection threshold, warm detection threshold, mechanical detection threshold, vibration perception threshold, current perception threshold, pinprick sensibility, deep tendon reflexes and grip strength.

Embodiment III-16

The method of Embodiment III-13, wherein the neurotoxicity is assessed by measuring sensory nerve action potential in one of radial, dorsal sural, sural and ulnar nerves.

Embodiment III-17

The method of any of Embodiments III-13-16, further compromising establishing the subject's baseline prior to administration of the platinum drug.

Embodiment III-18

The method of any of Embodiments III-13-16, wherein the platinum drug-induced neurotoxicity is assessed near the midpoint of treatment.

Embodiment III-19

The method of any of Embodiments III-13-16, wherein the platinum drug-induced neurotoxicity is assessed after treatment with a cumulative dose of 200 mg/m$^2$.

Embodiment III-20

The method of Embodiment III-1, wherein toxicity is nephrotoxicity.

Embodiment III-21

The method of any of Embodiments III-1-8, wherein the selective OCT2 inhibitor is selected from the group consisting of buflomedil, a buflomedil salt, dolutegravir, and a dolutegravir salt.

Embodiment III-22

The method of Embodiment III-21, wherein the selective OCT2 inhibitor is buflomedil, or a buflomedil salt.

Embodiment III-23

The method of Embodiment III-22, wherein the dose of buflomedil or a buflomedil salt administered in a subject is adjusted based on at least one of the factors of the said subject, body weight, body surface area, height, age, gender, alcohol use, tobacco use, life style, renal function, liver function, genetic polymorphism and co-medications.

Embodiment III-24

The method of Embodiments III-22 or 23, wherein the dose of buflomedil or a buflomedil salt results in its plasma level during the period of platinum administration at least 0.43 mg/l, 0.86 mg/l, 1.29 mg/l, 1.72 mg/l or 2.15 mg/l.

Embodiment III-25

The method of any of Embodiments III-22-24, wherein the dose of buflomedil or a buflomedil salt is at least 100 mg, 200 mg, 300 mg, 400 mg, 500 mg or 600 mg.

Embodiment III-26

The method of any of Embodiments III-22-25, wherein the dose of buflomedil or a buflomedil salt is at least 1 mg/kg, 2 mg/kg, 3 mg/kg, 4 mg/kg, 5 mg/kg, 6 mg/kg, 8 mg/kg or 10 mg/kg.

Embodiment III-27

The method of Embodiment III-21, wherein the selective OCT2 inhibitor is dolutegravir or a dolutegravir salt.

Embodiment III-28

The method of Embodiment III-27, wherein the dose of dolutegravir or a dolutegravir salt results in its plasma level during the period of platinum administration at least 1.4 mg/l, 2.8 mg/l, 4.2 mg/l, 5.6 mg/l or 7.0 mg/l.

Embodiment III-29

The method of Embodiment III-27 or 28, wherein the dose of dolutegravir or a dolutegravir salt is at least 50 mg, 100 mg, 150 mg, 200 mg, 250 mg, 300 mg or 400 mg.

Embodiment III-30

The method of any of Embodiments III-27-29, wherein the dose of dolutegravir or a dolutegravir salt is at least 1 mg/kg, 2 mg/kg, 3 mg/kg, 4 mg/kg, 5 mg/kg or 6 mg/kg.

Embodiment III-31

The method of any of Embodiments III-1-30, wherein the selective OCT2 inhibitor does not reduce the efficacy of the platinum drug.

Embodiment III-32

The method of any of Embodiments III-1-31, wherein the selective OCT2 inhibitor is administered at a dose that results in its plasma concentration during the period of platinum drug administration less than its maximum tolerated plasma concentration (MTC) and greater than 1×, 2×, 3×, 4× of its IC$_{50}$ value for OCT2-mediated transport of 20 µM oxaliplatin assessed in human serum or an assay buffer containing 4% bovine serum albumin.

Embodiment III-33

The method of any of Embodiments III-1-19, 31 or 32, wherein the selective OCT2 inhibitor has an IC$_{50}$ for OCT2- mediated transport of 20 µM oxaliplatin in human serum or an assay solution containing 4% bovine serum albumin, of less than or equal to 5 µM.

Embodiment III-34

The method of Embodiment III-33, wherein the selective OCT2 inhibitor has an $IC_{50}$ for OCT2-mediated transport of 20 µM oxaliplatin in human serum or an assay solution containing 4% bovine serum albumin that is at least 10-fold less than the selective OCT2 inhibitor $IC_{50}$ for 20 µM oxaliplatin transport in human serum or an assay solution containing 4% bovine serum albumin mediated by one or more of OCT1-. OCT-3, or MATE-1.

Embodiment III-35

The method of any of Embodiments III-1-34, wherein the subject in need thereof has a cancer expressing at least one of Organic Cation Transporter 1 (OCT1) or Organic Cation Transporter 3 (OCT3).

Embodiment III-36

The method of any of Embodiments III-1-26 or 31-35, wherein the selective OCT2 inhibitor is buflomedil, or a buflomedil salt.

Embodiment III-37

The method of any of Embodiments III-1-20 or 27-35, wherein the selective OCT2 inhibitor is dolutegravir, or a dolutegravir salt.

Embodiment III-38

The method of any of Embodiments III-1-37, wherein the platinum drug and the selective OCT2 inhibitor are administered at the same time.

Embodiment III-39

The method of any of Embodiments III-1-37, wherein the selective OCT2 inhibitor is administered before the platinum drug.

Embodiment III-40

The method of any of Embodiments III-1-37, wherein the selective OCT2 inhibitor is administered after the platinum drug.

Embodiment III-41

The method of any of Embodiments III-1-40, wherein the amount of platinum drug administered to the subject during one treatment session is greater than what is administered under standard clinical practices.

Embodiment III-42

The method of any of Embodiments III-1-41, wherein the cumulative amount of platinum drug administered to the subject in need thereof over the entire course of treatment is greater than what is administered under standard clinical practices.

Embodiment III-43

The method of any of Embodiments III-1-42, wherein the platinum drug is administered at a greater frequency than under standard clinical practices.

Embodiment III-44

The method of any of Embodiments III-1 or 3-43, wherein the neurotoxicity is peripheral neuropathy.

Embodiment III-45

The method of Embodiment III-44, wherein the peripheral neuropathy is Grade 3 or Grade 4 peripheral neuropathy.

Embodiment III-46

The method of any of Embodiments III-1-45, wherein the subject in need thereof is a human or a non-human animal.

Embodiment III-47

The method of any of Embodiments III-1-46, wherein the selective OCT2 inhibitor is administered enterally, intravenously, intramuscularly, intraperitoneally, orally, or parenterally.

Embodiment III-48

The method of any of Embodiments III-1-47, wherein the selective OCT2 inhibitor is administered via more than one route of administration.

Embodiment III-49

The method of any of Embodiments HIII-1-47, wherein the platinum drug and the selective OCT2 inhibitor are administered via the same route of administration.

Embodiment III-50

The method of any of Embodiments III-1-47, wherein the selective OCT2 inhibitor is administered via intravenous infusion.

Embodiment III-51

The method of any of Embodiments III-1-47, wherein the selective OCT2 inhibitor is administrated via intravenous injection and intravenous infusion.

Embodiment III-52

The method of Embodiments III-50 or 51, wherein intravenous infusion is over a period of time at least 1 hour.

Embodiment III-53

The method of Embodiments III-50 or 51, wherein the rate of intravenous infusion is constant.

Embodiment III-54

The method of Embodiments III-50 or 51, wherein the rate of intravenous infusion is variable.

Embodiment III-55

The method of any of Embodiments III-1-54, wherein the cancer expresses OCT1.

Embodiment III-56

The method of any of Embodiments III-1-55, wherein the cancer expresses OCT3.

Embodiment III-57

The method of any of Embodiments III-1-56, wherein the cancer expresses OCT1 and OCT3.

Embodiment III-58

The method of any one of Embodiments III-1-57, wherein the cancer is selected from the group consisting of adenocarcinoma of the pancreas, ampullary and periampullary carcinoma, adenocarcinoma of the anus, appendiceal carcinoma, hepatocellular carcinoma, carcinoma of the colon or rectum, epithelial ovarian carcinoma, fallopian tube carcinoma, primary peritoneal cancer, esophageal or esophagogastric junction carcinoma, gastric carcinoma, small bowel carcinoma, testicular cancer, cholangiocarcinoma, pancreatic adenocarcinoma, carcinoma of unknown primary origin, chronic lymphocytic leukemia/small lymphocytic lymphoma, non-Hodgkin's lymphoma, adult T-cell leukemia/lymphoma, AIDS-related B-cell lymphoma, diffuse large B-cell lymphoma, follicular lymphoma, gastric MALT lymphoma, nongastric MALT lymphoma, mantle cell lymphoma, mycosis fungoides/Sezary syndrome, splenic marginal zone lymphoma, peripheral T cell lymphoma, primary cutaneous B-cell lymphoma, primary cutaneous anaplastic large cell lymphoma (ALCL), lung cancer, liver cancer, head and neck cancer, prostate cancer, smooth muscle cancer and gallbladder cancer.

Embodiment III-59

The method of Embodiment III-58, wherein the cancer is ovarian cancer.

Embodiment III-60

The method of Embodiment II-58, wherein the cancer is head and neck cancer.

Embodiment III-61

The method of Embodiment III-58, wherein the cancer is prostate cancer.

Embodiment III-62

The method of Embodiment III-58, wherein the cancer is lymphoma.

Embodiment III-63

The method of Embodiment III-58, wherein the cancer is smooth muscle cancer.

Embodiment III-64

The method of Embodiment III-58, wherein the cancer is carcinoma of the colon or rectum.

Embodiment III-65

The method of Embodiment III-58, wherein the cancer is liver cancer.

Embodiment III-66

The method of Embodiment III-58, wherein the cancer is lung cancer.

Embodiment III-67

The method of any of Embodiments III-1-66, further comprising administering to the subject in need thereof a therapeutically effective amount of one or more additional cancer chemotherapeutic agents in addition to the platinum drug.

Embodiment III-68

The method of Embodiment III-67, wherein the one or more additional chemotherapeutic agents is selected from the group consisting of 5-fluorouracil, bevacizumab, capecetabine, gemcitabine, irinotecan, and leucovorin.

Embodiment III-69

A pharmaceutical composition formulated for intravenous administration comprising
a platinum drug that is cisplatin,
a selective OCT2 inhibitor selected from the group consisting of buflomedil, a buflomedil salt, dolutegravir, and a dolutegravir salt, and
a pharmaceutically acceptable carrier.

Embodiment III-70

The pharmaceutical composition of Embodiment III-69, wherein the selective OCT2 inhibitor is buflomedil, or a buflomedil salt.

Embodiment III-71

The pharmaceutical composition of Embodiment III-69, wherein the OCT2 inhibitor is dolutegravir, or a dolutegravir salt.

Embodiment III-72

The pharmaceutical composition of any of Embodiments III-69-71, wherein the amount of the platinum drug is greater than what is present in a standard pharmaceutical composition comprising the platinum drug.

Embodiment III-73

The pharmaceutical composition of any of Embodiments III-69-72, further comprising a therapeutically effective amount of one or more additional cancer chemotherapeutic agents in addition to the platinum drug.

Embodiment III-74

The pharmaceutical composition of Embodiment III-73, wherein the one or more additional chemotherapeutic agents is selected from the group consisting of 5-fluorouracil, bevacizumab, capecetabine, gemcitabine, irinotecan, and leucovorin.

Embodiment III-75

A kit comprising a therapeutically effective amount of a platinum drug that is cisplatin; a selective OCT2 inhibitor and instructions for use.

Embodiment III-76

The kit of Embodiment III-75, further comprising instructions for determining a desirable dose of the selective OCT2 inhibitor for a subject in need.

Embodiment III-77

The kit of Embodiment III-76, wherein the dose is determined based on at least one factor of the said subject selected from body weight, body surface area, height, age, gender, alcohol use, tobacco use, life style, renal function, liver function, genetic polymorphism and co-medications.

Embodiment III-78

The kit of Embodiment III-76, wherein the dose is determined by monitoring plasma level of the OCT2 inhibitor in the said subject.

Embodiment III-79

The kit of any one of Embodiments III-75-78, wherein the selective OCT2 inhibitor is buflomedil or a buflomedil salt.

Embodiment III-80

The kit of Embodiment III-79, wherein buflomedil or a buflomedil salt is present in an amount greater than 300 mg, 450 mg, 600 mg, 800 mg or 1000 mg.

Embodiment III-81

The kit of any of Embodiments III-75-78, wherein the selective OCT2 inhibitor is dolutegravir or a dolutegravir salt.

Embodiment III-82

The kit of Embodiment III-81, wherein dolutegravir or a dolutegravir salt is present in an amount greater than 50 mg, 75 mg, 100 mg, 150 mg, 200 mg or 300 mg.

Embodiment II-83

The kit of any of Embodiments II-75-82, wherein the instructions state that the kit is intended for use in reducing platinum drug-induced neurotoxicity.

Embodiment III-84

The kit of any of Embodiments-75-83, wherein the instructions state that the kit is intended for use in treating cancer.

Embodiment III-85

The kit of any of Embodiments III-75-84, further comprising a therapeutically effective amount of one or more additional cancer chemotherapeutic agents in addition to the platinum drug.

Embodiment II-86

The kit of Embodiment III-85, wherein the one or more additional chemotherapeutic agents is selected from the group consisting of 5-fluorouracil, bevacizumab, capecetabine, gemcitabine, irinotecan, and leucovorin.

Exemplar Embodiments of Method with Determining Step

Embodiment IV-1

In one embodiment, the present disclosure provides a method for reducing platinum drug-induced toxicity in a subject in need thereof comprising determining an effective dose to achieve a plasma level of a selective Organic Cation Transporter 2 (OCT2) inhibitor that is buflomedil or a buflomedil salt in the subject in need thereof, wherein the plasma level is two to five times $IC_{50}$ of the selective Organic Cation Transporter 2 (OCT2) inhibitor that is buflomedil or a buflomedil salt:
    administering a platinum drug selected from the group consisting of oxaliplatin and cisplatin to the subject in need thereof; and
    administering an effective dose of a selective Organic Cation Transporter 2 (OCT2) inhibitor that is buflomedil or a buflomedil salt to the subject in need thereof,
    wherein the toxicity is nephrotoxicity, ototoxicity or peripheral neuropathy, and
    wherein the subject in need thereof has a cancer.

Embodiment IV-2

In one embodiment, the present disclosure provides a method for treating cancer in a subject in need thereof comprising
    determining an effective dose to achieve a plasma level of a selective Organic Cation Transporter 2 (OCT2) inhibitor that is buflomedil or a buflomedil salt in the subject in need thereof, wherein the plasma level is two to five times $IC_{50}$ of the selective Organic Cation Transporter 2 (OCT2) inhibitor that is buflomedil or a buflomedil salt;
    administering a therapeutically effective amount of a platinum drug selected from the group consisting of oxaliplatin and cisplatin to the subject in need thereof; and
    administering an effective dose of a selective Organic Cation Transporter 2 (OCT2) inhibitor that is buflomedil or a buflomedil salt to the subject in need thereof.

Embodiment IV-3

In one embodiment, the present disclosure provides a method for increasing patient compliance for treating cancer in a subject in need thereof comprising determining an effective dose to achieve a plasma level of a selective Organic Cation Transporter 2 (OCT2) inhibitor that is buflomedil or a buflomedil salt in the subject in need thereof, wherein the plasma level is two to five times $IC_{50}$ of the selective Organic Cation Transporter 2 (OCT2) inhibitor that is buflomedil or a buflomedil salt;

administering a therapeutically effective amount of a platinum drug selected from the group consisting of oxaliplatin and cisplatin to the subject in need thereof; and administering a selective Organic Cation Transporter 2 (OCT2) inhibitor that is buflomedil or a buflomedil salt to the subject in need thereof in a dose effective to reduce platinum drug-induced toxicity in said subject in need thereof, whereby said subject completes treatment with a cumulative dose of at least 100 mg/m².

Embodiment IV-4

The method of any one of Embodiments IV-1-3, wherein the step of determining an effective dose to achieve a plasma level of a selective Organic Cation Transporter 2 (OCT2) inhibitor is performed by administering a pre-dose of the selective Organic Cation Transporter 2 (OCT2) inhibitor.

Embodiment IV-5

The method of any one of Embodiments IV-1-3, wherein the step of determining an effective dose to achieve a plasma level of a selective Organic Cation Transporter 2 (OCT2) inhibitor is determined by a reference data chart based on subject characteristics.

Embodiment IV-6

The method of any one of Embodiments IV-2 or 3-5, wherein the therapeutically effective amount of platinum drug administered is known to cause platinum drug-induced neurotoxicity in subjects.

Embodiment IV-7

The method of Embodiment IV-6, wherein the neurotoxicity is peripheral neurotoxicity.

Embodiment IV-8

The method of Embodiment IV-6, wherein the neurotoxicity is damage to a sensory neuron.

Embodiment IV-9

The method of Embodiment IV-6, wherein the neurotoxicity is damage to a motor neuron.

Embodiment IV-9a

The method of any of Embodiments IV-1-9, wherein the neurotoxicity is chronic neurotoxicity.

Embodiment IV-9b

The method of any of Embodiments IV-1-9, wherein the neurotoxicity is acute syndrome transient neurotoxicity.

Embodiment IV-9c

The method of any of Embodiments IV-1-9, wherein the neurotoxicity occurs 1 hour to seven days after first treatment.

Embodiment IV-9d

The method of any of Embodiments II-1-9, wherein the neurotoxicity occurs after a subject completes treatment with a cumulative dose of at least 500 mg/m²

Embodiment IV-10

The method of Embodiment IV-6, wherein the neurotoxicity is damage to dorsal root ganglia (DRG).

Embodiment IV-11

The method of any of Embodiments IV-1-10, wherein the dose of selective OCT2 inhibitor is effective to minimize platinum drug-induced neurotoxicity in said subject in need thereof.

Embodiment IV-12

The method of any of Embodiments IV-1-10, wherein the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale. Total Neuropathy Score clinical version (TNSc) and European Organization for Research and Treatment of Cancer CIPN specific self-report questionnaire (EORTC QOL-CIPN20), in patients treated with a cumulative dose of at least 100 mg/m².

Embodiment IV-13

The method of any of Embodiments IV-1-10, wherein the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in patients treated with a platinum drug dose intensity of at least 30 mg/week/m².

Embodiment IV-14

The method of any of Embodiments IV-1-10, wherein the dose of selective OCT2 inhibitor is effective to prevent platinum drug-induced neurotoxicity of Grade 3 or higher, as assessed by a method selected from National Cancer Institute-Common Toxicity Criteria (NCI-CTC) sensory scale, National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20), in patients treated with a platinum drug dose of at least 80 mg/m².

Embodiment IV-15

The method of any of Embodiments IV-1-14, further comprising assessing platinum drug-induced neurotoxicity in a subject after administration of the platinum drug.

Embodiment IV-16

The method of Embodiment IV-15, wherein the neurotoxicity is assessed by a method selected from National Cancer Institute-Common Toxicity Criteria (NCI-CTC) sensory scale. National Cancer Institute-Common Toxicity Criteria (NCI-CTC) motor scale, Total Neuropathy Score clinical version (TNSc) and European Organization for Research and Treatment of Cancer CIPN specific self-report questionnaire (EORTC QOL-CIPN20).

Embodiment IV-17

The method of Embodiment IV-15, wherein the neurotoxicity is assessed by a measurement selected from sensory nerve action potential, sensory nerve conduction velocity, cold pain threshold, heat pain threshold, mechanical pain threshold, cold detection threshold, warm detection threshold, mechanical detection threshold, vibration perception threshold, current perception threshold, pinprick sensibility, deep tendon reflexes and grip strength.

Embodiment IV-18

The method of Embodiment IV-15, wherein the neurotoxicity is assessed by measuring sensory nerve action potential in one of radial, dorsal sural, sural and ulnar nerves.

Embodiment IV-19

The method of any of Embodiments IV-15-18, further compromising establishing the subject's baseline prior to administration of the platinum drug.

Embodiment IV-20

The method of any of Embodiments IV-15-18, wherein the platinum drug-induced neurotoxicity is assessed near the midpoint of treatment.

Embodiment IV-21

The method of any of Embodiments IV-15-18, wherein the platinum drug-induced neurotoxicity is assessed after treatment with a cumulative dose of 200 mg/m$^2$.

Embodiment IV-22

The method of Embodiment IV-1, wherein toxicity is nephrotoxicity.

Embodiment IV-23

The method of any of Embodiments IV-1-22, wherein the dose of buflomedil or a buflomedil salt administered in a subject is adjusted based on at least one of the factors of the said subject, body weight, body surface area, height, age, gender, alcohol use, tobacco use, life style, renal function, liver function, genetic polymorphism and co-medications.

Embodiment IV-24

The method of any of Embodiments IV-1-23, wherein the dose of buflomedil or a buflomedil salt results in its plasma level during the period of platinum administration at least 0.43 mg/l, 0.86 mg/l, 1.29 mg/l, 1.72 mg/l or 2.15 mg/l.

Embodiment IV-25

The method of any of Embodiments IV-1-24, wherein the dose of buflomedil or a buflomedil salt is at least 100 mg, 200 mg, 300 mg, 400 mg, 500 mg or 600 mg.

Embodiment IV-26

The method of any of Embodiments IV-1-25, wherein the dose of buflomedil or a buflomedil salt is at least 1 mg/kg, 2 mg/kg, 3 mg/kg, 4 mg/kg, 5 mg/kg, 6 mg/kg, 8 mg/kg or 10 mg/kg.

Embodiment IV-27

The method of any of Embodiments IV-1-26, wherein the selective OCT2 inhibitor does not reduce the efficacy of the platinum drug.

Embodiment IV-28

The method of any of Embodiments IV-1-27, wherein the selective OCT2 inhibitor is administered at a dose that results in its plasma concentration during the period of platinum drug administration less than its maximum tolerated plasma concentration (MTC) and greater than 1×, 2×, 3×, 4× of its IC$_{50}$ value for OCT2-mediated transport of 20 μM oxaliplatin assessed in human serum or an assay buffer containing 4% bovine serum albumin.

Embodiment IV-29

The method of any of Embodiments IV-1-28, wherein the selective OCT2 inhibitor has an IC$_{50}$ for OCT2-mediated transport of 201 μM oxaliplatin in human serum or an assay solution containing 4% bovine serum albumin, of less than or equal to 5 μM.

Embodiment IV-30

The method of Embodiment IV-29, wherein the selective OCT2 inhibitor has an IC$_{50}$ for OCT2-mediated transport of 20 μM oxaliplatin in human serum or an assay solution containing 4% bovine serum albumin that is at least 10-fold less than the selective OCT2 inhibitor IC$_{50}$ for 20 μM oxaliplatin transport in human serum or an assay solution containing 4% bovine serum albumin mediated by one or more of OCT1-, OCT-3, or MATE-1.

Embodiment IV-31

The method of any of Embodiments IV-1-30, wherein the subject in need thereof has a cancer expressing at least one of Organic Cation Transporter 1 (OCT1) or Organic Cation Transporter 3 (OCT3).

Embodiment IV-32

The method of any of Embodiments IV-1-31, wherein the platinum drug and the selective OCT2 inhibitor are administered at the same time.

Embodiment IV-33

The method of any of Embodiments IV-1-31, wherein the selective OCT2 inhibitor is administered before the platinum drug.

Embodiment IV-34

The method of any of Embodiments IV-1-31, wherein the selective OCT2 inhibitor is administered after the platinum drug.

Embodiment IV-35

The method of any of Embodiments IV-1-34, wherein the amount of platinum drug administered to the subject during one treatment session is greater than what is administered under standard clinical practices.

Embodiment IV-36

The method of any of Embodiments IV-1-35, wherein the cumulative amount of platinum drug administered to the subject in need thereof over the entire course of treatment is greater than what is administered under standard clinical practices.

Embodiment IV-37

The method of any of Embodiments IV-1-36, wherein the platinum drug is administered at a greater frequency than under standard clinical practices.

Embodiment IV-38

The method of any of Embodiments IV-1 or 3-37, wherein the neurotoxicity is peripheral neuropathy.

Embodiment IV-39

The method of Embodiment IV-38, wherein the peripheral neuropathy is Grade 3 or Grade 4 peripheral neuropathy.

Embodiment IV-40

The method of any of Embodiments IV-1-39, wherein the subject in need thereof is a human or a non-human animal.

Embodiment IV-41

The method of any of Embodiments IV-1-40, wherein the selective OCT2 inhibitor is administered enterally, intravenously, intramuscularly, intraperitoneally, orally, or parenterally.

Embodiment IV-42

The method of any of Embodiments IV-1-41, wherein the selective OCT2 inhibitor is administered via more than one route of administration.

Embodiment IV-43

The method of any of Embodiments IV-1-42, wherein the platinum drug and the selective OCT2 inhibitor are administered via the same route of administration.

Embodiment IV-44

The method of any of Embodiments IV-1-43, wherein the selective OCT2 inhibitor is administered via intravenous infusion.

Embodiment IV-45

The method of any of Embodiments IV-1-43, wherein the selective OCT2 inhibitor is administrated via intravenous injection and intravenous infusion.

Embodiment IV-46

The method of Embodiment IV-44 or 45, wherein intravenous infusion is over a period of time at least 1 hour.

Embodiment IV-47

The method of Embodiment IV-44 or 45, wherein the rate of intravenous infusion is constant.

Embodiment IV-48

The method of Embodiments IV-44 or 45, wherein the rate of intravenous infusion is variable.

Embodiment IV-49

The method of any of Embodiments IV-1-48, wherein the cancer expresses OCT1.

Embodiment IV-50

The method of any of Embodiments IV-1-49, wherein the cancer expresses OCT3.

Embodiment IV-51

The method of any of Embodiments IV-1-50, wherein the cancer expresses OCT1 and OCT3.

Embodiment IV-52

The method of any one of Embodiments IV-1-51, wherein the cancer is selected from the group consisting of adenocarcinoma of the pancreas, ampullary and periampullary carcinoma, adenocarcinoma of the anus, appendiceal carcinoma, hepatocellular carcinoma, carcinoma of the colon or rectum, epithelial ovarian carcinoma, fallopian tube carcinoma, primary peritoneal cancer, esophageal or esophagogastric junction carcinoma, gastric carcinoma, small bowel carcinoma, testicular cancer, cholangiocarcinoma, pancreatic adenocarcinoma, carcinoma of unknown primary origin, chronic lymphocytic leukemia/small lymphocytic lymphoma, non-Hodgkin's lymphoma, adult T-cell leukemia/lymphoma. AIDS-related B-cell lymphoma, diffuse large B-cell lymphoma, follicular lymphoma, gastric MALT lymphoma, nongastric MALT lymphoma, mantle cell lymphoma, mycosis fungoides/Sezary syndrome, splenic marginal zone lymphoma, peripheral T cell lymphoma, primary cutaneous B-cell lymphoma, primary cutaneous anaplastic large cell lymphoma (ALCL), lung cancer, liver cancer, head and neck cancer, prostate cancer, smooth muscle cancer and gallbladder cancer.

Embodiment IV-53

The method of Embodiment IV-52, wherein the cancer is ovarian cancer.

Embodiment IV-54

The method of Embodiment IV-52, wherein the cancer is head and neck cancer.

Embodiment IV-55

The method of Embodiment IV-52, wherein the cancer is prostate cancer.

Embodiment IV-56

The method of Embodiment IV-52, wherein the cancer is lymphoma.

Embodiment IV-57

The method of Embodiment IV-52, wherein the cancer is smooth muscle cancer.

Embodiment IV-58

The method of Embodiment IV-52, wherein the cancer is carcinoma of the colon or rectum.

Embodiment IV-59

The method of Embodiment IV-52, wherein the cancer is liver cancer.

Embodiment IV-60

The method of Embodiment IV-52, wherein the cancer is lung cancer.

Embodiment IV-61

The method of any of Embodiments IV-1-60, further comprising administering to the subject in need thereof a therapeutically effective amount of one or more additional cancer chemotherapeutic agents in addition to the platinum drug.

Embodiment IV-62

The method of Embodiment IV-61, wherein the one or more additional chemotherapeutic agents is selected from the group consisting of 5-fluorouracil, bevacizumab, capecetabine, gemcitabine, irinotecan, and leucovorin.

Embodiment IV-63

A pharmaceutical composition formulated for intravenous administration comprising
a platinum drug that is oxaliplatin or cisplatin,
a selective OCT2 inhibitor selected from the group consisting of buflomedil and a buflomedil salt, and
a pharmaceutically acceptable carrier.

Embodiment IV-64

The pharmaceutical composition of Embodiment IV-63, wherein the amount of the platinum drug is greater than what is present in a standard pharmaceutical composition comprising the platinum drug.

Embodiment IV-65

The pharmaceutical composition of Embodiment IV-63 or 64, further comprising a therapeutically effective amount of one or more additional cancer chemotherapeutic agents in addition to the platinum drug.

Embodiment IV-66

The pharmaceutical composition of Embodiment IV-65, wherein the one or more additional chemotherapeutic agents is selected from the group consisting of 5-fluorouracil, bevacizumabh, capecetabine, gemcitabine, irinotecan, and leucovorin.

Embodiment IV-67

A kit comprising a therapeutically effective amount of a platinum drug that is oxaliplatin or cisplatin: a selective OCT2 inhibitor and instructions for use.

Embodiment IV-68

The kit of Embodiment IV-67, further comprising instructions for determining a desirable dose of the selective OCT2 inhibitor for a subject in need.

Embodiment IV-69

The kit of Embodiment IV-67 or 68, wherein the dose is determined based on at least one factor of the said subject selected from body weight, body surface area, height, age, gender, alcohol use, tobacco use, life style, renal function, liver function, genetic polymorphism and co-medications.

Embodiment IV-70

The kit of any of Embodiments IV-67-69, wherein the dose is determined by monitoring plasma level of the OCT2 inhibitor in the said subject.

Embodiment IV-71

The kit of any of Embodiments IV-67-70, wherein buflomedil or a buflomedil salt is present in an amount greater than 300 mg, 450 mg, 600 mg, 800 mg or 1000 mg.

Embodiment IV-72

The kit of any of Embodiments IV-67-71, wherein the instructions state that the kit is intended for use in reducing platinum drug-induced neurotoxicity.

Embodiment IV-73

The kit of Embodiment IV-67-72, wherein the instructions state that the kit is intended for use in treating cancer.

Embodiment IV-74

The kit of any of Embodiments IV-67-73 further comprising a therapeutically effective amount of one or more additional cancer chemotherapeutic agents in addition to the platinum drug.

Embodiment IV-75

The kit of Embodiment IV-74, wherein the one or more additional chemotherapeutic agents is selected from the group consisting of 5-fluorouracil, bevacizumab, capecitabine, gemcitabine, irinotecan, and leucovorin.

Exemplary Embodiments-Selective OCT2 Inhibitor for Use in Treatment

Embodiment V-1

In one embodiment, the present disclosure provides a selective OCT2 inhibitor for use in the treatment of cancer in a subject in need thereof, wherein the OCT2 inhibitor is for use in combination with a platinum drug that is oxaliplatin.

Embodiment V-2

The selective OCT2 inhibitor according to Embodiment V-1, wherein the OCT2 inhibitor is for administration at a dose capable of reducing platinum drug-induced toxicity.

Embodiment V-3

In one embodiment, the present disclosure provides a selective OCT2 inhibitor for use in the treatment of cancer in a subject in need thereof, wherein the OCT2 inhibitor is for use in combination with a platinum drug that is cisplatin.

Embodiment V-4

The selective OCT2 inhibitor according to Embodiment V-3, wherein the OCT2 inhibitor is for administration at a dose capable of reducing platinum drug-induced toxicity.

Embodiment V-5

In one embodiment, the present disclosure provides a selective OCT2 inhibitor that is buflomedil or a buflomedil salt for use in the treatment of cancer in a subject in need thereof, wherein the OCT2 inhibitor is for use in combination with a platinum drug that is oxaliplatin or cisplatin.

Embodiment V-6

The selective OCT2 inhibitor according to Embodiment V-5, wherein the OCT2 inhibitor is for administration at a dose capable of reducing platinum drug-induced toxicity.

Embodiment V-7

In one embodiment, the present disclosure provides a selective OCT2 inhibitor for use in reducing platinum drug toxicity in a subject in need thereof, wherein the OCT2 inhibitor is for use in combination with a platinum drug that is oxaliplatin.

Embodiment V-8

In one embodiment, the present disclosure provides a selective OCT2 inhibitor for use in reducing platinum drug toxicity in a subject in need thereof, wherein the OCT2 inhibitor is for use in combination with a platinum drug that is cisplatin.

Embodiment V-9

In one embodiment, the present disclosure provides a selective OCT2 inhibitor that is buflomedil or a buflomedil salt for use in reducing platinum drug toxicity in a subject in need thereof, wherein the OCT2 inhibitor is for use in combination with a platinum drug that is oxaliplatin or cisplatin.

Embodiment V-10

In one embodiment, the present disclosure provides a selective OCT2 inhibitor for use in increasing patient compliance in the treatment of cancer in a subject in need thereof, wherein the OCT2 inhibitor is for use in combination with a platinum drug that is oxaliplatin.

Embodiment V-11

In one embodiment, the present disclosure provides a selective OCT2 inhibitor for use in increasing patient compliance in the treatment of cancer in a subject in need thereof, wherein the OCT2 inhibitor is for use in combination with a platinum drug that is cisplatin.

Embodiment V-12

In one embodiment, the present disclosure provides a selective OCT2 inhibitor that is buflomedil or a buflomedil salt for use in increasing patient compliance in the treatment of cancer in a subject in need thereof, wherein the OCT2 inhibitor is for use in combination with a platinum drug that is oxaliplatin or cisplatin.

Exemplary Embodiments—Use of Selective OCT2 Inhibitor

Embodiment VI-1

In one embodiment, the present disclosure provides use of a selective OCT2 inhibitor in the preparation of a medicament for the treatment of cancer, wherein the medicament is for use in combination with a platinum drug that is oxaliplatin.

Embodiment VI-2

The use according to Embodiment VI-1, wherein the OCT2 inhibitor is for administration at a dose capable of reducing platinum drug-induced toxicity.

Embodiment VI-3

In one embodiment, the present disclosure provides use of a selective OCT2 inhibitor in the preparation of a medicament for the treatment of cancer, wherein the medicament is for use in combination with a platinum drug that is cisplatin.

Embodiment VI-4

The use according to Embodiment VI-3, wherein the OCT2 inhibitor is for administration at a dose capable of reducing platinum drug-induced toxicity.

Embodiment VI-5

In one embodiment, the present disclosure provides use of a selective OCT2 inhibitor that is buflomedil or a buflomedil salt in the preparation of a medicament for the treatment of cancer, wherein the medicament is for use in combination with a platinum drug that is oxaliplatin or cisplatin.

Embodiment VI-6

The use according to Embodiment VI-5, wherein the OCT2 inhibitor is for administration at a dose capable of reducing platinum drug-induced toxicity.

Embodiment VI-7

In one embodiment, the present disclosure provides use of a selective OCT2 inhibitor in the preparation of a medicament for reducing platinum drug toxicity, wherein the medicament is for use in combination with a platinum drug that is oxaliplatin.

Embodiment VI-8

In one embodiment, the present disclosure provides use of a selective OCT2 inhibitor in the preparation of a medicament for reducing platinum drug toxicity, wherein the medicament is for use in combination with a platinum drug that is cisplatin.

Embodiment VI-9

In one embodiment, the present disclosure provides use of a selective OCT2 inhibitor that is buflomedil or a buflomedil salt in the preparation of a medicament for reducing platinum drug toxicity, wherein the medicament is for use in combination with a platinum drug that is oxaliplatin or cisplatin.

Embodiment VI-10

In one embodiment, the present disclosure provides use of a selective OCT2 inhibitor in the preparation of a medicament for increasing patient compliance in the treatment of cancer, wherein the medicament is for use in combination with a platinum drug that is oxaliplatin.

Embodiment VI-11

In one embodiment, the present disclosure provides use of a selective OCT2 inhibitor in the preparation of a medicament for increasing patient compliance in the treatment of cancer, wherein the medicament is for use in combination with a platinum drug that is cisplatin.

Embodiment VI-12

In one embodiment, the present disclosure provides use of a selective OCT2 inhibitor that is buflomedil or a buflomedil salt in the preparation of a medicament for increasing patient compliance in the treatment of cancer, wherein the medicament is for use in combination with a platinum drug that is oxaliplatin or cisplatin.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

It understood that Embodiments V-1 to V-6 and VI-1 to VI-6 can be used in combination with any of Embodiments I-1 to I-105; II-1 to III-85; III-1 to III-86; or IV-1 to IV-75.

EXAMPLES

The following Examples are merely illustrative and are not meant to limit any aspects of the present disclosure in any way.

Example A—Protocol for Evaluation of the Protective Effect of OPV-3003 in a Balb/c Mice Model of Oxaliplatin-Induced Peripheral Neuropathy The protocol in this example is discussed in Renn, C. L.; Carozzi, V. A.; Rhee. P.; Gallop, D.; Dorsey. S. G.; Cavaletti, G., Multimodal assessment of painful peripheral neuropathy induced by chronic oxaliplatin-based chemotherapy in mice. *Mol Pain*, 2011, 7, 29; and Boehmerle, W., et. al., Scientific Reports 4:6370, p 1-9, 2014.

Aim

The aim is to assess the neuroprotective effects of OPV-3003 in Balb/c mice exposed to chronic treatment with Oxaliplatin (OHP).

Animals

Male Balb/c mice, 20 grams on arrival (Envigo, Italy)

Housing and Treatments

The care and husbandry of animals were in conformity with the institutional guidelines in compliance with national (D.L, n. 26/2014) and international laws and policies (EEC Council Directive 86/609. OJ L 358, 1, Dec. 12, 1987; Guide for the Care and Use of Laboratory Animals, U.S. National Research Council, 1996).

Drugs

OXALIPLATIN (OHP), 3.5 mg/kg, intravenously, twice a week for 4 weeks.

OPV-3003 (OPV), 30 mg/kg intraperitoneally 15 minutes before OHP administration, and 15 mg/kg intravenously co-administrated with OHP, twice a week for 4 weeks.

Experimental Protocol

Randomization

GROUP 1: NAÏVE (N=12)
GROUP 2: OPV (N=12)
GROUP 3: OHP (N=12)
GROUP 4: OHP+OPV (n=12)
Total number of animals: 48

Figure 18:
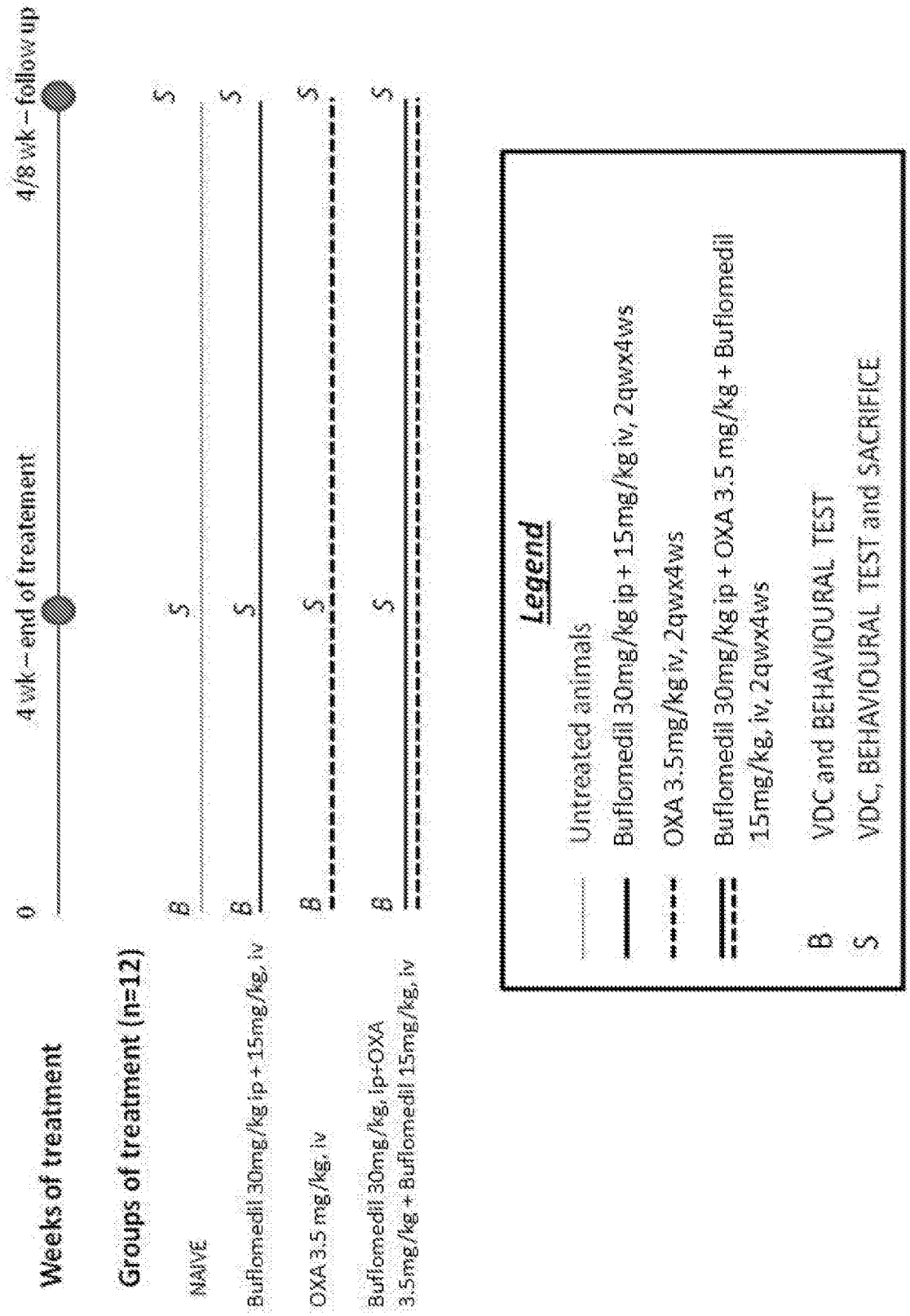
FIG. 18 depicts one study design of evaluating buflomedil's effects on peripheral neuropathy in an established mouse OXAIPN model.

As shown in the flow-chart in FIG. 18:

- at baseline, at the end of treatment and at the end of follow-up period nerve conduction velocity and behavioral test will be performed in all the animals;
- 15 min after the first and the last iv administration the serum sample will be collected for pharmacokinetic analysis;
- 24 h after the first iv administration the cold plate test will be performed;
- at the end of treatment and at the end of follow-up period sciatic nerve, caudal nerve, L4-L5 DRG and skin biopsies will be collected by 4 animals groups;
- the body weight will be measured twice a week; mortality and clinical signs will be monitored every day.

EXPERIMENTAL PLAN

Phase 1: Pharmacological Treatments

OHP and OPV will be administered for 4 weeks. In the group co-administered with OHP and OPV, OPV intraperitoneally will be injected 15 min before the co-administration of OHP and OPV intravenously.

4 animals in each group will be sacrificed four days after the last drug administration.

Phase 2: Follow-Up Period

The animals will be observed for 4 and 8 weeks after the last administration. After 4 weeks of follow-up the analysis of NCV will be performed to decide if sacrifice the animals or observe the animal for other 4 weeks.

Assessments and Timing

Nerve Conduction Velocity

The caudal and digital NCV will be evaluated at baseline, at the end of the pharmacological treatment and after 4 and 8 weeks of follow-up. Sensory/motor and sensory nerve conduction velocities (NCVs) are determined stimulating respectively the caudal and the digital nerves by using an electromyography apparatus (Myto2 ABN Neuro, Firenze, Italy). The caudal NCV will be determined by placing a couple of recording needle electrodes at the base of the tail and a couple of stimulating needle electrodes 3.5 cm distally to the recording points. The digital NCV will be determined by placing the positive recording electrode in the thigh, the negative recording electrode close to ankle bone and the positive and negative stimulating electrodes close to the fourth toe near the digital nerve and under the paw respectively.

The intensity, duration and frequency of stimulation will be set up in order to obtain optimal results.

All the neurophysiological determinations will be performed under standard conditions in a temperature-controlled room (22+/−2° C.).

Behavioral Test

The Plantar Test. Dynamic Plantar Aesthesiometer Test and Cold Plate Test will be used to determine the alterations in pain perception and their changes due to pharmacological treatment. These behavioral tests will be performed at baseline, at the end of pharmacological treatment and after 4 and 8 weeks of follow-up.

The thermal nociceptive threshold of the plantar rear paw will be assessed using a Plantar Test (model 37370; Ugo Basile Biological Instruments, Comerio, Italy). An infra-red light source is located under the glass floor and positioned under the center of the mice's rear paw. Once in position, the heat source was activated and a photo cell automatically shut off the heat source and recorded the time to withdrawal (withdrawal latency). To avoid causing thermal injury in the event that the animal did not withdraw its paw voluntarily, there was an upper limit cutoff of 30 seconds, after which the heat was automatically terminated.

The mechanical nociceptive threshold will be assessed using a Dynamic Aesthesiometer Test (model 37450. Ugo Basile Biological Instruments. Comerio, Italy), which generated a linearly increasing mechanical force.

At each time point, after the acclimatization period, a pointed metallic filament (0.5-mm diameter) will be applied to the plantar surface of the hind paw, which exerted a progressively increasing punctuate pressure, reaching up to 15 g within 15 seconds. The pressure evoking a clear voluntary hind-paw withdrawal response will be recorded automatically and taken as representing the mechanical nociceptive threshold index. The results represent the maximal pressure (expressed in grams) tolerated by the animals. There was an upper limit cutoff of 30 seconds, after which the mechanical stimulus was automatically terminated.

Cold plate test is performed by using an apparatus (35100—Hot/Cold Plate. Ugo Basile instruments) composed by a Plexiglas cylinder and a thermostatic plate, able to reach variable temperatures. The animal is placed on the plate set at +4° C., free to move and walk. Two blinded experimenters simultaneously determine the number of pain signs (ex: jumping, licking, increase anxiety etc. . . . ) in a trial of 5 minutes.

Morphological Analysis of DRG, Sciatic and Caudal Nerves

Left sciatic nerves, caudal nerves. L4-L5 DRG, will be harvested and processed for the morphological analysis. The tissues will be fixed for 3 hours at room temperature in paraformaldehyde 4%/glutaraldehyde 2% (DRG) or in glutaraldehyde 3% (peripheral nerves), post-fixed in $OsO_4$ and epoxy resin embedded. Morphological analysis will be carried out on 1 µm-thick semi-thin sections stained with toluidine blue. At least two tissue blocks for each animal will be sectioned and then examined with a light microscope.

Morphometrical Analysis of Drug and Nerves

Harvested DRG will be used for the morphometric examinations on toluidine blue stained 1-µm-thick semithin sections. DRG will be analyzed with a computer-assisted image analyzer (ImageJ NIH software) and the somatic, nuclear and nucleolar size of DRG sensory neurons measured in randomly selected sections on at least 300 DRG neurons/mouse.

For the morphometric analysis of myelinated fibers, sections will be observed with a photomicroscope (Nikon Eclipse E200; Leica Microsystems GmbH. Wetzlar. Germany) at a magnification of 60× and the morphometric analysis was performed using a QWin automatic image analyzer (Leica Microsystems GmbH). In randomly selected sections collected from all specimens, all myelinated fibers evaluable in the analyzed space will be counted and the external (total) and internal (axonal) diameters of myelinated fibers will be measured, on at least 500 myelinated fibers/nerves. From both axonal and total fiber diameters, the histogram of fiber distribution will be calculated and the ratio between the two diameters, the g-ratio (a well-established measure of degree of myelination [Boehmerle 2014]), will be automatically calculated for each set of individual axon and fiber diameter.

Example 1

The following example relates to the identification of inhibitors of oxaliplatin cellular uptake through the OCT2 transporter.

Oxaliplatin is among the most actively used tumor chemotherapeutics, particularly in colorectal cancer. However, along with its antitumor efficacy, oxaliplatin has been associated with adverse effects including peripheral neuropathy, ototoxicity and nephrotoxicity. Although the exact mechanism of these toxicities remains poorly understood, it has been proposed that OCT2 mediated cellular accumulation may be a cause [1]. A library of prescription drugs against oxaliplatin uptake in OCT2-expressing cells was screened and a number of drugs as inhibitors of OCT2-mediated oxaliplatin cellular uptake were identified.

Materials and Methods

Madin-Darby canine kidney type II (MDCK-II) cells maintained in Dulbecco's Modified Eagle's Medium (DMEM) were seeded at 60±10K per well on 96-well PCF porous membrane insert 24 h prior to transfection. Fully confluent MDCK cell monolayers were transfected with either cDNA plasmids encoding the human transporter to be tested or a GFP control. A transport assay was initiated 48 h later by incubating cells with the probe substrate mixed with varying concentrations of the test drug at 37° C. for 5 or 30 min. The cells were then washed with ice-cold PBS and lysed with 50:50 acetonitrile:H2O. Intracellular content of the substrate was quantified by LC/MS/MS or a MicroBeta radiometric plate reader.

Fifteen drugs were selected and evaluated for their potencies in inhibiting OCT2-mediated oxaliplatin uptake at 5 and 50 μM to obtain estimated $IC_{50}$ values (Table 1).

was also not predictive of a drug's effect on OCT2-mediated oxaliplatin uptake. Applicants screened 70 compounds for OCT2-mediated transport of metformin. For example, miconazole, erlotinib, pentamidine, epinastine, exemestrane, tiotropium and propantheline demonstrated over 10-fold higher potencies in inhibiting OCT2-mediated transport of oxaliplatin than that of metformin (Table 1). For example, leuprolide and miconazole demonstrated about 39-fold differences in metformin transport ($IC_{50}$=3.62 and 141.60 μM), but displayed similar potency in inhibiting oxaliplatin uptake ($IC_{50}$=1.57 and 1.55 μM, respectively).

TABLE 1

Inhibition profile of drugs with respect to OCT2-mediated substrate uptake

| | Oxaliplatin | | | Substrate used ASP+ | | Metformin | | |
|---|---|---|---|---|---|---|---|---|
| Compound | Inhibition % @ 5 μM | Inhibition % @ 50 μM | $IC_{50}$ (μM)** | Inhibition % @ 20 μM* | $IC_{50}$ (μM)** | Inhibition % @ 5 μM | Inhibition % @ 50 μM | $IC_{50}$ (μM)** |
| Buflomedil | 87 | 105 | 0.78 | 104 | <0.1 | | | 5.7 ± 0.8 |
| Chlorphenesin | 14 | 30 | 117.7 | 96 | 0.86 | | | no inhibition at 100 uM |
| Miconazole | 39 | 97 | 1.55 | 91 | 2.0 | | | 141.6 ± 50.2 |
| Leuprolide | 76 | 97 | 1.57 | 88 | 2.8 | 58 | 91 | 3.62 |
| Erlotinib | 93 | 106 | 0.37 | Unkn | | | | 94.4 ± 18.0 |
| Cimetidine | 34 | 83 | 9.7 | 43 | 26.4 | | | 57.6 ± 6.9 |
| Chlorphenesin Carbamate | 28 | 36 | 90.4 | Unkn | | | | no inhibition at 100 uM |
| Ipratropium•Br | 107 | 104 | <0.1 | 96 | 0.81 | 94 | 97 | 0.32 |
| Propantheline•Br | 103 | 102 | <0.1 | 107 | <0.1 | 75 | 96 | 1.7 |
| Tiotropium•Br | 98 | 102 | 0.12 | Unkn | | 77 | 95 | 1.5 |
| Dolutagravir*** | 83 | 97 | 0.20 | Unkn | | | | 0.54 ± 0.09 |
| Exemestane | 96 | 102 | 0.19 | 100 | <0.1 | 66 | 94 | 2.6 |
| Epinastine | 96 | 100 | 0.19 | 97 | 0.58 | 56 | 92 | 3.9 |
| Pentamidine | 99 | 99 | 0.07 | 102 | <0.1 | 67 | 91 | 2.5 |
| Imatinib | 57 | 95 | 3.7 | 103 | <0.1 | | | |

ASP+ was used at 5 μM in Hanks' Balanced Salt Solution (HBSS). Meformin and oxaliplatin were dosed at 10 μM in HBSS for 5 and 30 min, respectively.
ASP+: 4-(4-(Dimethylamino)styryl)-N-methylpyridinium iodide
Unkn: unknown
*Kido Y et al. J Med Chem 2011; 54 (13): 4548-58.
**$IC_{50}$ is estimated based on the inhibition induced by the single concentration (20 or 50 μM) tested, or calculated by nonlinear regression of seven concentrations tested (in bold, ±SEM).
***$IC_{50}$ values were adjusted with measured inhibitor recovery rate.

Many prescription drugs have been screened against human OCT2 expressed in various cell lines using different OCT2 substrates. For example, using ASP+ as an OCT2 substrate, the Giacomini group [2] identified 244 prescription drugs as OCT2 inhibitors, some of which are listed in Table 1. However, the extent to which various inhibitors reduced OCT2-mediated transport of other substrates, such as metformin and oxaliplatin, varies widely, possibly due to the fact that these substrates interact with distinct binding sites of OCT2 [3]. Thus there exists no direct correlation between the inhibition potencies of OCT2-mediated ASP+ uptake and OCT2-mediated uptake of oxaliplatin and metformin. For example, chlorphenesin carbamate and imatinib were shown by the Giacomini group to be a potent inhibitor of OCT2-mediated ASP+ uptake, but their potencies as an inhibitor of OCT2-mediated metformin and oxaliplatin uptake are more than 100 and 30 fold less, respectively. In another example, miconazole exhibited similar potency against OCT2 transport of ASP+ and oxaliplatin, but is approximately 70 fold less potent in inhibiting OCT2-mediated metformin transport (Table 1).

Metformin is a more commonly used probe substrate for OCT2. The inhibition of metformin transport through OCT2

The data indicated that in order to determine the inhibition potency of drugs against OCT2-mediated oxaliplatin transport, oxaliplatin must be used as the OCT2 substrate. Therefore, previously reported studies [2,3] based on in vitro OCT2 assays using substrates other than oxaliplatin cannot be used to determine whether compounds inhibit OCT2-mediated oxaliplatin transport.

Using oxaliplatin as the OCT2 substrate, a number of drugs were identified, including buflomedil, as potent inhibitors ($IC_{50}$<2 μM) of OCT2-mediated oxaliplatin transport. Under in vivo conditions, non-specific binding of inhibitors to serum proteins can affect their apparent inhibition potencies in blood plasma. To further confirm their potencies in blood plasma, which are reflected by $IC_{50,app}$, serial concentrations of these drugs were tested against 20 μM or 100 μM oxaliplatin transport mediated through OCT2 in either 100% human serum or HBSS containing 4% bovine serum albumin (BSA), which closely represents serum in terms of protein binding of drugs. The regressed $IC_{50}$ and apparent serum $IC_{50,app}$ values of part of the drugs are shown in Table 2.

TABLE 2

Identification of clinically relevant inhibitors of OCT2 mediated oxaliplatin uptake by $C_{max,u}/IC_{50}$ or $C_{max}/IC_{50,app}$ ratio

| Compound | $IC_{50}$ or Ki (μM)* | $IC_{50,app}$ (μM)** | Plasma peak total concentration $C_{max}$ (μM) | Plasma protein binding (%) | Plasma peak unbound concentration $C_{max,u}$ (μM) | $C_{max,u}/IC_{50}$ | $C_{max}/IC_{50,app}$ |
|---|---|---|---|---|---|---|---|
| Buflomedil | 0.78 | 1.45 | 6.8 | 70 | 2.04 | 2.62 | 4.69 |
| Miconazole | 1.55 | 3.30 | 14.9 | 92 | 1.19 | 0.77 | 4.52 |
| Erlotinib | 0.37 | 2.08 | 5.4 | 93 | 0.38 | 1.02 | 2.60 |
| Propantheline•Br | <0.1 | 0.24 | 0.134 | unkn | | | 0.56 |
| Epinastine | 0.19 | | 0.12 | 64.2 | 0.04 | 0.23 | |
| Cimetidine | 9.71 | 36.75 | 12 | 20 | 9.60 | 0.99 | 0.33 |
| Tiotropium Br | 0.12 | 1.10 | 0.034 | 72 | 0.01 | 0.08 | 0.03 |
| Exemestane | 0.19 | | 0.091 | 90 | 0.01 | 0.05 | |
| Pentamidine | 0.067 | | 0.730 | 69 | 0.23 | 3.38 | |
| Dolutegravir | 0.20 | 3.37 | 10.90 | 99.5 | 0.05 | 0.28 | 3.23 |
| Leuprolide | 1.57 | | 0.017 | 46 | 0.01 | 0.01 | |
| Ipratropium•Br | <0.1 | | Inhalation aerosol with very low plasma exposure | NA | | | |

*Intrinsic inhibition constant assessed in protein free HBSS.
**Apparent inhibition constant measured in 100% human serum or HBSS containing 4% bovine serum albumin (BSA).

Example 2

The following example relates to the identification of clinically relevant inhibitors of OCT2-mediated oxaliplatin uptake.

The FDA has published guidance in predicting if a drug is likely to be a transporter inhibitor in clinics by using data attained in in vitro models [4]. $C_{max,u}$ denotes the maximum free, unbound plasma concentration of a drug. If the ratio between $C_{max,u}$ and in vitro $IC_{50}$ assessed in protein-free buffer is <0.1, the drug is unlikely to inhibit the transporter in vivo. Thus, characteristics of the in vitro model may be used to predict in vivo effectiveness.

Accordingly, qualified inhibitors identified using the in vitro methods described above were examined for a potential effect on OCT2-mediated oxaliplatin cellular uptake clinically by using published clinical pharmacokinetic data of these drugs. Using this data, seven compounds had calculated $C_{max,u}/IC_{50}$ ratios that are >0.1 (Table 2). These drugs are buflomedil, miconazole, erlotinib, propantheline, epinastine, pentamidine, dolutegravir, and cimetidine. Among them, pentamidine, buflomedil and erlotinib had the highest $C_{max,u}/IC_{50}$ ratios (>1), suggesting that at their maximal clinical plasma concentrations, these drugs may inhibit over 50% OCT2-mediated oxaliplatin cellular uptake in vivo. However, a clinical dose of pentamidine can cause nephrotoxicity in nearly 25% of patients, hence it may be a less desirable OCT2 inhibitor for reducing platinum drug toxicity.

For other drugs, their low (<1) $C_{max,u}/IC_{50}$ ratios suggest that these drugs may have to be administered at a dose that is much higher than their normal clinical dose in order to achieve >50% OCT2 mediated oxaliplatin uptake in vivo. For example, Tiotropium and epinastine are ophthalmic drugs that were shown as very potent OCT2 inhibitors with a measured $IC_{50}$ of 0.12 μM and 0.19 μM respectively. However, their systemic/plasma levels are also very low (Table 2), therefore, when administered at their approved clinical dose, they are likely to have minimal inhibitory effects on OCT2 activities in organs other than the eye. Alternatively, changing their formulation and/or route of administration may increase their plasma exposure, which may induce unexpected systemic toxicities not observed at low plasma exposure.

In addition, another method was used to identify compounds that can potentially affect OCT2-mediated oxaliplatin cellular uptake clinically. Instead of $C_{max,u}/IC_{50}$ ratio, $C_{max}/IC_{50,app}$ ratio was used, where $C_{max}$ denotes the total plasma concentration of a drug and $IC_{50,app}$ denotes the apparent half-maximal inhibition constant measured in vitro in 100% serum or assay buffer containing physiological concentrations of serum binding proteins, such as albumin. This approach was demonstrated to have more accurate prediction of in vivo transporter inhibition effects of highly protein bound (>90%) compounds [17].

Using $C_{max,u}/IC_{50,app}$ ratio, it was further demonstrated that buflomedil and erlotinib are likely to be clinically relevant inhibitors of OCT2-mediated oxaliplatin cellular uptake. Moreover, it was demonstrated that two highly serum protein bound drugs miconazole and dolutegravir, which had $C_{max,u}/IC_{50}$ of less than 1 (Table 2), may exhibit much higher inhibition of OCT2-mediated oxaliplatin cellular uptake in vivo because of their high $C_{max,u}/IC_{50,app}$ ratios (4.52 and 3.23 respectively. Table 2).

In addition to looking at $C_{max,u}/IC_{50}$ or $C_{max}/IC_{50,app}$ ratios, it is also important to factor in other pharmacokinetic (PK) parameters in order to find an inhibitor with optimal clinical effects when inhibiting OCT2 mediated oxaliplatin uptake.

TABLE 3

Clinical pharmacokinetic parameters of buflomedil, miconazole, erlotinib, dolutegravir, and pentamidine

| Drug and typical clinical dose | Mean $C_{max}$ (ug/mL) | Mean $C_{max}$ (uM) | Mean $T_{1/2}$ (hour) | Reference | $C_{max}/IC_{50,app}$ ratio |
|---|---|---|---|---|---|
| Buflomedil (300 mg po, bid) | 2.1 | 6.8 | 3.4 | [9] | 4.69 |
| Buflomedial (600 mg slow-release, po, qd) | 2.2 | 7.2 | >10 | [9] | 4.97 |

TABLE 3-continued

Clinical pharmacokinetic parameters of buflomedil, miconazole, erlotinib, dolutegravir, and pentamidine

| Drug and typical clinical dose | Mean $C_{max}$ (ug/mL) | Mean $C_{max}$ (uM) | Mean $T_{1/2}$ (hour) | Reference | $C_{max}/IC_{50, app}$ ratio |
|---|---|---|---|---|---|
| Miconazole (800 mg IV) | 5 | 12 | 0.4 (distribution phase), 8.9 (terminal phase) | [7, 8] | 3.64 |
| Erlotinib (150 mg po, single dose) | 1.14 | 2.9 | 20 | [10] | 1.39 |
| Erlotinib (150 mg po, day 24) | 2.12 | 5.4 | 18.2 | [10] | 2.60 |
| Dolutegravir (50 mg po qd, single dose) | 4.56 | 10.9 | 14.2 | [15] | 3.23 |
| Dolutegravir (50 mg po qd, day 10) | 6.16 | 14.7 | ~15 | [15] | 4.36 |

In clinical oncology, oxaliplatin is typically dosed through intravenous infusion over a few hours. As shown in FIG. 1A, the plasma concentration of oxaliplatin remains high within three hours after the start of the two hour infusion. As a drugs' efficacy and toxicity are typically closely related to their plasma concentration, oxaliplatin may induce more toxicity during this period. Therefore, to best reduce oxaliplatin toxicities that are be attributed to OCT2-mediated cellular uptake, an inhibitor of OCT2-mediated oxaliplatin uptake should maintain sufficient plasma concentration at least during this period. In the case of miconazole, 600 mg dosed IV bolus (FIG. 1B) has a high maximal plasma concentration; however, its plasma concentration drops rapidly with a half-time of 0.4 hour (initial phase), resulting in nearly five-fold decrease at 3 hour. Such a PK profile with short half-time may not be ideal for sustaining the inhibition of OCT2-mediated oxaliplatin uptake (and thus inhibition of toxicity) in a clinical setting, unless miconazole is infused over time or the administration of cisplatin/oxaliplatin is shorter. For instance, it is possible to administer both cisplatin and oxaliplatin by bolus or by shorter infusion time. In contrast to miconazole IV injection, buflomedil, dolutegravir and erlotinib oral administration have long half-times (Table 3), which means their plasma concentration can be maintained at desirable concentrations for longer period of time (FIG. 1C, FIG. 1D and FIG. 1E). Buflomedil 600 mg slow-release tablet qd (FIG. 1C(2)) seems to be particularly well adapted to protecting from 2 hour infusion of platinum derivatives, particularly for oxaliplatin infusion.

Example 3

The following example relates to the inhibition selectivity for OCT2 over other major transporters involved in oxaliplatin handling.

Figure 2:
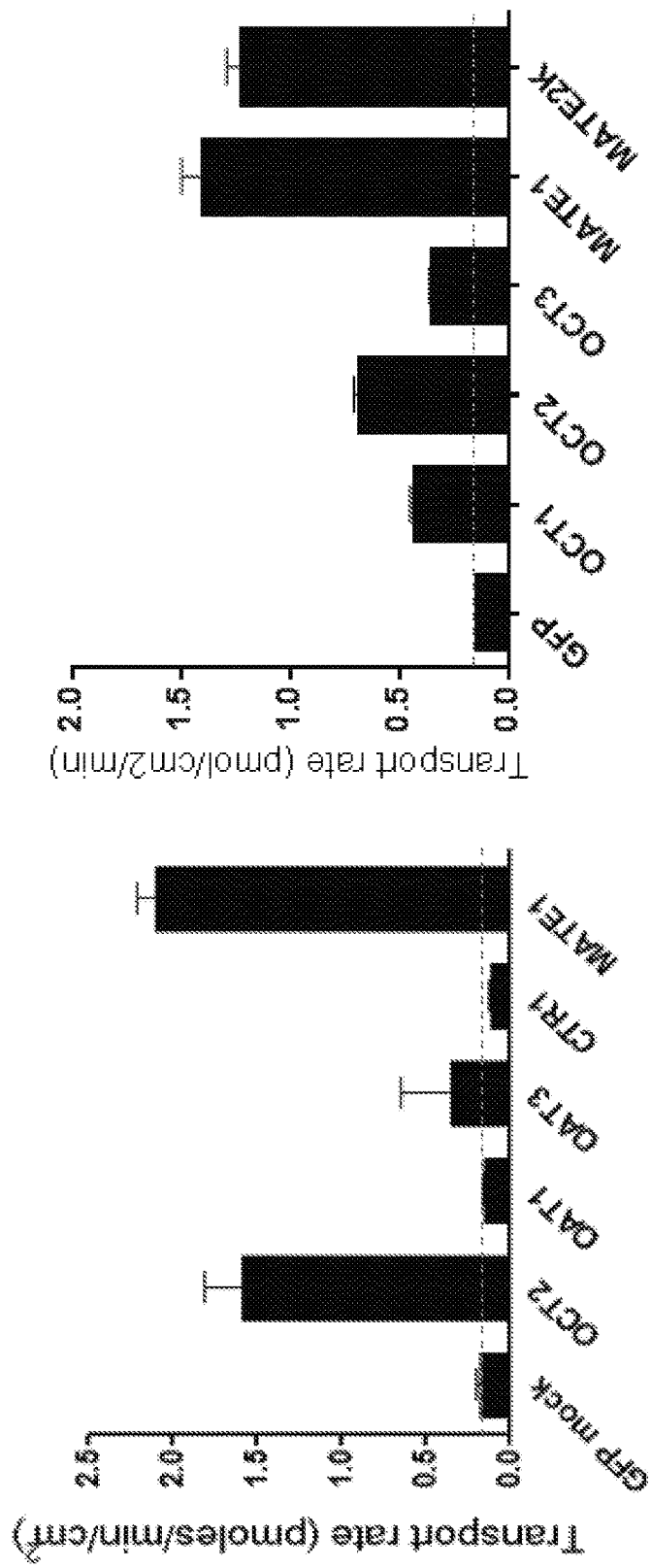
FIG. 2 depicts the transport of oxaliplatin by different transporters expressed in MDCK cells. (Left: oxaliplatin 20 μM in protein-free HBSS; Right: oxaliplatin 20 μM in 100% human serum).

In addition to OCT2, oxaliplatin is also thought to interact with other uptake transporters, mainly OCT1 and OCT3. Efflux transporters including MATE1 and MATE2K are also involved in controlling the cellular accumulation of oxaliplatin. Applicants have confirmed the transportability of oxaliplatin by transporters including OCT1, OCT2. OCT3 and MATE1 and MATE2K (FIG. 2).

These transporters have different roles in modulating oxaliplatin efficacy and toxicity. For example, OCT and OCT3 have been linked to oxaliplatin efficacy in tumor cells. However, MATE1 and MATE2K are believed to reduce oxaliplatin and cisplatin's toxicity in the kidney. Therefore, it is important to have a drug that specifically inhibits OCT2 so that it will not affect oxaliplatin efficacy and/or aggravate oxaliplatin nephrotoxicity.

Using buflomedil as an example, the importance of selectivity in interacting with oxaliplatin transporters was demonstrated. Erlotinib and cimetidine, two OCT2 inhibitors which have been tested in clinical trials for their ability to protect patients from platinum drug-induced toxicity, were used as comparison. Using a similar in vitro transporter method as described above, the $IC_{50}$ of these drugs against OCT1, OCT2. OCT3. MATE1 and MATE2K was determined. Table 4 lists the measured or estimated serum apparent $IC_{50,app}$ values for buflomedil, erlotinib, cimetidine, miconazole, and dolutegravir against oxaliplatin (20 μM in 100% human serum or 100 μM in HBSS containing 4% BSA) transport mediated by these transporters.

Figure 3:
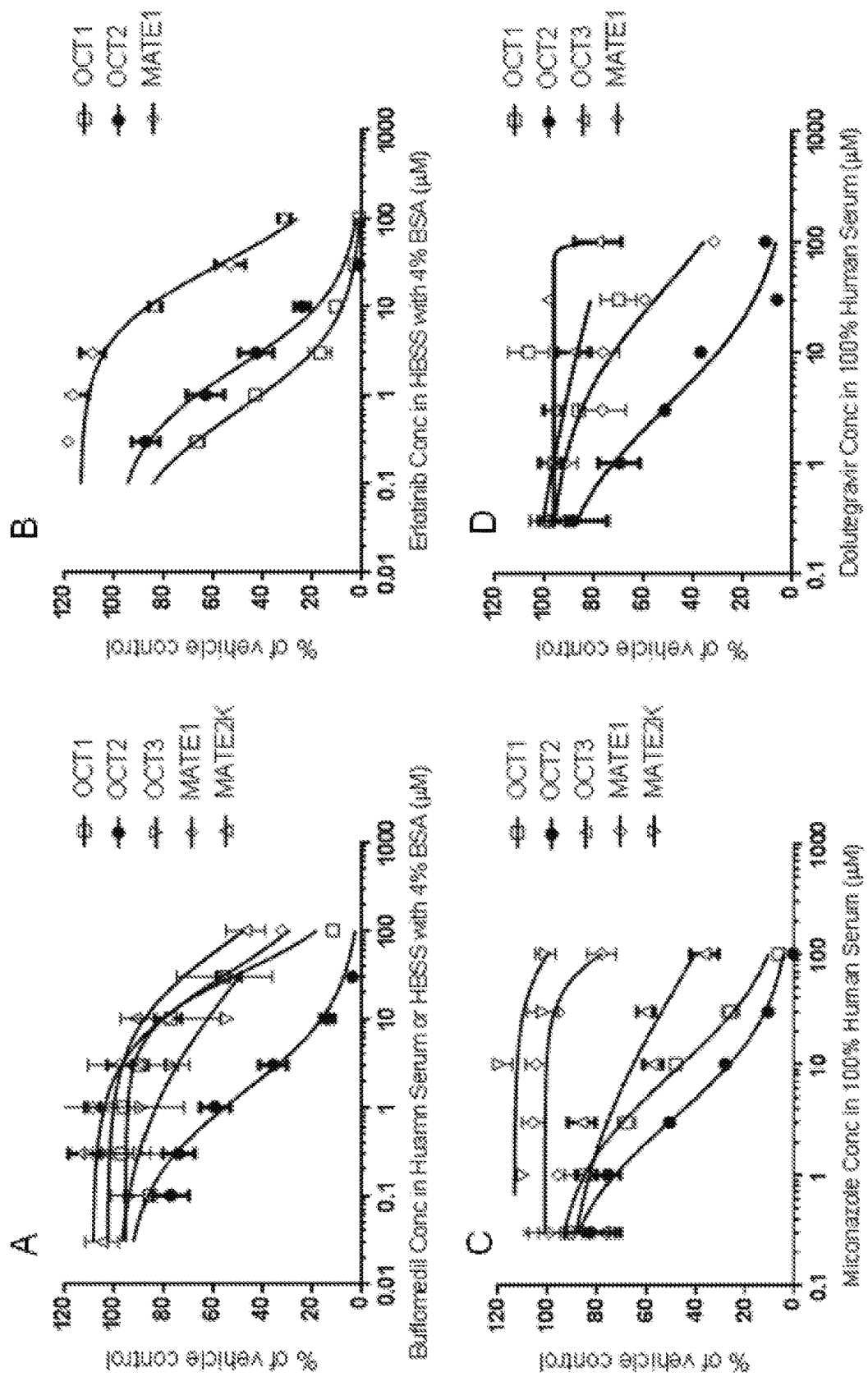
FIG. 3 depicts the inhibition of buflomedil (FIG. 3A), erlotinib (FIG. 3B), miconazole (FIG. 3C), and dolutegravir (FIG. 3D) on oxaliplatin transport in human serum or alike assay buffer by different transporters.

Buflomedil was demonstrated to be a selective inhibitor of OCT2 in transporting oxaliplatin, with at least 20-fold higher potency over OCT1, OCT3, MATE1 and MATE2K (FIG. 3A, Table 4). Dolutegravir was also demonstrated to be a potent selective inhibitor of OCT2 in transporting oxaliplatin, with at least 10-fold higher potency over OCT1. OCT3 and MATE1 (FIG. 3D, Table 4). Miconazole was demonstrated to be a potent inhibitor of OCT2 in transporting oxaliplatin, with at least 2-fold higher potency over OCT1. OCT3. MATE1 and MATE2K (FIG. 3C, Table 4). Erlotinib was also demonstrated to be potent in suppressing OCT1 as well as OCT2 (FIG. 3B, Table 4). Cimetidine was shown to be an inhibitor of OCT2, but with even more preference towards inhibiting oxaliplatin transport through MATE1 (Table 3). These data suggested that compared to erlotinib and cimetidine, buflomedil, miconazole and dolutegravir are a better agent, as they are more selective inhibitors of OCT2-mediated oxaliplatin transport. Particularly, buflomedil and dolutegravir, which showed >10× selectivity between OCT2 and other relevant transporters (OCT1, OCT3, MATE1).

Compared to buflomedil and dolutegravir, miconazole has low (<2×) selectivity between OCT2 and OCT1, suggesting it is more likely to interfere with oxaliplatin efficacy than the other two drugs in OCT1 expressing tumors such as colon and liver cancers. Nevertheless, because miconazole has high selectivity (>10×) between OCT2 and other relevant transporters (OCT3, MATE1 and MATE2K), it may still be a promising candidate when OCT1 play a minimal role in therapeutic efficacy (e.g., when a chemo drug is an OCT2 substrate but not OCT1, and/or the tumor express low level of OCT1).

The same methods can be used to determine the transporter inhibition selectivity of imidazole and other drugs.

Despite that buflomedil was discovered first by us to be a potent and selective inhibitor of OCT2 mediated oxaliplatin transport. FIG. 15A shows that buflomedil had no inhibition selectivity between OCT2 and MATE1 when metformin was used as the substrate. The result further demonstrates the critical importance of using oxaliplatin as the transporter substrate in order to screen for the appropriate drugs for minimizing OCT2 mediated oxaliplatin toxicity.

In contrast, buflomedil was further evaluated for its OCT2 and MATE1 inhibition potencies using cisplatin as the transporter substrate. FIG. 15B shows that buflomedil has nearly identical $IC_{50}$s for OCT2 or MATE1 mediated oxaliplatin and cisplatin transport. This result suggest that cisplatin and oxaliplatin may interact with the same transporter binding sites, leading to no or little substrate-dependent (oxaliplatin vs. cisplatin) buflomedil potency and selectivity as demonstrated.

reduction of oxaliplatin cytotoxicity with buflomedil was tested with an in vitro MDCK (canine proximal epithelia cells) model overexpressing OCT2, MATE1 and MATE2K.

TABLE 4

Apparent inhibition constants of oxaliplatin transport mediated through different transporters

| Compound | OCT1 $IC_{50, app}$ (μM) | OCT2 $IC_{50, app}$ (μM) | OCT3 $IC_{50, app}$ (μM) | MATE1 $IC_{50, app}$ (μM) | MATE2K $IC_{50, app}$ (μM) |
|---|---|---|---|---|---|
| Buflomedil | 34.6 ± 7.6 | 1.4 ± 0.2 | 28.0 ± 11.4 | 32.7 ± 5.4 | 84.0 ± 23.1 |
| Erlotinib | 0.67 ± 0.06 | 2.1 ± 0.5 | | 30.7 ± 4.9 | no inhibition at 10 μM |
| Cimetidine | | 36.8 ± 13.6 | | | |
| Miconazole | 8.4 ± 1.5 | 3.3 ± 0.6 | 49.2 ± 22.6 | >100 | >100 |
| Dolutegravir | >100 | 3.4 ± 1.0 | >100 | 42.7 ± 12.0 | |

Apparent inhibition constant, $IC_{50, app}$, was determined in 100% human serum or in HBSS containing 4% BSA, against transport of 20 μM or 100 μM oxalipaltin.

Example 4

The following example relates to the inhibition of intracellular oxaliplatin accumulation by buflomedil in cells co-expressing uptake and efflux transporters.

In most naturally occurring cells, uptake transporters co-exist with efflux transporters. It is the interplay between the uptake and efflux transporters that determines the net intracellular accumulation of a substrate. One example is in the proximal tubule epithelial cells in the kidney, where the basolaterally expressed transporters, mainly OCT2, work in concert with the apically expressed MATE1 and MATE2K [5]. To measure how buflomedil can affect the net intracellular content of oxaliplatin, a multi-transporter cell system was constructed by concomitantly transfecting and expressing OCT2 and MATE1 at cDNA plasmid concentrations of 40 and 10 ng/p L respectively. Cells were dosed with oxaliplatin 100 μM mixed with varying concentrations of buflomedil in 4% BSA HBSS for 90 min. At the end of the experiment, the intracellular content of oxaliplatin was quantified by LC/MS/MS. Cells with single expression of OCT2 or GFP mock were also used as a control.

Figure 4:
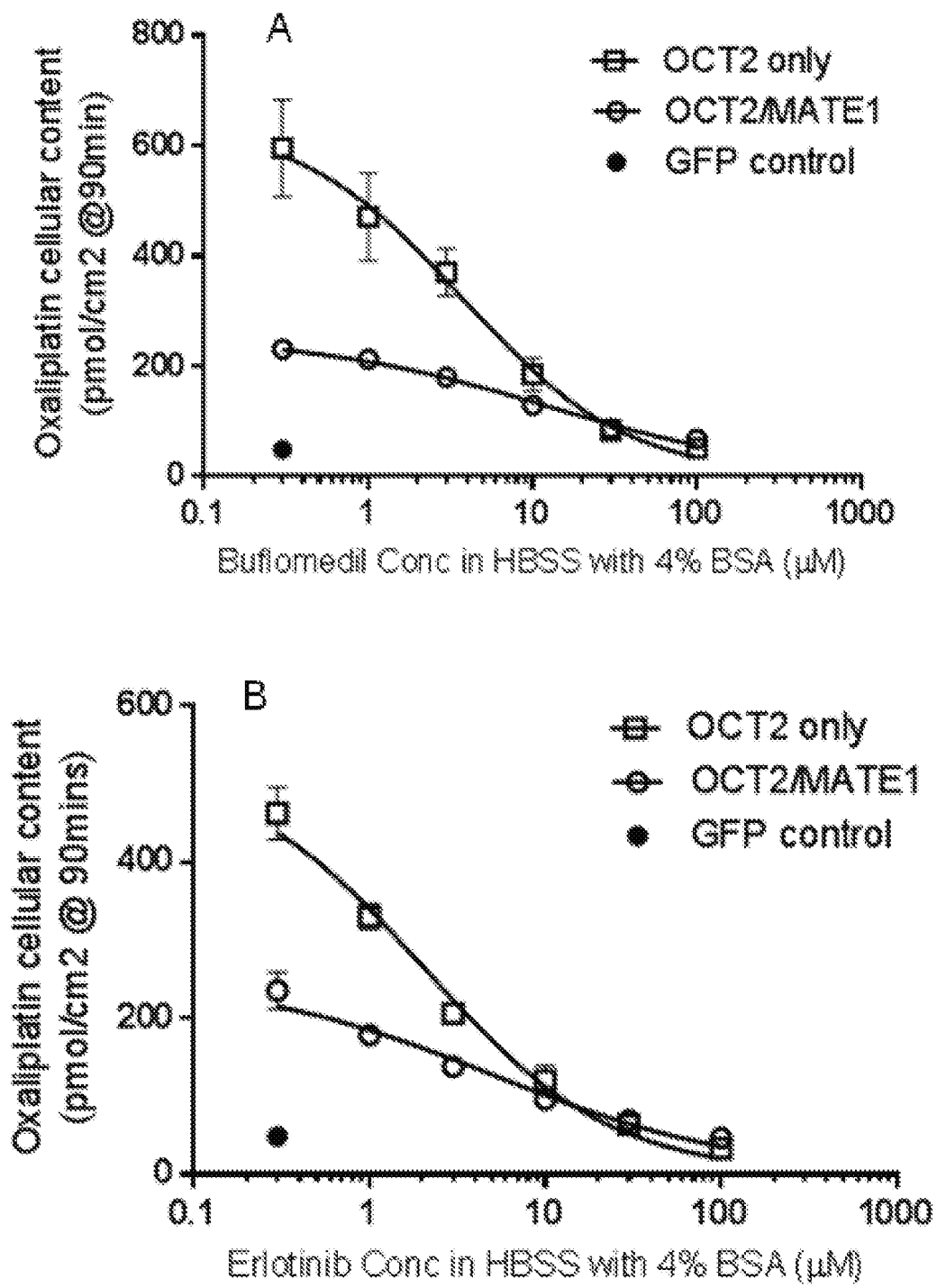
FIG. 4 depicts the inhibition of intracellular content of oxaliplatin in cells co-expressed with OCT2, or OCT2 and MATE1, by buflomedil (FIG. 4A) and erlotinib (FIG. 4B).

As shown in FIG. 4, the intracellular content of OCT2-expressing cells was significantly higher than cells expressing GFP mock control, suggesting OCT2 can potentiate oxaliplatin nephrotoxicity. However, cells expressing both MATE1 with OCT2 had significantly reduced cellular content of oxaliplatin in comparison with OCT2 only, suggesting that MATE1 plays a role in protecting renal tubular cells from oxaliplatin assault. Because both buflomedil and erlotinib are more potent inhibitors of OCT2 than MATE1 (Table 4), they reduced cellular accumulation of oxaliplatin in cells co-expressing OCT2 and MATE1, suggesting that they should also potentially reduce nephrotoxicity induced by oxaliplatin. This is in contrast to cimetidine, a more potent inhibitor of MATE1 than OCT2, which may increase oxaliplatin accumulation in renal tubular cells through preferential inhibition of MATE1, hence potentially aggravating oxaliplatin induced nephrotoxicity.

Example 5

The following example relates to the discovery that buflomedil reduces cytotoxicity of oxaliplatin by inhibiting its OCT2-mediated uptake.

Previous studies demonstrated that buflomedil is a potent inhibitor of OCT2-mediated uptake of oxaliplatin. Here, Materials and Methods A triple-transporter model for OCT2(SLC22A2), MATE1 (SLC47A1), and MATE2-K(SLC47A2) was created by transfecting fully confluent MDCK-II cell monolayers with DNA mixture containing the plasmids encoding OCT2, MATE1, and MATE-2K at concentrations of 40, 15, and 5 ng/μl, respectively. The OCT2 was expressed on the basolateral cell membrane, and MATE1 and MATE2-K were expressed on the apical side of the cells. To demonstrate the effects of MATE1/MATE2K efflux transporters, a model expressing similar level of OCT2 was also used. This systems were cultured in complete medium consisting of Dulbecco's modified Eagle's medium without phenyl-red with 10% fetal bovine serum in an atmosphere of 5% CO2-95% air at 37° C. The apical medium was adjusted to pH 6.7 with 25 mM of 2-(N-morpholino) ethanesulfonic acid (MES).

Both basolateral and apical sides were treated with various concentrations of buflomedil ranging from 3-1000 μM during the treatment, and oxaliplatin was only added in basolateral side and fixed at 100 μM. Cells were pre-incubated with or without inhibitors for 30 min, and then co-administered with oxaliplatin for further 4 hours. After removal of the media, a drug-free medium was added in both sides. After incubation 24 hours, the medium was collected, and the lactate dehydrogenase (LDH) activity in the medium was measured using an LDH cytotoxicity assay kit (G-Biosciences. St. Louis, Mo.; or Biochain, Newark, Calif.), according to the manufacturers' instructions. Cytotoxicity was evaluated by measuring the LDH activity in the medium.

Further, the concentration of an OCT2 inhibitor was fixed at a concentration that is close to the drug's clinical $C_{max}$, and co-administered with various concentrations of oxaliplatin ranging from 1-1000 μM. Buflomedil was tested 3p and 6 μM. Dolutegravir was tested at 10 μM. One competitor, erlotinib, was selected due to its great potency on the inhibition of OCT2 uptake of oxaliplatin in previous studies. Another competitor, cimetidine, was also tested because it is a widely known non-selective OCT2 inhibitor, and because it has been studied both in vitro and in vivo for reducing platinum induced toxicities, including nephrotoxicity and neurotoxicity. Cytotoxicity was tested using the same procedure described above. In addition, cisplatin was reported as a substrate of OCT2 transporter. Therefore, cisplatin was also tested at 100, 300 and 1000 μM along with or without 6 μM of buflomedil in this triple model. In another similar experiment, oxaliplatin cytotoxicity was evaluated in OCT2 expressing cells with and without MATE1 and MATE2K transporters, to demonstrate the protective role of these efflux transporters.

Results and Discussion

Figure 5:
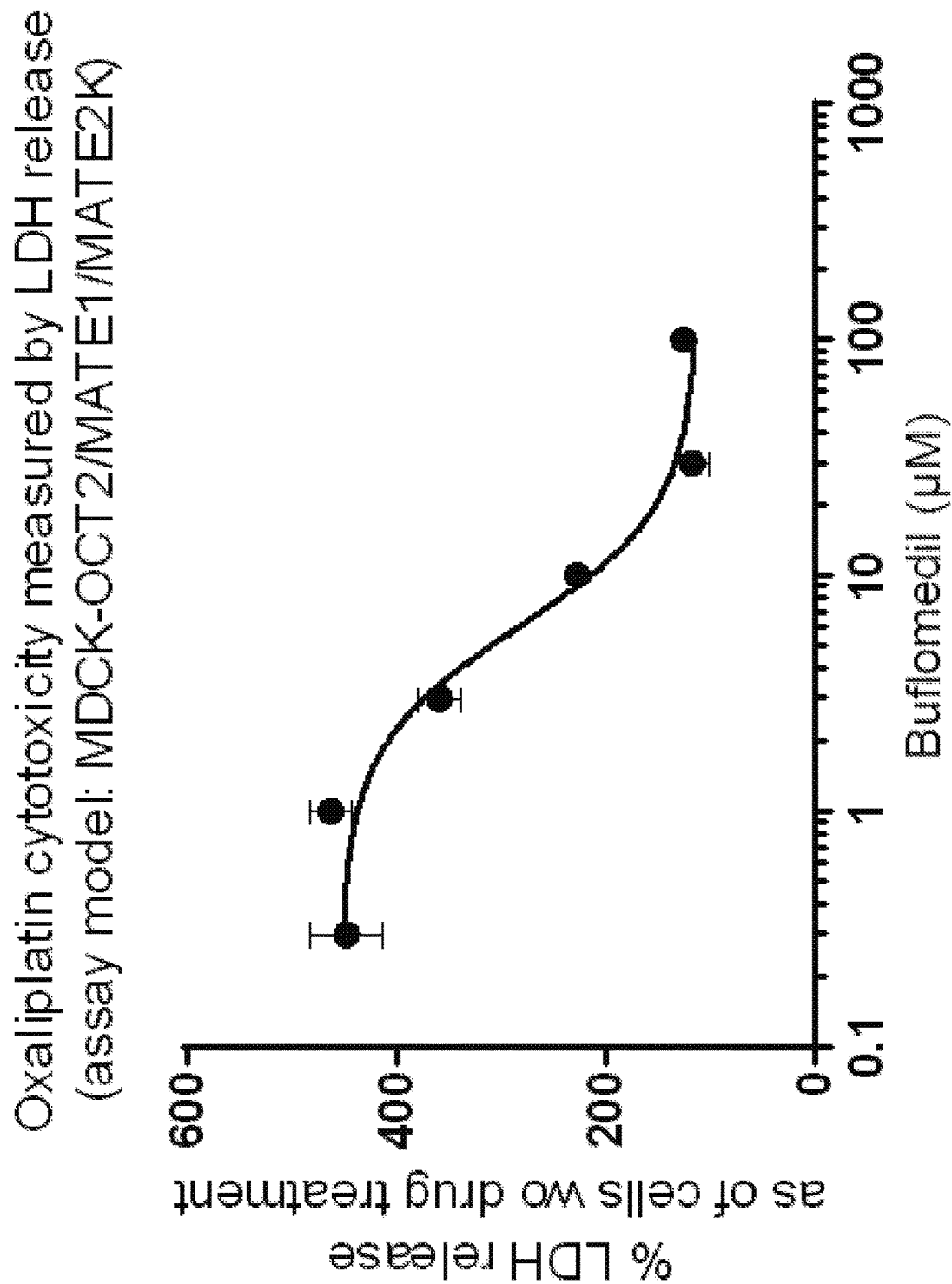
FIG. 5 depicts that buflomedil reduced cytotoxicity of 100 μM Oxaliplatin in OCT2-expressing cells in a dose-dependent fashion.
Figure 6:
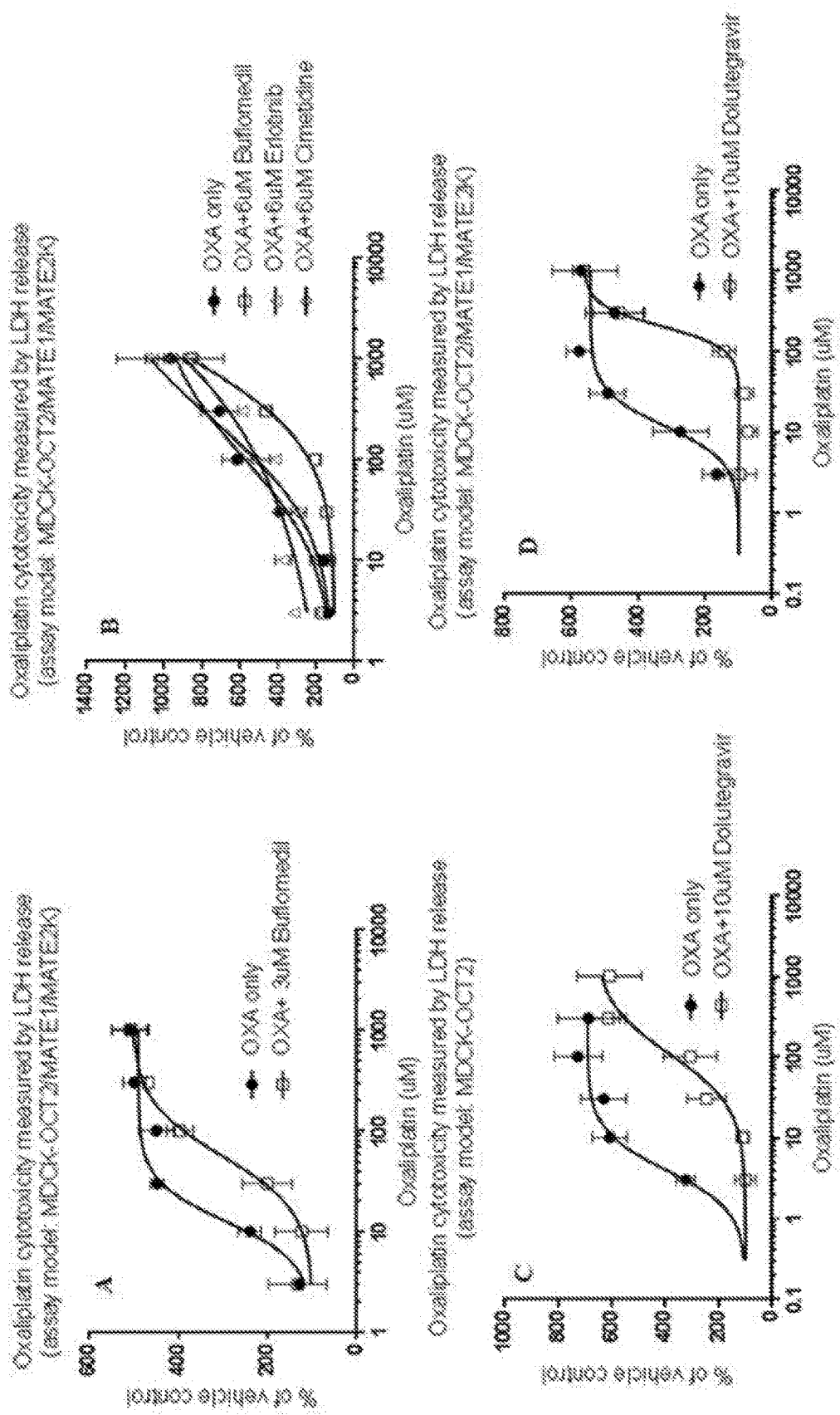
FIG. 6 depicts that buflomedil at 3 μm and 6 μM (FIG. 6A.

FIGS. 5 and 6 show that buflomedil and dolutegravir effectively reduced oxaliplatin-induced cytotoxicity in cells expressing OCT2, When 100 µM oxaliplatin was applied with buflomedil at different concentrations, buflomedil reduced oxaliplatin-induced cytotoxicity in a dose-dependent manner, with a clinically relevant $IC_{50}$ value of 6 µM (FIG. 5).

To determine oxaliplatin cytotoxicity $EC_{50}$ values, cells were treated with various concentrations of oxaliplatin, in the presence and absence of buflomedil, buflomedil, cimetidine or erlotinib at a fixed concentration. FIG. 6A-B shows that compared to oxaliplatin treatment alone, co-treatment with 3 µM and 6 µM buflomedil drastically reduced oxaliplatin cytotoxicity in cells expressing OCT2. MATE1 and MATE2K, with $EC_{50}$ values increased by 4.5× and 10× respectively, suggesting that buflomedil at clinically relevant concentrations can significantly alleviate oxaliplatin-induced toxicity in OCT2 expressing cells. Similarly, 10 µM dolutegravir drastically reduced oxaliplatin cytotoxicity in cells expressing OCT2, with and without MATE1 and MATE2K (FIG. 6C-D), with $EC_{50}$ values increased by 17.3× and 27.4× respectively.

Erlotinib showed cytotoxicity itself without adding oxaliplatin (FIG. 6B). Although a reduction in toxicity of high concentration oxaliplatin (>100 1M) was observed in the presence of 6 µM erlotinib, its $EC_{50}$ value could not be obtained due to an ambiguous fitting. In contrast to buflomedil and dolutegravir, 6 µM cimetidine did not reduce oxaliplatin cytotoxicity in the triple transporter model, likely because it is a strong inhibitor of MATE1 and MATE2K but not OCT2. Overall, buflomedil and dolutegravir showed superior effects compared to erlotinib and cimetidine in reduction of oxaliplatin cytotoxicity in the OCT2-expressing cells.

It should be noted that the triple-transporter model is particularly useful to model the disposition and toxicity of platinum drugs in renal tubular cells with abundant expression of OCT2 on the basolateral/plasma side, and MATE1 and MATE2-K on the apical/tubular side. Hence, these studies particularly suggest that selective inhibitors of OCT2-mediated oxaliplatin transport, such as buflomedil, can be used to reduce nephrotoxicity associated with oxaliplatin.

Figure 7:
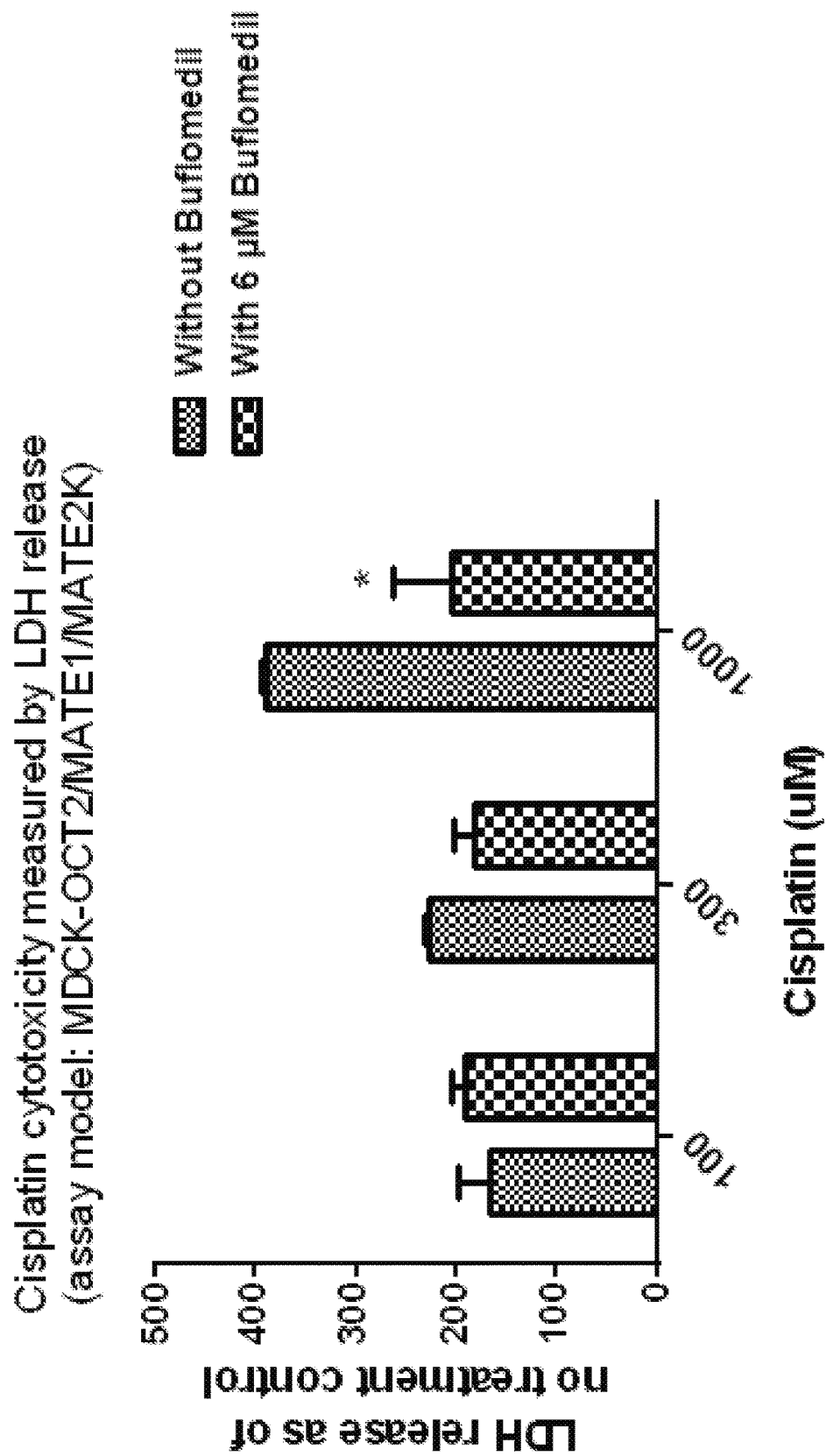
FIG. 7 depicts that buflomedil significantly reduced cytotoxicity from 1 mM of cisplatin in MDCK cells expressing OCT2, MATE1 and MATE2K (* indicates $p<0.05$).

In addition. FIG. 7 also suggests that buflomedil can reduce cisplatin-induced cytotoxicity in cells expressing OCT2. MATE1 and MATE2K. The cisplatin-induced toxicity showed a dose-response relationship after 30 µM treatment (data not shown). Three concentrations of cisplatin at 100, 300, and 1000 µM were compared. Compared to cisplatin alone, 6 µM buflomedil significantly reduced cytotoxicity of 1 mM cisplatin, suggesting buflomedil could be used to reduce cisplatin induced nephrotoxicity.

Figure 16:
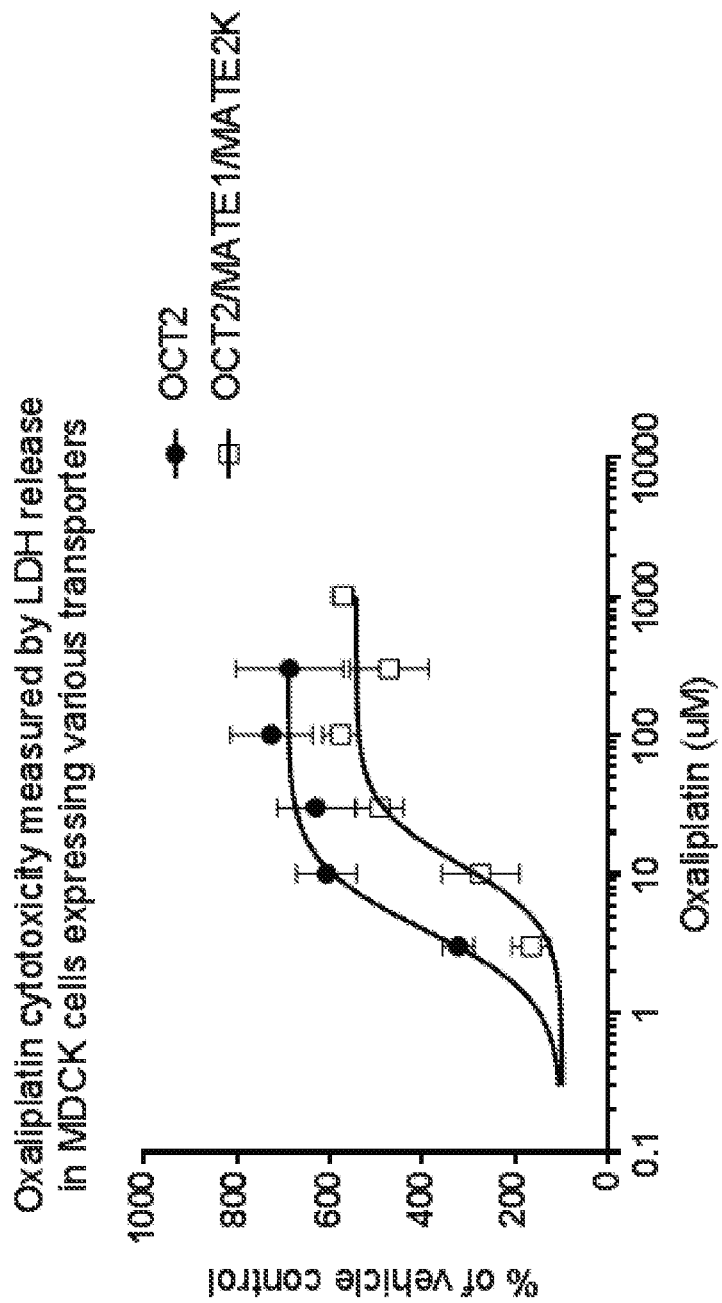
FIG. 16 depicts that efflux transporters MATE1 and MATE2K was effective on reducing severity and potency of oxaliplatin cytotoxicity in MDCK cells.

FIG. 16 shows MATE1 and MATE2K were effective on reducing oxaliplation cytotoxicity in OCT2 expressing cells. The presence of MATE1 and MATE2K not only increased the EC50 of oxaliplatin cytotoxicity by 3×, but also reduced the maximum level of cell damage. These results were in agreement with the oxaliplatin accumulation study presented in Example 4 and FIG. 4, further substantiating the hypothesis that MATE transporters play an protective organs especially the kidney against toxicities induced by oxaliplatin and cisplatin.

Example 6

The following example relates to the effects of buflomedil, dolutegravir and other drugs on in vitro anti-tumor effects of chemotherapeutic agents in tumor cell lines.

To evaluate whether buflomedil and dolutegravir could interfere with anti-tumor efficacy of oxaliplatin, cisplatin and chemotherapeutics used along with oxaliplatin, cytotoxicity assays were conducted in tumor cell lines.

Materials and Methods

Anti-Proliferation Study in HT-29 and HepG2 Cells

HT-29 (a colorectal cancer cell line) and HepG2 (a hepatocarcinoma cell line) cells were selected to examine the potency of oxaliplatin when co-administered with buflomedil, dolutegravir, cimetidine or erlotinib. The potency was determined by the sulforhodamine B (SRB) assay in 96-well plates. HT-29 cells and HepG2 cells were maintained in McCOY's 5A and Eagle's MEM media with 10% fetal bovine serum, respectively, in an atmosphere of 5% $CO_2$-95% air at 37° C. Seeding density was 3000 cells/well for both cell lines. After overnight incubation. 3 µM or 6 µM buflomedil, 3 µM-9 µM dolutegavir, 3 µM or 6 µM of erlotinib, or 6 µM of cimetidine were added to cells for pre-incubation for 30 min, and then various concentrations of oxaliplatin ranging from 0.1 to 100 µM were added to the culture medium for further incubation of 72 hours.

Results and Discussion

Figure 8:
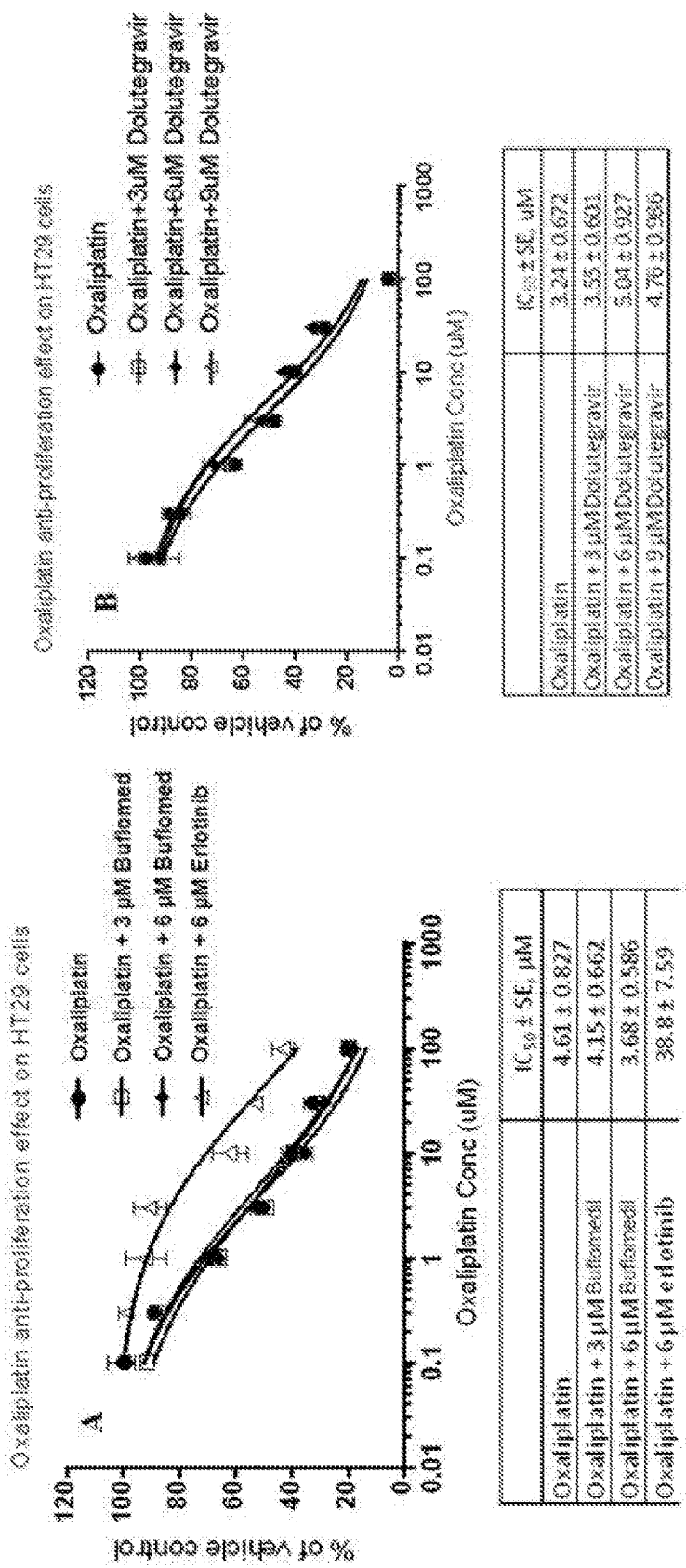
FIG. 8 depicts that erlotinib at 6 uM (FIG. 8A) drastically reduced (~8×) oxaliplatin anti-tumor potency in HT-29 cells, whereas buflomedil at 3 μM and 6 μM (FIG. 8A), dolutegravir at 3 uM, 6 uM and 9 uM (FIG. 8B) didn't affect oxaliplatin efficacy.
Figure 9:
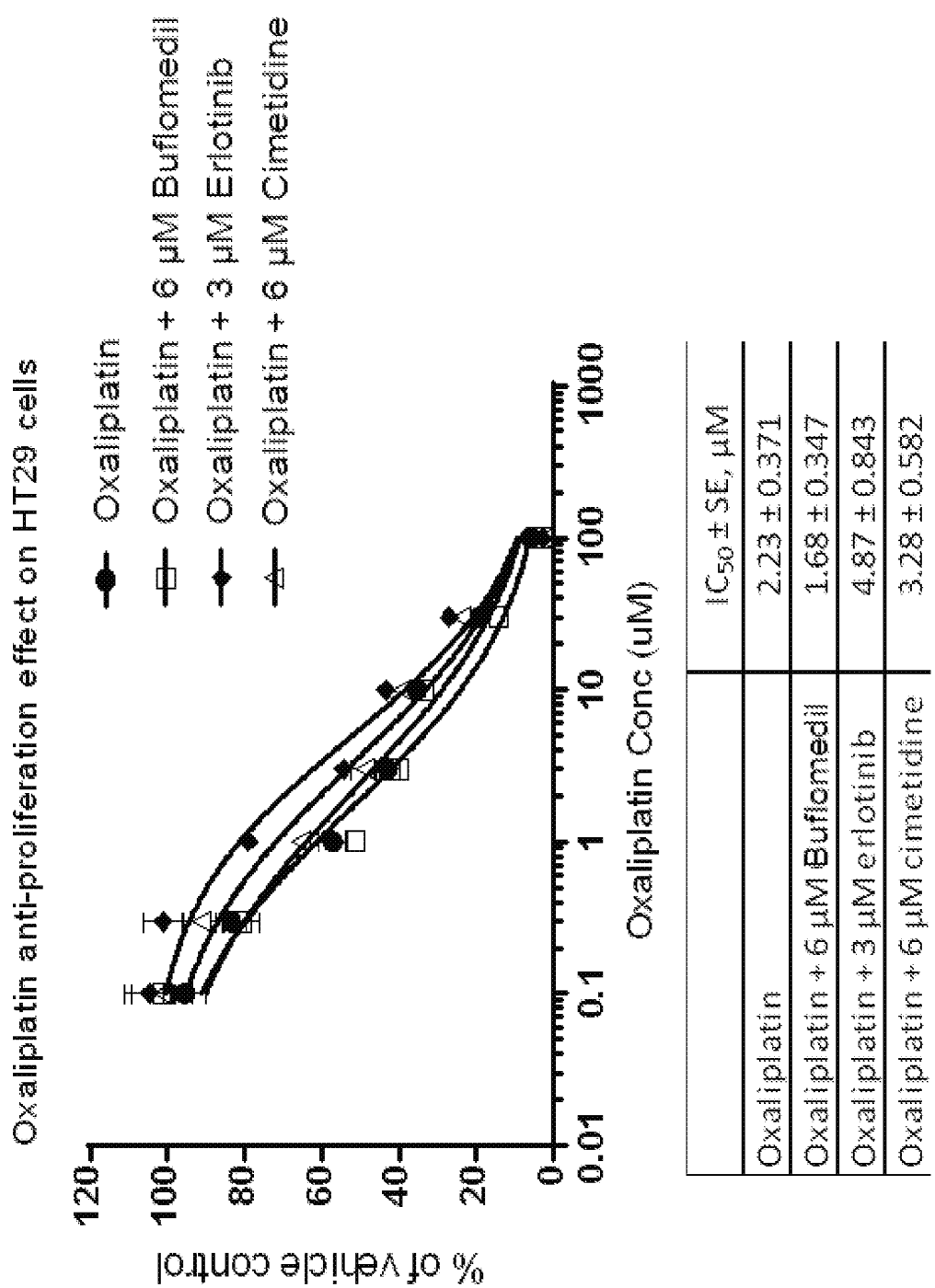
FIG. 9 depicts erlotinib at 3 μM significantly reduced anti-tumor potency of oxaliplatin ($p<0.05$) in HT-29 cells. Whereas 6 μM buflomedil and 6 μM cimetidine did not affect oxaliplatin anti-tumor activity.
Figure 10:
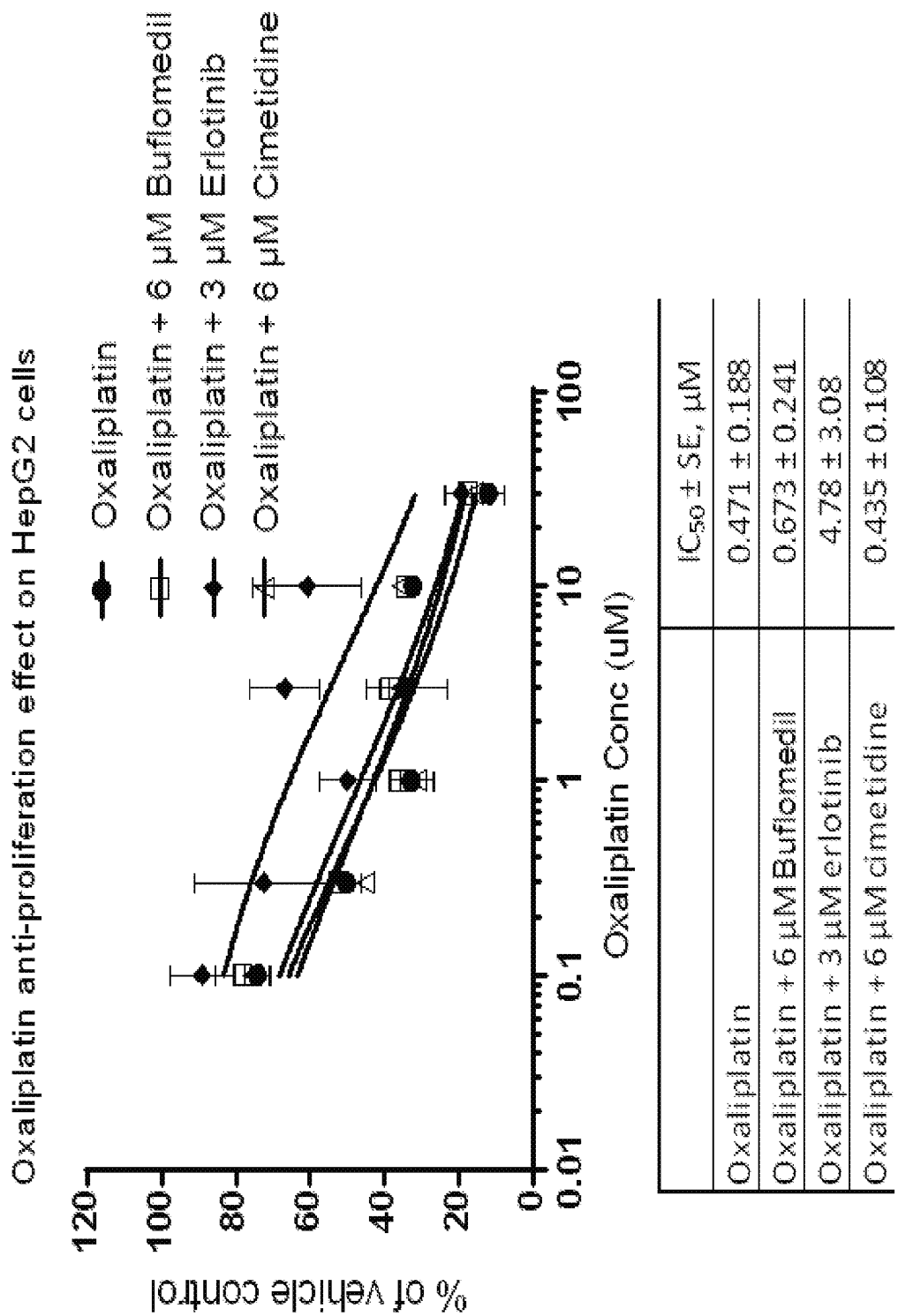
FIG. 10 depicts that erlotinib, not buflomedil nor cimetidine, drastically reduced (~10×) anti-tumor potency of oxaliplatin in HepG2 cells.

Buflomedil, Dolutegravir and Cimetidine, not Erlolinib, Maintained the Potency of Oxaliplatin in HT-29 (Human Colorectal Adenocarcinoma) and HepG2 (Human Liver Carcinoma) Cells as Tested by Anti-Proliferative Studies:

The anti-proliferative studies showed that 3 or 6 µM buflomedil, 3 µM or 6 µM or 9 µM dolutegravir, did not affect oxaliplatin anti-proliferation $IC_{50}$ values compared to the treatment of oxaliplatin alone in HT-29 (FIG. 8). In contrast, 6 µM erlotinib shifted oxaliplatin $IC_{50}$ by 8.4-fold, suggesting that erlotinib may reduce the cytotoxicity of oxaliplatin in HT-29 cells (FIG. 8A). A side-by-side comparison of co-administration of oxaliplatin with buflomedil (6 µM), erlotinib (3 µM), or cimetidine (6 µM) was also conducted. Only treatment of erlotinib with oxaliplatin significantly reduced the potency of oxaliplatin (FIG. 9). In addition, the same results were obtained with HepG2 cells; the $IC_{50}$ value was shifted 10-fold when co-administered with erlotinib and oxaliplatin compared to treatment with oxaliplatin alone (FIG. 10). Without wishing to be bound by theory, it is hypothesized that both HT-29 and HepG2 cells express high levels of OCT1. Therefore, oxaliplatin potency was reduced by erlotinib, which is a strong OCT1 inhibitor.

It is noteworthy that buflomedil and dolutegravir were shown to be a strong inhibitor of OCT2, but not OCT1 nor OCT3, in previous studies. Therefore, the potency of oxaliplatin remained the same when buflomedil or dolutegravir was co-administered. Although cimetidine does not reduce oxaliplatin potency when it was co-administered with oxaliplatin, it may not effectively reduce cytotoxicity mediated by OCT2 due to its weak inhibitory effect on OCT2. Overall, the data suggested that buflomedil and dolutegravir did not affect the anti-proliferation potency of oxaliplatin on HT-29 and HepG2 cells due to weak or ignorable inhibition of OCT1 or OCT3 in these cancer cells.

Figure 11:
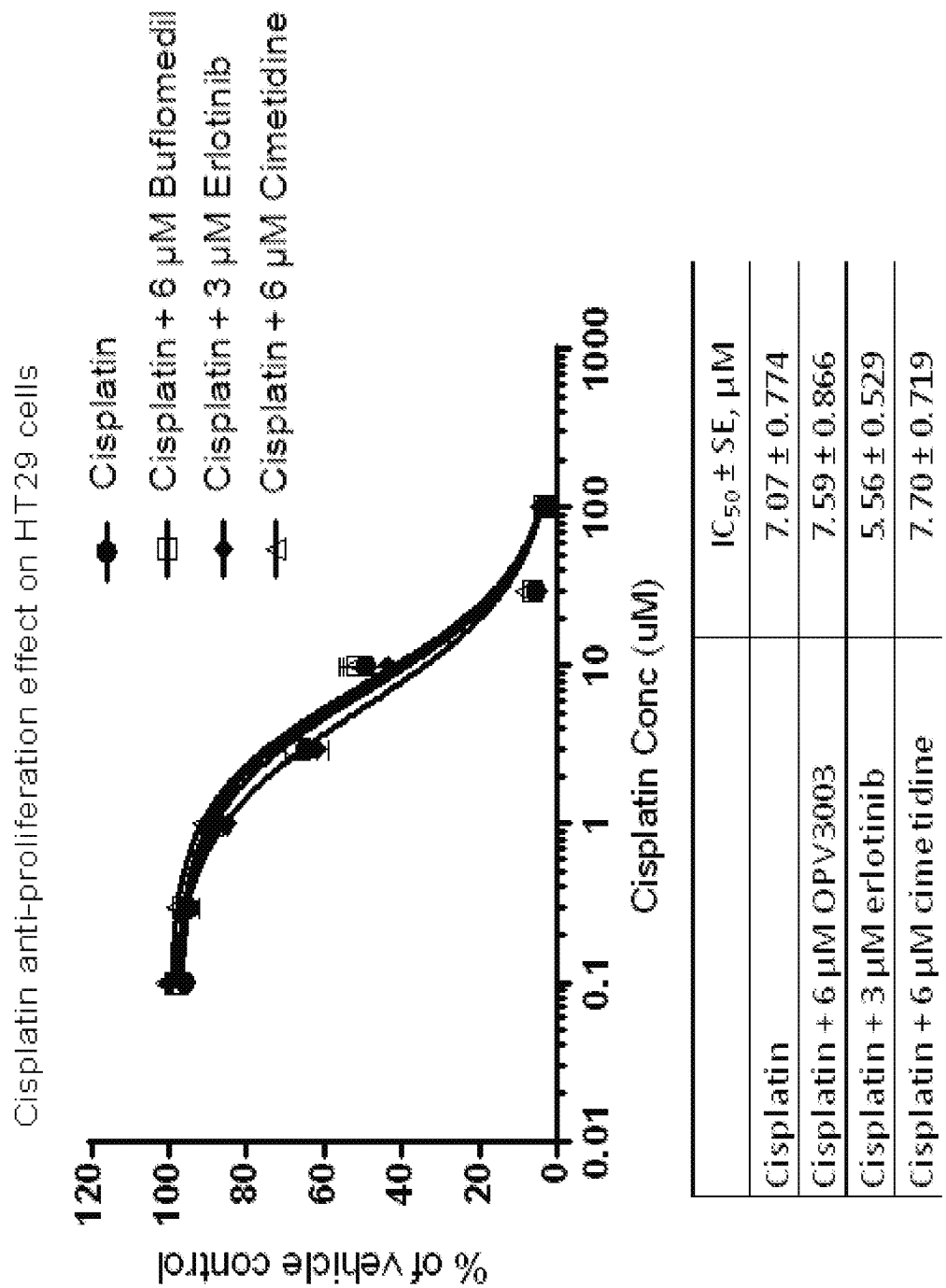
FIG. 11 depicts the anti-tumor effect of cisplatin in HT-29 cells was not affected by co-treatment with buflomedil, erlotinib, or cimetidine.
Figure 14:
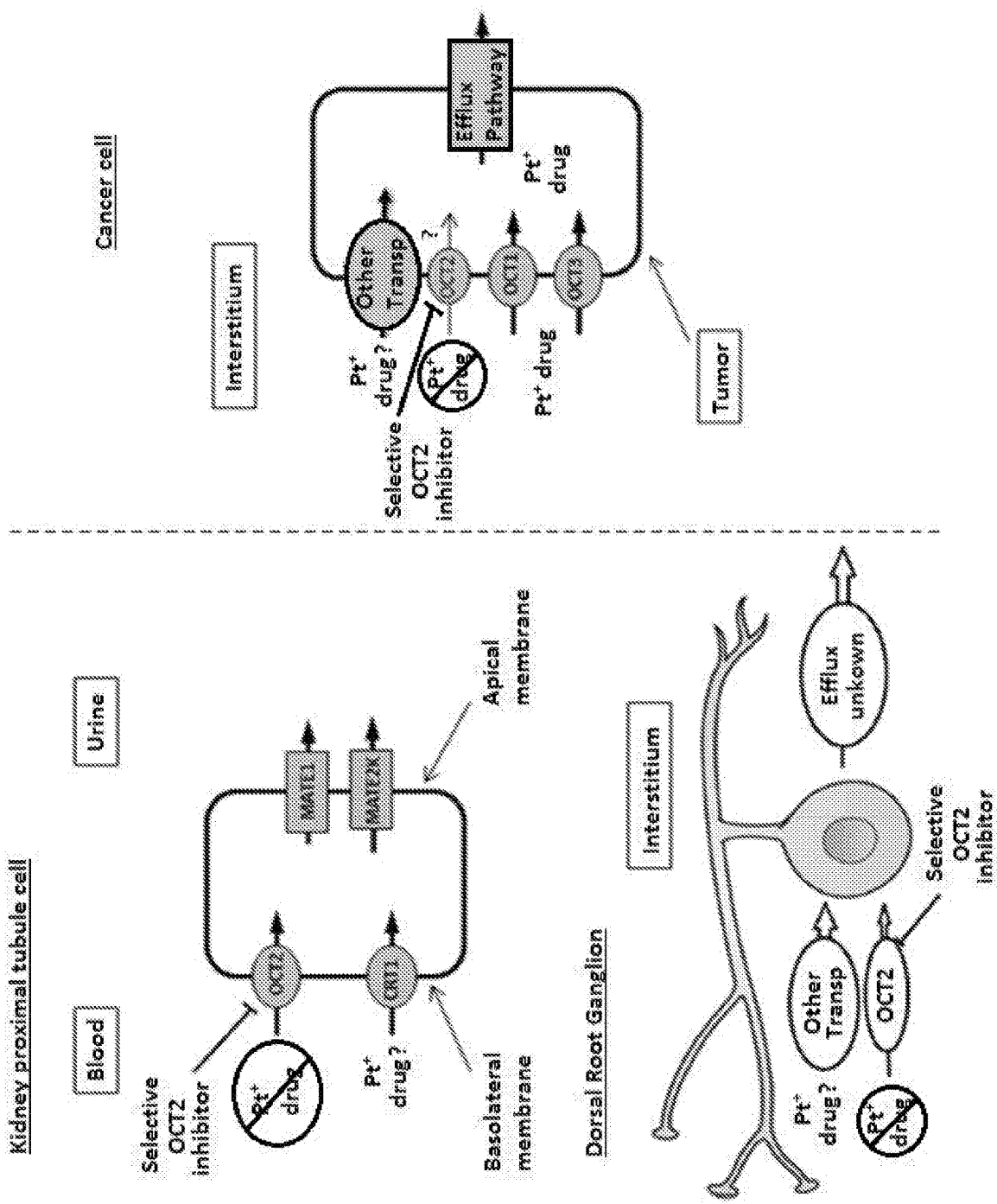
FIG. 14 depicts inhibition of the uptake of platinum drug by selective OCT2 inhibitor into a kidney proximal tubule cell or a dorsal root ganglion cell, and minimal inhibition of the uptake of platinum drug into a cancer cell which primarily relies on mechanisms/transporters other than OCT2 to take up platinum drug. The contribution of several transporters like CTR1 to the uptake of platinum derivatives in various cells has not been validated. The presence of OCT2 on cancer cells will vary according to the nature of tumor but the presence of OCT1 and/or OCT3 will guarantee uptake of platinum drug into the cells.

Cisplatin has also been reported as a substrate of OCTs. Therefore it was tested whether these inhibitors reduce the potency of cisplatin in HT-29. None of the three inhibitors reduced cisplatin anti-proliferation potency in HT-29 cells (FIG. 11). Interestingly, it was previously shown that erlotinib can reduce the potency of oxaliplatin, possibly by inhibiting OCT1-mediated oxaliplatin uptake in tumor cells. These results suggested that OCT1-mediated cisplatin transport may not be an important mechanism of cisplatin accumulation in HT-29 cells. Thus, erlotinib has ignorable impact on cisplatin cytotoxicity in HT-29 cells.

In addition to oxaliplatin and cisplatin, buflomedil was tested for its potential interference with 5-FU and gemcitabine, two chemotherapeutics commonly used in combination with oxaliplatin in treating various tumors including colorectal cancer and hepatocellular carcinoma. Again, as illustrated in FIGS. 12 and 13, buflomedil and dolutegravir did not impact the anti-tumor effect of 5-FU and gemcitabine in HT-29 cells, suggesting co-administration of buflomedil and dolutegravir should not reduce efficacies of 5-FU and gemcitabine.

Example 7

The following example relates to platinum-induced neuropathy.

General methodologies known to the art are used to assess the activity of buflomedil following induction of various toxicities by platinum drugs in selected neuropathy mice models. Other methods are available. Modifications of these methods are available as well.

Materials and Methods

Evaluation of General Toxicity

Mouse body weight is determined at baseline, before each drug administration and every week up to 8 weeks. In addition, mice are also examined daily for evaluation of general health including observation for signs of hair loss, piloerection, general gait weakness, condition of the hind paws and tail skin, and gastrointestinal disorders.

Ear cavity temperature is measured using an infrared thermometer (model IRT303HACCP, National Product, MD) at baseline and after weeks 1, 3, 6, and 8 prior to performing the behavioral tests. Core body temperature is measured using a rectal probe (Thermalert TH-5 and TCAT-IA Controller, Physitemp Instruments, Inc.) at baseline and after weeks 1, 3, and 6 in two mice from each drug treatment group after brief anesthesia with isoflurane or equivalent.

The nephrotoxicity of cisplatin and oxaliplatin is assessed by blood urea nitrogen (BUN) levels in samples collected at the end of the 3-week drug treatment. Based on normal mouse BUN values (8-33 mg/dL according to normal reference laboratory values from Research Animal Resources at the University of Minnesota-http://www.ahc.umn.edu/rar/refvalues.html; values as reported for normal untreated C57BL/6 mice). BUN levels >40 mg/dL were used as an indication of developing nephrotoxicity.

Behavioral Testing

The order of testing is designed to ensure that the least stressful test is done first and to minimize the influence of one test on the next test. After a 2-week acclimation, the mice are trained five times over one week with the specific training protocols to familiarize them with testing procedures prior to entering the study. For the von Frey and paw radiant heat test, mice are allowed to run freely in the apparatus for 20 min before beginning the test. For the tail immersion test, each mouse is loosely wrapped in a partially rolled, moist paper towel for one min; the practice episode is repeated for 3-4 times. For the grip strength test, each mouse is guided for 5 min to pull the trapeze of the grip strength meter 3-4 times. No training is used for the cold plate apparatus. All behavioral tests are carried out in groups of 4-6 experimental mice at baseline, after completion of each drug treatment cycle at weeks 1 and 3, and follow up evaluation at weeks 6 and 8. All behavioral tests are conducted at room temperature (25° C.) and between the hour of 0900 and 1600 by one experimenter who is blinded to the drug treatment condition.

Activity Monitoring

Monitoring of locomotor activity is carried out at baseline, during drug treatment at weeks 1, 2, 3, and after treatment at weeks 6, 8, and 10 using VersaMax Animal Activity Monitors (AccuScan Model RXYZCM-16, Columbus, Ohio). The activities of six mice are simultaneously evaluated in six individual open chambers. Mice are allowed to run freely for 5 min prior to behavioral recording for 20 min in the open chamber made of a Plexiglas box (42×42×30 cm) with wood chip bedding. The VersaMax monitor has infrared sensors located every 2.54 cm along the perimeter (16 infrared beams along each side) and 2.5 cm above the floor. Although the VersaMax monitor collects information in 21 behavioral categories, distance traveled is collected in 1-min intervals, collapsed into 10 2-min blocks, averaged and presented as group means±SEM.

Grip Strength Test

Grip strength is measured using a grip strength meter (Stoelting, Wood Dale, Il) as previously described. The grip strength meter consists of a force transducer with digital display and a metal plate with a trapeze. Each mouse is placed on the plate and is pulled by its tail with increasing force until it is unable to grasp the trapeze and the grip is broken. The instrument digitally captures and displays the peak pull-force achieved. Muscle strength is defined as the peak weight (g) indicated on the display. The value is determined individually as the mean of three trials and presented as group mean±SEM.

Cold Plate Assay

Temperatures ranging from −5° C. to 4° C. at 1° C. intervals are used to examine the threshold for cold hyperalgesia in mice. Greater reproducibility is obtained when counting the number of paw lifts in a defined period. In preliminary dosing studies, oxaliplatin-treated mice developed significant cold hyperalgesia between −5° C. and −3° C. A temperature sensor is placed directly on the surface of the metal plate to ensure accurate temperature reading (TECA, Chicago, Ill.). For each cold testing session, mice are brought to the testing room and allowed to acclimate for 10 min prior to being individually placed onto the cold metal surface enclosed within a clear plexiglass barrier of 8 cm W×14 cm D×14 cm H with a top cover. To ensure the accuracy of paw lift counting, each cold plate testing session is videotaped using a video camcorder (Sony DCR-PC 1000) and the video is replayed in slow motion. The total number of brisk lifts of either hind paw or jumping is counted as the response to cold hyperalgesia. Movements associated with locomotion are distinct, involving coordinated movement of all four limbs and these should be excluded. Mice are only tested once on any given test day to avoid any possible anesthetic or tissue damage effects that could be produced by repeated exposure to a cold surface. A maximum cut off time of 5 min is used to prevent tissue damage. Three separate trials are carried out on three separate days at base line and two separate trials during and after drug treatment at weeks 1, 3, 6, and 8 are averaged and presented as the mean number of paw lifts.

Von Frey Filament Assay

For the assessment of mechanical allodynia, an Ugo Basile Dynamic Plantar Aesthesiometer (Stoclting. Wood Dale, Il) using the von Frey filament principle is used. Mice are placed under clear plastic boxes above a wire mesh floor that allowed full access to the paws. Acclimation and exploratory behavior are observed for up to two hours until mice become calm and close to motionless. The operator then places the touch stimulator apparatus under each mouse's hind paw and positions the calibrated metal filament below the target area of the hind paw. After pressing the start key, an electrodynamic actuator of the apparatus lifts the metal filament (diameter of 0.5 mm). The filament touches the plantar surface and exerts a continuous vertical force of 0 to 5 g over a 10 s interval until the hind paw withdraws and activates a stop signal. The instrument automatically registers the weight intensity threshold in g that triggers paw withdrawal. Each hind paw is tested alternately with an interval of 5 min for four trials. Paw movement associated with locomotion or weight shifting is not counted as withdrawal responses. Paw withdrawal threshold of eight trials from both hind paws of each mouse are averaged and recorded as mean±SEM.

Radiant Heat Assay

For the assessment of thermal hyperalgesia, a Hargreaves' test [16] is conducted using a Plantar Ugo Basile apparatus (Stoelting, Wood Dale. II). Mice can move freely in this apparatus on an elevated glass surface with plastic boxes above as the top cover. Mice are given a two hour acclimation period prior to testing until they become calm and motionless. A calibrated infrared light source of high intensity is applied perpendicular on the plantar surface of each mouse's hind paw. The rising temperature on the bottom of the hind paw causes the mouse to move its paw; the change in paw position alters reflected light and stops the timer. Latency to paw withdrawal is automatically recorded for each trial. If the mouse does not withdraw its hind paw within 15 s, the testing trial terminates to prevent tissue damage and 15 s is recorded. Each hind paw is tested alternately with an interval of 5 min for four trials. Paw withdrawal latency of eight trials from both hind paws of each mouse is averaged and recorded as mean±SEM.

Tail Immersion Assay

For assessment of tail thermal hyperalgesia, a tail immersion test is conducted as previously described with modifications. For each testing session, mice are brought to the testing room and each is individually acclimatized three to four times in a moist paper towel for a minute duration without tail immersion. Next, each mouse is swiftly and gently wrapped in a slightly moist paper towel and held in the investigator's hand with minimal restraint to allow the distal one-third of the tail to be immersed in a water bath. The water bath is preset at 50.5°±0.5° C. and the temperature is verified with an independent extra temperature sensor. Only when the mouse is calm and its tail is relaxed, is the next step of tail immersion pursued. If the mouse becomes agitated, it is unwrapped and the testing protocol restarted. Latency to vigorous tail flick is recorded during three trials separated by at least 30 min, and three trials are averaged and presented as mean±SEM. Cutoff time is set at 20 s, after which mouse is removed regardless of behavioral response.

Use of Buflomedil to Prevent or Treat Neurotoxicity of Oxaliplatin in Mice

How buflomedil will prevent or treat neurotoxicity in oxaliplatin induced peripheral neuropathy model of mice will be measured as described above and using the complete methodology described in Ta et al 2009[18]).

Thermal sensitivity associated with a single IP dose of oxaliplatin (40 or 5 mg/kg) in male wild-type mice is assessed by a cold-plate test. The number of paw lifts and licks when exposed to a temperature of −4, 4, or 30° C. for 5 min is obtained for each mouse at 120 and 24 h before receiving oxaliplatin to determine the number of baseline events. Data are recorded as the percentage change in the number of paw lifts or paw licks compared with baseline values when the animals are exposed to the same temperature 24 or 48 h after the administration of oxaliplatin. Mechanical allodynia is determined by a Von Frey Hairs test. Mice are left to acclimate on a mesh platform and in 100×60 mm cylindrical tubes before the force necessary for a rigid Von Frey hair filament (IITC Life Science) to induce paw withdrawal of the hind limbs is assessed for each mouse at 120 and 24 h before receiving oxaliplatin to determine baseline events. Paw withdrawal is assessed in triplicate on each hind paw with 5-min intervals between repeating the test on each mouse and alternating from the left paw to the right paw. Data are also recorded as the percent change of force (in grams) necessary to promote paw withdrawal before and after the administration of oxaliplatin. In subsequent experiments, the administration of oxaliplatin (5 mg/kg) is preceded by IV injection of buflomedil at several doses. Alternatively, buflomedil can also be administered orally. In other experiments, buflomedil is actually administered 24 h before the administration of oxaliplatin, such that prevention properties could be observed.

Example 8

The following example relates to the use of buflomedil to prevent or treat neurotoxicity of oxaliplatin in Oct1/2(−/−) mice.

Whether buflomedil will prevent or treat neurotoxicity in oxaliplatin induced peripheral neuropathy model of mice with both wild type and Oct1/2(−/−) mice is measured using the materials and methods are described above in Example 7 and the complete methodology is described in [18].

Thermal sensitivity associated with a single IP dose of oxaliplatin (40 or 5 mg/kg) in male wild-type mice and age-matched male Oct1/2(−/−) mice is assessed by a cold-plate test. The number of paw lifts and licks when exposed to a temperature of −4, 4, or 30° C. for 5 min is obtained for each mouse at 120 and 24 h before receiving oxaliplatin to determine the number of baseline events. Data are recorded as the percentage change in the number of paw lifts or paw licks compared with baseline values when the animals are exposed to the same temperature 24 or 48 h after the administration of oxaliplatin. Mechanical allodynia is determined by a Von Frey Hairs test. Mice are left to acclimate on a mesh platform and in 100×60 mm cylindrical tubes before the force necessary for a rigid Von Frey hair filament (IITC Life Science) to induce paw withdrawal of the hind limbs is assessed for each mouse at 120 and 24 h before receiving oxaliplatin to determine baseline events. Paw withdrawal is assessed in triplicate on each hind paw with 5-min intervals between repeating the test on each mouse and alternating from the left paw to the right paw. Data are also recorded as the percent change of force (in grams) necessary to promote paw withdrawal before and after the administration of oxaliplatin. In subsequent experiments, the administration of oxaliplatin (5 mg/kg) is preceded by IV injection of buflomedil at several doses. Alternatively, buflomedil can also be administered orally. In other experiments, buflomedil is actually administered 24 h before the administration of oxaliplatin, such that prevention properties can be observed.

Example 9

The following example relates to the use of buflomedil to protect against cisplatin nephrotoxicity.

Male wistar rats are treated systemically (IV) with PBS, cisplatin (11 mg/kg), buflomedil (dose to be determined)+ Cisplatin (11 mg/kg) or buflomedil (5.5 mg/kg) alone, 72 hrs post treatment blood is collected and analyzed for serum BUN (blood urea nitrogen) and serum creatinine values.

It is expected that serum BUN values will increase with cisplatin treatment, while co-administration of buflomedil with cisplatin lowers the BUN values. Serum creatinine values should also increase significantly with cisplatin treatment, however buflomedil co-administration with cisplatin should result in lower creatinine levels. Buflomedil treatment alone should not change the serum creatinine values significantly when compared to control PBS-treated values.

Example 10

The following example relates to the use of buflomedil to prevent ototoxicity for both oxaliplatin and cisplatin in trans-tympanic rat models.

Platinum drugs cause ototoxicity. Auditory brainstem responses (ABRs) have been measured prior to cisplatin or oxaliplatin administration (pretreatment ABRs), and 72 hours following cisplatin administration (post-treatment ABRs). A bar graph of auditory brainstem responses (ABR) threshold shifts (dB) observed under the different treatment conditions indicating that cisplatin induces hearing loss, as evidenced by 20-35 dB shifts in thresholds, has been shown by others. It is expected that these threshold shifts could be abolished by buflomedil treatment at all frequencies tested. Treatment with buflomedil alone should not affect the ABR thresholds.

Buflomedil can be administered trans-tympanically to limit the concern that it could interfere with the anticancer effects of platinum drugs. Trans-tympanic administration of drugs is the use of localized application of drugs to prevent hearing loss. This route of drug administration reduces the likelihood that the drug will get into the systemic circulation and produce side effects or cause drug-drug interactions. The ease of drug delivery via the trans-tympanic route means that it can be readily performed on individuals in the out-patient setting. The use of ventilation tubes in the tympanic membrane would allow for more episodic administration of buflomedil in children prior to administering chemotherapeutic regimen with oxalipatin.

Pre-treatment ABRs are conducted on Wistar rats, which are then pre-treated with vehicle or trans-tympanic buflomedil (dose of the solution to be determined) followed by cisplatin (11 mg/kg, IP) or by oxaliplatin over a 30 min infusion period. Post-treatment ABRs are conducted 72 h later.

It is expected that trans-tympanic buflomedil will abolish cisplatin and oxaliplatin-induced hearing loss in rat model over all the three frequencies tested in the vehicle-pretreated groups. Scanning electron photomicrographs will provide a morphological analysis of the three rows of outer hair cells of the organ of Corti to detect substantial outer hair cell damage. This damage should be abrogated by trans-tympanic administration of buflomedil.

Example 11

The following example relates to a xenograft showing that both the reduction of nephrotoxicity of cisplatin and retention of cisplatin activity in osteosarcoma cells is applicable to other cell lines including cell lines from colon and liver cancer.

Materials and Methods

Seven-week-old male Fischer rats and male Wistar rats are divided into four groups (3 to 5 rats in a group): saline-injected control group (saline), buflomedil-alone group intravenously (IV) injected buflomedil via a jugular vein by bolus injection (dose to be determined mg/kg) and continuous infusion using a microsyringe pump under light ether anesthesia (buflomedil alone), cisplatin-alone group intraperitoneally (IP) injected 1.75 mg/kg of cisplatin for tumor bearing rats or 7 mg/kg of cisplatin for rats without tumor (cisplatin alone) and combined treatment group injected cisplatin just before buflomedil injection (cisplatin buflomedil). The doses of cisplatin for tumor-bearing and un-bearing animals are the doses that show moderate antitumor effect against SOSN2 osteosarcoma and marked nephrotoxicity, based on the results of the preliminary experiments. Similar studies can be conducted to determine what dose of cisplatin is required to have an effect on various cell lines including HT-29 for colon cancer and selected liver cancer cell lines (see ref for full review [1]) for hepatocellular carcinoma.

The animals are housed in a climate- and light-controlled environment with free access to water and food. Male Fischer rats are inoculated with a SOSN2 tumor block (about 10 mm3) subcutaneously on the back. Alternatively they are inoculated with colon or liver cancer cell lines. When tumor size reached about 300 $mm^3$, drug treatments (cisplatin; 1.75 mg/kg. IP, buflomedil according to the protocol) are performed. The tumor size is measured every day for 16 d, as below.

Tumor size $(mm^3) = \frac{1}{2} \times$ major axis $\times$ (short diameter)$^2$ Male Wistar rats without tumors are treated with cisplatin (7 mg/kg) and buflomedil (according to the protocol indicated), and blood samples (400 ml) are collected from the tail vein under light anesthesia every day: the rats are killed by cervical dislocation under deep ether anesthesia on day 5. Urine is collected for 24 h on the last day of the experiment. Creatinine and blood urine nitrogen (BUN) are measured in our laboratory using commercial kits, and other biochemical analyses are performed.

Measurement of Buflomedil Serum Concentration

One hundred microliters of the serum sample, 25 ml of the internal standard ranitidine (100 mg/ml), and 100 ml NaOH (5 N) are mixed and buflomedil is extracted with 3 ml methylene chloride, dissolved with 100 ml of the mobile phase (5% acetonitrile/0.002 M triethylamine and 0.025% acetic acid), and measured using high-performance liquid chromatography at 228 nm. Cells are cultured in RPMI-1640 medium (Sigma) supplemented with 10% fetal bovine serum (Sigma) and 600 mg/ml kanamycin sulfate (Meiji Seika Co., Tokyo, Japan) in an atmosphere of 5% CO2 at 37° C. Cells (2.5-5103 cells/100 ml/well) are seeded onto 96-well plates, and after 24 h, treated with varying concentrations of cisplatin in the presence or absence of buflomedil (0.5, 1 mM) or NAC (3 mM) for 48 h. After treatment, cell viability is measured using the Cell Counting Kit-8, based on the reduction activity of mitochondria dehydrogenases, according to the manufacturer's instructions.

Cellular Uptake of Cisplatin

For the measurement of cisplatin uptake, confluent growing cells in 100 mm culture dishes are incubated with medium containing cisplatin (500 mM) with or without buflomedil (1 mM) for 2 h. After treatment, the cells are rapidly washed twice with phosphate-buffered saline, then solubilized by 0.5 N NaOH, and the protein content of the cell is determined with a Dc Protein Assay Kit (Bio-Rad Laboratories, Richmond. Calif., U.S.A.). Cell fluid solubilized with NaOH is diluted with deionized Milli-Q water (Millipore, Billerica, Mass., U.S.A.) five times. Elemental platinum concentrations are measured by flame atomic absorption spectrometry on a model AA-6800 Atomic Absorption Spectrometer (Shimadzu Corporation, Kyoto. Japan). The absorbance of atomized platinum is measured at 14 mA and a wavelength of 265.9 nm with a 0.5-nm slit width. Integrated absorbance with a read time of 5 s is recorded. The standard curves are linear over a range of 0.5 to 50 mg/ml. All measurements are performed in triplicate. The cellular platinum levels are expressed as mg platinum per mg protein. Other technologies including mass spectrometry using platinum chelates could be used as well to measure the platinum concentrations.

In Vivo Experiments

In experiments described by others [14], serum concentrations of cisplatin after IP injection (3.5 mg/kg) into rats resulted in a 24 h half-life, but cisplatin accumulated in the kidney for 48 h. Due to this rapid clearance documented in rats, high serum concentrations of buflomedil after cisplatin injection should be maintained by an IV bolus injection and continuous infusion for 4 h. The serum concentration of buflomedil can be maintained at adequate levels for 4 h using this injection protocol.

Initially, whether this buflomedil dosage influences the antitumor effect of cisplatin will be examined. Typically, cisplatin significantly inhibits tumor growth, and at 16 d after treatment, the tumor mass of the cisplatin-alone group is one-third that of the control group. We expect that buflomedil should have little influence on tumor growth in the control group or in combination with cisplatin.

Next, a nephrotoxic dose of cisplatin (7 mg/kg, IP) is administered to non-tumor rats, and the effect of buflomedil on the kidney function will be examined. After administering cisplatin, kidney weight is typically significantly elevated, and this increase should be restrained by the addition of buflomedil, which when administered alone should not affect kidney weight. The serum creatinine and BUN levels should significantly increase after the third day of cisplatin injection, and buflomedil co-administration should significantly inhibit the increase of these biomarkers. As a result, rats are expected to suffer serious renal damage 5 d after treatment with cisplatin, and the combined treatment with buflomedil should clearly reduce the damage.

In histopathology, necrotic and apoptotic changes in the epithelium cell of the renal tubule in the cisplatin treated group should be analyzed and the degree and range of the injury should decrease by the combination of buflomedil.

Example 12

The following example relates to a assessing neurotoxicity in tumor-bearing mice treated with oxaliplatin in the presence or absence of buflomedil. A similar experiment could be performed with dolutegravir or miconazole or any other imidazole derivatives The Use of Mice Models Several studies have examined the neurophysiological, behavioral and pathological characteristics of oxaliplatin-induced peripheral neurotoxicity using rat models (Authier N. et al. Neurotherapeutics, 2009; 6:620-629), and most of the oxaliplatin-induced pain studies have been done after a single injection of the drug. While rats developed significant cold and mechanical allodynia following a single dose of oxaliplatin, these models are not representative of the chronic neurotoxicity experienced in clinical practice (Joseph E K, Levine J D. J Pain. 2009; 10:534-541). Cavaletti et al. (Eur J Cancer. 2001; 37:2457-2463) have demonstrated that chronic oxaliplatin treatment in rats induced atrophy of dorsal root ganglia (DRG) neurons and decreased peripheral sensory nerve conduction velocities (NCV). Moreover, chronic oxaliplatin treatment induced cold and heat hypersensitivity along with mechanical allodynia that persisted for 3 weeks after drug treatment ended (Ling B et al. Pain. 2007:128:225-234). The use of rat models to study oxaliplatin-induced neurotoxicity has been very informative. However, since it is difficult to implant tumors in rats, most studies of the anticancer properties of oxaliplatin have used mice. Thus, rat models have limited efficacy for investigations of peripheral neurotoxicity in the same experimental paradigms used to evaluate the anticancer activity of oxaliplatin.

The Use of Sophisticated Neuropathic Mice Models are More Representative of the Pathology Observed in Humans Recently, several mouse models of oxaliplatin-induced pain have been developed using an acute, single dose or chronic, repeated doses of oxaliplatin (Gauchan P et al. Neurosci Lett. 2009; 458:93-95). While these studies demonstrated the development of mechanical and cold allodynia after oxaliplatin treatment, the characterization of peripheral neurotoxicity was limited. To address these limitations various studies performed in BALB/c mice treated with a schedule of oxaliplatin were able to induce the onset of a painful neuropathy with the aim to achieve a more complete characterization of the peripheral and central nervous system events induced by the chronic treatment (Renn. C. L. et al., Mol Pain, 2011, 7, 29).

The following experiments can be conducted in tumor-bearing mice both in the presence and absence of buflomedil or other OCT-2 inhibitors with the goal to reduce neurotoxicity while preserving anti-tumor properties of oxaliplatin.

General Appearance and Body Weight Change

To generate the model of oxaliplatin-induced painful peripheral neuropathy used in this study, the mice are given tail vein injections of oxaliplatin (3.5 mg/kg) twice weekly (separated by either 3 or 4 days) for four weeks. The control group is naïve mice that do not receive drug or vehicle injections. The duration of this study is 21 days, preferably 30 days during which the mice are continuously allodynic after receiving oxaliplatin. The oxaliplatin is generally well-tolerated by the mice. The mice are weighed on drug administration days and, over the course of the study, the oxaliplatin-treated mice will have a significant decrease in body weight compared to the naïve mice reaching about 15% by the completion of the study.

Neuropathological Analysis

Nerve conduction velocities (NCV) and action potential amplitude are measured in the caudal and digital nerves 4 days after the final oxaliplatin dose. Chronic oxaliplatin treatment should induce a significant decrease in the caudal NCV with a concomitant significant decrease in action potential amplitude compared to the naïve group.

Morphological Analysis of DRG and Sciatic Nerve

To determine whether the altered function of peripheral neurons after oxaliplatin are accompanied by structural changes in the DRG cell bodies and axons of the sciatic nerve, thin sections through the L4-L5 DRGs and sciatic nerve from naïve and oxaliplatin-treated mice are examined at the light and electron microscope levels two days after the final dose of drug in week four. Particular attention will be given to differences between oxaliplatin treated and non-treated animals. Examination of sciatic nerves by light microscope will allow clear observation of the state of myelinated fibers in the sciatic nerve of oxaliplatin-treated mice compared to naïve animals.

Previous work in rat models demonstrated that platinum-derived compounds induce DRG neuron cell body shrinkage (Carozzi V A et al. Exp Neurol. 2010; 226:301-309). Since finding that oxaliplatin induced changes to the nucleoli of DRG neurons in mice model, a morphometric analysis was performed to examine the cell bodies of DRG neurons from oxaliplatin-treated (3.5 mg/kg/iv twice weekly for four weeks) and naïve control mice for evidence of cell body shrinkage similar to that seen in rats. The morphometric analysis revealed that DRG neurons from oxaliplatin-treated mice had a significant decrease in the area (mm2) of their cell bodies and nucleoli but not nuclei, compared to DRG neurons from naïve mice (black bars). Morphological analyses are therefore recommended both in presence and absence of OCT2 inhibitors like buflomedil, dolutegravir and miconazole to demonstrate potential protection from oxaliplatin toxicity.

Reducing Neurotoxicity with Buflomedil Concurrent with Retention of Anti-Tumor Activity in Tumor Bearing Mice Model Treated with Oxaliplatin.

As shown in the previous examples, buflomedil clearly reduced the neurotoxicity induced by oxaliplatin in several mice models. The intent now is to demonstrate that such reduction of neurotoxicity does not interfere with the anti-tumor activity of oxaliplatin in both colon and liver xenografts mice models.

Four-week-old male BALB/c nude mice are used for that particular experiment. Mice are housed under specific pathogen-free conditions; food and water are provided ad libitum. After the animals have been in quarantine for one week, they are implanted subcutaneously with a human colorectal tumor cell line like HT-29 or HepG2 (human liver carcinoma) cells, the volume of which is approximately 8 mm3.

To evaluate the antitumor activity, the mice are grouped according to the tumor volume once the mean tumor volume reached about 150 to 200 mm3 (day 0). Each group consisted of 7 to 9 mice.

The tumor diameters are measured twice a week until day 21, and the tumor volume is estimated as 0.5×length×width2. The relative tumor volume (RTV) is calculated using the following formula: RTV=(tumor volume on measured day)/(tumor volume on day 0). On day 15, the tumor growth inhibition ratio (TGI) is calculated using the following formula: TGI=[1−(mean tumor volume of treated group)/(mean tumor volume of control group)]×100. The body weight change (BWC; %) is calculated as [(body weight on day 15)−(body weight on day 0)]/(body weight on day 0)×100(%). The growth delay period (GDP), which indicates the difference in the period during which the RTV grew to 4 (corresponding to 50% of the size of the control tumors at the endpoint on day 21), is determined according to a previously reported procedure (Balin-Gauthier D, et al, Cancer Chemother Pharmacol 7: 709-718, 2006)

Toxicity is defined as a 20% or more body weight loss or toxic death. Whether buflomedil will prevent or treat neurotoxicity in oxaliplatin-induced peripheral neuropathy model of mice with tumor bearing mice is measured using the materials and methods described above in Examples 7 and 8. Neurotoxicity can also be measured by any of the experimental methods described at the beginning of this example and comprising morphological analysis of DRG and neurons, neuropathological analysis, measure of body weight, and general appearances.

More specifically, neurotoxicity could be assessed by thermal sensitivity associated with a single IP dose of oxaliplatin (40 or 5 mg/kg) in tumor bearing mice using a cold-plate test. The number of paw lifts and licks when exposed to a temperature of −4, 4, or 30° C. for 5 min is obtained for each mouse at 120 and 24 h before receiving oxaliplatin to determine the number of baseline events. Data are recorded as the percentage change in the number of paw lifts or paw licks compared with baseline values when the animals are exposed to the same temperature 24 or 48 h after the administration of oxaliplatin. Mechanical allodynia is determined by a Von Frey Hairs test. Mice are left to acclimate on a mesh platform and in 100×60 mm cylindrical tubes before the force necessary for a rigid Von Frey hair filament (IITC Life Science) to induce paw withdrawal of the hind limbs is assessed for each mouse at 120 and 24 h before receiving oxaliplatin to determine baseline events. Paw withdrawal is assessed in triplicate on each hind paw with 5-min intervals between repeating the test on each mouse and alternating from the left paw to the right paw. Data are also recorded as the percent change of force (in grams) necessary to promote paw withdrawal before and after the administration of oxaliplatin. In subsequent experiments, the administration of oxaliplatin (5 mg/kg) is preceded by IV injection of buflomedil at several doses. Alternatively, buflomedil can also be administered orally. In other experiments, buflomedil is actually administered 24 h before the administration of oxaliplatin, such that prevention properties can be observed. The assessment of neurotoxicity is performed in parallel with the assessment of tumor reduction, therefore, in addition to the measures performed prior to adding oxaliplatin, it is recommended to perform such assessment at 24, 48, 72 hours and at day 7, 14 and 21. After initial treatment, the tumor volume is measured twice a week continuously until day 21.

It is expected that administration of oxaliplatin will show significant antitumor activity against both colon and liver xenograft models. It is also expected that several mice could die from oxaliplatin exposure independently from the effect on neurotoxicity. Finally, it is expected that anti-tumor activity of oxaliplatin observed by measuring change in tumor volume and body weight for both colon and liver tumor cells measured in absence of buflomedil will be similar to the anti-tumor activity of oxaliplatin in presence of buflomedil, preferentially with measurable reduction of neurotoxicity as defined in the examples above and in at the beginning of this example.

Example 13

The following example relates to the measurement of buflomedil plasma concentration in Balb/C mice via intravenous (IV) and intraperitoneal (IP) administration.

Experiments

Test article Buflomedil was prepared in 5% glucose formulation at 2 mg/mL (for IV) or 4 mg/ml (for IP). Male mice of 7-8 weeks of age were allowed to acclimate for 6 days. Three mice were administered 10 mg/kg of buflomedil via intravenous injection. Three mice were administered 20 mg/kg, three mice were administered 40 mg/kg of buflomedil intraperitoneal injection. Blood was collected at 0.083, 0.5, and 1 hour into Heparin tubes. The plasma was obtained through centrifugation of the blood at 4000 rpm at 4° C.

For plasma sample analysis, the samples were thawed and mixed well before 20 L aliquots were processed using protein precipitation by internal standard (Verapamil) containing organic solution, methanol: acetonitrile 5:95 (v/v).

After vigorous vortexing and refrigerated centrifugation at 4000 rpm, 50 μL of the extract from each sample was reconstituted with 70 μL of 0.1% formic acid in water. Calibration standards were prepared by first serial diluting the 2 mg/mL Buflomedil stock solution with 70% acetonitrile and then spiking the solutions into blank plasma. The calibration curve was extracted in the same way as the plasma samples. The final extracts were analyzed by LC-MS/MS using positive electrospray ionizations under the multiple-reaction-monitoring (MRM) mode for the detection of buflomedil. The standard curve fitted by linear regression was used to quantify the analyte in the matrix using Analyst 1.5.2 software (AB Sciex) Results The bioanalytical method was successfully established to measure buflomedil concentrations in mouse plasma. The lower limit of quantitation (LLOQ) was 0.5 ng/mL. The buflomedil plasma levels are represented in FIG. 17A. The results show the average buflomedil plasma concentration in the mice of each group remained above 2 mg/l at 10 minutes after IV/IP administration. The results further suggest that the estimated bioavailability of IP administration is between 40-60%.

Example 15

The following example relates to the measurement of dolutegravir plasma concentration in Balb/C mice via oral (PO), intravenous (IV) and intraperitoneal (IP) administration.

Experiments

Test article dolutegravir was prepared in DMSO:50 mM N-methylglucamine with 3% Mannitol formulation (1:19 v/v) at 1 mg/mL. Male mice of 6-7 weeks of age were obtained from Charles River and allowed to acclimate for 3-5 days. The mice were weighed and individually identified (tail marked). The mice (n=3) in the oral (PO) group were fasted overnight and orally gavaged with 10 mg/kg of Dolutegravir. The second group of mice (n=3) were intravenously (IV) injected with 4 mg/kg of Dolutegravir. The third group of mice (n=3) were intraperitoneally (IP) injected with 4 mg/kg of Dolutegravir. At 10 min, 0.5 h, 1 h post dosing, ~120 μl of blood sample was collected from the IV and IP mice by orbital venous sinus bleeding. At 1 h, 2 h, 4 h post dosing, ~120 μl of blood sample was collected from the PO mice by orbital venous sinus bleeding. The plasma was harvested by centrifugation of blood samples at 4000 rpm at 4° C. for 10 minutes and stored in dry ice.

For analysis, the plasma samples were diluted into the calibration range as needed. Aliquot of 20 μL of each plasma sample was treated with 100 μL of internal standard (Verapamil) containing organic solution, methanol: acetonitrile 5:95 (v/v). After vigorous vortexing and refrigerated centrifugation at 4000 rpm, 50 μL of the supernatant from each sample was transferred to the injection plate and reconstituted with 70 μL of 0.1% formic acid in water. Calibration standards were prepared by first serial diluting 2 mg/mL Dolutegravir stock solution with 70% acetonitrile and then spiking the solutions into blank plasma. The calibration curve was extracted in the same way as the unknown samples. The final extracts were analyzed by LC-MS/MS using positive electrospray ionizations under the multiple-reaction-monitoring (MRM) mode for the detection of Dolutegravir. The standard curve fitted by linear regression was used to quantify the analyte in the matrix using Analyst 1.6.2 software (AB Sciex).

Results

The dolutegravir plasma levels are represented in FIG. 17B. The results demonstrate that the route of administration significantly affected dolutegravir plasma exposure in mice.

Example 14

The following example relates to assess the neuroprotective effects of buflomedil, administered via IV and IP injection, in Balb/c mice exposed to chronic treatment with Oxaliplatin.

SUMMARY

At the beginning of the study, 48 male Balb/c mice were randomized into 4 experimental groups: one group was left untreated (CTRL, n=12), one group was treated with Buflomedil (BFMD, n=12), one group was treated with Oxaliplatin (OXA, n=12), and one group was co-treated with Oxaliplatin and Buflomedil (OXA+BFMD, n=12).

At baseline (before drug treatment) and at the end of treatment, caudal nerve conduction study (NCS), behavioral tests (Dynamic and Cold Plate), histopathology study were performed. Serum samples were collected at the end of treatment.

Figure 24:
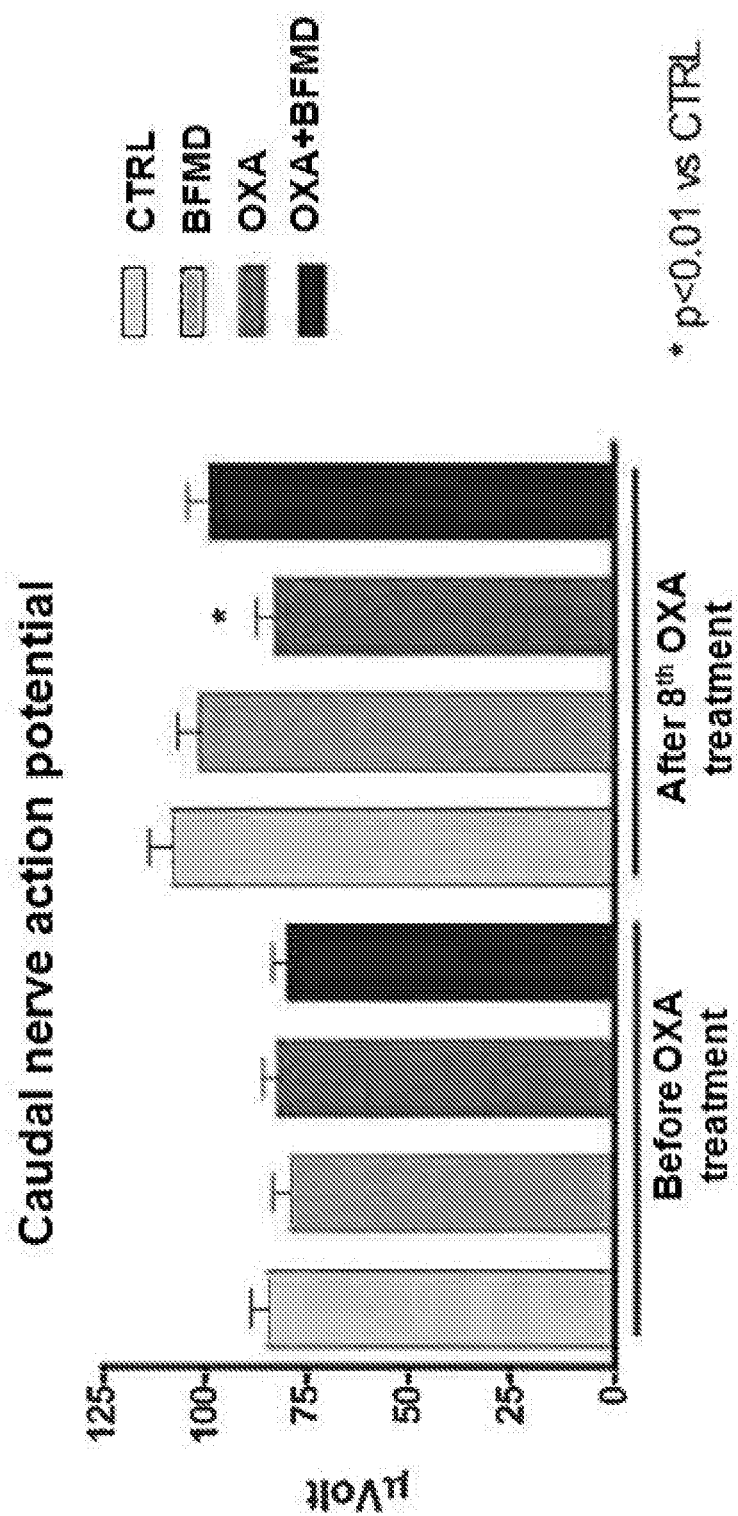
FIG. 24 depicts buflomedil was effective on reducing peripheral neurotoxicity in mice after 8 cycles of oxaliplatin treatment, based on electrophysiological assessment of caudal nerve action potential.
Figure 25:
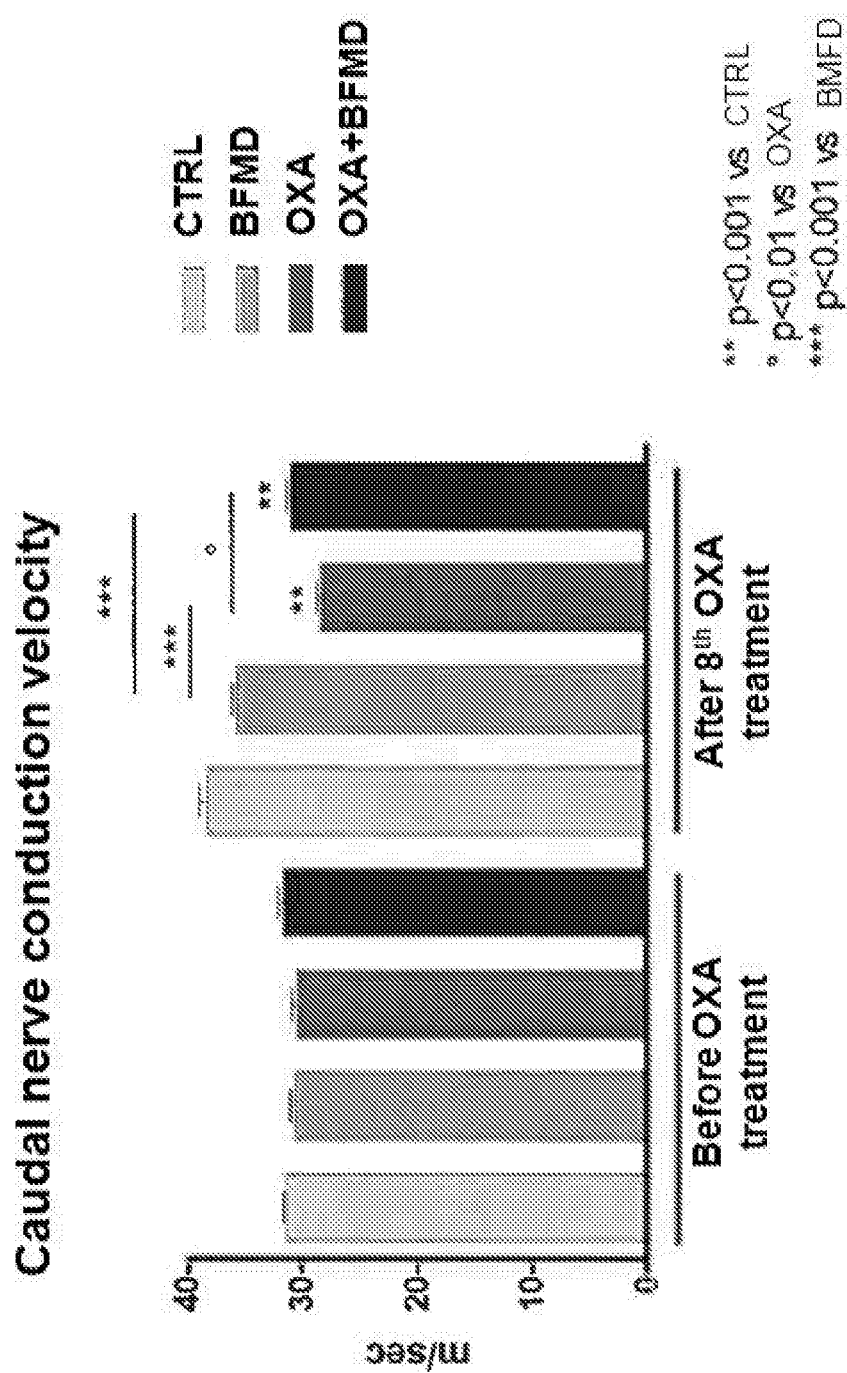
FIG. 25 depicts buflomedil is effective on reducing peripheral neuropathy in mice after 8 cycles of oxaliplatin treatment, based on electrophysiological assessment of caudal nerve conduction velocity (NCV).

This study showed that oxaliplatin induced peripheral neuropathy in the group of mice repeatedly treated with oxaliplatin, as evidenced by DRG nerve injury (FIG. 19-20), sciatic nerve injury (FIG. 21), mechanical allodynia (FIG. 22), cold allodynia (FIG. 23), and reduced caudal nerve action potential (FIG. 24) and nerve conduction velocity (FIG. 25). Buflomedil was effective on reducing OXAIPN in the OXA+BFMD group, compared with the OXA only group. Particularly, morphology examination and morphometric assessment of DRG nerves showed that BFMD nearly completely prevented OXA's induced DRG neuronal injury, which is the hallmark of OXAIPN. Behavioral and NCS tests also demonstrated that Buflomedil was effective on reducing OXAIPN.

Plasma level analysis of Buflomedil and Oxaliplatin confirmed that Buflomedil was at an effective level that was expected to significantly inhibit OCT2 mediated oxaliplatin transport, and oxaliplatin plasma level was not affected by buflomedil. All these results suggested that in this study, buflomedil might be effective on abolishing OCT2 mediated oxaliplatin accumulation in DRG, thus alleviating both the acute (cold allodynia) and chronic (mechanical allodynia and NCS) forms of OXAIPN through minimizing neural damage at least in DRG.

Study Aim

Buflomedil was discovered by us as a potent and specific inhibitor of OCT2-mediated OXA transport (EXAMPLE 1); for this reason the purpose of this study was to verify if the inhibition of OCT2-mediated OXA transport by Buflomedil is able to reduce the severity of OXA-induced neuropathy in an established OXAIPN model (Renn C L., Mol Pain, 2011, 7.29).

Materials and Methods

Animals were subjected to a physical examination (health check) shortly after arrival.

The care and husbandry of animals were in conformity with the institutional guidelines in compliance with national (D.L, n. 26/2014) and international laws and policies (EEC Council Directive 86/609, OJ L 358, 1. Dec. 12, 1987: Guide for the Care and Use of Laboratory Animals, U.S. National Research Council, 1996).

Study Design

The study designed is represented in FIG. 18

Overall Experimental Plan

| Treatment groups | Animal numbers |
|---|---|
| Control untreated animals (OXA) | 1-12 |
| Buflomedil 30 mg/kg, ip + 15 mg/kg, iv (BFMD) | 13-24 |
| Oxaliplatin 3.5 mk/kg (OXA) | 25-36 |
| Oxaliplatin 3.5 mk/kg + BFMD 30 mg/kg, ip + 15 mg/kg, iv (OXA + BFMD) | 37-48 |

OXA was administered via the tail vein (iv). Intraperitoneal Buflomedil (ip) was injected 15 min before the co-administration of OXA and BFMD intravenously (iv)

Dose Selection Justification

Dosage and route of administration of Buflomedil were determined, based on the data obtained from EXAMPLE 13, to achieve a target buflomedial plasma concentration greater than 1.72 mg/l during the course of oxaliplatin administration. At such concentration, buflomedil is estimated to achieve >90% OCT2 inhibition based on in vitro data from EXAMPLE 1. Dosage of Oxaliplatin was chosen based on previous experience and the literature data (Renn C L., Mol Pain, 2011, 7, 29).

Study Schedule

| Major activities | Study day/week/month, time point |
|---|---|
| Mortality | Daily |
| Clinical signs | Daily |
| Body weight | Two times a week |
| Tissue sampling | At the end of $4^{th}$ weeks of treatment |
| Behavioral testing: Dynamic, Plantar and Cold Plate Test | At baseline and after $4^{th}$ weeks from the beginning of the study |
| Neurophysiology | After $4^{th}$ weeks from the beginning of the study |
| Pharmacokinetic analysis | After $1^{st}$ and $8^{th}$ administration of OXA and BFMD |
| Euthanasia | $CO_2$ inhalation at sacrifice |

Test Methods

Nerve Conduction Velocity

The development of peripheral neuropathy after chronic administration of drugs was assessed by evaluating the nerve conduction velocity (NCV) along caudal and digital nerve using an electromyography apparatus (Myto2 ABN Neuro, Firenze, Italy). Caudal NCV was determined by placing a couple of recording needle electrodes at the base of the tail and a couple of stimulating needle electrodes 3.5 cm distally to the recording points. Similarly, the digital NCV was determined by placing the recording electrodes close to the ankle bone and the stimulating electrodes close to the fourth toe near the digital nerve. The intensity, duration and frequency of stimulation were set up in order to obtain optimal results. All the neurophysiological determinations were performed under standard conditions in a temperature-controlled room (22+/-2° C.) and the animal under isoflurane anesthesia along the whole procedure with continuous monitoring of vital signs.

Behavioral Test: Dynamic Plantar Aesthesiometer Test

The Dynamic Plantar Aesthesiometer Test was used to determine the alterations in mechanical pain perception and their changes due to pharmacological treatment. Mice were accustomed to the device 3 days before performing the tests after a 1 hour acclimatization period followed by testing. The mechanical nociceptive threshold was assessed using a Dynamic Aesthesiometer Test (model 37450, Ugo Basile Biological Instruments, Comerio. Italy), which generated a linearly increasing mechanical force. At each time point, after the acclimatization period, a servo-controlled mechanical stimulus (a pointed metallic filament, 0.5-mm diameter) was applied to the plantar surface of the hind paw, which exerted a progressively increasing punctuate pressure, reaching up to 15 g within 15 seconds. The pressure evoking a clear voluntary hind-paw withdrawal response was recorded automatically and taken as representing the mechanical nociceptive threshold index. The mechanical threshold was always assessed alternatively on each side every 2 minutes on 3 occasions to yield a mean value. The results represent the maximal pressure (expressed in grams) tolerated by the animals. There was an upper limit cutoff of 30 seconds, after which the mechanical stimulus was automatically terminated.

Behavioral Test: Cold Plate Test

Cold Plate Test was used to determine the alterations in cold temperature related pain perception and their changes due to pharmacological treatment. Cold Plate Test was performed by using an apparatus (35100—Hot/Cold Plate. Ugo Basile instruments) composed by a Plexiglas cylinder and a thermostatic plate, able to reach variable temperatures. The mice were placed on the plate set at +4° C., free to move and walk. Two blinded experimenters simultaneously determine the number of pain signs (e.g. jumping, licking, etc.) in a trial of 5 minutes.

Neuropathological Analysis of DRG and Sciatic Nerve

The investigator was blind to the nerve and DRG conditions for these analyses. Three animals from each group were sacrificed four days after the last oxaliplatin dose. The left sciatic nerves and the L4-L5 DRGs were harvested and processed following previously reported protocols, resin embedded and sectioned for light and electron microscope analysis. For the light microscopy analysis, 1 µm semithin sections were stained with toluidine blue and examined using a Nikon Eclipse E200 light microscope (Nikon, Firenze, Italy). For the electron microscopy analysis, ultrathin sections (80 nm) counterstained with uranyl acetate and lead citrate, were examined with a Philips CM 10 transmission electron microscope (Philips, Eindhoven, Netherlands).

Morphometric Analysis of DRG Neurons

The investigator was blind to the experimental conditions of the tissue for these experiments. One micron thick semithin sections stained with toluidine blue were used for morphometric examination of the DRGs from control (n=3) and oxaliplatin-treated mice (n=3). (Renn et al. Molecular Pain 2011, 7:29). Only the cells where the nucleolus was included in the section plane of 50 µm-spaced out sections were considered to avoid the overlapping of the same cell bodies and they were analyzed with computer-assisted image analysis (ImageJ, NIH) to measure the soma and nucleolus size of at least 300 DRG neurons per mouse.

Analysis of Sciatic Nerve Histology: Measure of G-Ratio

After completion of behavioral and electrophysiological analysis, animals were killed and sciatic nerves were dissected, fixed, stained for myelin and cut as semithin sections. Light microscopy was performed to capture an image of the entire nerve which was then subjected to semi-automatic software-based nerve morphometry in order to assess axon diameter and myelin thickness 20.

Statistical Evaluation

The differences in body weight, NCV, sensory potential amplitude and behavioral tests were statistically evaluated using the analysis of variance (ANOVA) and the Tukey-Kramer post-test (significance level set at $p<0.05$).

Data Acquisition

Data for all investigations were recorded, whenever possible, on-line using software packages specifically designed for the purposes of the test facility/site. Where on-line recording was not possible, handwritten raw data sheets were used. The data were subsequently entered manually into the computer and the raw data sheets are archived.

Results

Mortality

Two animals (BFMD and OXA+BFMD groups) died after the first administration; one animal (OXA+BFMD group) died after the last administration.

Clinical Observations

The administration of the test compounds was well-tolerated.

Body Weight

Body weight changes along the study. During the treatment all groups of treatment did not show significant difference in body weight if compared to untreated animals.

Morphometry and Histopathology Analysis

The morphometric analysis revealed that DRG neurons from oxaliplatin-treated mice (OXA, dark grey) had a significant decrease in the area ($\mu m^2$) of their cell bodies (FIG. 19A) and nucleoli (FIG. 19B), compared to DRG neurons from naïve mice (CTRL, pale grey bars). Furthermore the presence of BFMD clearly protected the DRG with both somatic and nucleoli showing no difference from the CTRL group, after 4 weeks of treatment with OXA (OXA+BFMD, black bars).

Figure 20:
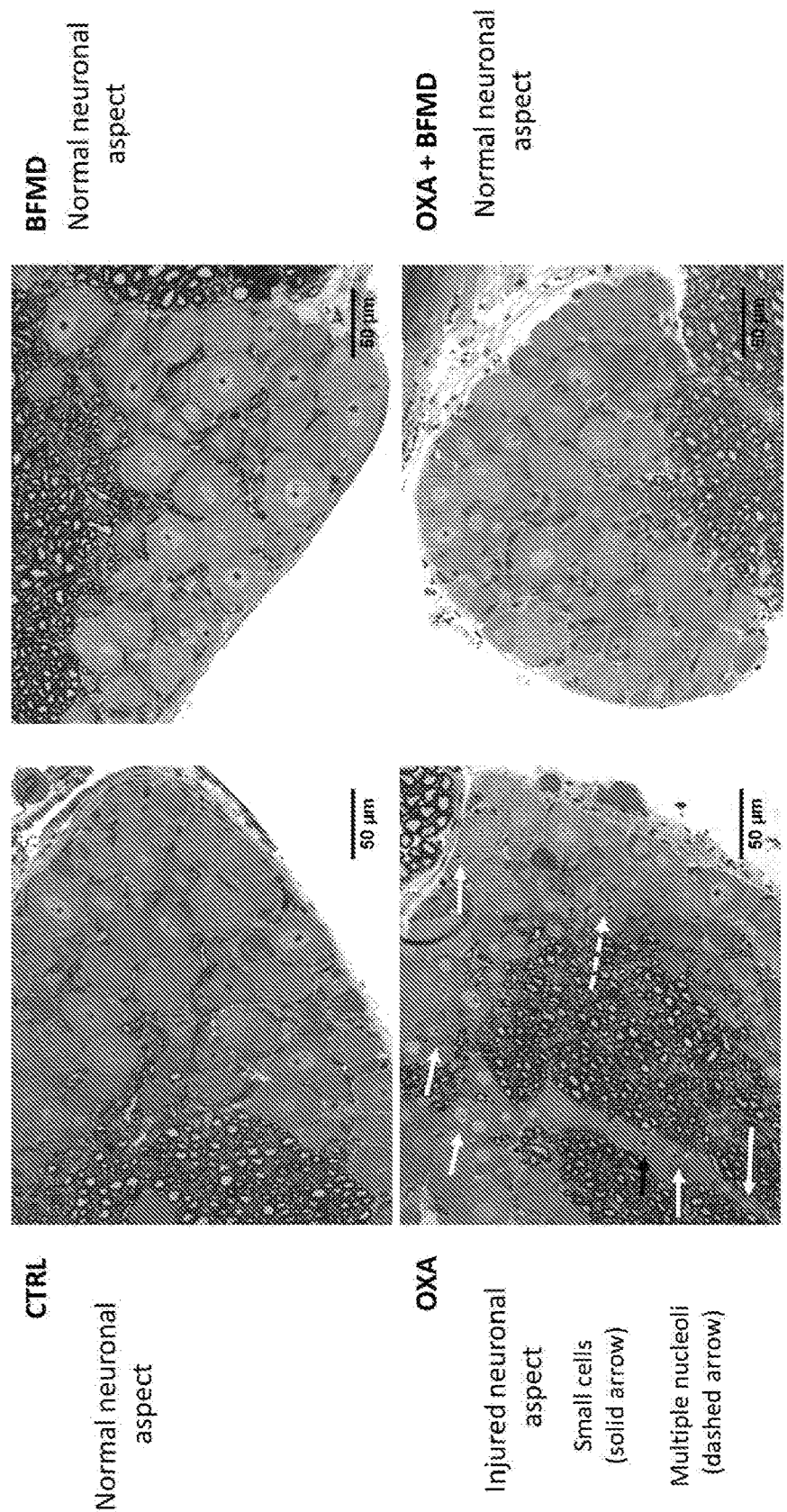
FIG. 20 depicts morphology of DRG nerve cells from histopathology samples of mice after 8 cycles of treatment with vehicle control (top left), oxaliplatin (bottom left), buflomedil (top right) and oxaliplatin+buflormedil (bottom right).

Thin sections through the L4-L5 DRGs and sciatic nerve from naïve, oxaliplatin-treated mice in presence or absence of BFMD treatment were examined at the light and electron microscope levels two days after the final dose of drug in week four (FIG. 20). Altered function of peripheral neurons after oxaliplatin was accompanied by structural changes in the DRG cell bodies as it is clearly represented in (FIG. 20: OXA). Light microscopy revealed that DRG neurons from oxaliplatin-treated mice had a high incidence of multinucleolated cell bodies with eccentric nucleoli compared to naïve DRG neurons. In all experimental groups, the cytoplasm of neurons and satellite cells appeared normal. BFMD groups in presence or absence of OXA look clearly similar to the control and therefore further establish the protective properties of BFMD during treatment with OXA.

In summary, the presence of BFMD during treatment with OXA clearly protects DRG as observed both with cellular morphometry and histopathology.

Neuropathological Analysis Sciatic Nerve

Figure 21:
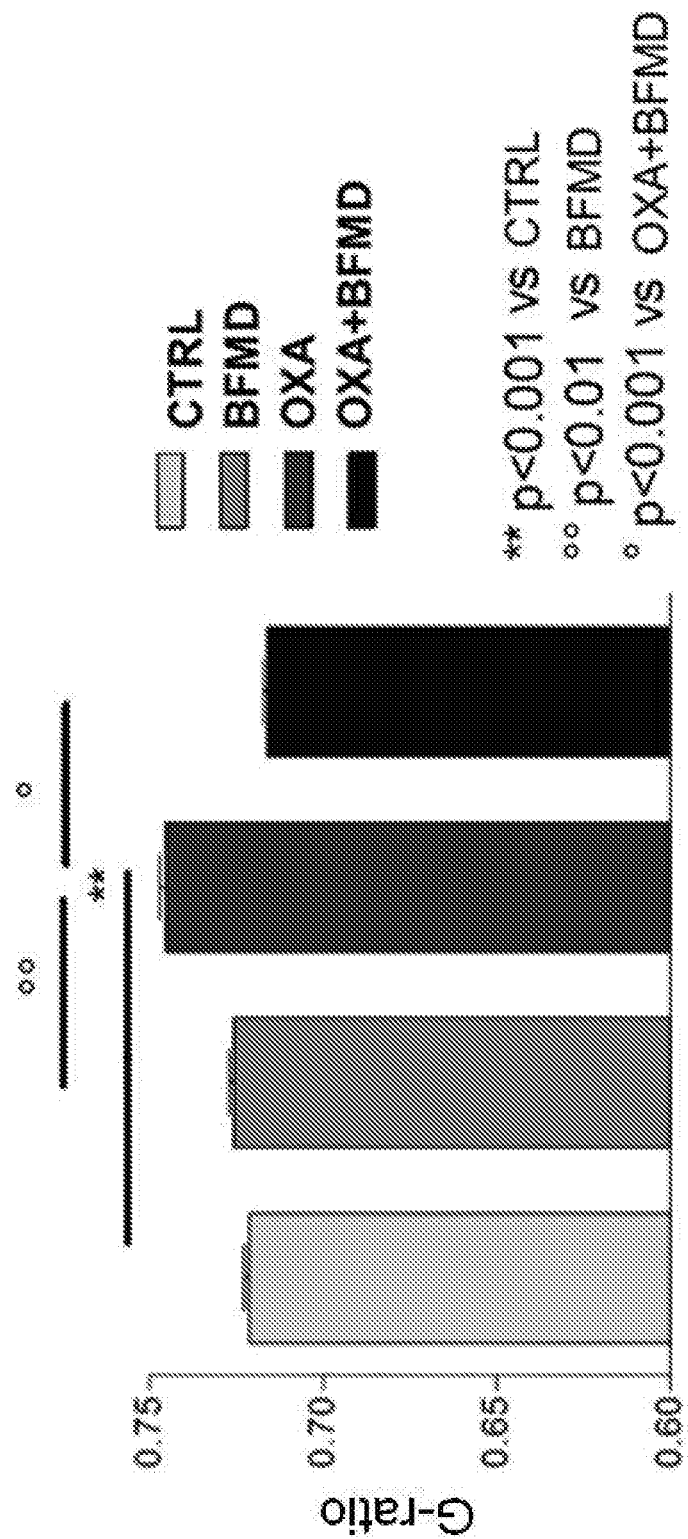
FIG. 21 depicts buflomedil was effective on reducing sciatic nerve damage in mice treated with 8 cycles of oxaliplatin at 3.5 mg/kg, based on morphometric assessment of sciatic nerve samples.
Figure 22:
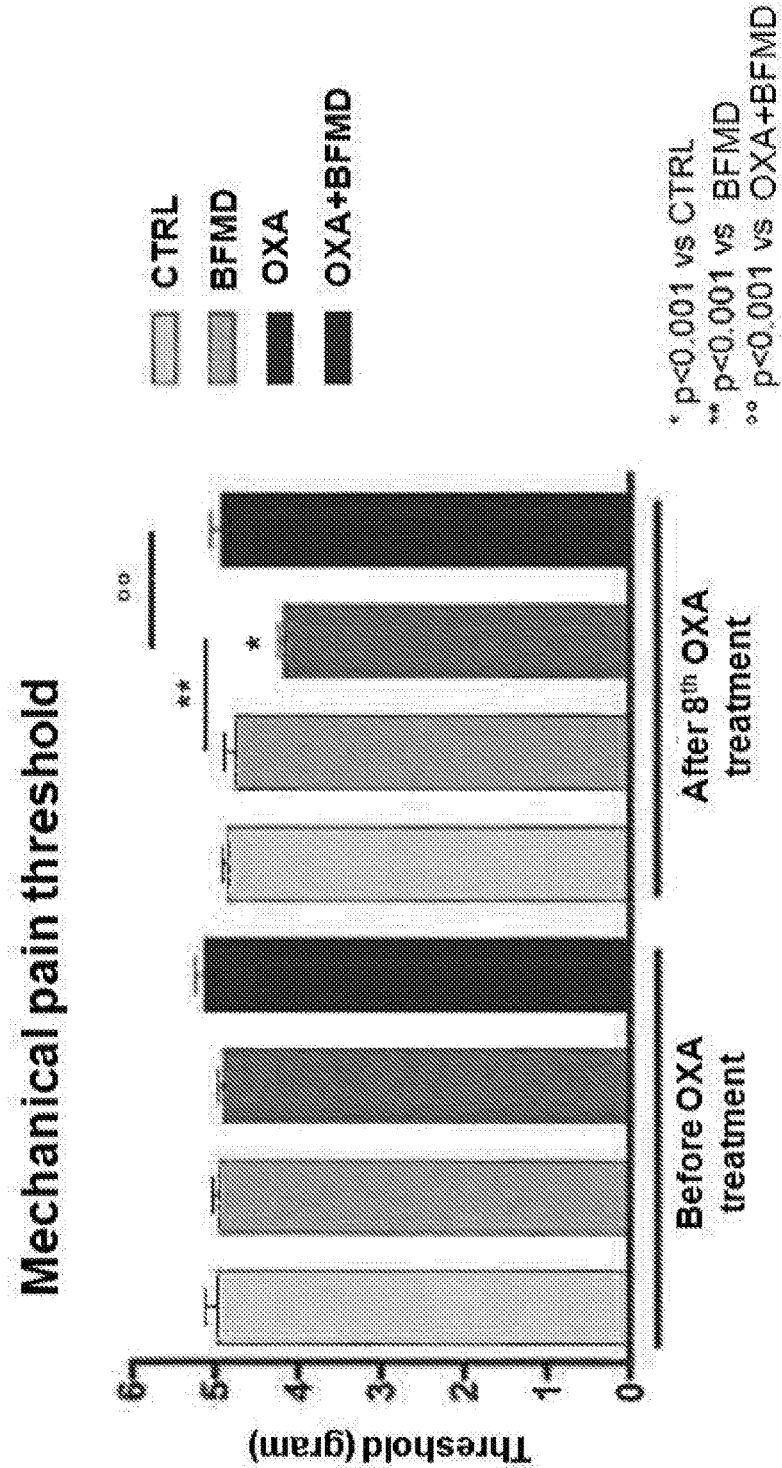
FIG. 22 depicts buflomedil was effective on preventing mechanical allodynia in mice after 8 cycles of oxaliplatin treatment.

To assess changes in nerve cell myelination, we calculated the g ratio of nerve fibers (g-ratio denominates the numerical ratio between the diameter of the axon and the outer diameter of the myelinated fiber; hypomyelination in sciatic nerves, which is associated with platinum neurotoxicity (Boehmerle, W., et al. Sci. Rep. 4, 6370), would thus cause an increase of the g-ratio). As shown in FIG. 21, a mild hypomyelination, reflected as a small but statistically significant increase in G-ratio, was evident in the OXA group as compared with CTRL. Treating with BFMD minimized such damage, showed as a reduction in G-ratio of the OXA+BFMD group vs OXA group. This data further confirmed the protective effect of BFMD against nerve damage caused by OXA.

Dynamic Aesthesiometer Test

Dynamic Aesthesiometer Test results (FIG. 22) at baseline and at the end of the study are reported in Fig. O. At the end of treatment only the groups treated with OXA alone showed the development of mechanical allodynia with a reduction in the latency until withdrawal vs CTRL, BFMD and OXA+BFMD (p<0.001).

Cold Plate Test

Figure 23:
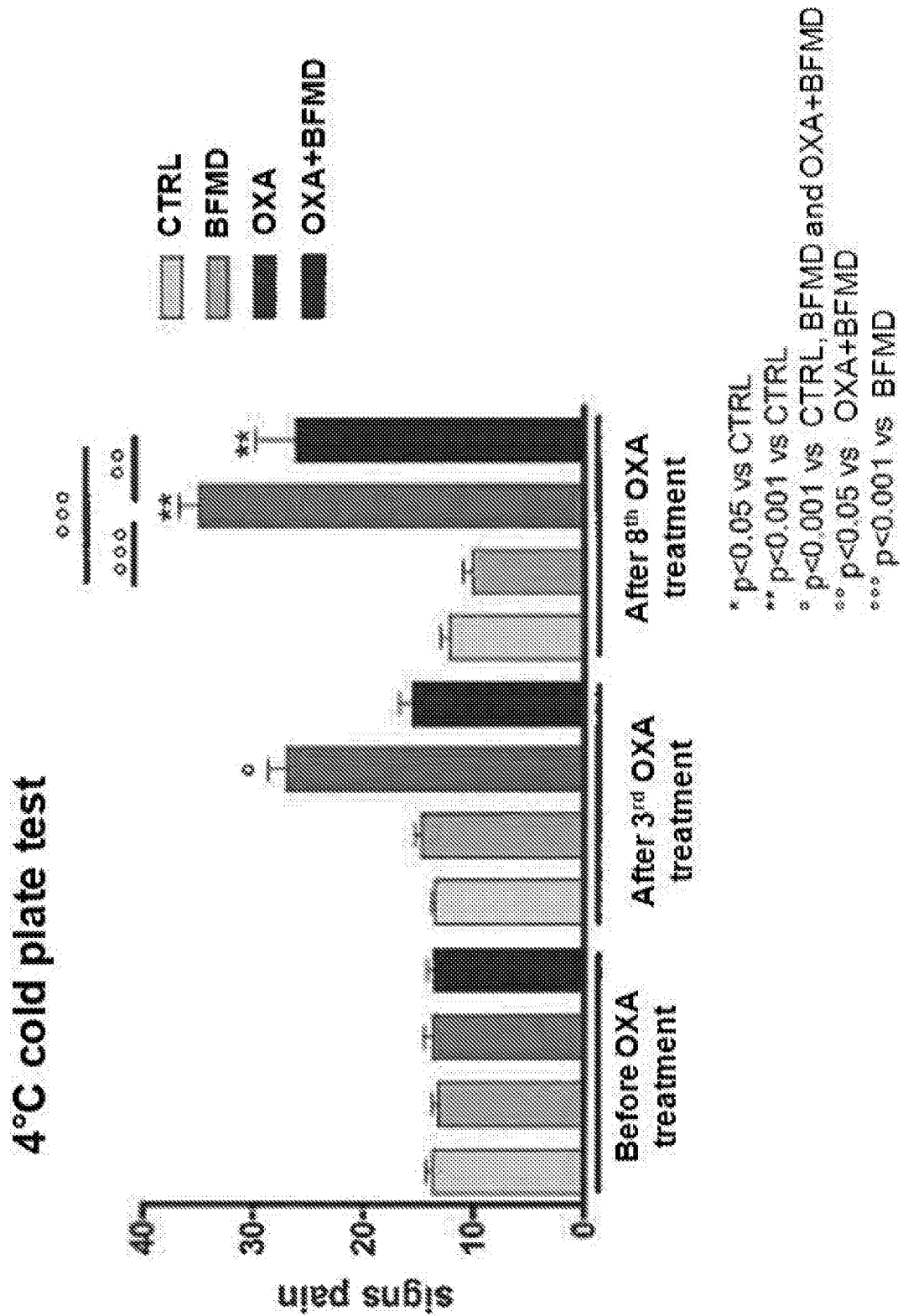
FIG. 23 depicts buflomedil was effective on reducing cold allodynia in mice after 3 and 8 cycles of oxaliplatin treatment.

Cold Plate Test results at baseline, after third injection and the end of the study (eight injections) are reported in FIG. 23. After third injection only the group treated with OXA alone showed a significant increase in pain signs versus CTRL and all groups of treatment (p<0.001). At the end of treatment both groups treated with OXA alone or in co-administration of BFMD showed a significant increase in pain signs versus CTRL and BFMD (p<0.001). The co-treated group showed a significant decrease in pain signs versus OXA alone (p<0.05).

Neurophysiological Results

The administration of Oxaliplatin, induced a significant reduction in caudal nerve conduction velocity vs. control mice, the group treated with OXA+BFMD showed a reduction compared to CTRL and BFMD groups, but showed a small but statistically significant increase when compared to OXA alone (FIG. 24). Only the OXA group showed a significant decrease in caudal amplitude (p<0.01 vs CTRL) (FIG. 25), whereas there was no statistically significant difference among CTRL. BFMD and OXA+BFMD groups.

Plasma Levels

Figure 26:
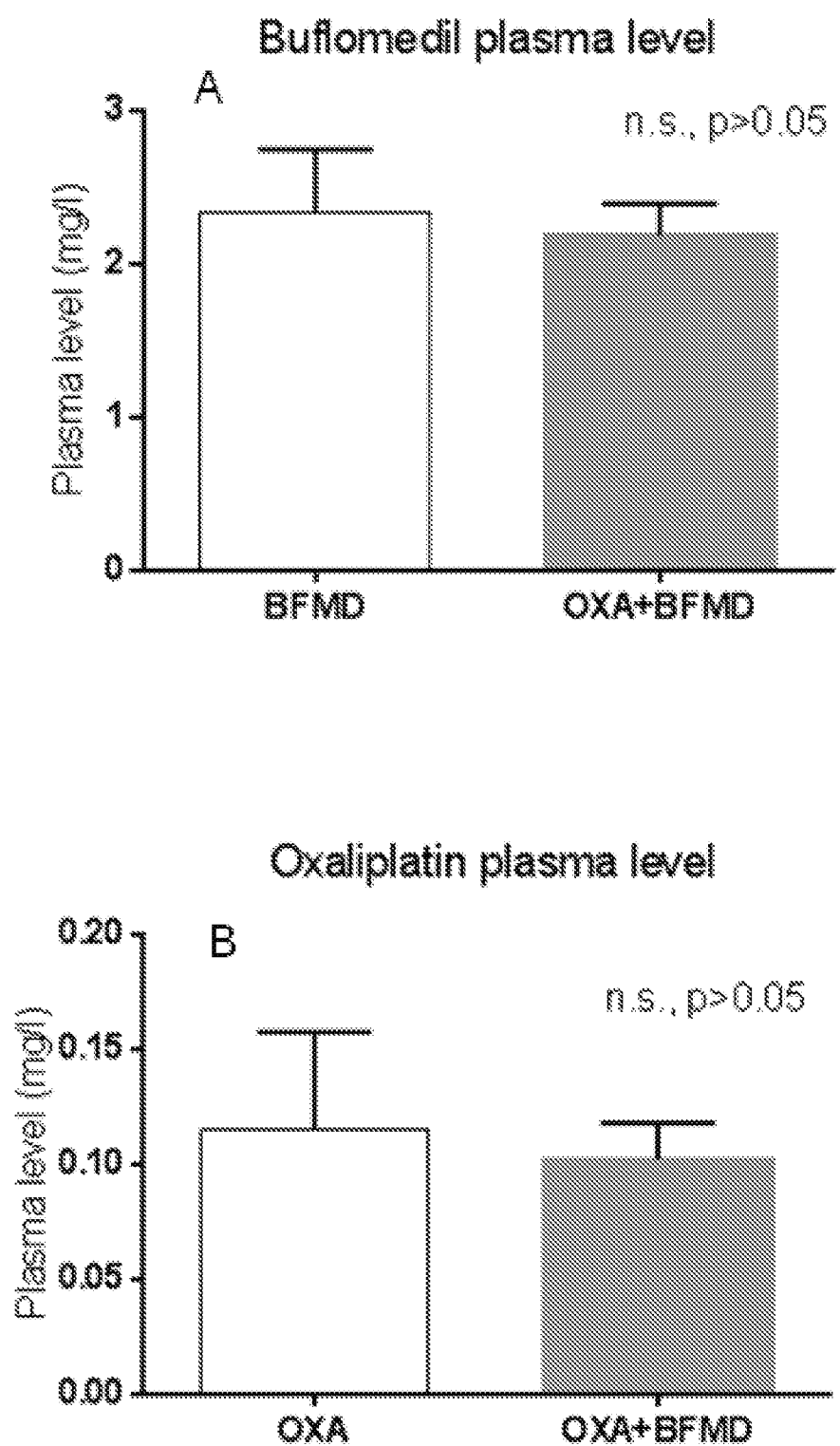
FIG. 26 depicts plasma levels of buflomedil and oxaliplatin in mice 15 minutes after the $8^{th}$ cycle of oxaliplatin (3.5 mg/kg) treatment.

Plasma levels for both OXA and BFMD were measured at the end of the study. Plasma levels for BFMD were consistently above an expected level (1.72 mg/l) (FIG. 26A). No pharmacokinetic interaction was observed in vivo between BFMD and OXA as shown in FIG. 26A, whereby both levels of BFMD and BFMD in presence of OXA are sensibly equivalent. Furthermore plasma levels of OXA seems unaffected by the presence of BFMD (FIG. 26B)

Example 16

The following example relates to evaluating and comparison of the effect of Dolutegravir (DTG) and chlorphenesin (CTC) on acute peripheral neuropathy induced by a single administration of Oxaliplatin Aim The aim of this study is to assess the effects of Dolutegravir and Chlorphenesin Carbamate in Balb/c mice exposed to acute treatment with Oxaliplatin (OXA). Both dolutegravir and chlorphenesin are known OCT2 inhibitors. However, in our experiments, we have previously established (EXAMPLE 1) that Dolutegravir is a selective OCT2 inhibitor whereas Chlorphenesin does not inhibit OCT2 mediated Oxaliplatin transport, despite it was reported as a very potent inhibitor of OCT2 mediated transport of a non-platinum compound ASP+. Based on findings from EXAMPLE 15, we expect Dolutegravir should block oxaliplatin uptake in DRG whereas Chrlophenesin should not. It is therefore our aim to observe how Dolutegravir and Chlorphenesis could differently protect male Balb/c mice in an acutely induced peripheral neuropathy Study Design At the beginning of the study, 30 male Balb/c mice were randomized (FIG. 27) into 6 experimental groups: one group was left untreated (CTRL, n=5), one group was treated with Oxaliplatin iv 3.5 mg/kg (OXA, n=5), one group was treated with Dolutegravir 4 mg/kg ip (DTG, n=5), one group was treated with Chlorphenesin 4 mg/kg ip (CPC, n=5), one group was co-treated with Oxaliplatin 3.5 mg/kg iv and Dolutegravir administered ip 60 min before the OXA administration (OXA+BFMD, n=12) and the last group was treated with Chlorphenesin 4 mg/kg ip Oxaliplatin 3.5 mg/kg and Dolutegravir administered ip 60 min before the OXA administration (OXA+CPC).

The dose and route of administration of dolutegravir used in this study were determined based on PK study in EXAMPLE 14, such that DTG plasma level should be sufficient to block OCT2 significantly (>90%).

At baseline and at the end of treatment behavioral tests (Dynamic and Cold Plate) and serum collection were performed. The behavioral tests evidenced the development of allodynia in the animals treated with OXA alone.

Drug Dosage and Formulation

Oxaliplatin (OXA), 3.5 mg/kg$^a$, intravenously, dissolved in glucosate 5%

Dolutegravi (DTG), 4 mg/kg$^b$, intraperitoneally, formulated as a solution in DMSO diluted with 50 mM N-methylglucamine in 3% aqueous mannitol (1/19 v/v).

Chlorphenesin Carbamate (CPC), 4 mg/kg, intravenously, dissolved in glucosate 5%

Pharmacological Treatment

OXA vehicle, OXA, CPC, DTG, DTG+OXA and CPC+OXA were administered once time. In the group co-administered with OXA and DTG. DTG was injected intraperitoneally 1 hour before the administration of OXA. In the group co-administered with OXA and CPC, CPC was co-administered with OXA intravenously. Mechanical allodynia and cold sensory threshold (dynamic test and cold plate test) were performed 24 and 48 hours after the treatment, respectively, using the methods described in EXAMPLE 15

Plasma Sample Collection 15 min after the iv administration of oxaliplatin the serum sample were collected for pharmacokinetic analysis from each group.

Results

Figure 28:
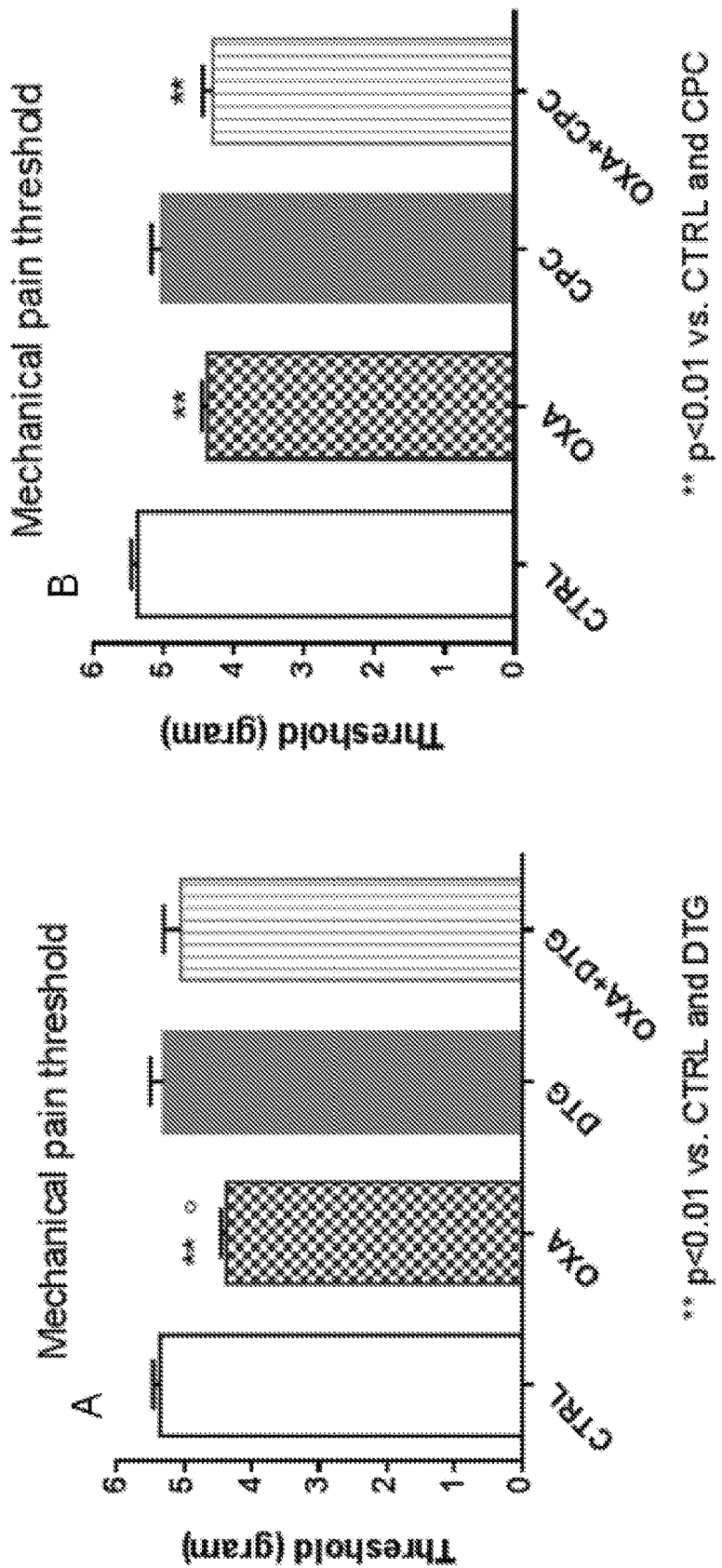
FIG. 28 depicts dolutegravir (FIG. 28A), but not chlophenesin (FIG. 28B), was effective on reducing mechanical hypersensitivity in mice after a single oxaliplatin treatment, based on measuring mechanical pain threshold.

FIG. 28A shows that a single injection of 3.5 mg/kg oxaliplatin induced mechanical allodynia evidenced by a significant decrease in Mechanical Pain Threshold (MPT) in the OXA group, as compared to the CTRL group, as well as the DTG alone and OXA+DTG. There was no statistically significant difference among the CTRL, DRG and OXA+DTG groups, suggesting DTG was effective in nearly completely alleviated mechanical hypersensitivity acutely induced by oxaliplatin. In contrast, CPC was shown to have no such effect as shown in FIG. 28B, which was an expected result for compounds that do not protect against OCT2 mediated platinum uptake in the DRG.

Figure 29:
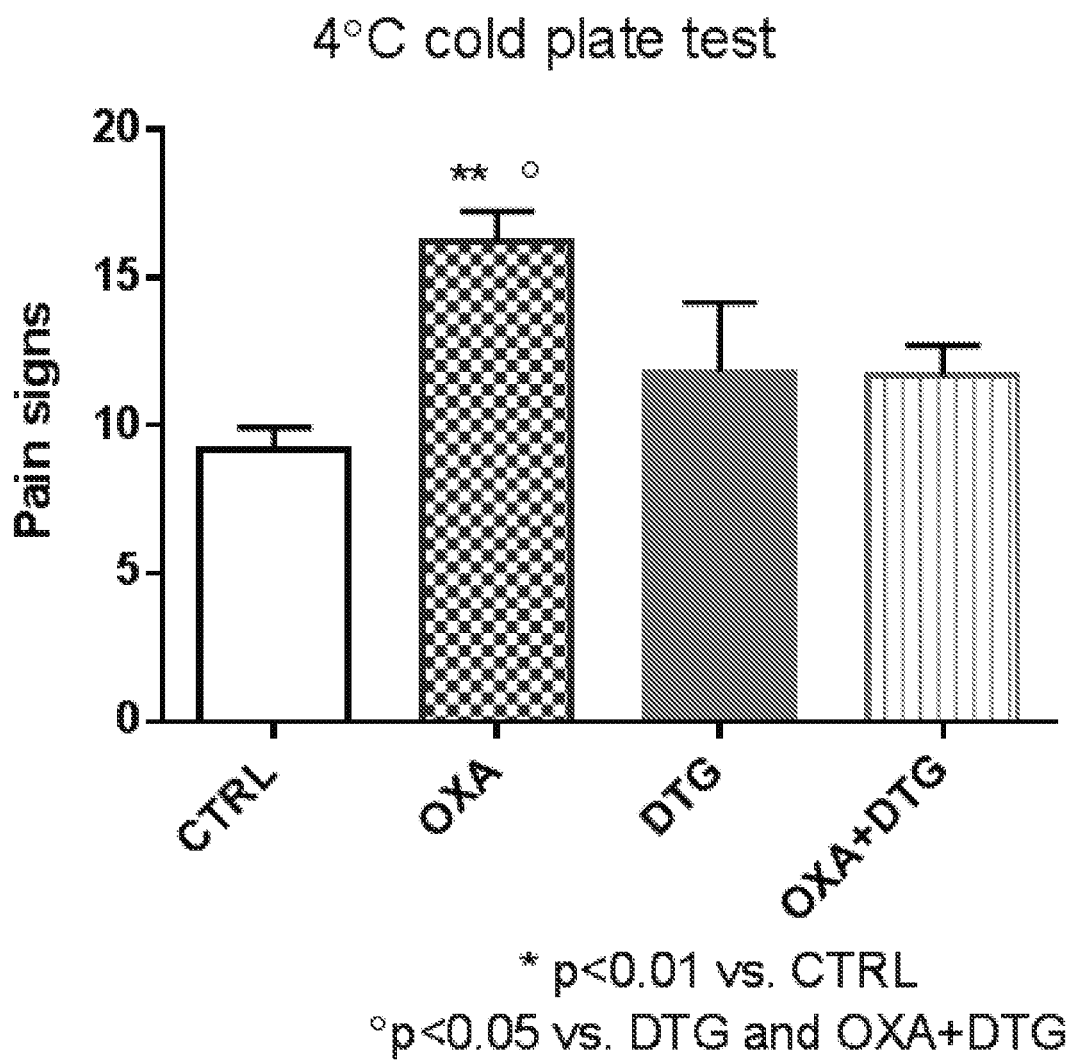
FIG. 29 depicts dolutegravir was effective on reducing cold hypersensitivity in mice after a single oxaliplatin treatment.

Similarly, cold plate assays results clearly show that DTG (FIG. 29) added to OXA protects the animal from cold allodynia.

These results clearly show that DTG, as expected, had a protective effect on both types of allodynia and therefore could be used to minimize both acute and chronic side effects of CIPN and more specifically OXA-IPN.

Example 16

The following example relates to correlating oxaliplatin accumulation with OXAIPN in mice treated with eight cycles of oxaliplatin, with and without orally administered buflomedil Study Design This study had the same design as that described in EXAMPLE 15 except that Buflomedil was administered by oral gavage (PO), 80 mg/kg, 2 hours before oxaliplatin administration.

At the end of 8 cycles of treatment, cold plate test, dynamic test and NCS test were conducted in all mice. Platinum content in DRG, Sciatic nerves and kidney of 3 mice each in the OXA and OXA+BFMD groups, was measured using the method below.

Platinum Accumulation Measurement

The tissue total platinum concentration was determined on frozen sciatic nerve. DRG, kidney, and plasma specimens collected from 3 animals/group killed 24 h after the last administration of the drugs. For each tissue, a calibration with control standard tissue was generated. All frozen test samples and standards were treated for a digestion process with a specific $HNO_3$: HCl solution (1:3). The samples obtained after digestion were analyzed by "Atomic Absorption" (Analyst 600 Perkin Elmer, Monza, Italy), and platinum tissue concentration was calculated accordingly.

Results

Figure 30:
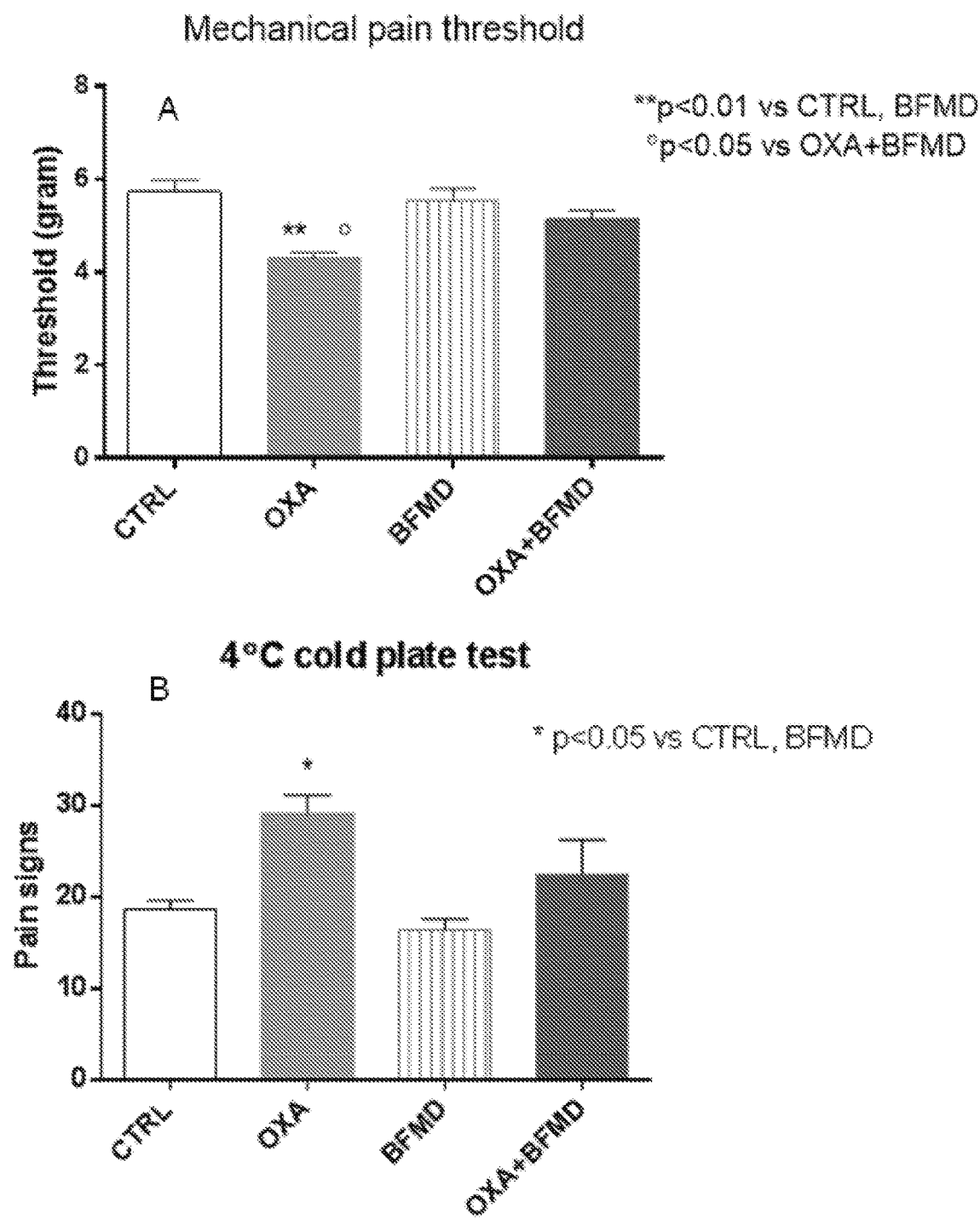
FIG. 30 depicts buflomedil (80 mg/kg po (orally)) was effective on reducing mechanical (FIG. 30A) and cold (FIG. 30B) allodynia in mice (n=3/group) after 8 cycles of oxaliplatin treatment.
Figure 31:
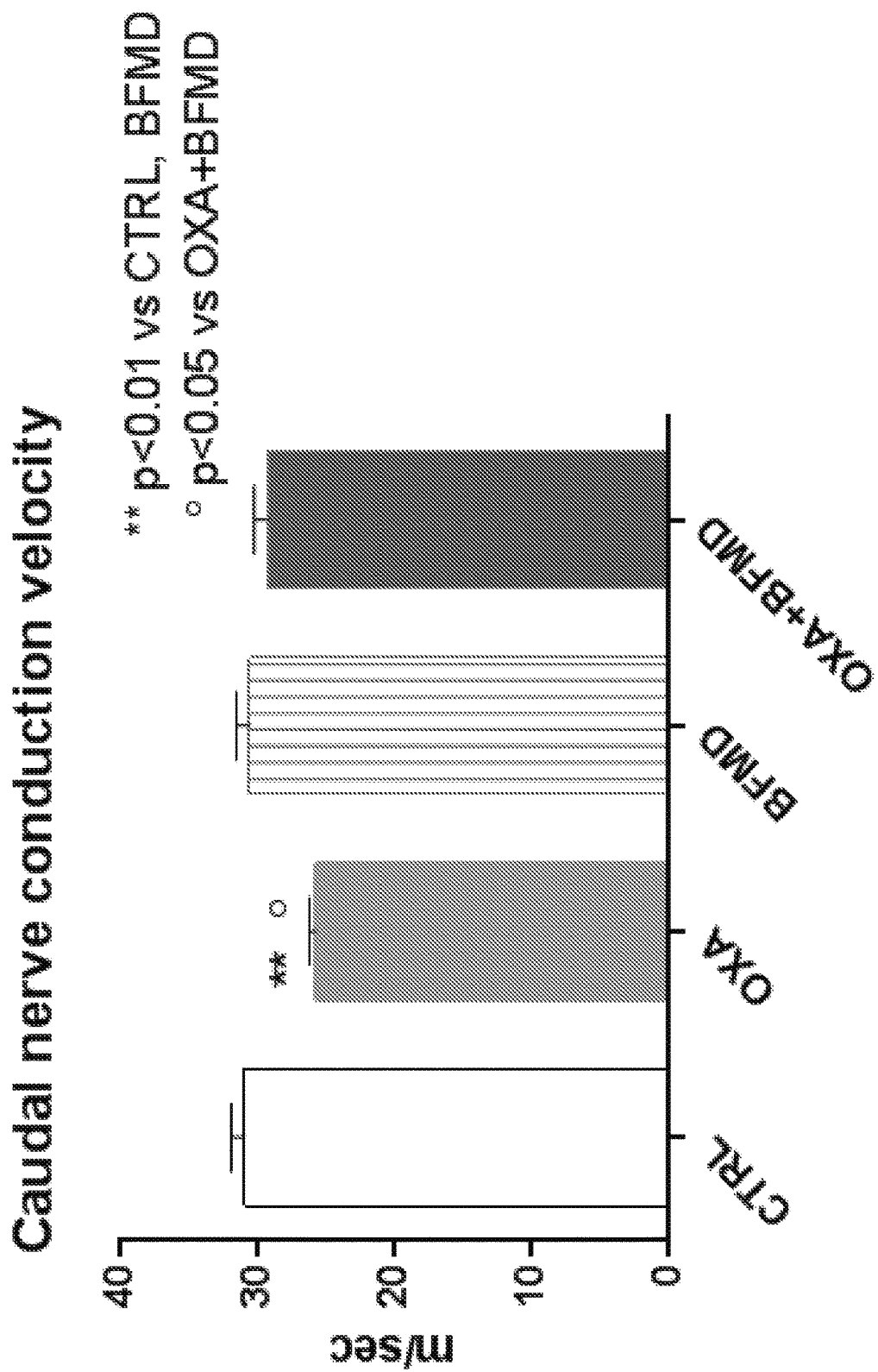
FIG. 31 depicts buflomedil (80 mg/kg po) was effective on reducing nerve injury, assessed by caudal NCV, in mice (n=3/group) after 8 cycles of oxaliplatin treatment.
Figure 32:
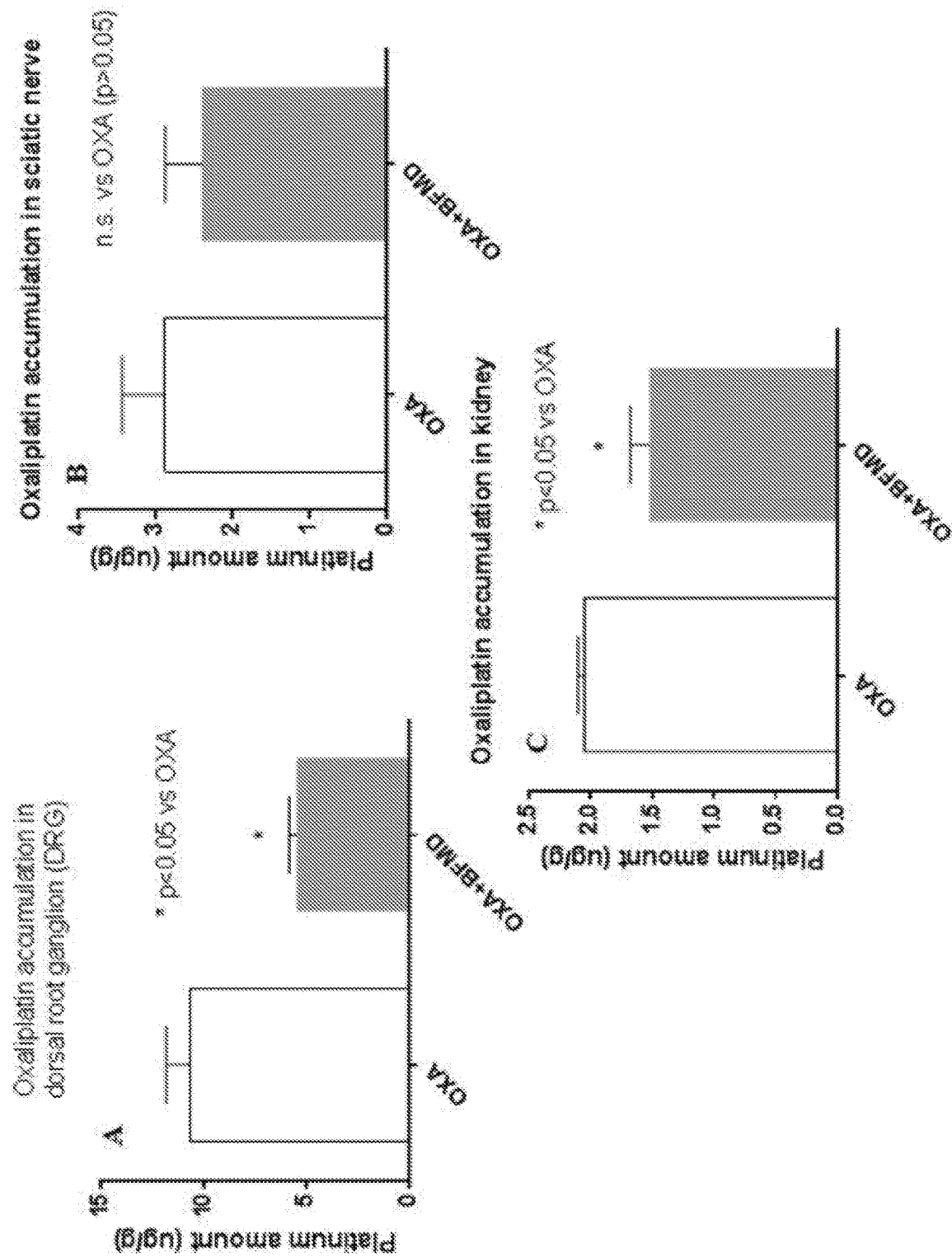
FIG. 32 depicts buflomedil was effective on reducing platinum accumulation in DRG (FIG. 32A) and kidney (FIG. 32C), but not in sciatic nerves (FIG. 32B).

Similar to the results presented in EXAMPLE 15, orally administrated buflomedil, at 80 mg/kg, showed protective effects against OXAIPN based both behavioral tests (mechanical pain threshold and cold plate test) (FIG. 30) and nerve conduction velocity measurement (FIG. 31). Moreover, buflomedil treatment resulted in a significant decrease in oxaliplatin accumulation in DRG (FIG. 32A), whereas such decrease was not seen in sciatic nerves that may not express high level of OCT2. The result further support that buflomedil may protect oxaliplatin induced DRG damage through reducing oxaliplatin accumulation via OCT2. Interestingly, buflomedil also reduced oxaliplatin accumulation in the kidney, suggesting in this study, buflomedil was able to block OCT2 in the kidney. This result, together with ones shown in previous examples, further suggest that buflomedil and other selective OCT2 inhibitors, such as dolutegravir, are very likely to have a protective role against cisplatin induced nephorotixity through reducing cisplatin accumulation in the kidney.

REFERENCES

1. Sprowl J A, Ciarimboli G, Lancaster C S et al. Proc Natl Acad Sci USA. 2013; 110(27):11199-204
2. Kido Y. Matsson P, Giacomini K M. J Med Chem 2011; 54(13):4548-58
3. Belzer M. Morales M, Jagadish B et al. J Pharmacol Exp Ther 2013; 346(2):300-10
4. Guidance for Industry Drug Interaction Studies-Study Design, Data Analysis, Implications for Dosing, and Labeling Recommendations] available at www.fda.gov/downloads/drugs/guidancecomplianceregulatoryinformation/guidances/ucm292362.pdf
5. Zhang Y, Warren M S. Zhang X et al. Drug Metab Dispos. 2015; 43(4):485-9.
6. H. Ehrsson, et. al, Medical Oncology, vol. 19, no. 4, 261-265, 2002
7. Sung J P, Grendahl J G, Levine H B, West J Med 126:5-13, January 1977
8. Mikamo. H., et. al., International Journal of Antimicrobial Agents 9 (1998) 207-211
9. Molinaro, M., et. al., Journal of Clinical Pharmacy and Therapeutics (1994) 19, 111-115
10. Hidalgo, M., Bloedow, D., Seminars in Oncology, Vol 30, No 3, Suppl 7 (June), 2003: pp 25-33
11. Heise et al. BMC Cancer 2012, 12:109
12. Yonesawa A, Inui K-I. Biochem Pharmacology (2011) 81; 563-568.
13. Ta et al., Mol Pain (2009) February 26, 5-9.
14. Katsuda et al., Biol Pharm Bull (2010) 33, 1867-71
15. Min et. al., ANTIMICROBIAL AGENTS AND CHEMOTHERAPY, January 2010, p. 254-258
16. K. M. Hargreaves et al Pain 32: 77-88, 1988.

17. Jahic. M., Baik, J., et. al., 13$^{th}$ European ISSX meeting, Glasgow. 2015, P164.
18. Ta et al. Mol Pain (2009) February 26, 5-9.
19. Carozzi, V. A., et al., Neurophysiological and neuropathological characterization of new murine models of chemotherapy-induced chronic peripheral neuropathies. Exp Neurol, 2010, 226(2): p. 301-9.
20. Cavaletti G. Chemotherapy-induced peripheral neurotoxicity (CIPN): what we need and what we know. J Peripher Nerv Syst. 2014 June; 19(2):66-76.
22. Renn C L. Carozzi V A, Rhee P, Gallop D. Dorsey S G. Cavaletti G. Multimodal assessment of painful peripheral neuropathy induced by chronic oxaliplatin-based chemotherapy in mice. Mol Pain. 2011 Apr. 26; 7:29

ADDITIONAL REFERENCES

Griffith, K. A., et al. *Support Care Cancer.* 2014 May; 22(5): 1161-1169
Jensen, T. S. *Lancet Neural.* 2014; 13: 924-35
Argyriou, A. A., et al. *Critical Reviews in Oncology/Hematology.* 82 (2012) 51-77
Boehmerle, W., et al. *Sci. Rep.* 4, 6370
Avan, A., et al. *The Oncologist.* 2015; 20: 411-432
Argyriou. A. A., *Toxics.* 2015, 3, 187-197
Zhang J., et al. *British Journal of Clinical Pharmacology.* 2015; 80:3, 502-514
Bourguinon, L., et al. *Fundamental & Clinical Pharmacology.* 26 (2012) 279-285
Gunder-Remy. U., et al. *European Journal of Clinical Pharmacology* (1981) 20: 459-463
Velasco, R., et al. *J Neurol Neurosurg Psychiatry* 2014; 85: 392-398
Yao, X., et al. *The American Journal of the Medical Sciences.* 2007; 334(2): 115-124
Miller, R. P., et al. *Toxins* 2010, 2, 2490-2518
Karasawa. T., et al. *Toxicology Letters* 237 (2015) 219-227
Sada, H., et al. *Journal of Pharmacological Sciences* 118, 547-551 (2012)
Seretny. M., et al. *PAIN* 115 (2014) 2461-2470
Kawashiri, T., et al. *European Journal of Pain* 15 (2011) 344-350
Cavaletti. G., et al. *Annals of Oncology* 24: 454-462, 2013
Wolf. S. L., et al. *Support Care Cancer.* 2012 March; 20(3): 625-632
Langer, Thorsten, et al. *Trends in Pharmacological Sciences* August 2013. Vol. 34, No. 8
Barbas, K., et al. *Veterinary and Comparative Oncology*, 6, 1, 1-18
Gauchan, P., et al. *Bio. Pharm. Bull.* 32 (4) 732-734 (2009)
Ushio, S., et al. *European Journal of Cancer* 48 (2012) 1407-1413
Authier, N., et al. *Neurotherapeutics*, Vol. 6, No. 4, 2009
Han, Y., et al. Frontiers in Pharmacology. 18, December 2013; Vol. 4: 156
Saif, M., et al. *Therapeutics and Clinical Risk Management* 2005: 1(4) 249-258
Miltenburg, N. C., et al. *Cancer Treatment Reviews.* 40 (2014) 872-882
Cavaletti, G., et al. *European Journal of Cancer* 46 (2010) 479-494
Karasawa, K., Steyger. P., Toxicology Letters 237 (0.2015) 219-227
Holmes, J., et. al., Toxicological Sciences 46, 342-351 (1998)
Hershman, D. et. al., and American Society of Clinical Oncology (ASCO), J of Clinical Oncology, v32:18 (2014) 1941-1970,
Wolfgang, B., et, al, *Scientific Reports* 4:6370 1-9 (2014)
Argyriou. A., et. al., *Cancer* January 2013, 438-444
Albers, J W. et. al., *Cochrane Database Syst Rev* (2) 2011 February 16, CD005228, doi: 10.1002/14651858.CD005228.pub3
Kautio A L. et. al., *Anticancer Res* 29:2601-2606 (2009)
Kautio A L. et. al., *J Pain Symptom Manage* 35:31-39 (2008)
Kottschade et al. *Support Care Cancer.* 2011 November; 19(11): 1769-77
Pace A., et. al., *J Clin Oncol* 21:927-931 (2003)
Werling, L., Experimental neurology (2007) 207:2 pg:248-257
Sprowl, J A., et. al., Proc Natl Acad Sci USA. 2013 Jul. 2; 110(27):11199-204
Hellberg et al., Laryngoscope 125: E320-325 (2015)
Burger H., Drug Resist Updat. 2011 February; 14(1):22-34
Harrach, S., Ciarimboli, G., Front. Pharmacol., v6:86 1-7 (0.2015)
Tashima, J Carcinog Mutagen 2015, 6:4
Li and Shu Molecular and Cellular Therapies 2014, 2:15
Nakanishi, T., CANCER GENOMICS & PROTEOMICS 4: 241-254 (2007)

What is claimed is:

1. A method for reducing oxaliplatin-induced neurotoxicity in a human subject in need thereof comprising
   administering oxaliplatin to the subject in need thereof; and
   administering to the subject in need thereof an effective dose of a second agent selected from the group consisting of buflomedil, a buflomedil salt, dolutegravir, and a dolutegravir salt, wherein the subject in need thereof has colorectal cancer or liver cancer; wherein the colorectal cancer or liver cancer expresses at least one of Organic Cation Transporter 1 (OCT1) and Organic Cation Transporter 3 (OCT3); and wherein the neurotoxicity is damage to dorsal root ganglia (DRG).

2. The method of claim 1, wherein the neurotoxicity is peripheral neurotoxicity.

3. The method of claim 1, wherein the neurotoxicity is damage to a sensory neuron.

4. The method of claim 1, wherein the neurotoxicity is chronic neurotoxicity.

5. The method of claim 1, wherein the neurotoxicity occurs after a subject completes treatment with a cumulative dose of the oxaliplatin of at least 500 mg/m$^2$.

6. The method of claim 1, wherein the dose of the second agent is effective to minimize oxaliplatin-induced neurotoxicity in said subject in need thereof.

7. The method of claim 1, further comprising assessing oxaliplatin-induced neurotoxicity in a subject after administration of the oxaliplatin.

8. The method of claim 1, wherein the oxaliplatin and the second agent are administered at the same time.

9. The method of claim 1, wherein the second agent is administered before the oxaliplatin.

10. The method of claim 1, wherein the second agent is administered after the oxaliplatin.

11. The method of claim 1, wherein
   a) the amount of oxaliplatin administered to the subject during one treatment session is greater than 60 mg/m$^2$;
   b) the cumulative amount of oxaliplatin administered to the subject in need thereof over the entire course of treatment is greater than 780 mg/m$^2$; or c) the oxaliplatin is administered at a greater frequency than every three weeks.

12. The method of claim 1, wherein the neurotoxicity is Grade 3 peripheral neuropathy or Grade 4 peripheral neuropathy.

13. The method of claim 1, wherein the second agent is administered enterally, intravenously, intramuscularly, intraperitoneally, orally, or parenterally.

14. A method for reducing cisplatin-induced neurotoxicity in a human subject in need thereof comprising
administering cisplatin to the subject in need thereof; and
administering to the subject in need thereof an effective dose of a second agent selected from the group consisting of buflomedil, a buflomedil salt, dolutegravir, and a dolutegravir salt,
wherein the subject in need thereof has colorectal cancer or liver cancer; wherein the colorectal cancer or liver cancer expresses at least one of Organic Cation Transporter 1 (OCT1) and Organic Cation Transporter 3 (OCT3); and wherein the neurotoxicity is damage to dorsal root ganglia (DRG).

15. The method of claim 1, wherein the neurotoxicity is Grade 2 or higher peripheral neuropathy.

16. The method of claim 1, wherein the colorectal cancer or liver cancer expresses OCT1.

17. The method of claim 1, wherein the colorectal cancer or liver cancer expresses OCT3.

18. The method of claim 1, wherein the colorectal cancer or liver cancer expresses OCT1 and OCT3.

19. The method of claim 1, wherein the colorectal cancer or liver cancer does not express OCT2.

20. The method of claim 1, wherein the neurotoxicity is acute syndrome transient neurotoxicity.

21. The method of claim 1, wherein the neurotoxicity is chronic peripheral neuropathy.

22. The method of claim 1, wherein the neurotoxicity is acute syndrome transient peripheral neuropathy.

* * * * *